(12) United States Patent
Boye et al.

(10) Patent No.: US 9,816,108 B2
(45) Date of Patent: Nov. 14, 2017

(54) RAAV-GUANYLATE CYCLASE COMPOSITIONS AND METHODS FOR TREATING LEBERS CONGENITAL AMAUROSIS-1 (LCA1)

(75) Inventors: Shannon Elizabeth Boye, Gainesville, FL (US); William W. Hauswirth, Gainesville, FL (US); Sanford Leon Boye, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/643,074

(22) PCT Filed: Apr. 22, 2011

(86) PCT No.: PCT/US2011/033669
§ 371 (c)(1),
(2), (4) Date: Feb. 1, 2013

(87) PCT Pub. No.: WO2011/133933
PCT Pub. Date: Oct. 27, 2011

(65) Prior Publication Data
US 2013/0210895 A1 Aug. 15, 2013

Related U.S. Application Data

(60) Provisional application No. 61/327,521, filed on Apr. 23, 2010.

(51) Int. Cl.
| | |
|---|---|
| *C12N 15/861* | (2006.01) |
| *A61K 48/00* | (2006.01) |
| *C12N 9/88* | (2006.01) |
| *C12N 15/86* | (2006.01) |
| *A61K 38/00* | (2006.01) |

(52) U.S. Cl.
CPC .......... *C12N 15/861* (2013.01); *A61K 48/005* (2013.01); *C12N 9/88* (2013.01); *C12N 15/86* (2013.01); *C12Y 406/01002* (2013.01); *A61K 38/00* (2013.01); *C12N 2750/14143* (2013.01); *C12N 2830/008* (2013.01); *C12N 2830/85* (2013.01)

(58) Field of Classification Search
CPC ........ C12N 15/861; C12N 2750/14143; C12N 9/88; C12N 2830/85; C12N 15/86; C12N 2830/008; A61K 48/005; A61K 38/00; C12Y 406/01002
See application file for complete search history.

(56) References Cited

U.S. PATENT DOCUMENTS

| | | | |
|---|---|---|---|
| 6,225,291 B1 | 5/2001 | Lewin et al. | |
| 2003/0003582 A1* | 1/2003 | Wakefield et al. | 435/456 |
| 2004/0022766 A1* | 2/2004 | Acland et al. | 424/93.2 |
| 2005/0255089 A1* | 11/2005 | Chiorini | C12N 15/86 424/93.2 |
| 2007/0042462 A1* | 2/2007 | Hildinger | 435/69.1 |
| 2008/0003204 A1 | 1/2008 | Flotte et al. | |
| 2010/0069467 A1 | 3/2010 | Boye et al. | |

FOREIGN PATENT DOCUMENTS

| | | |
|---|---|---|
| EP | 2021499 | 7/2007 |
| WO | 2002/082904 A2 | 10/2002 |
| WO | WO 2002/082904 A2 | 10/2002 |
| WO | WO 2004065576 A2 * | 8/2004 |
| WO | 2007/127428 A2 | 11/2007 |
| WO | WO 2009/046059 A1 | 4/2009 |

OTHER PUBLICATIONS

Yokoi et al. "Ocular Gene Transfer with Self-Complementary AAV Vectors." Invest Ophthalmol Vis Sci. (2007);48: pp. 3324-3328.*
Weleber et al. "Inherited and Orphan Retinal Diseases: Phenotypes, Genotypes, and ProbableTreatment Groups."RETINA, The Journal of Retinal and Vitreous Diseases, vol. 25, No. 8, Supplement (2005).*
Lotery et al. "Mutation analysis of 3 genes in patients with Leber congenital amaurosis." Arch Ophthalmol. Apr. 2000;118(4):538-43.*
Baehr, Wolfgang, et al., "The Function of Guanylate Cyclase 1 and Guanylate Cyclase 2 in Rod and Cone Photoreceptors," Journal of Biological Chemistry, The American Society for Biochemistry and Molecular biology, Inc., vol. 282, No. 12, pp. 8837-8847, Mar. 23, 2007.
Beltran, W. A., et al., "Efficiency of rAAV5 Vectors Containing Three Different Promoters for Rod Transduction in the Canine Retina," Investigative Ophthalmology & Visual Science 2010; 51; E-Abstract 3115, 2010 ARVO.
Beltran, William A., et al. "rAAV2/5 Gene-Targeting to Rods; Dose-Dependent Efficiency and Complications Associated With Different Promoters," Gene Ther. Sep. 2010; 17(9); 1162-1174. Doi;10.1038/gt.2010.56; National Institute of Health; pp. 1-23.
Boye, Shannon E., et al. "AAv-mediated Gene Therapy Restores Visual Function and Behavior to a Mouse Model or Leger Congenital Amaurosis-1 (LCA1)," Final Program American Sociaty of Gene & Cell Therapy, 13th Annual Meeting, Washington, DC USA, May 19-22, 2012, Abstract No. 17.
Boye, Sanford L., et al. "Long-Term Preservation of Cone Photoreceptors and Restoration of Cone Function by Gene Therapy in the Guanylate Cyclase-1 Knockout (GC1KO) Mouse," Investigative Ophthalmology & Visual Science, Sep. 2011, vol. 52, No. 10; The Association for Research in Vision and Ophthalmology, Inc. 2011; pp. 7098-7108.

(Continued)

*Primary Examiner* — Titilayo Moloye
(74) *Attorney, Agent, or Firm* — Wolf, Greenfield & Sacks, P.C.

(57) ABSTRACT

Disclosed are viral vector compositions comprising polynucleotide sequences that express one or more biologically-active mammalian guanylate cyclase proteins. Also disclosed are methods for their use in preventing, treating, and/or ameliorating at least one or more symptoms of a disease, disorder, abnormal condition, or dysfunction resulting at least in part from a guanylate cyclase deficiency in vivo. In particular embodiments, the use of recombinant adeno-associated viral (rAAV) vectors to treat or ameliorate symptoms of Leber's congenital amaurosis, as well as other conditions caused by an absence or reduction in the expression of a functional retinal-specific guanylate cyclase 1 (retGC1).

7 Claims, 25 Drawing Sheets

(56) References Cited

OTHER PUBLICATIONS

Boye, Shanon E., et al., "Functional and Behavioral Restoration of Vision by Gene Therapy in the Guanylate Cyclase-1 (GC1) Knockout Mouse," PLoS One 5(6); e11306. Doi:10:1371/ journal.pone. 0011306, pp. 1-13, 2010.
Chen, Junping, et al., "Light Threshold-Controlled Cone α-Transducin Translocation," Investigative Ophthalmology & Visual Science, Jul. 2007, vol. 48, No. 7, Association for Research in Vision and Ophthalmology, pp. 3350-3355.
Deng, Wen-Tao, et al., Functional Interchangeability of Rod and Cone Transducin α-Subunits, PNAS USA. Oct. 20, 2009;106(42):17681-6.
Haire, Shannon, E., et al., "Light-Driven Cone ArrestinTranslocation in Cones of Postnatal Guanylate Cyclase-1 Knockout Mouse Retina Treated With AAV-GC1," Investigative Ophthalmology & Visual Science, Sep. 2006, vol. 47, No. 9, Association for Research in Vision and Ophthalmology, pp. 3745-3753.
Jiang, L., et al., "Knock-Down of GCAP1 by RNA Interference Delays Photoreceptor Degeneration in GCAP1-Y99C Transgenic Mice," Investigative Ophthalmology & Visual Science 2010; 51; E-Abstract 4488, 2010 ARVO.
Kelsell, Rosemary E., et al., Mutations in the Retinal Guanylate Cyclase (RETGC-1) Gene in Dominant Cone-Rod Dystrophy, 1998 Oxford University Press; Human Molecular Genetics, 1998, vol. 7, No. 7, pp. 1179-1184.
Kong, Fansheng, et al., Self-Complementary AAV5 Vector Facilitates Quicker Transgene Expression in Photoreceptor and Retinal Pigment Epithelial Cells or Normal Mouse, Exp. Eye Res. May 2010; 90(5); 546-554. Doi; 10.1016/j.exer.2010.01.011; National Institutes of Health.
Li, Wensheng, et al., "Gene Therapy following Subretinal AAV5 Vector Delivery is Not Affected by a Previous Intravitreal AAV5 Vector Administration in the Partner Eye," Molecular Vision 2009; 15:267-275.
Pang, Ji-jing, et al., "AAV-Mediated Gene Therapy for Retinal Degeneration in the rd10 Mouse Containing a Recessive PDEβ Mutation," Investigative Ophthalmology & Visual Science, Oct. 2008, vol. 49, No. 10; Association for Research in Vision and Ophthalmology.
Pang, J., et al., "Self-Complementary AAV-Mediated Gene Therapy Restores Cone Function and Prevents Cone Degeneration in Two Models of Rpe65 Deficiency," Gene Therapy (2010), 1-12; 2010 Macmillan Publishers Limited.
Roman, Alejandro, et al., "Electroretinographic Analyses of Rpe65-Mutant rd12 Mice: Developing an in Vivo Bioassay for Human Gene Therapy Trials of Leber Cogenital Amaurosis," Molecular Vision 2007; 13:1701-10, Sep. 18, 2007.
Simonelli, Francesca, et al., "Gene Therapy for Leger's Congenital Amaurosis is Safe and Effective Through 1.5 Years After Vector Administration," The American Society of Gene & Cell Therapy, Molecular Therapy vol. 18, No. 3, 643-650, Mar. 2010.
Takemoto, Norihiko, et al., "High cGMP Synthetic Activity in Carp Cones," PNAS, Jul. 14, 2009, vol. 106, No. 28, pp. 11788-11793.
Williams, Melissa L., et al., "Lentiviral Expression of RetinalGuanylate Cyclase-1 (RetGC1) Restores Vision in an Avian Model of Childhood Blindness," PLoS Medicine, Jun. 2006, vol. 3, Issue 6, e201, pp. 0904-0917.
Zheng, Q., et al. "Proteomic Analysis Following AAV-Mediated Gene Therapy in rd12 Mice, a Model of Leber Congenital Amaurosis With Rpe65 Mutation," Investigative Ophthalmology & Visual Science, 2010; 51: E-Abstract 4491-A463, ARVO.
International Search Report and Written Opinion of the International Searching Authority issued in Application No. PCT/US2011/033669 dated Oct. 18, 2011.
Australian Office Action, dated Jul. 31, 2014, 2011242527, 3 pages.
Chinese Office Action, dated Sep. 28, 2014, 201180020530.7, 4 pages (with translation).
Japanese Office Action, dated Aug. 15, 2014, 2013-506347, 4 pages (with translation).
New Zealand First Examination Report, dated Aug. 21, 2014, 628121, 2 pages.
Examination Report dated Nov. 5, 2013 in copending Chinese Patent Application 201180020530.7.
International Search Report and Written Opinion for International Application No. PCT/US2011/033669 dated Nov. 18, 2011.
International Preliminary Report on Patentability for International Application No. PCT/US2011/033669 dated Nov. 1, 2012.
Accession No. Q02846. Jul. 1, 1993. 12 pages.
Accession No. P52785. Oct. 1, 1996. 8 pages.
Khani, AAV-mediated expression targeting of rod and cone photoreceptors with a human rhodopsin kinase promoter. Biochemistry and Molecular Biology. Sep. 2007; 48: 3954-61.
Lowe, Cloning and expression of a second photoreceptor-specific membrane retina guanylyl cyclase (RetGC), RetGC-2. Proc. Natl. Acad. Sci. Neurobiology. Jun. 1995; 92: 5535-9.
Pang et al., Self-complementary AAV-mediated gene therapy restores cone function and prevents cone degeneration in two models of Rpe65 deficiency. Gene Ther. Jul. 2010;17(7):815-26. doi: 10.1038/gt.2010.29. Epub Mar. 18, 2010.
Young, A short, highly active photoreceptor-specific enhancer/promoter region upstream of the human rhodopsin kinase gene. Investigative Ophthalmology & Visual Science. Sep. 2003; 44(9): 4076-85.
Zhong et al., Next generation of adeno-associated virus 2 vectors: point mutations in tyrosines lead to high-efficiency transduction at lower doses. Proc Natl Acad. Sci. USA. Jun. 3, 2008;105(22):7827-32.
Allocca et al., AAV-mediated gene replacement, either alone or in combination with physical and pharmacological agents, results in partial and transient protection from photoreceptor degeneration associated with betaPDE deficiency. Invest Ophthalmol Vis Sci. Jul. 29, 2011;52(8):5713-9. doi: 10.1167/iovs.10-6269.
Bemelmans et al., Lentiviral gene transfer of RPE65 rescues survival and function of cones in a mouse model of Leber congenital amaurosis. PLoS Med. Oct. 2006;3(10):e347.
Boye et al., AAV-mediated gene therapy in the guanylate cyclase (RetGC1/RetGC2) double knockout mouse model of Leber congenital amaurosis. Hum Gene Ther. Feb. 2013;24(2):189-202. doi: 10.1089/hum.2012.193.
Boye et al., The human rhodopsin kinase promoter in an AAV5 vector confers rod- and cone-specific expression in the primate retina. Hum Gene Ther. Oct. 2012;23(10):1101-15. doi: 10.1089/hum.2012.125. Epub Sep. 20, 2012.
Chen et al., RPE65 gene delivery restores isomerohydrolase activity and prevents early cone loss in Rpe65-/- mice. Invest Ophthalmol Vis Sci. Mar. 2006;47(3):1177-84.
Coleman et al., Cone cell survival and downregulation of GCAP1 protein in the retinas of GC1 knockout mice. Invest Ophthalmol Vis Sci. Oct. 2004;45(10):3397-403.
Conley et al, Nanoparticles for retinal gene therapy. Prog Retin Eye Res. Sep. 2010;29(5):376-97. doi: 10.1016/j.preteyeres.2010.04. 004. Epub May 7, 2010.
Flannery et al., Efficient photoreceptor-targeted gene expression in vivo by recombinant adeno-associated virus. Proc Natl Acad Sci U S A. Jun. 24, 1997;94(13):6916-21.
Koirala et al., S/MAR-containing DNA nanoparticles promote persistent RPE gene expression and improvement in RPE65-associated LCA. Hum Mol Genet. Apr. 15, 2013;22(8):1632-42. doi: 10.1093/hmg/ddt013. Epub Jan. 18, 2013.
Milam et al., Clinicopathologic effects of mutant GUCY2D in Leber congenital amaurosis. Ophthalmology. Mar. 2003;110(3):549-58.
Porto et al., Prenatal human ocular degeneration occurs in Leber's congenital amaurosis (LCA1 and 2). In Retinal Degenerations: Mechanisms and Experimental Therapy. Edited by LaVail et al. 2003; 59-60.
Puppo et al., Retinal transduction profiles by high-capacity viral vectors. Gene Ther. Oct. 2014; 21(10):855-65. doi: 10.1038/gt. 2014.57. Epub Jul. 3, 2014.

\* cited by examiner

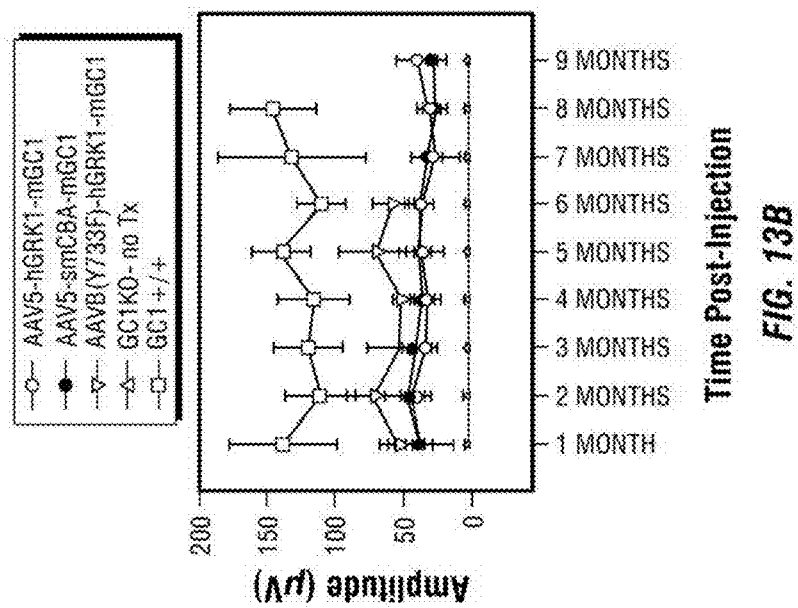
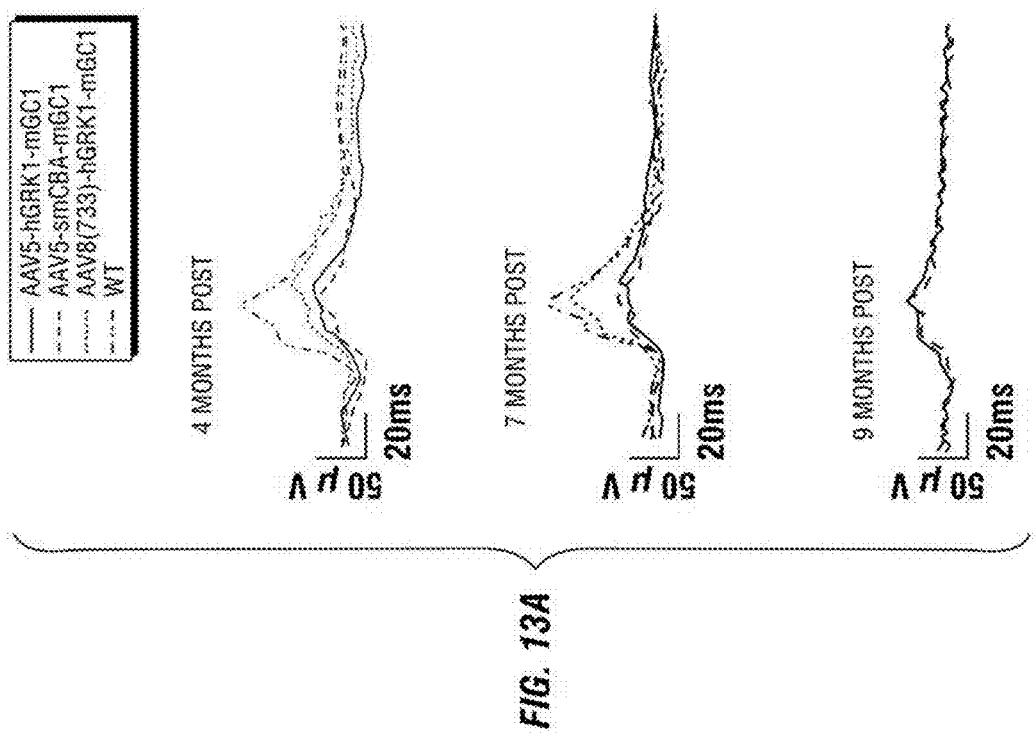
FIG. 13A
FIG. 13B

| DETECTION OF rAAV VECTOR SEQUENCES BY PCR IN GC1KO TISSUE SAMPLES | | | | | | | | | | | | |
|---|---|---|---|---|---|---|---|---|---|---|---|---|
| | M1a | M2b | M3b | M4c | M5c | M6c | M7c | M8c | M9b | M10c | M11b | M12c |
| | AAV8(733)-hGRK1 | AAV8(733)-hGRK1 | AAV5-smCBA | AAV5-smCBA | AAV5-smCBA | AAV5-smCBA | AAV5-smCBA | AAV5-smCBA | AAV5-hGRK1 | AAV5-hGRK1 | no Tx | no Tx |
| OPTIC NERVE R | na | na | +160 | +1000 | +970 | +1890 | NA | +395 | +3140 | +1695 | - | - |
| OPTIC NERVE L | +632 | +25,885 | - | na | na | na | na | na | - | na | na | na |
| BRAIN R | - | - | - | - | - | - | - | - | - | - | - | - |
| BRAIN L | - | - | - | - | - | - | - | +252 | - | - | - | - |

M, ANIMAL; R, RIGHT; L, LEFT; Tx, TREATMENT; -, NO PCR AMPLIFICATION; +, PCR AMPLIFICATION OF VECTOR SEQUENCE (REPLICATED VALUE SHOWN IS AVERAGE), COPY NUMBER PER MG OF DNA; NA, NOT AVAILABLE (NOT DETERMINABLE BECAUSE OF AN UNACCEPTABLE SPIKE-IN)
A. 4 MONTHS POST-INJECTION
B. 7 MONTHS POST-INJECTION
C. 10 MONTHS POST-INJECTION

*FIG. 17*

SEQUENCE LISTING

```
<160> NUMBER OF SEQ ID NOS: 18

<210> SEQ ID NO 1
<211> LENGTH: 1103
<212> TYPE: PRT
<213> ORGANISM: Homo sapiens

<400> SEQUENCE: 1

Met Thr Ala Cys Ala Arg Arg Ala Gly Gly Leu Pro Asp Pro Gly Leu
1               5                   10                  15

Cys Gly Pro Ala Trp Trp Ala Pro Ser Leu Pro Arg Leu Pro Arg Ala
            20                  25                  30
```

```
Leu Pro Arg Leu Pro Leu Leu Leu Leu Leu Leu Gln Pro Pro
        35                  40                  45

Ala Leu Ser Ala Val Phe Thr Val Gly Val Leu Gly Pro Trp Ala Cys
 50                  55                  60

Asp Pro Ile Phe Ser Arg Ala Arg Pro Asp Leu Ala Ala Arg Leu Ala
 65                  70                  75                  80

Ala Ala Arg Leu Asn Arg Asp Pro Gly Leu Ala Gly Gly Pro Arg Phe
                 85                  90                  95

Glu Val Ala Leu Leu Pro Glu Pro Cys Arg Thr Pro Gly Ser Leu Gly
                100                 105                 110

Ala Val Ser Ser Ala Leu Ala Arg Val Ser Gly Leu Val Gly Pro Val
                115                 120                 125

Asn Pro Ala Ala Cys Arg Pro Ala Glu Leu Leu Ala Glu Glu Ala Gly
130                 135                 140

Ile Ala Leu Val Pro Trp Gly Cys Pro Trp Thr Gln Ala Glu Gly Thr
145                 150                 155                 160

Thr Ala Pro Ala Val Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
                180                 185                 190

Leu Trp Val Glu Ala Gly Arg Ser Leu Ser Thr Ala Leu Arg Ala Arg
                195                 200                 205

Gly Leu Pro Val Ala Ser Val Thr Ser Met Glu Pro Leu Asp Leu Ser
                210                 215                 220

Gly Ala Arg Glu Ala Leu Arg Lys Val Arg Asp Gly Pro Arg Val Thr
225                 230                 235                 240

Ala Val Ile Met Val Met His Ser Val Leu Leu Gly Gly Glu Glu Gln
                245                 250                 255

Arg Tyr Leu Leu Glu Ala Ala Glu Glu Leu Gly Leu Thr Asp Gly Ser
                260                 265                 270

Leu Val Phe Leu Pro Phe Asp Thr Ile His Tyr Ala Leu Ser Pro Gly
                275                 280                 285

Pro Glu Ala Leu Ala Ala Leu Ala Asn Ser Ser Gln Leu Arg Arg Ala
290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Glu Leu Pro Ser
                325                 330                 335

Asp Leu Asn Leu Gln Gln Val Ser Pro Leu Phe Gly Thr Ile Tyr Asp
                340                 345                 350

Ala Val Phe Leu Leu Ala Arg Gly Val Ala Glu Ala Arg Ala Ala Ala
                355                 360                 365

Gly Gly Arg Trp Val Ser Gly Ala Ala Val Ala Arg His Ile Arg Asp
                370                 375                 380

Ala Gln Val Pro Gly Phe Cys Gly Asp Leu Gly Gly Asp Glu Glu Pro
385                 390                 395                 400

Pro Phe Val Leu Leu Asp Thr Asp Ala Ala Gly Asp Arg Leu Phe Ala
                405                 410                 415

Thr Tyr Met Leu Asp Pro Ala Arg Gly Ser Phe Leu Ser Ala Gly Thr
                420                 425                 430

Arg Met His Phe Pro Arg Gly Gly Ser Ala Pro Gly Pro Asp Pro Ser
                435                 440                 445

Cys Trp Phe Asp Pro Asn Asn Ile Cys Gly Gly Gly Leu Glu Pro Gly
```

-continued

```
            450                 455                 460
Leu Val Phe Leu Gly Phe Leu Val Val Gly Met Gly Leu Ala Gly
465                 470                 475                 480

Ala Phe Leu Ala His Tyr Val Arg His Arg Leu Leu His Met Gln Met
                    485                 490                 495

Val Ser Gly Pro Asn Lys Ile Ile Leu Thr Val Asp Asp Ile Thr Phe
            500                 505                 510

Leu His Pro His Gly Gly Thr Ser Arg Lys Val Ala Gln Gly Ser Arg
            515                 520                 525

Ser Ser Leu Gly Ala Arg Ser Met Ser Asp Ile Arg Ser Gly Pro Ser
530                 535                 540

Gln His Leu Asp Ser Pro Asn Ile Gly Val Tyr Glu Gly Asp Arg Val
545                 550                 555                 560

Trp Leu Lys Lys Phe Pro Gly Asp Gln His Ile Ala Ile Arg Pro Ala
                565                 570                 575

Thr Lys Thr Ala Phe Ser Lys Leu Gln Glu Leu Arg His Glu Asn Val
                    580                 585                 590

Ala Leu Tyr Leu Gly Leu Phe Leu Ala Arg Gly Ala Glu Gly Pro Ala
                595                 600                 605

Ala Leu Trp Glu Gly Asn Leu Ala Val Val Ser Glu His Cys Thr Arg
610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
                660                 665                 670

Ile Val Asp Gly Arg Phe Val Leu Lys Ile Thr Asp His Gly His Gly
                675                 680                 685

Arg Leu Leu Glu Ala Gln Lys Val Leu Pro Glu Pro Arg Ala Glu
            690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
                    725                 730                 735

Gln Glu Val Val Cys Arg Ser Ala Pro Tyr Ala Met Leu Glu Leu Thr
                740                 745                 750

Pro Glu Glu Val Val Gln Arg Val Arg Ser Pro Pro Leu Cys Arg
                755                 760                 765

Pro Leu Val Ser Met Asp Gln Ala Pro Val Glu Cys Ile Leu Leu Met
            770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
                820                 825                 830

Asp Leu Ile Arg Glu Arg Thr Glu Glu Leu Glu Leu Glu Lys Gln Lys
                835                 840                 845

Thr Asp Arg Leu Leu Thr Gln Met Leu Pro Pro Ser Val Ala Glu Ala
            850                 855                 860

Leu Lys Thr Gly Thr Pro Val Glu Pro Glu Tyr Phe Glu Gln Val Thr
865                 870                 875                 880
```

```
Leu Tyr Phe Ser Asp Ile Val Gly Phe Thr Thr Ile Ser Ala Met Ser
            885                 890                 895

Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
            915                 920                 925

Asp Ala Tyr Met Val Ala Ser Gly Leu Pro Gln Arg Asn Gly Gln Arg
            930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
            965                 970                 975

Ile Gly Leu His Ser Gly Pro Cys Val Ala Gly Val Val Gly Leu Thr
            980                 985                 990

Met Pro Arg Tyr Cys Leu Phe Gly Asp Thr Val Asn Thr Ala Ser Arg
            995                 1000                1005

Met Glu Ser Thr Gly Leu Pro Tyr Arg Ile His Val Asn Leu Ser
     1010            1015                1020

Thr Val Gly Ile Leu Arg Ala Leu Asp Ser Gly Tyr Gln Val Glu
     1025            1030                1035

Leu Arg Gly Arg Thr Glu Leu Lys Gly Lys Gly Ala Glu Asp Thr
     1040            1045                1050

Phe Trp Leu Val Gly Arg Arg Gly Phe Asn Lys Pro Ile Pro Lys
     1055            1060                1065

Pro Pro Asp Leu Gln Pro Gly Ser Ser Asn His Gly Ile Ser Leu
     1070            1075                1080

Gln Glu Ile Pro Pro Glu Arg Arg Arg Lys Leu Glu Lys Ala Arg
     1085            1090                1095

Pro Gly Gln Phe Ser
     1100

<210> SEQ ID NO 2
<211> LENGTH: 1108
<212> TYPE: PRT
<213> ORGANISM: Mus musculus

<400> SEQUENCE: 2

Met Ser Ala Trp Leu Leu Pro Ala Gly Gly Leu Pro Gly Ala Gly Phe
1               5                   10                  15

Cys Val Pro Ala Arg Gln Ser Pro Ser Ser Phe Ser Arg Val Leu Arg
            20                  25                  30

Trp Pro Arg Pro Gly Leu Pro Gly Leu Leu Leu Leu Leu Leu Leu Pro
            35                  40                  45

Ser Pro Ser Ala Leu Ser Ala Val Phe Lys Val Gly Val Leu Gly Pro
50                  55                  60

Trp Ala Cys Asp Pro Ile Phe Ala Arg Ala Arg Pro Asp Leu Ala Ala
65                  70                  75                  80

Arg Leu Ala Ala Asn Arg Leu Asn Arg Asp Phe Ala Leu Asp Gly Gly
            85                  90                  95

Pro Arg Phe Glu Val Ala Leu Leu Pro Glu Pro Cys Leu Thr Pro Gly
            100                 105                 110

Ser Leu Gly Ala Val Ser Ser Ala Leu Ser Arg Val Ser Gly Leu Val
            115                 120                 125

Gly Pro Val Asn Pro Ala Ala Cys Arg Pro Ala Glu Leu Leu Ala Gln
```

```
            130                 135                 140
Glu Ala Gly Val Ala Leu Val Pro Trp Gly Cys Pro Gly Thr Arg Ala
145                 150                 155                 160

Ala Gly Thr Thr Ala Pro Ala Val Thr Pro Ala Ala Asp Ala Leu Tyr
                165                 170                 175

Val Leu Leu Arg Ala Phe Arg Trp Ala Arg Val Ala Leu Ile Thr Ala
            180                 185                 190

Pro Gln Asp Leu Trp Val Glu Ala Gly Arg Ala Leu Ser Thr Ala Leu
        195                 200                 205

Arg Ala Arg Gly Leu Pro Val Ala Leu Val Thr Ser Met Glu Thr Ser
    210                 215                 220

Asp Arg Ser Gly Ala Arg Glu Ala Leu Gly Arg Ile Arg Asp Gly Pro
225                 230                 235                 240

Arg Val Arg Val Val Ile Met Val Met His Ser Val Leu Leu Gly Gly
                245                 250                 255

Glu Glu Gln Arg Tyr Leu Leu Glu Ala Ala Glu Glu Leu Ala Leu Thr
            260                 265                 270

Asp Gly Ser Leu Val Phe Leu Pro Phe Asp Thr Leu His Tyr Ala Leu
        275                 280                 285

Ser Pro Gly Pro Glu Ala Leu Ala Ala Phe Val Asn Ser Ser Gln Leu
    290                 295                 300

Arg Arg Ala His Asp Ala Val Leu Thr Leu Thr Arg Arg Cys Pro Pro
305                 310                 315                 320

Gly Gly Ser Val Gln Asp Ser Leu Arg Arg Ala Gln Glu His Gln Glu
                325                 330                 335

Leu Pro Leu Asp Leu Asn Leu Lys Gln Val Ser Pro Leu Phe Gly Thr
            340                 345                 350

Ile Tyr Asp Ala Val Phe Leu Leu Ala Gly Gly Val Lys Arg Ala Arg
        355                 360                 365

Thr Ala Val Gly Gly Gly Trp Val Ser Gly Ala Ser Val Ala Arg Gln
    370                 375                 380

Val Arg Glu Ala Gln Val Ser Gly Phe Cys Gly Val Leu Gly Arg Thr
385                 390                 395                 400

Glu Glu Pro Ser Phe Val Leu Leu Asp Thr Asp Ala Ser Gly Glu Gln
                405                 410                 415

Leu Phe Ala Thr His Leu Leu Asp Pro Val Leu Gly Ser Leu Arg Ser
            420                 425                 430

Ala Gly Thr Pro Met His Phe Pro Arg Gly Gly Pro Ala Pro Gly Pro
        435                 440                 445

Asp Pro Ser Cys Trp Phe Asp Pro Asp Val Ile Cys Asn Gly Gly Val
450                 455                 460

Glu Pro Gly Leu Val Phe Val Gly Phe Leu Leu Val Ile Gly Met Gly
465                 470                 475                 480

Leu Thr Gly Ala Phe Leu Ala His Tyr Leu Arg His Arg Leu Leu His
                485                 490                 495

Met Gln Met Ala Ser Gly Pro Asn Lys Ile Ile Leu Thr Leu Glu Asp
            500                 505                 510

Val Thr Phe Leu His Pro Pro Gly Gly Ser Ser Arg Lys Val Val Gln
        515                 520                 525

Gly Ser Arg Ser Ser Leu Ala Thr Arg Ser Ala Ser Asp Ile Arg Ser
    530                 535                 540

Val Pro Ser Gln Pro Gln Glu Ser Thr Asn Val Gly Leu Tyr Glu Gly
545                 550                 555                 560
```

```
Asp Trp Val Trp Leu Lys Lys Phe Pro Gly Glu His His Met Ala Ile
                565                 570                 575

Arg Pro Ala Thr Lys Thr Ala Phe Ser Lys Leu Arg Glu Leu Arg His
                580                 585                 590

Glu Asn Val Ala Leu Tyr Leu Gly Leu Phe Leu Ala Gly Thr Ala Asp
                595                 600                 605

Ser Pro Ala Thr Pro Gly Glu Gly Ile Leu Ala Val Val Ser Glu His
610                 615                 620

Cys Ala Arg Gly Ser Leu His Asp Leu Leu Ala Gln Arg Glu Ile Lys
625                 630                 635                 640

Leu Asp Trp Met Phe Lys Ser Ser Leu Leu Asp Leu Ile Lys Gly
                645                 650                 655

Met Arg Tyr Leu His His Arg Gly Val Ala His Gly Arg Leu Lys Ser
                660                 665                 670

Arg Asn Cys Val Val Asp Gly Arg Phe Val Leu Lys Val Thr Asp His
                675                 680                 685

Gly His Gly Arg Leu Leu Glu Ala Gln Arg Val Leu Pro Glu Pro Pro
                690                 695                 700

Ser Ala Glu Asp Gln Leu Trp Thr Ala Pro Glu Leu Leu Arg Asp Pro
705                 710                 715                 720

Ser Leu Glu Arg Arg Gly Thr Leu Ala Gly Asp Val Phe Ser Leu Ala
                725                 730                 735

Ile Ile Met Gln Glu Val Val Cys Arg Ser Thr Pro Tyr Ala Met Leu
                740                 745                 750

Glu Leu Thr Pro Glu Glu Val Ile Gln Arg Val Arg Ser Pro Pro Pro
                755                 760                 765

Leu Cys Arg Pro Leu Val Ser Met Asp Gln Ala Pro Met Glu Cys Ile
                770                 775                 780

Gln Leu Met Thr Gln Cys Trp Ala Glu His Pro Glu Leu Arg Pro Ser
785                 790                 795                 800

Met Asp Leu Thr Phe Asp Leu Phe Lys Ser Ile Asn Lys Gly Arg Lys
                805                 810                 815

Thr Asn Ile Ile Asp Ser Met Leu Arg Met Leu Glu Gln Tyr Ser Ser
                820                 825                 830

Asn Leu Glu Asp Leu Ile Arg Glu Arg Thr Glu Glu Leu Glu Gln Glu
                835                 840                 845

Lys Gln Lys Thr Asp Arg Leu Leu Thr Gln Met Leu Pro Pro Ser Val
                850                 855                 860

Ala Glu Ala Leu Lys Met Gly Thr Ser Val Glu Pro Glu Tyr Phe Glu
865                 870                 875                 880

Glu Val Thr Leu Tyr Phe Ser Asp Ile Val Gly Phe Thr Thr Ile Ser
                885                 890                 895

Ala Met Ser Glu Pro Ile Glu Val Val Asp Leu Leu Asn Asp Leu Tyr
                900                 905                 910

Thr Leu Phe Asp Ala Ile Ile Gly Ala His Asp Val Tyr Lys Val Glu
                915                 920                 925

Thr Ile Gly Asp Ala Tyr Met Val Ala Ser Gly Leu Pro Gln Arg Asn
                930                 935                 940

Gly Gln Arg His Ala Ala Glu Ile Ala Asn Met Ser Leu Asp Ile Leu
945                 950                 955                 960

Ser Ala Val Gly Ser Phe Arg Met Arg His Met Pro Glu Val Pro Val
                965                 970                 975
```

```
Arg Ile Arg Ile Gly Leu His Ser Gly Pro Cys Val Ala Gly Val Val
            980                 985                 990

Gly Leu Thr Met Pro Arg Tyr Cys Leu Phe Gly Asp Thr Val Asn Thr
        995                 1000                1005

Ala Ser Arg Met Glu Ser Thr Gly Leu Pro Tyr Arg Ile His Val
    1010                1015                1020

Asn Met Ser Thr Val Arg Ile Leu Arg Ala Leu Asp Gln Gly Phe
    1025                1030                1035

Gln Met Glu Cys Arg Gly Arg Thr Glu Leu Lys Gly Lys Gly Ile
    1040                1045                1050

Glu Asp Thr Tyr Trp Leu Val Gly Arg Leu Gly Phe Asn Lys Pro
    1055                1060                1065

Ile Pro Lys Pro Pro Asp Leu Gln Pro Gly Ala Ser Asn His Gly
    1070                1075                1080

Ile Ser Leu Gln Glu Ile Pro Pro Glu Arg Arg Lys Lys Leu Glu
    1085                1090                1095

Lys Ala Arg Pro Gly Gln Phe Thr Gly Lys
    1100                1105

<210> SEQ ID NO 3
<211> LENGTH: 1108
<212> TYPE: PRT
<213> ORGANISM: Rattus norvegicus

<400> SEQUENCE: 3

Met Ser Ala Trp Leu Leu Pro Ala Gly Gly Phe Pro Gly Ala Gly Phe
1               5                   10                  15

Cys Ile Pro Ala Trp Gln Ser Arg Ser Ser Leu Ser Arg Val Leu Arg
            20                  25                  30

Trp Pro Gly Pro Gly Leu Pro Gly Leu Leu Leu Leu Leu Leu Pro
        35                  40                  45

Ser Pro Ser Ala Phe Ser Ala Val Phe Lys Val Gly Val Leu Gly Pro
    50                  55                  60

Trp Ala Cys Asp Pro Ile Phe Ala Arg Ala Arg Pro Asp Leu Ala Ala
65                  70                  75                  80

Arg Leu Ala Thr Asp Arg Leu Asn Arg Asp Leu Ala Leu Asp Gly Gly
                85                  90                  95

Pro Trp Phe Glu Val Thr Leu Leu Pro Glu Pro Cys Leu Thr Pro Gly
            100                 105                 110

Ser Leu Gly Ala Val Ser Ser Ala Leu Thr Arg Val Ser Gly Leu Val
        115                 120                 125

Gly Pro Val Asn Pro Ala Ala Cys Arg Pro Ala Glu Leu Leu Ala Gln
    130                 135                 140

Glu Ala Gly Val Ala Leu Val Pro Trp Gly Cys Pro Gly Thr Arg Ala
145                 150                 155                 160

Ala Gly Thr Thr Ala Pro Ala Val Thr Pro Ala Ala Asp Ala Leu Tyr
                165                 170                 175

Val Leu Leu Lys Ala Phe Arg Trp Ala Arg Val Ala Leu Ile Thr Ala
            180                 185                 190

Pro Gln Asp Leu Trp Val Glu Ala Gly Arg Ala Leu Ser Thr Ala Leu
        195                 200                 205

Arg Ala Arg Gly Leu Pro Val Ala Leu Val Thr Ser Met Val Pro Ser
    210                 215                 220

Asp Leu Ser Gly Ala Arg Glu Ala Leu Arg Arg Ile Arg Asp Gly Pro
225                 230                 235                 240
```

-continued

```
Arg Val Arg Val Val Ile Met Val Met His Ser Val Leu Leu Gly Gly
                245                 250                 255

Glu Glu Gln Arg Tyr Leu Leu Glu Ala Ala Glu Leu Gly Leu Thr
            260                 265                 270

Asp Gly Ser Leu Val Phe Leu Pro Phe Asp Thr Leu His Tyr Ala Leu
            275                 280                 285

Ser Pro Gly Pro Glu Ala Leu Ala Ala Phe Val Asn Ser Ser Lys Leu
        290                 295                 300

Arg Arg Ala His Asp Ala Val Leu Thr Leu Thr Arg Arg Cys Pro Pro
305                 310                 315                 320

Gly Gly Ser Val Gln Asp Ser Leu Arg Arg Ala Gln Glu His Gln Glu
                325                 330                 335

Leu Pro Leu Asp Leu Asp Leu Lys Gln Val Ser Pro Leu Phe Gly Thr
            340                 345                 350

Ile Tyr Asp Ala Val Phe Leu Leu Ala Gly Gly Val Thr Arg Ala Arg
            355                 360                 365

Ala Ala Val Gly Gly Gly Trp Val Ser Gly Ala Ser Val Ala Arg Gln
        370                 375                 380

Met Arg Glu Ala Gln Val Phe Gly Phe Cys Gly Ile Leu Gly Arg Thr
385                 390                 395                 400

Glu Glu Pro Ser Phe Val Leu Leu Asp Thr Asp Ala Ala Gly Glu Arg
                405                 410                 415

Leu Phe Thr Thr His Leu Leu Asp Pro Val Leu Gly Ser Leu Arg Ser
            420                 425                 430

Ala Gly Thr Pro Val His Phe Pro Arg Gly Ala Pro Ala Pro Gly Pro
            435                 440                 445

Asp Pro Ser Cys Trp Phe Asp Pro Asp Val Ile Cys Asn Gly Gly Val
        450                 455                 460

Glu Pro Gly Leu Val Phe Val Gly Phe Leu Leu Val Ile Val Val Gly
465                 470                 475                 480

Leu Thr Gly Ala Phe Leu Ala His Tyr Leu Arg His Arg Leu Leu His
                485                 490                 495

Met Gln Met Val Ser Gly Pro Asn Lys Ile Ile Leu Thr Leu Glu Asp
            500                 505                 510

Val Thr Phe Leu His Pro Gln Gly Gly Ser Ser Arg Lys Val Ala Gln
            515                 520                 525

Gly Ser Arg Ser Ser Leu Ala Thr Arg Ser Thr Ser Asp Ile Arg Ser
        530                 535                 540

Val Pro Ser Gln Pro Gln Glu Ser Thr Asn Ile Gly Leu Tyr Glu Gly
545                 550                 555                 560

Asp Trp Val Trp Leu Lys Lys Phe Pro Gly Glu His His Met Ala Ile
                565                 570                 575

Arg Pro Ala Thr Lys Met Ala Phe Ser Lys Leu Arg Glu Leu Arg His
            580                 585                 590

Glu Asn Val Ala Leu Tyr Leu Gly Leu Phe Leu Ala Gly Thr Ala Asp
            595                 600                 605

Ser Pro Ala Thr Pro Gly Glu Gly Ile Leu Ala Val Val Ser Glu His
        610                 615                 620

Cys Ala Arg Gly Ser Leu His Asp Leu Leu Ala Gln Arg Asp Ile Lys
625                 630                 635                 640

Leu Asp Trp Met Phe Lys Ser Ser Leu Leu Leu Asp Leu Ile Lys Gly
                645                 650                 655
```

```
Met Arg Tyr Leu His His Arg Gly Val Ala His Gly Arg Leu Lys Ser
            660                 665                 670

Arg Asn Cys Val Val Asp Gly Arg Phe Val Leu Lys Val Thr Asp His
        675                 680                 685

Gly His Gly Arg Leu Leu Glu Ala Gln Arg Val Leu Pro Glu Pro Pro
    690                 695                 700

Ser Ala Glu Asp Gln Leu Trp Thr Ala Pro Glu Leu Arg Asp Pro
705                 710                 715                 720

Ala Leu Glu Arg Arg Gly Thr Leu Ala Gly Asp Val Phe Ser Leu Gly
                725                 730                 735

Ile Ile Met Gln Glu Val Val Cys Arg Ser Thr Pro Tyr Ala Met Leu
            740                 745                 750

Glu Leu Thr Pro Glu Glu Val Ile Gln Arg Val Arg Ser Pro Pro Pro
        755                 760                 765

Leu Cys Arg Pro Leu Val Ser Met Asp Gln Ala Pro Met Glu Cys Ile
770                 775                 780

Gln Leu Met Ala Gln Cys Trp Ala Glu His Pro Glu Leu Arg Pro Ser
785                 790                 795                 800

Met Asp Leu Thr Phe Asp Leu Phe Lys Gly Ile Asn Lys Gly Arg Lys
                805                 810                 815

Thr Asn Ile Ile Asp Ser Met Leu Arg Met Leu Glu Gln Tyr Ser Ser
            820                 825                 830

Asn Leu Glu Asp Leu Ile Arg Glu Arg Thr Glu Glu Leu Glu Gln Glu
        835                 840                 845

Lys Gln Lys Thr Asp Arg Leu Leu Thr Gln Met Leu Pro Pro Ser Val
850                 855                 860

Ala Glu Ala Leu Lys Met Gly Thr Ser Val Glu Pro Glu Tyr Phe Glu
865                 870                 875                 880

Glu Val Thr Leu Tyr Phe Ser Asp Ile Val Gly Phe Thr Thr Ile Ser
                885                 890                 895

Ala Met Ser Glu Pro Ile Glu Val Val Asp Leu Leu Asn Asp Leu Tyr
            900                 905                 910

Thr Leu Phe Asp Ala Ile Ile Gly Ser His Asp Val Tyr Lys Val Glu
        915                 920                 925

Thr Ile Gly Asp Ala Tyr Met Val Ala Ser Gly Leu Pro Gln Arg Asn
    930                 935                 940

Gly Gln Arg His Ala Ala Glu Ile Ala Asn Met Ser Leu Asp Ile Leu
945                 950                 955                 960

Ser Ala Val Gly Ser Phe Arg Met Arg His Met Pro Glu Val Pro Val
                965                 970                 975

Arg Ile Arg Ile Gly Leu His Ser Gly Pro Cys Val Ala Gly Val Val
            980                 985                 990

Gly Leu Thr Met Pro Arg Tyr Cys Leu Phe Gly Asp Thr Val Asn Thr
        995                 1000                1005

Ala Ser Arg Met Glu Ser Thr Gly Leu Pro Tyr Arg Ile His Val
    1010                1015                1020

Asn Met Ser Thr Val Arg Ile Leu Arg Ala Leu Asp Gln Gly Phe
    1025                1030                1035

Gln Met Glu Cys Arg Gly Arg Thr Glu Leu Lys Gly Lys Gly Val
    1040                1045                1050

Glu Asp Thr Tyr Trp Leu Val Gly Arg Val Gly Phe Asn Lys Pro
    1055                1060                1065

Ile Pro Lys Pro Pro Asp Leu Gln Pro Gly Ala Ser Asn His Gly
```

```
                        1070                1075                1080
         Ile  Ser  Leu  Gln  Glu  Ile  Pro  Pro  Glu  Arg  Arg  Lys  Lys  Leu  Glu
                   1085                     1090                1095

Lys  Ala  Arg  Pro  Gly  Gln  Phe  Thr  Gly  Lys
                   1100                     1105

<210> SEQ ID NO 4
<211> LENGTH: 1110
<212> TYPE: PRT
<213> ORGANISM: Bos taurus

<400> SEQUENCE: 4

Met  Thr  Ala  Cys  Thr  Phe  Leu  Ala  Gly  Gly  Leu  Arg  Asp  Pro  Gly  Leu
 1                  5                   10                  15

Cys  Ala  Pro  Thr  Arg  Trp  Ser  Pro  Ser  Pro  Gly  Leu  Pro  Pro  Ile
            20                  25                  30

Pro  Pro  Arg  Pro  Arg  Leu  Arg  Leu  Arg  Pro  Pro  Leu  Leu  Leu  Leu
         35                  40                  45

Leu  Leu  Pro  Arg  Ser  Val  Leu  Ser  Ala  Val  Phe  Thr  Val  Gly  Val  Leu
 50                 55                  60

Gly  Pro  Trp  Ala  Cys  Asp  Pro  Ile  Phe  Ala  Arg  Ala  Arg  Pro  Asp  Leu
 65                 70                  75                  80

Ala  Ala  Arg  Leu  Ala  Ala  Ser  Arg  Leu  Asn  His  Ala  Ala  Ala  Leu  Glu
            85                  90                  95

Gly  Gly  Pro  Arg  Phe  Glu  Val  Ala  Leu  Leu  Pro  Glu  Pro  Cys  Arg  Thr
           100                 105                 110

Pro  Gly  Ser  Leu  Gly  Ala  Val  Ser  Ser  Ala  Leu  Thr  Arg  Val  Ser  Gly
           115                 120                 125

Leu  Val  Gly  Pro  Val  Asn  Pro  Ala  Ala  Cys  Arg  Pro  Ala  Glu  Leu  Leu
130                 135                 140

Ala  Gln  Glu  Ala  Gly  Val  Ala  Leu  Val  Pro  Trp  Gly  Cys  Pro  Gly  Thr
145                 150                 155                 160

Arg  Ala  Ala  Gly  Thr  Thr  Ala  Pro  Val  Thr  Pro  Ala  Ala  Asp  Ala
                165                 170                 175

Leu  Tyr  Ala  Leu  Leu  Arg  Ala  Phe  Arg  Trp  Ala  His  Val  Ala  Leu  Val
           180                 185                 190

Thr  Ala  Pro  Gln  Asp  Leu  Trp  Val  Glu  Ala  Gly  His  Ala  Leu  Ser  Thr
           195                 200                 205

Ala  Leu  Arg  Ala  Arg  Gly  Leu  Pro  Val  Ala  Leu  Val  Thr  Ser  Met  Glu
210                 215                 220

Pro  Ser  Asp  Leu  Ser  Gly  Ala  Arg  Glu  Ala  Leu  Arg  Arg  Val  Gln  Asp
225                 230                 235                 240

Gly  Pro  Arg  Val  Arg  Ala  Val  Ile  Met  Val  Met  His  Ser  Val  Leu  Leu
                245                 250                 255

Gly  Gly  Glu  Glu  Gln  Arg  Cys  Leu  Leu  Glu  Ala  Ala  Glu  Leu  Gly
           260                 265                 270

Leu  Ala  Asp  Gly  Ser  Leu  Val  Phe  Leu  Pro  Phe  Asp  Thr  Leu  His  Tyr
           275                 280                 285

Ala  Leu  Ser  Pro  Gly  Pro  Asp  Ala  Leu  Ala  Val  Leu  Ala  Asn  Ser  Ser
           290                 295                 300

Gln  Leu  Arg  Lys  Ala  His  Asp  Ala  Val  Leu  Thr  Leu  Thr  Arg  His  Cys
305                 310                 315                 320

Pro  Leu  Gly  Gly  Ser  Val  Arg  Asp  Ser  Leu  Arg  Arg  Ala  Gln  Glu  His
                325                 330                 335
```

```
Arg Glu Leu Pro Leu Asp Leu Asn Leu Gln Gln Val Ser Pro Leu Phe
                340                 345                 350

Gly Thr Ile Tyr Asp Ser Val Phe Leu Ala Gly Gly Val Ala Arg
            355                 360                 365

Ala Arg Val Ala Ala Gly Gly Trp Val Ser Gly Ala Ala Val Ala
        370                 375                 380

Arg His Ile Arg Asp Ala Arg Val Pro Gly Phe Cys Gly Ala Leu Gly
385                 390                 395                 400

Gly Ala Glu Glu Pro Ser Phe Val Leu Leu Asp Thr Asp Ala Thr Gly
                405                 410                 415

Asp Gln Leu Phe Ala Thr Tyr Val Leu Asp Pro Thr Gln Gly Phe Phe
                420                 425                 430

His Ser Ala Gly Thr Pro Val His Phe Pro Lys Gly Arg Gly Pro
            435                 440                 445

Gly Pro Asp Pro Ser Cys Trp Phe Asp Pro Asp Thr Ile Cys Asn Gly
            450                 455                 460

Gly Val Glu Pro Ser Val Val Phe Ile Gly Phe Leu Val Val Gly
465                 470                 475                 480

Met Gly Leu Ala Gly Ala Phe Leu Ala His Tyr Cys Arg His Arg Leu
                485                 490                 495

Leu His Ile Gln Met Val Ser Gly Pro Asn Lys Ile Ile Leu Thr Leu
                500                 505                 510

Asp Asp Ile Thr Phe Leu His Pro His Gly Gly Asn Ser Arg Lys Val
            515                 520                 525

Ala Gln Gly Ser Arg Thr Ser Leu Ala Ala Arg Ser Ile Ser Asp Val
            530                 535                 540

Arg Ser Ile His Ser Gln Leu Pro Asp Tyr Thr Asn Ile Gly Leu Tyr
545                 550                 555                 560

Glu Gly Asp Trp Val Trp Leu Lys Lys Phe Pro Gly Asp Arg His Ile
                565                 570                 575

Ala Ile Arg Pro Ala Thr Lys Met Ala Phe Ser Lys Ile Arg Glu Leu
                580                 585                 590

Arg His Glu Asn Val Ala Leu Tyr Leu Gly Leu Phe Leu Ala Gly Gly
            595                 600                 605

Ala Gly Gly Pro Ala Ala Pro Gly Glu Gly Val Leu Ala Val Val Ser
    610                 615                 620

Glu His Cys Ala Arg Gly Ser Leu Gln Asp Leu Leu Ala Gln Arg Asp
625                 630                 635                 640

Ile Lys Leu Asp Trp Met Phe Lys Ser Ser Leu Leu Leu Asp Leu Ile
                645                 650                 655

Lys Gly Ile Arg Tyr Leu His His Arg Gly Val Ala His Gly Arg Leu
            660                 665                 670

Lys Ser Arg Asn Cys Val Val Asp Gly Arg Phe Val Leu Lys Val Thr
        675                 680                 685

Asp His Gly His Gly Arg Leu Leu Glu Ala Gln Arg Val Leu Pro Glu
        690                 695                 700

Pro Pro Ser Ala Glu Asp Gln Leu Trp Thr Ala Pro Glu Leu Leu Arg
705                 710                 715                 720

Asp Pro Val Leu Glu Arg Arg Gly Thr Leu Ala Gly Asp Val Phe Ser
                725                 730                 735

Leu Gly Ile Ile Met Gln Glu Val Val Cys Arg Ser Ala Pro Tyr Ala
                740                 745                 750

Met Leu Glu Leu Thr Pro Glu Glu Val Val Lys Arg Val Gln Ser Pro
```

-continued

```
                755                 760                 765
Pro Pro Leu Cys Arg Pro Ser Val Ser Ile Asp Gln Ala Pro Met Glu
770                 775                 780

Cys Ile Gln Leu Met Lys Gln Cys Trp Ala Glu Gln Pro Glu Leu Arg
785                 790                 795                 800

Pro Ser Met Asp Arg Thr Phe Glu Leu Phe Lys Ser Ile Asn Lys Gly
                805                 810                 815

Arg Lys Met Asn Ile Ile Asp Ser Met Leu Arg Met Leu Glu Gln Tyr
                820                 825                 830

Ser Ser Asn Leu Glu Asp Leu Ile Arg Glu Arg Thr Glu Glu Leu Glu
                835                 840                 845

Leu Glu Lys Gln Lys Thr Asp Arg Leu Leu Thr Gln Met Leu Pro Pro
850                 855                 860

Ser Val Ala Glu Ala Leu Lys Met Gly Thr Pro Val Glu Pro Glu Tyr
865                 870                 875                 880

Phe Glu Glu Val Thr Leu Tyr Phe Ser Asp Ile Val Gly Phe Thr Thr
                885                 890                 895

Ile Ser Ala Met Ser Glu Pro Ile Glu Val Val Asp Leu Leu Asn Asp
                900                 905                 910

Leu Tyr Thr Leu Phe Asp Ala Ile Ile Gly Ser His Asp Val Tyr Lys
                915                 920                 925

Val Glu Thr Ile Gly Asp Ala Tyr Met Val Ala Ser Gly Leu Pro Gln
                930                 935                 940

Arg Asn Gly His Arg His Ala Ala Glu Ile Ala Asn Met Ala Leu Asp
945                 950                 955                 960

Ile Leu Ser Ala Val Gly Thr Phe Arg Met Arg His Met Pro Glu Val
                965                 970                 975

Pro Val Arg Ile Arg Ile Gly Leu His Ser Gly Pro Cys Val Ala Gly
                980                 985                 990

Val Val Gly Leu Thr Met Pro Arg Tyr Cys Leu Phe Gly Asp Thr Val
                995                 1000                1005

Asn Thr Ala Ser Arg Met Glu Ser Thr Gly Leu Pro Tyr Arg Ile
1010                1015                1020

His Val Asn Arg Ser Thr Val Gln Ile Leu Ser Ala Leu Asn Glu
1025                1030                1035

Gly Phe Leu Thr Glu Val Arg Gly Arg Thr Glu Leu Lys Gly Lys
1040                1045                1050

Gly Ala Glu Glu Thr Tyr Trp Leu Val Gly Arg Arg Gly Phe Asn
1055                1060                1065

Lys Pro Ile Pro Lys Pro Pro Asp Leu Gln Pro Gly Ala Ser Asn
1070                1075                1080

His Gly Ile Ser Leu His Glu Ile Pro Pro Asp Arg Arg Gln Lys
1085                1090                1095

Leu Glu Lys Ala Arg Pro Gly Gln Phe Ser Gly Lys
1100                1105                1110

<210> SEQ ID NO 5
<211> LENGTH: 1109
<212> TYPE: PRT
<213> ORGANISM: Canis familiaris

<400> SEQUENCE: 5

Met Ser Ala Cys Ala Leu Leu Ala Gly Gly Leu Pro Asp Pro Arg Leu
1               5                   10                  15
```

```
Cys Ala Pro Ala Arg Trp Ala Arg Ser Pro Pro Gly Val Pro Gly Ala
                20                  25                  30
Pro Pro Trp Pro Gln Pro Arg Leu Arg Leu Leu Leu Leu Leu Leu Leu
            35                  40                  45
Leu Pro Pro Ser Ala Leu Ser Ala Val Phe Thr Val Gly Val Leu Gly
        50                  55                  60
Pro Trp Ala Cys Asp Pro Ile Phe Ala Arg Ala Arg Pro Asp Leu Ala
65                  70                  75                  80
Ala Arg Leu Ala Ala Arg Leu Asn Arg Asp Ala Ala Leu Glu Asp
                85                  90                  95
Gly Pro Arg Phe Glu Val Thr Leu Leu Pro Glu Pro Cys Arg Thr Pro
                100                 105                 110
Gly Ser Leu Gly Ala Val Ser Ser Ala Leu Gly Arg Val Ser Gly Leu
            115                 120                 125
Val Gly Pro Val Asn Pro Ala Ala Cys Arg Pro Ala Glu Leu Leu Ala
        130                 135                 140
Gln Glu Ala Gly Val Ala Leu Val Pro Trp Ser Cys Pro Gly Thr Arg
145                 150                 155                 160
Ala Gly Gly Thr Thr Ala Pro Ala Gly Thr Pro Ala Ala Asp Ala Leu
                165                 170                 175
Tyr Ala Leu Leu Arg Ala Phe Arg Trp Ala Arg Val Ala Leu Ile Thr
                180                 185                 190
Ala Pro Gln Asp Leu Trp Val Glu Ala Gly Arg Ala Leu Ser Ala Ala
            195                 200                 205
Leu Arg Ala Arg Gly Leu Pro Val Ala Leu Val Thr Thr Met Glu Pro
        210                 215                 220
Ser Asp Leu Ser Gly Ala Arg Glu Ala Leu Arg Arg Val Gln Asp Gly
225                 230                 235                 240
Pro Arg Val Arg Ala Val Ile Met Val Met His Ser Val Leu Leu Gly
                245                 250                 255
Gly Glu Glu Gln Arg Cys Leu Leu Gln Ala Ala Glu Glu Leu Gly Leu
                260                 265                 270
Ala Asp Gly Ser Leu Val Phe Leu Pro Phe Asp Thr Leu His Tyr Ala
            275                 280                 285
Leu Ser Pro Gly Pro Glu Ala Leu Ala Val Leu Ala Asn Ser Ser Gln
        290                 295                 300
Leu Arg Arg Ala His Asp Ala Val Leu Ile Leu Thr Arg His Cys Pro
305                 310                 315                 320
Pro Gly Gly Ser Val Met Asp Asn Leu Arg Arg Ala Gln Glu His Gln
                325                 330                 335
Glu Leu Pro Ser Asp Leu Asp Leu Gln Gln Val Ser Pro Phe Phe Gly
                340                 345                 350
Thr Ile Tyr Asp Ala Val Leu Leu Leu Ala Gly Gly Val Ala Arg Ala
            355                 360                 365
Arg Ala Ala Ala Gly Gly Trp Val Ser Gly Ala Thr Val Ala His
        370                 375                 380
His Ile Pro Asp Ala Gln Val Pro Gly Phe Cys Gly Thr Leu Gly Gly
385                 390                 395                 400
Ala Gln Glu Pro Pro Phe Val Leu Leu Asp Thr Asp Ala Ala Gly Asp
                405                 410                 415
Arg Leu Phe Ala Thr Tyr Met Leu Asp Pro Thr Arg Gly Ser Leu Leu
                420                 425                 430
Ser Ala Gly Thr Pro Val His Phe Pro Arg Gly Gly Gly Thr Pro Gly
```

-continued

```
            435                 440                 445
Ser Asp Pro Ser Cys Trp Phe Glu Pro Gly Val Ile Cys Asn Gly Gly
450                 455                 460

Val Glu Pro Gly Leu Val Phe Leu Gly Phe Leu Leu Val Gly Met
465                 470                 475                 480

Gly Leu Thr Gly Ala Phe Leu Ala His Tyr Leu Arg His Arg Leu Leu
                    485                 490                 495

His Ile Gln Met Val Ser Gly Pro Asn Lys Ile Ile Leu Thr Leu Asp
                500                 505                 510

Asp Val Thr Phe Leu His Pro His Gly Gly Ser Thr Arg Lys Val Val
            515                 520                 525

Gln Gly Ser Arg Ser Ser Leu Ala Ala Arg Ser Thr Ser Asp Ile Arg
530                 535                 540

Ser Val Pro Ser Gln Pro Leu Asp Asn Ser Asn Ile Gly Leu Phe Glu
545                 550                 555                 560

Gly Asp Trp Val Trp Leu Lys Lys Phe Pro Gly Asp Gln His Ile Ala
                565                 570                 575

Ile Arg Pro Ala Thr Lys Thr Ala Phe Ser Lys Leu Arg Glu Leu Arg
            580                 585                 590

His Glu Asn Val Val Leu Tyr Leu Gly Leu Phe Leu Gly Ser Gly Gly
            595                 600                 605

Ala Gly Gly Ser Ala Ala Gly Glu Gly Val Leu Ala Val Val Ser Glu
610                 615                 620

His Cys Ala Arg Gly Ser Leu His Asp Leu Leu Ala Gln Arg Asp Ile
625                 630                 635                 640

Lys Leu Asp Trp Met Phe Lys Ser Ser Leu Leu Leu Asp Leu Ile Lys
                645                 650                 655

Gly Met Arg Tyr Leu His His Arg Gly Val Ala His Gly Arg Leu Lys
            660                 665                 670

Ser Arg Asn Cys Val Val Asp Gly Arg Phe Val Leu Lys Val Thr Asp
            675                 680                 685

His Gly His Ala Arg Leu Met Glu Ala Gln Arg Val Leu Leu Glu Pro
            690                 695                 700

Pro Ser Ala Glu Asp Gln Leu Trp Thr Ala Pro Glu Leu Leu Arg Asp
705                 710                 715                 720

Pro Ala Leu Glu Arg Arg Gly Thr Leu Pro Gly Asp Val Phe Ser Leu
                725                 730                 735

Gly Ile Ile Met Gln Glu Val Val Cys Arg Ser Ala Pro Tyr Ala Met
                740                 745                 750

Leu Glu Leu Thr Pro Glu Glu Val Val Glu Arg Val Arg Ser Pro Pro
            755                 760                 765

Pro Leu Cys Arg Pro Ser Val Ser Met Asp Gln Ala Pro Val Glu Cys
            770                 775                 780

Ile Gln Leu Met Lys Gln Cys Trp Ala Glu His Pro Asp Leu Arg Pro
785                 790                 795                 800

Ser Leu Gly His Ile Phe Asp Gln Phe Lys Ser Ile Asn Lys Gly Arg
                    805                 810                 815

Lys Thr Asn Ile Ile Asp Ser Met Leu Arg Met Leu Glu Gln Tyr Ser
                820                 825                 830

Ser Asn Leu Glu Asp Leu Ile Arg Glu Arg Thr Glu Glu Leu Glu Leu
            835                 840                 845

Glu Lys Gln Lys Thr Asp Arg Leu Leu Thr Gln Met Leu Pro Pro Ser
850                 855                 860
```

```
Val Ala Glu Ala Leu Lys Met Gly Thr Pro Val Pro Glu Tyr Phe
865                 870                 875                 880

Glu Glu Val Thr Leu Tyr Phe Ser Asp Ile Val Gly Phe Thr Thr Ile
            885                 890                 895

Ser Ala Met Ser Glu Pro Ile Glu Val Val Asp Leu Leu Asn Asp Leu
            900                 905                 910

Tyr Thr Leu Phe Asp Ala Ile Ile Gly Ser His Asp Val Tyr Lys Val
            915                 920                 925

Glu Thr Ile Gly Asp Ala Tyr Met Val Ala Ser Gly Leu Pro Gln Arg
            930                 935                 940

Asn Gly Gln Arg His Ala Ala Glu Ile Ala Asn Met Ala Leu Asp Ile
945                 950                 955                 960

Leu Ser Ala Val Gly Ser Phe Arg Met Arg His Met Pro Glu Val Pro
                965                 970                 975

Val Arg Ile Arg Ile Gly Leu His Ser Gly Pro Cys Val Ala Gly Val
                980                 985                 990

Val Gly Leu Thr Met Pro Arg Tyr Cys Leu Phe Gly Asp Thr Val Asn
                995                 1000                1005

Thr Ala Ser Arg Met Glu Ser Thr Gly Leu Pro Tyr Arg Ile His
        1010                1015                1020

Val Asn Met Ser Thr Val Arg Ile Leu His Ala Leu Asp Glu Gly
        1025                1030                1035

Phe Gln Thr Glu Val Arg Gly Arg Thr Glu Leu Lys Gly Lys Gly
        1040                1045                1050

Ala Glu Asp Thr Tyr Trp Leu Val Gly Arg Arg Gly Phe Asn Lys
        1055                1060                1065

Pro Ile Pro Lys Pro Pro Asp Leu Gln Pro Gly Ala Ser Asn His
        1070                1075                1080

Gly Ile Ser Leu Gln Glu Ile Pro Leu Asp Arg Arg Trp Lys Leu
        1085                1090                1095

Glu Lys Ala Arg Pro Gly Gln Phe Ser Gly Lys
        1100                1105

<210> SEQ ID NO 6
<211> LENGTH: 1103
<212> TYPE: PRT
<213> ORGANISM: Macaca mulatta

<400> SEQUENCE: 6

Met Thr Ala Cys Ala Arg Arg Ala Gly Gly Leu Pro Asp Pro Arg Leu
1               5                   10                  15

Cys Gly Pro Ala Arg Trp Ala Pro Ala Leu Pro Arg Leu Pro Arg Ala
                20                  25                  30

Leu Pro Arg Leu Pro Leu Leu Leu Leu Leu Leu Leu Gln Pro Pro
            35                  40                  45

Ala Leu Ser Ala Val Phe Thr Val Gly Val Leu Gly Pro Trp Ala Cys
        50                  55                  60

Asp Pro Ile Phe Ser Arg Ala Arg Ala Asp Leu Ala Ala Arg Leu Ala
65                  70                  75                  80

Ala Ala Arg Leu Asn Arg Asp Pro Asp Leu Ala Gly Gly Pro Arg Phe
                85                  90                  95

Glu Val Ala Leu Leu Pro Glu Pro Cys Arg Thr Pro Gly Ser Leu Gly
            100                 105                 110

Ala Val Ser Ser Ala Leu Thr Arg Val Ser Gly Leu Val Gly Pro Val
```

```
               115                 120                 125
Asn Pro Ala Ala Cys Arg Pro Ala Glu Leu Leu Ala Glu Glu Ala Gly
            130                 135                 140

Ile Ala Leu Val Pro Trp Gly Cys Pro Gly Thr Gln Ala Ala Gly Thr
145                 150                 155                 160

Thr Ala Pro Ala Leu Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
            180                 185                 190

Leu Trp Val Glu Ala Gly His Ser Leu Ser Thr Ala Leu Arg Ala Arg
        195                 200                 205

Gly Leu Pro Val Ala Ser Val Thr Ser Met Glu Pro Leu Asp Leu Ser
    210                 215                 220

Gly Ala Arg Glu Ala Leu Arg Lys Val Arg Asp Gly Pro Arg Val Thr
225                 230                 235                 240

Ala Val Ile Met Val Met His Ser Val Leu Leu Gly Gly Glu Glu Gln
                245                 250                 255

Arg Tyr Leu Leu Glu Ala Ala Glu Glu Leu Gly Leu Thr Asp Gly Ser
            260                 265                 270

Leu Val Phe Leu Pro Phe Asp Thr Val His Tyr Ala Leu Ser Pro Gly
        275                 280                 285

Pro Glu Ala Leu Ala Ala Leu Ala Asn Ser Ser Gln Leu Arg Arg Ala
    290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Arg Glu Leu Pro Ser
                325                 330                 335

Asp Leu Asn Leu Gln Gln Val Ser Pro Leu Phe Gly Thr Ile Tyr Asp
            340                 345                 350

Ala Val Phe Leu Leu Val Arg Gly Val Ala Glu Ala Arg Ala Ala Ala
        355                 360                 365

Gly Gly Arg Trp Val Ser Gly Ala Ala Val Ala Arg His Val Trp Asp
    370                 375                 380

Ala Gln Val Pro Gly Phe Cys Gly Asp Leu Gly Gly Asp Glu Glu Pro
385                 390                 395                 400

Pro Phe Val Leu Leu Asp Thr Asp Ala Val Gly Asp Arg Leu Phe Ala
                405                 410                 415

Thr Tyr Met Leu Asp Pro Thr Arg Gly Ser Leu Leu Ser Ala Gly Thr
            420                 425                 430

Pro Met His Phe Pro Arg Gly Gly Ser Ala Pro Gly Pro Asp Pro Ser
        435                 440                 445

Cys Trp Phe Asp Pro Asn Asn Ile Cys Gly Gly Leu Glu Pro Gly
    450                 455                 460

Leu Val Phe Leu Gly Phe Leu Val Val Gly Met Gly Leu Ala Gly
465                 470                 475                 480

Ala Phe Leu Ala His Tyr Val Arg His Gln Leu Leu His Ile Gln Met
                485                 490                 495

Val Ser Gly Pro Asn Lys Ile Ile Leu Thr Val Asp Asp Ile Thr Phe
            500                 505                 510

Leu His Pro His Gly Gly Thr Ser Arg Lys Val Ala Gln Gly Ser Arg
        515                 520                 525

Ser Ser Leu Ala Ala Arg Ser Met Ser Asp Val Arg Ser Gly Pro Ser
    530                 535                 540
```

-continued

```
Gln Pro Thr Asp Ser Pro Asn Val Gly Val Tyr Glu Gly Asp Arg Val
545                 550                 555                 560

Trp Leu Lys Lys Phe Pro Gly Asp Gln His Ile Ala Ile Arg Pro Ala
                565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Gln Gly Ala Glu Gly Pro Ala
        595                 600                 605

Ala Leu Trp Glu Gly Asn Leu Ala Val Val Ser Glu His Cys Thr Arg
610                 615                 620

Gly Ser Leu Gln Asp Leu Leu Ala Gln Arg Glu Ile Lys Leu Asp Trp
625                 630                 635                 640

Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
            660                 665                 670

Ile Val Asp Gly Arg Phe Val Leu Lys Ile Thr Asp His Gly His Gly
        675                 680                 685

Arg Leu Leu Glu Ala Gln Lys Val Leu Pro Glu Pro Pro Arg Ala Glu
690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
                725                 730                 735

Gln Glu Val Val Cys Arg Ser Ala Pro Tyr Ala Met Leu Glu Leu Thr
            740                 745                 750

Pro Glu Glu Val Val Gln Arg Val Arg Ser Pro Pro Pro Leu Cys Arg
        755                 760                 765

Pro Leu Val Ser Met Asp Gln Ala Pro Val Glu Cys Ile His Leu Met
770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
            820                 825                 830

Asp Leu Ile Arg Glu Arg Thr Glu Glu Leu Glu Leu Glu Lys Gln Lys
        835                 840                 845

Thr Asp Arg Leu Leu Thr Gln Met Leu Pro Pro Ser Val Ala Glu Ala
850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
                885                 890                 895

Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
        915                 920                 925

Asp Ala Tyr Met Val Ala Ser Gly Leu Pro Gln Arg Asn Gly Gln Arg
930                 935                 940

His Ala Ala Glu Ile Ala Asn Met Ser Leu Asp Ile Leu Ser Ala Val
945                 950                 955                 960
```

```
Gly Thr Phe Arg Met Arg His Met Pro Glu Val Pro Val Arg Ile Arg
            965                 970                 975

Ile Gly Leu His Ser Gly Pro Cys Val Ala Gly Val Gly Leu Thr
        980                 985                 990

Met Pro Arg Tyr Cys Leu Phe Gly Asp Thr Val Asn Thr Ala Ser Arg
        995                 1000                1005

Met Glu Ser Thr Gly Leu Pro Tyr Arg Ile His Val Asn Leu Ser
        1010                1015                1020

Thr Val Gly Ile Leu Arg Ala Leu Asp Ser Gly Tyr Gln Val Glu
        1025                1030                1035

Leu Arg Gly Arg Thr Glu Leu Lys Gly Lys Gly Ala Glu Asp Thr
        1040                1045                1050

Phe Trp Leu Val Gly Arg Arg Gly Phe Asn Lys Pro Ile Pro Lys
        1055                1060                1065

Pro Pro Asp Leu Gln Pro Gly Ser Ser Asn His Gly Ile Ser Leu
        1070                1075                1080

Gln Glu Ile Pro Pro Glu Arg Arg Arg Lys Leu Glu Lys Ala Arg
        1085                1090                1095

Pro Gly Gln Phe Ser
        1100

<210> SEQ ID NO 7
<211> LENGTH: 1103
<212> TYPE: PRT
<213> ORGANISM: Pongo pygmaeus

<400> SEQUENCE: 7

Met Thr Ala Cys Ala Arg Arg Ala Gly Gly Leu Pro Asp Pro Gly Leu
1               5                   10                  15

Cys Gly Pro Ala Arg Trp Ala Pro Ser Leu Pro Arg Leu Pro Arg Ala
            20                  25                  30

Leu Pro Arg Leu Pro Leu Leu Leu Leu Leu Leu Gln Pro Pro
        35                  40                  45

Ala Leu Ser Ala Val Phe Thr Val Gly Val Leu Gly Pro Trp Ala Cys
    50                  55                  60

Asp Pro Ile Phe Ser Arg Ala Arg Pro Asp Leu Ala Ala Arg Leu Ala
65                  70                  75                  80

Ala Ala Arg Leu Asn Arg Asp Pro Gly Leu Ala Gly Gly Pro Arg Phe
                85                  90                  95

Glu Val Ala Leu Leu Pro Glu Pro Cys Arg Thr Pro Gly Ser Leu Gly
            100                 105                 110

Ala Val Ser Ser Ala Leu Ala Arg Val Ser Gly Leu Val Gly Pro Val
            115                 120                 125

Asn Pro Ala Ala Cys Arg Pro Ala Glu Leu Leu Ala Asp Asn Pro Gly
        130                 135                 140

Ile Ala Leu Val Pro Trp Gly Cys Pro Trp Thr Gln Ala Glu Gly Thr
145                 150                 155                 160

Thr Ala Pro Cys Val Thr Pro Ala Ala Asp Ala Leu Tyr Ala Leu Leu
                165                 170                 175

Arg Ala Phe Gly Trp Ala Arg Val Ala Leu Val Thr Ala Pro Gln Asp
            180                 185                 190

Leu Trp Val Glu Ala Gly Arg Ser Leu Ser Thr Ala Leu Arg Ala Arg
        195                 200                 205

Gly Leu Pro Val Ala Ser Val Thr Ser Met Glu Pro Leu Asp Leu Ser
    210                 215                 220
```

```
Gly Ala Arg Glu Ala Leu Arg Lys Val Arg Asp Gly Pro Arg Val Thr
225                 230                 235                 240

Ala Val Ile Met Val Met His Ser Val Leu Leu Gly Gly Glu Glu Gln
            245                 250                 255

Arg Tyr Leu Leu Glu Ala Ala Glu Glu Leu Gly Leu Thr Asp Gly Ser
        260                 265                 270

Leu Val Phe Leu Pro Phe Asp Thr Ile His Tyr Ala Leu Ser Pro Gly
    275                 280                 285

Pro Glu Ala Leu Ala Ala Leu Ala Asn Ser Ser Gln Leu Arg Arg Ala
290                 295                 300

His Asp Ala Val Leu Thr Leu Thr Arg His Cys Pro Ser Glu Gly Ser
305                 310                 315                 320

Val Leu Asp Ser Leu Arg Arg Ala Gln Glu Arg Arg Glu Leu Pro Ser
                325                 330                 335

Asp Leu Asn Leu Gln Gln Val Ser Pro Leu Phe Gly Thr Ile Tyr Asp
            340                 345                 350

Ala Val Phe Leu Leu Ala Arg Gly Val Ala Glu Ala Trp Ala Ala Ala
        355                 360                 365

Gly Gly Arg Trp Val Ser Gly Ala Ala Val Ala Arg His Ile Arg Asp
370                 375                 380

Ala Gln Val Pro Gly Phe Cys Gly Asp Leu Gly Gly Asp Gly Glu Pro
385                 390                 395                 400

Pro Phe Val Leu Leu Asp Thr Asp Ala Ala Gly Asp Arg Leu Phe Ala
                405                 410                 415

Thr Tyr Met Leu Asp Pro Ala Arg Gly Ser Phe Leu Ser Ala Gly Thr
            420                 425                 430

Arg Met His Phe Pro Arg Gly Gly Ser Ala Pro Gly Pro Asp Pro Ser
        435                 440                 445

Cys Trp Phe Asp Pro Asn Asn Ile Cys Gly Gly Gly Leu Glu Pro Gly
    450                 455                 460

Leu Val Phe Leu Gly Phe Leu Val Val Gly Met Gly Leu Ala Gly
465                 470                 475                 480

Ala Phe Leu Ala His Tyr Val Arg His Arg Leu Leu His Ile Gln Met
                485                 490                 495

Val Ser Gly Pro Asn Lys Ile Ile Leu Thr Val Asn Asp Ile Thr Phe
            500                 505                 510

Leu His Pro His Gly Gly Thr Ser Arg Lys Val Ala Gln Gly Ser Arg
        515                 520                 525

Ser Ser Leu Ala Ala Arg Ser Met Ser Asp Ile Arg Ser Gly Pro Ser
    530                 535                 540

Gln Pro Leu Asp Ser Pro Asn Val Gly Val Tyr Glu Gly Asp Arg Val
545                 550                 555                 560

Trp Leu Lys Lys Phe Pro Gly Asp Gln His Ile Ala Ile Arg Pro Ala
                565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Arg Gly Ala Glu Gly Pro Ala
        595                 600                 605

Ala Leu Trp Glu Gly Asn Leu Ala Val Val Ser Glu His Cys Thr Arg
    610                 615                 620

Gly Ser Leu Gln Asp Leu Leu Ser Gln Arg Glu Ile Lys Leu Asp Trp
625                 630                 635                 640
```

```
Met Phe Lys Ser Ser Leu Leu Leu Asp Leu Ile Lys Gly Ile Arg Tyr
                645                 650                 655

Leu His His Arg Gly Val Ala His Gly Arg Leu Lys Ser Arg Asn Cys
            660                 665                 670

Ile Val Asp Gly Arg Phe Val Leu Lys Ile Thr Asp His Gly His Gly
        675                 680                 685

Arg Leu Leu Glu Ala Gln Lys Val Leu Pro Glu Pro Pro Arg Ala Glu
    690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Ala Ile Ile Met
                725                 730                 735

Gln Glu Val Val Cys Arg Ser Ala Pro Tyr Ala Met Leu Glu Leu Thr
            740                 745                 750

Pro Glu Glu Val Val Gln Arg Val Arg Ser Pro Pro Pro Leu Cys Arg
        755                 760                 765

Pro Leu Val Ser Met Asp Gln Ala Pro Val Glu Cys Ile His Leu Met
    770                 775                 780

Lys Gln Cys Trp Ala Glu Gln Pro Glu Leu Arg Pro Ser Met Asp His
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
            820                 825                 830

Asp Leu Ile Arg Glu Arg Thr Glu Glu Leu Glu Leu Glu Lys Gln Lys
        835                 840                 845

Thr Asp Arg Leu Leu Thr Gln Met Leu Pro Pro Ser Val Ala Glu Ala
850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
                885                 890                 895

Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
        915                 920                 925

Asp Ala Tyr Met Val Ala Ser Gly Leu Pro Gln Arg Asn Gly Gln Arg
    930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
                965                 970                 975

Ile Gly Leu His Ser Gly Pro Cys Val Ala Gly Val Val Gly Leu Thr
            980                 985                 990

Met Pro Arg Tyr Cys Leu Phe Gly Asp Thr Val Asn Thr Ala Ser Arg
        995                 1000                1005

Met Glu Ser Thr Gly Leu Pro Tyr Arg Ile His Val Asn Leu Ser
    1010                1015                1020

Thr Val Gly Ile Leu Arg Ala Leu Asp Ser Gly Tyr Gln Val Glu
    1025                1030                1035

Leu Arg Gly Arg Thr Glu Leu Lys Gly Lys Gly Ala Glu Asp Thr
    1040                1045                1050

Phe Trp Leu Val Gly Arg Arg Gly Phe Asn Lys Pro Ile Pro Lys
```

```
            1055                1060                1065

Pro  Pro  Asp  Leu  Gln  Pro  Gly  Ser  Ser  Asn  His  Gly  Ile  Ser  Leu
     1070                1075                1080

Gln  Glu  Ile  Pro  Pro  Glu  Arg  Arg  Arg  Lys  Leu  Glu  Lys  Ala  Arg
     1085                1090                1095

Pro  Gly  Gln  Phe  Ser
     1100
```

<210> SEQ ID NO 8
<211> LENGTH: 1103
<212> TYPE: PRT
<213> ORGANISM: Callithrix jacchus
<400> SEQUENCE: 8

```
Met  Thr  Ala  Cys  Ala  Arg  Arg  Ala  Gly  Gly  Leu  Pro  Asp  Pro  Gly  Leu
1                  5                  10                 15

Cys  Gly  Pro  Ala  Arg  Trp  Ala  Pro  Ala  Leu  Ser  Arg  Leu  Pro  Arg  Ala
                    20                 25                 30

Leu  Pro  Arg  Leu  Pro  Leu  Leu  Leu  Leu  Leu  Leu  Leu  Gln  Pro  Pro
               35                 40                 45

Ala  Leu  Ser  Ala  Gln  Phe  Thr  Val  Gly  Val  Leu  Gly  Pro  Trp  Ala  Cys
50                       55                 60

Asp  Pro  Ile  Phe  Ser  Arg  Ala  Arg  Pro  Asp  Leu  Ala  Ala  Arg  Leu  Ala
65                       70                 75                      80

Ala  Ala  Arg  Leu  Asn  Arg  Asp  Pro  Ser  Leu  Ala  Gly  Gly  Pro  Arg  Phe
                    85                 90                 95

Glu  Val  Ala  Leu  Leu  Pro  Glu  Pro  Cys  Arg  Thr  Pro  Gly  Ser  Leu  Gly
                    100                105                110

Ala  Val  Ser  Ser  Ala  Leu  Ala  Arg  Val  Ser  Gly  Leu  Val  Gly  Pro  Val
               115                120                125

Asn  Pro  Ala  Ala  Cys  Arg  Pro  Ala  Glu  Leu  Leu  Ala  Glu  Glu  Ala  Gly
130                      135                140

Ile  Ala  Leu  Val  Pro  Trp  Gly  Cys  Pro  Gly  Thr  Gln  Ala  Ala  Gly  Thr
145                      150                155                     160

Thr  Ala  Pro  Val  Val  Thr  Pro  Ala  Ala  Asp  Ala  Leu  Tyr  Ala  Leu  Leu
                    165                170                175

Arg  Ala  Phe  Gly  Trp  Ala  Arg  Val  Ala  Leu  Val  Thr  Ala  Pro  Gln  Asp
                    180                185                190

Leu  Trp  Val  Glu  Ala  Gly  Leu  Ser  Leu  Ser  Thr  Ala  Leu  Arg  Ala  Arg
               195                200                205

Gly  Leu  Pro  Val  Val  Ser  Val  Thr  Ser  Met  Glu  Pro  Leu  Asp  Leu  Ser
210                      215                220

Gly  Ala  Arg  Glu  Ala  Leu  Arg  Lys  Val  Arg  Asn  Gly  Pro  Arg  Val  Thr
225                      230                235                     240

Ala  Val  Ile  Met  Val  Met  His  Ser  Val  Leu  Leu  Gly  Gly  Glu  Glu  Gln
                    245                250                255

Arg  Tyr  Leu  Leu  Glu  Ala  Ala  Glu  Glu  Leu  Gly  Leu  Thr  Asp  Gly  Ser
                    260                265                270

Leu  Val  Phe  Leu  Pro  Phe  Asp  Thr  Ile  His  Tyr  Ala  Leu  Ser  Pro  Gly
               275                280                285

Arg  Glu  Ala  Leu  Ala  Ala  Leu  Val  Asn  Ser  Ser  Gln  Leu  Arg  Arg  Ala
          290                295                300

His  Asp  Ala  Val  Leu  Thr  Leu  Thr  Arg  His  Cys  Ser  Ser  Glu  Gly  Ser
305                      310                315                     320
```

-continued

```
Val Leu Asp Ser Leu Arg Lys Ala Gln Gln Arg Arg Glu Leu Pro Ser
            325                 330                 335

Asp Leu Asn Leu Glu Gln Val Ser Pro Leu Phe Gly Thr Ile Tyr Asp
            340                 345                 350

Ala Val Val Leu Leu Ala Arg Gly Val Ala Asp Ala Arg Ala Ala Val
            355                 360                 365

Gly Gly Arg Trp Val Ser Gly Ala Ala Val Arg His Val Trp Asp
    370                 375                 380

Ala Gln Ala Ser Gly Phe Cys Gly Asp Leu Arg Asp Glu Glu Pro
385                 390                 395                 400

Ser Phe Val Leu Leu Asp Thr Asp Ala Ala Gly Asp Gln Leu Phe Ala
                405                 410                 415

Thr Tyr Met Leu Asp Pro Ala Arg Gly Ser Leu Leu Ser Ala Gly Thr
            420                 425                 430

Pro Met His Phe Pro Arg Gly Gly Pro Ala Pro Gly Pro Asp Pro Ser
            435                 440                 445

Cys Trp Phe Asp Pro Asn Asn Ile Cys Asp Gly Gly Leu Glu Pro Gly
    450                 455                 460

Phe Ile Phe Leu Gly Phe Leu Val Val Gly Met Gly Leu Ala Gly
465                 470                 475                 480

Ala Leu Leu Ala His Tyr Val Arg His Gln Leu Leu His Ile Gln Met
            485                 490                 495

Val Ser Gly Pro Asn Lys Ile Ile Leu Thr Val Asp Asp Ile Thr Phe
            500                 505                 510

Leu His Pro His Gly Gly Ala Ser Arg Lys Val Ala Gln Gly Ser Arg
            515                 520                 525

Ser Ser Leu Ala Ala His Ser Thr Ser Asp Ile Arg Ser Gly Pro Ser
    530                 535                 540

Gln Pro Ser Asp Ser Pro Asn Ile Gly Val Tyr Glu Gly Asp Arg Val
545                 550                 555                 560

Trp Leu Lys Lys Phe Pro Gly Glu Gln His Ile Ala Ile Arg Pro Ala
                565                 570                 575

Thr Lys Thr Ala Phe Ser Lys Leu Gln Glu Leu Arg His Glu Asn Val
            580                 585                 590

Ala Leu Tyr Leu Gly Leu Phe Leu Ala Gln Gly Ala Glu Gly Pro Ala
            595                 600                 605

Ala Leu Trp Glu Gly Asn Leu Ala Val Val Ser Glu His Cys Thr Arg
            610                 615                 620

Gly Ser Leu Gln Asp Leu Leu Ala Gln Arg Glu Ile Lys Leu Asp Trp
625                 630                 635                 640

Met Phe Lys Ser Ser Leu Leu Asp Leu Ile Lys Gly Ile Arg Tyr
                645                 650                 655

Leu His His Arg Gly Val Ala His Gly Arg Leu Lys Ser Arg Asn Cys
            660                 665                 670

Ile Val Asp Gly Arg Phe Val Leu Lys Ile Thr Asp His Gly His Gly
            675                 680                 685

Arg Leu Leu Glu Ala Gln Lys Val Leu Pro Glu Pro Pro Lys Ala Glu
            690                 695                 700

Asp Gln Leu Trp Thr Ala Pro Glu Leu Leu Arg Asp Pro Ala Leu Glu
705                 710                 715                 720

Arg Arg Gly Thr Leu Ala Gly Asp Val Phe Ser Leu Gly Ile Ile Met
                725                 730                 735

Gln Glu Val Val Cys Arg Ser Ala Pro Tyr Ala Met Leu Glu Leu Thr
```

```
                740                 745                 750
Pro Asp Glu Val Val Gln Arg Val Arg Ser Pro Pro Leu Cys Arg
        755                 760                 765

Pro Phe Val Ser Met Asp Gln Ala Pro Val Glu Cys Ile His Leu Met
    770                 775                 780

Lys Gln Cys Trp Ala Glu Gln Pro Glu Leu Arg Pro Ser Met Asp Leu
785                 790                 795                 800

Thr Phe Asp Leu Phe Lys Asn Ile Asn Lys Gly Arg Lys Thr Asn Ile
                805                 810                 815

Ile Asp Ser Met Leu Arg Met Leu Glu Gln Tyr Ser Ser Asn Leu Glu
            820                 825                 830

Asp Leu Ile Arg Glu Arg Thr Glu Glu Leu Glu Leu Glu Lys Gln Lys
        835                 840                 845

Thr Asp Arg Leu Leu Thr Gln Met Leu Pro Pro Ser Val Ala Glu Ala
    850                 855                 860

Leu Lys Thr Gly Thr Pro Val Glu Pro Glu Tyr Phe Glu Gln Val Thr
865                 870                 875                 880

Leu Tyr Phe Ser Asp Ile Val Gly Phe Thr Thr Ile Ser Ala Met Ser
                885                 890                 895

Glu Pro Ile Glu Val Val Asp Leu Leu Asn Asp Leu Tyr Thr Leu Phe
            900                 905                 910

Asp Ala Ile Ile Gly Ser His Asp Val Tyr Lys Val Glu Thr Ile Gly
        915                 920                 925

Asp Ala Tyr Met Val Ala Ser Gly Leu Pro Gln Arg Asn Gly Gln Arg
    930                 935                 940

His Ala Ala Glu Ile Ala Asn Met Ser Leu Asp Ile Leu Ser Ala Val
945                 950                 955                 960

Gly Thr Phe Arg Met Arg His Met Pro Glu Val Pro Val Arg Ile Arg
                965                 970                 975

Ile Gly Leu His Ser Gly Pro Cys Val Ala Gly Val Val Gly Leu Thr
            980                 985                 990

Met Pro Arg Tyr Cys Leu Phe Gly Asp Thr Val Asn Thr Ala Ser Arg
        995                 1000                1005

Met Glu Ser Thr Gly Leu Pro Tyr Arg Ile His Val Asn Leu Ser
    1010                1015                1020

Thr Val Gly Ile Leu Arg Ala Leu Asp Ser Gly Tyr Gln Val Glu
    1025                1030                1035

Leu Arg Gly Arg Thr Glu Leu Lys Gly Lys Gly Ala Glu Asp Thr
    1040                1045                1050

Phe Trp Leu Val Gly Arg Arg Gly Phe Asn Lys Pro Ile Pro Lys
    1055                1060                1065

Pro Pro Asp Leu Gln Pro Gly Ala Ser Asn His Gly Ile Ser Leu
    1070                1075                1080

Gln Glu Ile Pro Pro Glu Arg Arg Arg Lys Leu Glu Lys Ala Arg
    1085                1090                1095

Pro Gly Gln Phe Ser
    1100

<210> SEQ ID NO 9
<211> LENGTH: 1012
<212> TYPE: PRT
<213> ORGANISM: Ailuropoda melanoleuca
<220> FEATURE:
<221> NAME/KEY: misc_feature
<222> LOCATION: (80)..(88)
```

```
<223> OTHER INFORMATION: Xaa can be any naturally occurring amino acid
<220> FEATURE:
<221> NAME/KEY: misc_feature
<222> LOCATION: (964)..(971)
<223> OTHER INFORMATION: Xaa can be any naturally occurring amino acid

<400> SEQUENCE: 9

Met Arg Ala Cys Ala Leu Leu Ala Gly Gly Leu Pro Tyr Pro Arg Leu
1               5                   10                  15

Cys Ala Pro Thr Arg Trp Ala Pro Ala Arg Pro Gly Val Ser Arg Ala
            20                  25                  30

Leu Pro Trp Pro Arg Pro Arg Leu Arg Leu Leu Leu Leu Leu Leu Leu
            35                  40                  45

Arg Pro Pro Ser Val Leu Ser Ala Val Phe Thr Val Gly Val Leu Gly
50                  55                  60

Pro Trp Ala Cys Asp Pro Ile Phe Ala Arg Ala Arg Pro Asp Leu Xaa
65                  70                  75                  80

Xaa Xaa Xaa Xaa Xaa Xaa Xaa Asp Ala Leu Tyr Val Leu Leu Arg
                85                  90                  95

Ala Phe Arg Trp Ala Arg Val Ala Leu Val Thr Ala Pro Gln Asp Leu
            100                 105                 110

Trp Val Glu Ala Gly Arg Ala Leu Ser Ala Ala Leu Arg Ala Arg Gly
            115                 120                 125

Leu Pro Val Ala Leu Val Thr Thr Met Glu Pro Ser Asp Leu Ser Gly
130                 135                 140

Ala Arg Glu Ala Leu Arg Arg Val Gln His Gly Pro Arg Val Ser Ala
145                 150                 155                 160

Val Ile Met Val Met His Ser Val Leu Leu Gly Gly Glu Glu Gln Arg
                165                 170                 175

Cys Leu Leu Gln Ala Ala Glu Glu Leu Gly Leu Ala Asp Gly Ser Leu
            180                 185                 190

Val Phe Leu Pro Phe Asp Thr Leu His Tyr Ala Leu Ser Pro Gly Pro
            195                 200                 205

Glu Ala Leu Ala Ala Leu Ala Asn Ser Ser Gln Leu Arg Arg Ala His
210                 215                 220

Asp Ala Val Leu Thr Leu Thr Arg His Cys Pro Pro Gly Gly Ser Val
225                 230                 235                 240

Met Asp Ser Leu Arg Arg Ala Gln Glu Arg Gln Glu Leu Pro Ser Asp
                245                 250                 255

Leu Asn Leu Glu Gln Val Ser Pro Leu Phe Gly Thr Ile Tyr Asp Ala
            260                 265                 270

Val Phe Leu Leu Ala Gly Gly Val Ala Arg Ala Arg Ala Ala Ala Ala
            275                 280                 285

Asp Ser Arg Val Pro Gly Phe Cys Gly Ala Leu Gly Gly Ala Glu Glu
290                 295                 300

Pro Pro Phe Val Leu Leu Asp Thr Asp Ala Ala Gly Asp Arg Phe Phe
305                 310                 315                 320

Ala Thr Tyr Val Leu Asp Pro Thr Arg Gly Ser Leu His Ser Ala Gly
                325                 330                 335

Thr Pro Val His Phe Pro Arg Gly Gly Ala Pro Gly Pro Asp Pro
            340                 345                 350

Ser Cys Trp Phe Glu Pro Asp Ser Ile Cys Asn Gly Gly Val Glu Pro
            355                 360                 365

Gly Leu Val Phe Thr Gly Phe Leu Leu Val Val Gly Met Gly Leu Met
370                 375                 380
```

-continued

```
Gly Ala Phe Leu Ala His Tyr Val Arg His Arg Leu Leu His Ile Gln
385                 390                 395                 400

Met Val Ser Gly Pro Asn Lys Ile Ile Leu Thr Leu Asp Asp Ile Thr
            405                 410                 415

Phe Leu His Pro Gln Gly Gly Ser Ala Arg Lys Val Val Gln Gly Ser
        420                 425                 430

Arg Ser Ser Leu Ala Ala Arg Ser Thr Ser Asp Val Arg Ser Val Pro
    435                 440                 445

Ser Gln Pro Ser Asp Gly Gly Asn Ile Gly Leu Tyr Glu Gly Asp Trp
450                 455                 460

Val Trp Leu Lys Lys Phe Pro Gly Ser Gln His Ile Ala Ile Arg Pro
465                 470                 475                 480

Ala Thr Lys Thr Ala Phe Ser Lys Leu Arg Glu Leu Arg His Glu Asn
            485                 490                 495

Val Ala Leu Tyr Leu Gly Leu Phe Leu Gly Gly Glu Gly Gly Ser
            500                 505                 510

Ala Ala Ala Gly Gly Gly Met Leu Ala Val Val Ser Glu His Cys Thr
        515                 520                 525

Arg Gly Ser Leu His Asp Leu Leu Ala Gln Arg Asp Ile Lys Leu Asp
530                 535                 540

Trp Met Phe Lys Ser Ser Leu Leu Leu Asp Leu Ile Lys Gly Met Arg
545                 550                 555                 560

Tyr Leu His His Arg Gly Val Ala His Gly Arg Leu Lys Ser Arg Asn
            565                 570                 575

Cys Val Val Asp Gly Arg Phe Val Leu Lys Val Thr Asp His Gly His
            580                 585                 590

Gly Arg Leu Leu Glu Ala Gln Lys Val Leu Ala Glu Pro Pro Ser Ala
        595                 600                 605

Glu Asp Gln Leu Trp Thr Ala Pro Glu Leu Leu Arg Asp Pro Ala Leu
    610                 615                 620

Glu Arg Arg Gly Thr Leu Ala Gly Asp Val Phe Ser Leu Gly Ile Ile
625                 630                 635                 640

Met Gln Glu Val Val Cys Arg Ser Ser Pro Tyr Ala Met Leu Glu Leu
            645                 650                 655

Ser Ala Arg Glu Val Val Gln Arg Val Arg Ser Pro Pro Pro Leu Cys
            660                 665                 670

Arg Pro Ser Val Ser Val Asp Gln Ala Pro Ala Glu Cys Ile Gln Leu
        675                 680                 685

Met Lys Gln Cys Trp Ala Glu Gln Pro Glu Leu Arg Pro Ser Leu Asp
690                 695                 700

Arg Thr Phe Asp Gln Phe Lys Ser Ile Asn Lys Gly Arg Lys Thr Asn
705                 710                 715                 720

Ile Ile Asp Ser Met Leu Arg Met Leu Glu Gln Tyr Ser Ser Asn Leu
            725                 730                 735

Glu Gly Leu Ile Arg Glu Arg Thr Glu Leu Glu Leu Glu Leu Lys Arg
            740                 745                 750

Lys Thr Asp Arg Leu Arg Ala Ala Ser Leu Pro Ser Ser Val Ala Glu
        755                 760                 765

Ala Leu Lys Met Gly Thr Pro Val Glu Pro Glu Tyr Phe Glu Glu Val
    770                 775                 780

Thr Leu Tyr Phe Ser Asp Ile Val Gly Phe Thr Thr Ile Ser Ala Met
785                 790                 795                 800
```

```
Ser Glu Pro Ile Glu Val Val Asp Leu Leu Asn Asp Leu Tyr Thr Leu
                805                 810                 815

Phe Asp Ala Ile Ile Gly Ser His Asp Val Tyr Lys Val Glu Thr Ile
            820                 825                 830

Gly Asp Ala Tyr Met Val Ala Ser Gly Leu Pro Gln Arg Asn Gly Gln
            835                 840                 845

Arg His Ala Ala Glu Ile Ala Asn Met Ala Leu Asp Ile Leu Ser Ala
        850                 855                 860

Val Gly Ser Phe Arg Met Arg His Met Pro Glu Val Pro Val Arg Ile
865                 870                 875                 880

Arg Ile Gly Leu His Ser Gly Pro Cys Val Ala Gly Val Val Gly Leu
                885                 890                 895

Thr Met Pro Arg Tyr Cys Leu Phe Gly Asp Thr Val Asn Thr Ala Ser
                900                 905                 910

Arg Met Glu Ser Thr Gly Leu Pro Tyr Arg Ile His Val Asn Met Ser
            915                 920                 925

Thr Val Arg Ile Leu Arg Ala Leu Asp Glu Gly Phe Gln Thr Glu Val
        930                 935                 940

Arg Gly Arg Thr Glu Leu Lys Gly Lys Gly Ala Glu Asp Thr Tyr Trp
945                 950                 955                 960

Leu Val Gly Xaa Xaa Xaa Xaa Xaa Xaa Xaa Pro Ile Pro Lys Pro
                965                 970                 975

Pro Asp Leu Gln Pro Gly Ala Ser Asn His Gly Ile Ser Leu Gln Glu
                980                 985                 990

Ile Pro Leu Asp Arg Arg Gln Lys Leu Glu Lys Ala Arg Pro Gly Gln
            995                 1000                1005

Phe Ser Gly Lys
    1010

<210> SEQ ID NO 10
<211> LENGTH: 1093
<212> TYPE: PRT
<213> ORGANISM: Monodelphis domestica

<400> SEQUENCE: 10

Met Leu Val Pro Ser Ile Asn Gly Leu Phe His Pro Pro Trp Cys
1               5                   10                  15

Phe Pro Pro Leu Pro Leu Pro Leu Phe Phe Leu Phe Leu Leu Leu
                20                  25                  30

Leu Pro Val Pro Val Leu Pro Ala Thr Phe Thr Ile Gly Val Leu Gly
            35                  40                  45

Pro Trp Ser Cys Asp Pro Ile Phe Ser Arg Ala Arg Pro Asp Leu Ala
50                  55                  60

Ala Arg Leu Ala Ala Thr Arg Met Asn His Asp Gln Ala Leu Glu Gly
65                  70                  75                  80

Gly Pro Trp Phe Glu Val Ile Leu Leu Pro Glu Pro Cys Arg Thr Ser
                85                  90                  95

Gly Ser Leu Gly Ala Leu Ser Pro Ser Leu Ala Arg Val Ser Gly Leu
            100                 105                 110

Val Gly Pro Val Asn Pro Ala Ala Cys His Pro Ala Glu Leu Leu Ala
        115                 120                 125

Gln Glu Ala Gly Val Pro Leu Val Pro Trp Gly Cys Pro Gln Gly Lys
130                 135                 140

Ala Arg Thr Thr Ala Pro Ala Leu Pro Leu Ala Leu Asp Ala Leu Tyr
145                 150                 155                 160
```

```
Ala Leu Leu Arg Ala Phe His Trp Ala Lys Val Ala Leu Ile Thr Ala
                165                 170                 175
Pro Gln Asp Leu Trp Val Glu Ala Gly Gln Ala Leu Ala Gly Gly Leu
            180                 185                 190
Arg Ser Arg Gly Leu Pro Val Ala Met Val Thr Ser Leu Glu Thr Thr
        195                 200                 205
Asp Leu Glu Ser Ala Lys Asn Ala Leu Lys Arg Val Arg Asp Gly Pro
    210                 215                 220
Lys Val Lys Val Leu Ile Met Val Met His Ser Val Leu Leu Gly Gly
225                 230                 235                 240
Glu Glu Gln Arg Leu Leu Glu Ala Ala Glu Glu Leu Gly Leu Val
                245                 250                 255
Glu Gly Thr Met Val Phe Leu Pro Phe Asp Thr Leu His Tyr Ala Leu
                260                 265                 270
Pro Pro Gly Pro Glu Ala Leu Arg Pro Ile Thr Asn Ser Ser Arg Leu
            275                 280                 285
Arg Lys Ala His Asp Ala Val Leu Thr Leu Thr Arg Tyr Cys Pro Lys
        290                 295                 300
Gly Ser Val Ser Ala Ser Leu Arg Gln Ala Gln Glu His Arg Glu Leu
305                 310                 315                 320
Pro Leu Asp Leu Lys Pro Gln Gln Val Ser Pro Leu Phe Gly Thr Ile
                325                 330                 335
Tyr Asp Ala Ile Tyr Leu Leu Ala Gly Ala Val Ala Gly Ala Gln Val
                340                 345                 350
Ala Gly Gly Gly Trp Val Ser Gly Ala Ala Val Ala Arg His Ile
            355                 360                 365
Pro Asn Thr Leu Val Ser Gly Phe Cys Gly Asp Leu Gly Gly Thr Lys
        370                 375                 380
Glu Pro Pro Phe Val Leu Leu Asp Thr Asp Gly Met Arg Asp Gln Leu
385                 390                 395                 400
Leu Pro Thr Tyr Thr Leu Asp Pro Ala Gln Gly Val Leu His His Ala
                405                 410                 415
Gly Asn Pro Ile His Phe Pro His Gly Gly Gln Gly Pro Gly Pro Asp
            420                 425                 430
Pro Pro Cys Trp Phe Asp Pro Asn Val Ile Cys Ser Gly Gly Ile Glu
        435                 440                 445
Pro Arg Phe Ile Leu Leu Val Ile Leu Ile Ile Ile Gly Gly Gly Leu
    450                 455                 460
Val Val Ala Thr Leu Ala Tyr Tyr Val Arg Arg Gln Leu Leu His Ala
465                 470                 475                 480
Gln Met Val Ser Gly Pro Asn Lys Met Ile Leu Thr Leu Glu Asp Ile
                485                 490                 495
Thr Phe Phe Pro Arg Gln Gly Ser Ser Arg Lys Ala Thr Glu Gly
            500                 505                 510
Ser Arg Ser Ser Leu Ile Ala His Ser Ala Ser Asp Met Arg Ser Ile
        515                 520                 525
Pro Ser Gln Pro Pro Asp Asn Ser Asn Ile Gly Met Tyr Glu Gly Asp
    530                 535                 540
Trp Val Trp Leu Lys Lys Phe Pro Gly Glu His Tyr Thr Glu Ile Arg
545                 550                 555                 560
Pro Ala Thr Lys Met Ala Phe Ser Lys Leu Arg Glu Leu Arg His Glu
                565                 570                 575
```

```
Asn Val Ala Val Gln Met Gly Leu Phe Leu Ala Gly Ser Met Glu Gly
            580                 585                 590

Ala Ala Ala Gly Gly Leu Gly Gly Ile Leu Ala Val Val Ser Glu
        595                 600                 605

Tyr Cys Ser Arg Gly Ser Leu Gln Asp Leu Leu Ile Gln Arg Asp Ile
        610                 615                 620

Lys Leu Asp Trp Met Phe Lys Ser Ser Leu Leu Leu Asp Leu Ile Lys
625                 630                 635                 640

Gly Leu Arg Tyr Leu His His Arg Gly Val Ala His Gly Arg Leu Lys
                645                 650                 655

Ser Arg Asn Cys Val Val Asp Gly Arg Phe Val Leu Lys Ile Thr Asp
            660                 665                 670

His Ala His Gly Arg Leu Leu Glu Ala Gln Arg Val Ser Leu Glu Pro
                675                 680                 685

Pro Gln Ala Glu Asp Arg Leu Trp Thr Ala Pro Glu Leu Leu Arg Asn
        690                 695                 700

Glu Ala Leu Glu Arg Gln Gly Thr Leu Gln Gly Asp Val Phe Ser Val
705                 710                 715                 720

Gly Ile Ile Met Gln Glu Val Val Cys Arg Cys Glu Pro Tyr Ala Met
                725                 730                 735

Leu Glu Leu Thr Pro Glu Glu Ile Ile Gln Lys Val Gln Ser Pro Pro
            740                 745                 750

Pro Met Cys Arg Pro Ser Val Ser Val Asp Gln Ala Pro Met Glu Cys
            755                 760                 765

Ile Gln Leu Met Lys Gln Cys Trp Ala Glu Gln Pro Asp Leu Arg Pro
770                 775                 780

Asn Met Asp Thr Thr Phe Asp Leu Phe Lys Asn Ile Asn Lys Gly Arg
785                 790                 795                 800

Lys Thr Asn Ile Ile Asp Ser Met Leu Arg Met Leu Glu Gln Tyr Ser
                805                 810                 815

Ser Asn Leu Glu Asp Leu Ile Arg Glu Arg Thr Glu Glu Leu Glu Leu
            820                 825                 830

Glu Lys Gln Lys Thr Asp Lys Leu Leu Thr Gln Met Leu Pro Pro Ser
        835                 840                 845

Val Ala Glu Ala Leu Lys Leu Gly Ile Pro Val Glu Pro Glu Tyr Phe
850                 855                 860

Glu Glu Val Thr Leu Tyr Phe Ser Asp Ile Val Gly Phe Thr Thr Ile
865                 870                 875                 880

Ser Ala Met Ser Glu Pro Ile Glu Val Val Asp Leu Leu Asn Asp Leu
                885                 890                 895

Tyr Thr Leu Phe Asp Ala Ile Ile Gly Ser His Asp Val Tyr Lys Val
            900                 905                 910

Glu Thr Ile Gly Asp Ala Tyr Met Val Ala Ser Gly Leu Pro Lys Arg
        915                 920                 925

Asn Gly Gln Arg His Ala Ala Glu Ile Ala Asn Met Ser Leu Asp Ile
        930                 935                 940

Leu Ser Ser Val Gly Ser Phe Arg Met Arg His Met Pro Glu Val Pro
945                 950                 955                 960

Val Arg Ile Arg Ile Gly Leu His Ser Gly Pro Cys Val Ala Gly Val
                965                 970                 975

Val Gly Leu Thr Met Pro Arg Tyr Cys Leu Phe Gly Asp Thr Val Asn
            980                 985                 990

Thr Ala Ser Arg Met Glu Ser Thr  Gly Leu Pro Tyr Arg  Ile His Val
```

-continued

```
              995                 1000                1005
Asn Leu Ser Thr Val Lys Ile Leu Gln Gly Leu Asn Glu Gly Phe
        1010                1015                1020

Gln Ile Glu Ile Arg Gly Arg Thr Glu Leu Lys Gly Lys Gly Val
        1025                1030                1035

Glu Asp Thr Tyr Trp Leu Val Gly Arg Lys Gly Phe Asp Lys Pro
        1040                1045                1050

Ile Pro Ile Pro Pro Asp Leu Pro Gly Ala Ser Asn His Gly
        1055                1060                1065

Ile Ser Leu Gln Glu Ile Pro Glu Asp Arg Arg Lys Lys Leu Glu
        1070                1075                1080

Lys Ala Arg Pro Gly Gln Pro Leu Gly Lys
        1085                1090

<210> SEQ ID NO 11
<211> LENGTH: 862
<212> TYPE: PRT
<213> ORGANISM: Equus caballus

<400> SEQUENCE: 11

Met Val Met His Ser Val Leu Leu Gly Gly Glu Glu Gln Arg Cys Leu
1               5                   10                  15

Leu Glu Ala Ala Glu Glu Leu Gly Leu Ala Asp Gly Ser Leu Val Phe
            20                  25                  30

Leu Pro Phe Asp Thr Leu His Tyr Ala Leu Ser Pro Gly Pro Glu Ala
        35                  40                  45

Leu Ala Val Leu Ala Asn Asn Ser Gln Leu Arg Arg Ala His Asp Ala
    50                  55                  60

Val Leu Thr Leu Thr Arg His Cys Pro Leu Gly Gly Ser Val Leu Asp
65                  70                  75                  80

Ser Leu Arg Arg Ala Gln Glu His Gln Glu Leu Pro Ser Asp Leu Asn
                85                  90                  95

Leu Gln Gln Val Ser Pro Leu Phe Gly Thr Ile Tyr Asp Ala Val Tyr
            100                 105                 110

Leu Leu Ala Gly Gly Val Ala Arg Ala Arg Ala Ala Ala Gly Gly Ser
        115                 120                 125

Trp Val Ser Gly Ala Ala Val Ala His His Val Arg Asp Ala Gln Val
    130                 135                 140

Pro Gly Phe Cys Gly Ala Leu Gly Gly Ala Glu Glu Pro Gln Phe Val
145                 150                 155                 160

Leu Leu Asp Thr Asp Ala Ala Gly Asp Arg Leu Phe Ala Thr Tyr Met
                165                 170                 175

Leu Asp Pro Thr Arg Gly Ser Leu Trp Ser Ala Gly Thr Pro Val His
            180                 185                 190

Phe Pro Arg Gly Gly Arg Gly Pro Gly Pro Asp Pro Trp Cys Trp Phe
        195                 200                 205

Asp Pro Asp Asp Ile Cys Asn Gly Gly Val Glu Pro Arg Leu Val Phe
    210                 215                 220

Ile Gly Phe Leu Leu Ala Val Gly Met Gly Leu Ala Gly Val Phe Leu
225                 230                 235                 240

Ala His Tyr Val Arg His Arg Leu Leu His Ile Gln Met Ala Ser Gly
                245                 250                 255

Pro Asn Lys Ile Ile Leu Thr Leu Asp Asp Ile Thr Phe Leu His Pro
            260                 265                 270
```

```
Gln Gly Gly Ser Ser Arg Lys Val Ile Gln Gly Ser Arg Ser Ser Leu
            275                 280                 285

Ala Ala Arg Ser Val Ser Asp Ile Arg Ser Val Pro Ser Gln Pro Met
        290                 295                 300

Asp Ser Ser Asn Ile Gly Leu Tyr Glu Gly Asp Trp Val Trp Leu Lys
305                 310                 315                 320

Lys Phe Pro Gly Asp Gln His Ile Ala Ile Arg Pro Ala Thr Lys Thr
                325                 330                 335

Ala Phe Ser Lys Leu Arg Glu Leu Arg His Glu Asn Val Ala Leu Tyr
            340                 345                 350

Leu Gly Leu Phe Leu Ala Gly Gly Ser Ser Gly Ala Ala Ala Pro Arg
        355                 360                 365

Glu Gly Met Leu Ala Val Val Ser Glu His Cys Ala Arg Gly Ser Leu
    370                 375                 380

His Asp Leu Leu Ala Gln Arg Asp Ile Lys Leu Asp Trp Met Phe Lys
385                 390                 395                 400

Ser Ser Leu Leu Leu Asp Leu Ile Lys Gly Met Arg Tyr Leu His His
                405                 410                 415

Arg Gly Val Ala His Gly Arg Leu Lys Ser Arg Asn Cys Val Val Asp
            420                 425                 430

Gly Arg Phe Val Leu Lys Val Thr Asp His Gly His Gly Arg Leu Leu
        435                 440                 445

Glu Ala Gln Lys Val Leu Pro Glu Pro Ser Ala Glu Asp Gln Leu
    450                 455                 460

Trp Thr Ala Pro Glu Leu Leu Arg Asp Pro Ala Leu Glu Arg Gln Gly
465                 470                 475                 480

Thr Leu Ala Gly Asp Val Phe Ser Leu Gly Ile Ile Gln Glu Val
                485                 490                 495

Val Cys Arg Ser Thr Pro Tyr Ala Met Leu Glu Leu Thr Pro Glu Glu
            500                 505                 510

Val Val Gln Arg Leu Gln Ser Pro Pro Leu Cys Arg Pro Ser Val
        515                 520                 525

Ser Met Asp Gln Ala Pro Met Glu Cys Ile Gln Leu Met Lys Gln Cys
    530                 535                 540

Trp Ala Glu Gln Pro Asp Leu Arg Pro Ser Met Asp Arg Thr Phe Asp
545                 550                 555                 560

Leu Phe Lys Ser Ile Asn Lys Gly Arg Lys Thr Asn Ile Ile Asp Ser
                565                 570                 575

Met Leu Arg Met Leu Glu Gln Tyr Ser Ser Asn Leu Glu Asp Leu Ile
            580                 585                 590

Arg Glu Arg Thr Glu Glu Leu Glu Leu Glu Lys Gln Lys Thr Asp Arg
        595                 600                 605

Leu Leu Thr Gln Met Leu Pro Pro Ser Val Ala Glu Ala Leu Lys Met
    610                 615                 620

Gly Thr Pro Val Glu Pro Glu Tyr Phe Glu Glu Val Thr Leu Tyr Phe
625                 630                 635                 640

Ser Asp Ile Val Gly Phe Thr Thr Ile Ser Ala Met Ser Glu Pro Ile
                645                 650                 655

Glu Val Val Asp Leu Leu Asn Asp Leu Tyr Thr Leu Phe Asp Ala Ile
            660                 665                 670

Ile Gly Ser His Asp Val Tyr Lys Val Glu Thr Ile Gly Asp Ala Tyr
        675                 680                 685

Met Val Ala Ser Gly Leu Pro Gln Arg Asn Gly Gln Arg His Ala Ala
```

```
                    690             695             700
Glu Ile Ala Asn Met Ala Leu Asp Ile Leu Ser Ala Val Gly Ser Phe
705                 710             715                 720

Arg Met Arg His Met Pro Glu Val Pro Val Arg Ile Arg Ile Gly Leu
                725             730             735

His Ser Gly Pro Cys Val Ala Gly Val Val Gly Leu Thr Met Pro Arg
            740             745             750

Tyr Cys Leu Phe Gly Asp Thr Val Asn Thr Ala Ser Arg Met Glu Ser
            755             760             765

Thr Gly Leu Pro Tyr Arg Ile His Val Asn Met Ser Thr Val Arg Ile
    770             775             780

Leu Arg Ala Leu Asp Glu Gly Phe Gln Val Glu Val Arg Gly Arg Thr
785             790             795                 800

Glu Leu Lys Gly Lys Gly Val Glu Asp Thr Tyr Trp Leu Val Gly Arg
                805             810             815

Arg Gly Phe Asn Lys Pro Ile Pro Lys Pro Pro Asp Leu Gln Pro Gly
                820             825             830

Ala Ser Asn His Gly Ile Ser Leu Gln Glu Ile Pro Pro Glu Arg Arg
            835             840             845

Gln Lys Leu Glu Lys Ala Arg Pro Gly Gln Phe Ser Gly Lys
    850             855             860

<210> SEQ ID NO 12
<211> LENGTH: 292
<212> TYPE: DNA
<213> ORGANISM: Homo sapiens

<400> SEQUENCE: 12 ggccccaga agcctggtgg ttgtttgtcc ttctcagggg aaaagtgagg cggccccttg      60
gaggaagggg ccgggcagaa tgatctaatc ggattccaag cagctcaggg gattgtcttt     120
ttctagcacc ttcttgccac tcctaagcgt cctccgtgac cccggctggg atttagcctg    180
gtgctgtgtc agccccggtc tcccaggggc ttcccagtgg tccccaggaa ccctcgacag    240
ggcccggtct ctctcgtcca gcaagggcag ggacgggcca caggccaagg gc             292

<210> SEQ ID NO 13
<211> LENGTH: 953
<212> TYPE: DNA
<213> ORGANISM: Artificial Sequence
<220> FEATURE:
<223> OTHER INFORMATION: hybrid CBA/CMV promoter

<400> SEQUENCE: 13
aattcggtac cctagttatt aatagtaatc aattacgggg tcattagttc atagcccata     60
tatggagttc cgcgttacat aacttacggt aaatggcccg cctggctgac cgcccaacga    120
cccccgccca ttgacgtcaa taatgacgta tgttcccata gtaacgccaa tagggacttt    180
ccattgacgt caatgggtgg actatttacg gtaaactgcc cacttggcag tacatcaagt    240
gtatcatatg ccaagtacgc cccctattga cgtcaatgac ggtaaatggc ccgcctggca    300
ttatgcccag tacatgacct tatgggactt tcctacttgg cagtacatct acgtattagt    360
catcgctatt accatggtcg aggtgagccc cacgttctgc ttcactctcc ccatctcccc    420
cccctcccca cccccaattt tgtatttatt tattttttaa ttattttgtg cagcgatggg    480 ggcgggggg ggggggggc gcgcgccagg cgggcgggg cggggcgagg ggcgggcgg        540 ggcgaggcgg agaggtgcgg cggcagccaa tcagagcggc gcgctccgaa agtttccttt    600
```

```
tatggcgagg cggcggcggc ggcggcccta taaaaagcga agcgcgcggc gggcgggagt    660
cgctgcgacg ctgccttcgc cccgtgcccc gctccgccgc cgcctcgcgc cgcccgcccc    720
ggctctgact gaccgcgtta ctcccacagg tgagcgggcg ggacggccct tctcctccgg    780
gctgtaatta gcgcttggtt taatgacggc ttgtttcttt tctgtggctg cgtgaaagcc    840
ttgaggggct ccgggagcta gagcctctgc taaccatgtt catgccttct tctttttcct    900
acagctcctg ggcaacgtgc tggttattgt gctgtctcat cattttggca aag           953
```

```
<210> SEQ ID NO 14
<211> LENGTH: 36
<212> TYPE: DNA
<213> ORGANISM: Artificial Sequence
<220> FEATURE:
<223> OTHER INFORMATION: Forward Primer

<400> SEQUENCE: 14
aaaagcggcc gcatgagcgc ttggctcctg ccagcc                                36

<210> SEQ ID NO 15
<211> LENGTH: 36
<212> TYPE: DNA
<213> ORGANISM: Artificial Sequence
<220> FEATURE:
<223> OTHER INFORMATION: Reverse Primer

<400> SEQUENCE: 15
aaaagcggcc gctcacttcc cagtaaactg gcctgg                                36

<210> SEQ ID NO 16
<211> LENGTH: 24
<212> TYPE: DNA
<213> ORGANISM: Artificial Sequence
<220> FEATURE:
<223> OTHER INFORMATION: Forward Primer

<400> SEQUENCE: 16
gacccttcct gctggttcga tcca                                             24

<210> SEQ ID NO 17
<211> LENGTH: 25
<212> TYPE: DNA
<213> ORGANISM: Artificial Sequence
<220> FEATURE:
<223> OTHER INFORMATION: Reverse Primer

<400> SEQUENCE: 17
ctgcatgtgt agcagcctgt gcctc                                            25

<210> SEQ ID NO 18
<211> LENGTH: 992
<212> TYPE: PRT
<213> ORGANISM: Artificial Sequence
<220> FEATURE:
<223> OTHER INFORMATION: Consensus Sequence

<400> SEQUENCE: 18
```

Met Ser Ala Ala Gly Gly Leu Gly Cys Pro Arg Ala Pro Ser Ile Pro
1               5                   10                  15

Arg Leu Leu Leu Leu Leu Leu Ser Leu Ser Ala Val Phe Val Gly
            20                  25                  30

Val Leu Gly Pro Trp Ala Cys Asp Pro Ile Phe Ala Arg Ala Arg Pro
        35                  40                  45

```
Asp Ile Ala Ala Arg Leu Ala Ala Arg Leu Asn Ala Leu Asp Gly Gly
    50                  55                  60

Pro Arg Phe Glu Val Ala Leu Leu Pro Glu Pro Cys Thr Pro Gly Ser
65                  70                  75                  80

Leu Gly Ala Val Ser Ser Ala Ser Arg Val Ser Gly Leu Val Gly Pro
                85                  90                  95

Val Asn Pro Ala Ala Cys Arg Pro Ala Glu Leu Leu Ala Gln Glu Ala
                100                 105                 110

Gly Val Ala Leu Val Pro Trp Gly Val Pro Gly Thr Arg Ala Ala Gly
                115                 120                 125

Thr Thr Ala Pro Val Thr Pro Ala Ala Asp Ala Leu Tyr Leu Leu Arg
            130                 135                 140

Ala Phe Arg Trp Ala Val Ala Leu Ile Thr Ala Pro Gln Asp Leu Trp
145                 150                 155                 160

Val Glu Ala Gly Ala Leu Ser Thr Ala Leu Arg Ala Arg Gly Leu Pro
                165                 170                 175

Val Ala Leu Val Thr Ser Met Glu Val Arg Val Ile Met Val Met Gly
                180                 185                 190

Ser Val Leu Leu Gly Gly Glu Glu Gln Arg Leu Leu Glu Ala Ala Glu
                195                 200                 205

Glu Leu Ala Leu Asp Gly Ser Leu Val Phe Leu Pro Phe Asp Thr Leu
            210                 215                 220

His Trp Ala Leu Ser Pro Gly Pro Asp Ala Ile Ala Asn Ser Ser Gln
225                 230                 235                 240

Leu Arg Lys Ala His Asp Ala Val Leu Thr Leu Thr Arg Cys Pro Gly
                245                 250                 255

Gly Ser Val Asp Ser Leu Arg Arg Ala Gln Glu His Glu Leu Pro Leu
                260                 265                 270

Asp Leu Asn Leu Gln Val Ser Pro Leu Phe Gly Thr Ile Tyr Asp Ala
            275                 280                 285

Val Phe Leu Leu Ala Gly Gly Thr Ala Thr Ala Gly Gly Gly Trp Val
    290                 295                 300

Ser Gly Ala Ala Val Ala Arg Ile Arg Asp Ala Val Gly Phe Cys Gly
305                 310                 315                 320

Leu Gly Glu Glu Pro Ser Phe Val Leu Ile Asp Thr Asp Ala Ser Gly
                325                 330                 335

Asp Gln Leu Phe Ala Thr His Leu Leu Asp Pro Gly Ser Ala Gly Thr
            340                 345                 350

Pro Met His Phe Pro Lys Gly Gly Ala Pro Gly Pro Asp Pro Ser Cys
            355                 360                 365

Trp Phe Asp Pro Asp Ile Cys Asn Gly Gly Val Glu Pro Leu Val Phe
    370                 375                 380

Ile Gly Phe Leu Leu Val Ile Gly Met Gly Leu Gly Ala Phe Leu Ala
385                 390                 395                 400

Phe Leu Ala His Tyr Arg His Arg Leu Leu His Ile Gln Met Ser Gly
                405                 410                 415

Pro Asn Lys Ile Ile Leu Thr Leu Asp Asp Ile Thr Phe Leu His Pro
            420                 425                 430

Gly Gly Ser Arg Lys Val Gln Gly Ser Arg Ser Ser Leu Ala Arg Ser
            435                 440                 445

Ser Asp Ile Arg Ser Ile Ser Gln Asp Thr Asn Ile Gly Leu Tyr Glu
    450                 455                 460
```

```
Gly Asp Trp Val Trp Leu Lys Lys Phe Pro Gly Asp His Ile Ala Ile
465                 470                 475                 480

Arg Pro Ala Thr Lys Ala Phe Ser Lys Ile Arg Glu Leu Arg His Glu
                485                 490                 495

Asn Val Ala Leu Tyr Leu Gly Leu Phe Leu Ala Gly Ala Gly Ala Pro
            500                 505                 510

Ala Pro Gly Glu Gly Ile Leu Ala Val Val Ser Glu His Cys Ala Arg
        515                 520                 525

Gly Ser Leu Asp Leu Leu Ala Gln Arg Asp Ile Lys Leu Asp Trp Met
    530                 535                 540

Phe Lys Ser Ser Leu Leu Leu Asp Leu Ile Lys Gly Ile Arg Tyr Leu
545                 550                 555                 560

His His Arg Gly Val Ala His Gly Arg Leu Lys Ser Arg Asn Cys Val
                565                 570                 575

Val Asp Gly Arg Phe Val Leu Lys Val Thr Asp His Gly His Gly Arg
            580                 585                 590

Leu Leu Glu Ala Gln Arg Val Leu Pro Glu Pro Ser Ala Glu Asp
        595                 600                 605

Gln Leu Trp Thr Ala Pro Glu Leu Leu Arg Asp Pro Leu Glu Arg Arg
    610                 615                 620

Arg Gly Thr Leu Ala Gly Asp Val Phe Ser Leu Ala Ile Ile Met Gln
625                 630                 635                 640

Glu Val Val Cys Arg Ser Pro Tyr Ala Met Leu Glu Leu Thr Pro Glu
                645                 650                 655

Glu Val Ile Arg Val Ser Pro Pro Leu Cys Arg Pro Val Ser Ile
            660                 665                 670

Asp Gln Ala Pro Met Glu Cys Ile Gln Leu Met Gln Val Trp Ala Glu
        675                 680                 685

Pro Glu Leu Arg Pro Ser Met Asp Thr Phe Asp Leu Phe Lys Ser Ile
    690                 695                 700

Asn Lys Gly Arg Lys Asn Ile Ile Asp Ser Met Leu Arg Met Leu Glu
705                 710                 715                 720

Gln Tyr Ser Ser Asn Leu Glu Asp Leu Ile Arg Glu Arg Thr Glu Glu
                725                 730                 735

Leu Glu Glu Glu Lys Gln Lys Thr Asp Arg Leu Leu Thr Gln Met Leu
            740                 745                 750

Pro Pro Ser Val Ala Glu Ala Leu Lys Met Gly Thr Val Glu Pro Glu
        755                 760                 765

Tyr Phe Glu Glu Val Thr Leu Tyr Phe Ser Asp Ile Val Gly Phe Thr
    770                 775                 780

Thr Ile Ser Ala Met Ser Glu Pro Ile Glu Val Val Asp Leu Leu Asn
785                 790                 795                 800

Asp Leu Tyr Thr Leu Phe Asp Ala Ile Ile Gly Ala His Asp Val Tyr
                805                 810                 815

Lys Val Glu Thr Ile Gly Asp Ala Tyr Met Val Ala Ser Gly Leu Pro
            820                 825                 830

Gln Arg Asn Gly Arg His Ala Ala Glu Ile Ala Asn Met Ala Leu Asp
        835                 840                 845

Ile Leu Ser Ala Val Gly Ser Phe Arg Phe Arg Met Arg His Met Pro
    850                 855                 860

Glu Val Pro Val Arg Ile Arg Ile Gly Leu His Ser Gly Pro Cys Val
865                 870                 875                 880

Ala Gly Val Val Gly Leu Thr Met Pro Arg Tyr Cys Leu Phe Gly Asp
```

-continued

```
                885                 890                 895
Thr Val Asn Thr Ala Ser Met Glu Ser Thr Gly Leu Pro Tyr Arg Ile
            900                 905                 910

His Val Asn Ser Thr Val Ile Leu Ala Leu Gly Phe Glu Arg Gly Arg
        915                 920                 925

Thr Glu Leu Lys Gly Lys Gly Glu Asp Thr Tyr Trp Leu Val Gly Arg
    930                 935                 940

Gly Phe Asn Lys Pro Ile Pro Lys Pro Pro Asp Leu Gln Pro Gly Ala
945                 950                 955                 960

Ser Asn His Gly Ile Ser Leu His Gly Ile Ser Leu Glu Ile Pro Pro
            965                 970                 975

Asp Arg Arg Lys Leu Glu Lys Ala Arg Pro Gly Gln Phe Ser Gly Lys
            980                 985                 990
```

RAAV-GUANYLATE CYCLASE COMPOSITIONS AND METHODS FOR TREATING LEBERS CONGENITAL AMAUROSIS-1 (LCA1)

CROSS-REFERENCE TO RELATED APPLICATIONS

The present application is the United States national stage of PCT International Patent Application No. PCT/US2011/033669, filed Apr. 22, 2011, which claims priority to U.S. Provisional Patent Application No. 61/327,521, filed Apr. 23, 2010, the contents of each of which is specifically incorporated herein in its entirety by express reference thereto.

STATEMENT REGARDING FEDERALLY SPONSORED RESEARCH OR DEVELOPMENT

This invention was made with government support under Grant Nos. EY011123 and EY008571 awarded by the National Institutes of Health (NIH). The government has certain rights in the invention.

NAMES OF THE PARTIES TO A JOINT RESEARCH AGREEMENT

Not Applicable.

BACKGROUND OF THE INVENTION

Field of the Invention

The present invention relates generally to the fields of molecular biology and virology, and in particular, to methods for using recombinant adeno-associated virus (rAAV) compositions that express at least a first nucleic acid segment encoding at least a first therapeutic gene product, and particularly those products useful in the prevention, treatment, or amelioration of one or more symptoms of diseases, disorders, trauma, injury, or dysfunction of the mammalian eye. In particular embodiments, the invention provides compositions including rAAV vectors that express a biologically-functional guanylate cyclase peptide, polypeptide, or protein for use in one or more investigative, diagnostic and/or therapeutic regimens, including, for example, the treatment of one or more disorders or diseases of the mammalian eye, and in particular, for treating congenital retinal blindness including, retinal dystrophy such as Leber's congenital amaurosis, type 1 (LCA1), in humans. Also provided are methods for preparing rAAV vector-based guanylate cyclase medicaments for use in viral vector-based gene therapies, including, for example rAAV-LCA1 vectors for treating or ameliorating one or more symptoms of guanylate cyclase deficiency in humans.

Description of Related Art

Leber's congenital amaurosis (LCA) (formerly "amaurosis congenita of Leber"), first described as a congenital type of retinitis pigmentosa (RP) by German ophthalmologist Dr. Theodor Leber in 1869, is the earliest and most severe form of inherited retinopathy, and accounts for about 6% of all inherited retinal dystrophies. LCA is a group of degenerative diseases of the retina, and is the most common cause of congenital blindness in children. This autosomal recessive condition is usually recognized at birth or during the first months of life in an infant with total blindness or greatly impaired vision, normal fundus and extinguished electroretinogram (ERG) (see e.g., Perrault et al., 1996). Despite these functional deficits, LCA1 patients retain some rod and cone photoreceptors in both their macular and peripheral retina for years. Symptoms of the disease include retinal dysfunction, wobbly eye movement (nystagmus), impaired vision, slow pupil response, and ultimately, blindness.

Through genetic analyses, mutations in guanylate cyclase-1 (Gucy2d), assigned to the LCA1 locus, have been shown to account for 20% of all reported cases of LCA (see e.g., Milam et al., 2003; Perrault et al., 1996; Perrault et al., 2000). The number of patients affected by LCA1 is approximately twice that of patients affected by defects in the Retinal pigment epithelium-specific 65-kDa protein (RPE65) version of the disease (LCA2), which has garnered much attention in the gene therapy community in recent years.

It is estimated that 200,000 Americans have type 1 Leber's. Gucy2d encodes guanylate cyclase (retGC1) which is expressed in photoreceptor outer segment membranes (see e.g., Dizhoor et al., 1994; Liu et al., 1994), and plays a role in the recovery phase of phototransduction. Mutations which reduce or abolish activity of this enzyme are thought to create the biochemical equivalent of chronic light exposure in rod and cone photoreceptors. LCA is usually regarded as the consequence of either impaired development of photoreceptors or extremely early degeneration of cells that have developed normally. The LCA1 locus (GUCY2D) has been mapped to human chromosome 17p13.1 (LCA1) by homozygosity mapping.

DEFICIENCIES IN THE PRIOR ART

Presently there are no effective prophylactics or therapeutics available to prevent or treat LCA1 in humans.

SUMMARY OF THE INVENTION

The present invention overcomes limitations inherent in the prior art by providing new, non-obvious, and useful rAAV-based genetic constructs that encode one or more therapeutic mammalian polypeptides, and particularly those proteins, peptides, polypeptides of the guanylate cyclase family, for the prophylaxis, treatment and/or amelioration of one or more mammalian diseases, disorders or dysfunctions, or one or more symptoms thereof, that result from, or are exacerbated by, a deficit in, or a deficiency of, biologically-active guanylate cyclase polypeptide activity. In particular, the invention provides genetic constructs encoding one or more mammalian retinal-specific guanylate cyclase (retGC1) polypeptides, for use in the treatment of such conditions as LCA1, and other conditions of the eye such as recessive and dominant forms of cone-rod dystrophy that manifest from a deficiency or absence of physiologically-normal levels of guanylate cyclase polypeptide.

In one embodiment, the invention provides a recombinant adeno-associated viral (rAAV) vector including at least a first polynucleotide that comprises a promoter operably linked to at least a first nucleic acid segment that encodes at least a first mammalian guanylate cyclase protein, peptide, or polypeptide. Preferably, the promoter is a photoreceptor-specific promoter (such as, for example, a human rhodopsin kinase promoter), or a ubiquitous promoter (such as, for example, a truncated chimeric CMV-chicken β-actin promoter). Preferably the first nucleic acid segment encodes at least a first mammalian guanylate cyclase protein, peptide, or polypeptide that comprises, consists essentially of, or alternatively, consists of, at least a first contiguous amino acid sequence region that is at least about 80%, about 85%, or about 90% or greater in identity with at least a first sequence region of at least about 60, about 70, about 80, about 90, or about 100 or more contiguous amino acids of a sequence as set forth in any one or more of the mammalian guanylate cyclase proteins depicted in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

In certain embodiments, the at least a first nucleic acid segment preferably encodes at least a first mammalian guanylate cyclase protein, peptide, or polypeptide that includes at least a first contiguous amino acid sequence region that is at least about 91%, about 92%, about 93%, about 94%, or about 95% or greater in primary amino acid sequence identity with at least a first sequence region of at least about 100, about 110, about 120, about 130, about 140, or about 150 or more contiguous amino acids of a sequence as set forth in any one or more of the mammalian guanylate cyclase protein sequences recited in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

Preferably, the at least a first nucleic acid segment will encode at least one or more mammalian guanylate cyclase proteins, peptides, or polypeptides that each preferably include at least a first contiguous primary amino acid sequence that is at least about 95%, at least about 96%, at least about 97%, at least about 98%, or at least about 99% identical to at least a first sequence region that includes at least about 90, about 110, about 130, about 150, or about 170 or more contiguous amino acids of at least a first guanylate cyclase protein as shown in one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

Preferably the rAAV vectors of the present invention include at least a first nucleic acid segment encodes at least a first mammalian guanylate cyclase protein, peptide, or polypeptide that comprises, consists essentially of, or alternatively, consists of, the amino acid sequence of any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, or a polynucleotide sequence that is complementary to, or specifically hybridizes to one or more such sequences under stringent, to highly-stringent hybridization conditions. Preferably, the first mammalian guanylate cyclase protein, peptide, or polypeptide will possess guanylate cyclase activity in vitro and in vivo in transformed mammalian cells, and preferably, in transformed human host cells. In particular aspects, the guanylate cyclase protein, peptide, or polypeptide will possess significant biologically-active guanylate cyclase activity in vitro and in vivo in transformed mammalian cells, and preferably, in transformed human host cells when the nucleic acid segment encoding the peptide, protein, or polypeptide is operably linked to at least a first promoter capable of expressing the sequence in a mammalian, and preferably, human, host cell.

While the rAAV vectors of the present invention are not necessarily limited to a particular serotype, in certain embodiments, the inventors contemplate beneficial results can be achieved by utilizing an rAAV vector that is one or more of the following known serotypes: recombinant adeno-associated virus serotype 1 (rAAV1), recombinant adeno-associated virus serotype 2 (rAAV2), recombinant adeno-associated virus serotype 3 (rAAV3), recombinant adeno-associated virus serotype 4 (rAAV4), recombinant adeno-associated virus serotype 5 (rAAV5), recombinant adeno-associated virus serotype 6 (rAAV6), recombinant adeno-associated virus serotype 7 (rAAV7), recombinant adeno-associated virus serotype 8 (rAAV8), or a recombinant adeno-associated virus serotype 9 (rAAV) vector. In certain applications, the rAAV vectors of the present invention may be a self-complementary rAAV (scAAV) vector.

In embodiments in which a photoreceptor-specific promoter is desired, the rAAV vectors disclosed herein may include at least a first photoreceptor-specific rhodopsin kinase promoter. Exemplary such promoters include the human rhodopsin kinase promoter, which is illustrated in SEQ ID NO:12. In certain aspects of the invention, the use of a promoter sequence that includes at least about 20, at least about 25, at least about 30, at least about 35, at least about 40, at least about 45, or at least about 50 or more contiguous nucleotides from SEQ ID NO:12 is particularly preferred when tissue-specific (and in particular, photoreceptor-specific) expression of the therapeutic construct is desired.

Similarly, in embodiments in which a ubiquitous promoter is desired, the rAAV vectors disclosed herein may include at least a first truncated chimeric CMV-chicken β-actin promoter. Exemplary such promoters include the truncated chimeric CMV-chicken β-actin promoter, which is illustrated in SEQ ID NO:13. In certain aspects of the invention, the use of a promoter sequence that includes at least about 20, at least about 25, at least about 30, at least about 35, at least about 40, at least about 45, or at least about 50 or more contiguous nucleotides from SEQ ID NO:13 is particularly preferred when non-tissue specific expression of the therapeutic gene is desired.

In some embodiments, the promoter sequence employed in the disclosed therapeutic gene constructs may comprise, consist essentially of, or alternately, consist of, a nucleic acid sequence that includes at least 55, about 60, about 65, about 70, about 75, about 80, about 85, about 90, about 95, about 100, about 105, about 110, about 115, or about 120 or more contiguous nucleotides from the promoter sequences set forth in either SEQ ID NO:12 or SEQ ID NO:13.

The gene therapy vectors disclosed herein may also further optionally include one or more "upstream" or "downstream" regulatory sequences, such as a first enhancer operably linked to the at least a first nucleic segment, or a transcription regulatory region such as the woodchuck hepatitis virus post-transcriptional regulatory element. The constructs of the invention may also further optionally include one or more intron sequences operably linked to the at least a first nucleic segment encoding the therapeutic agent.

The nucleic acid segments encoding the mammalian guanylate cyclase proteins, peptides, and polypeptides of the invention may be derived from natural, semi-synthetic, or fully synthetic sequences, but will preferably be of mammalian origin. Exemplary mammalian sources include, without limitation, human, non-human primates, murines, felines, canines, porcines, ovines, bovine, equines, epine, caprine, lupines, and the like.

The rAAV vectors disclosed herein may optionally be comprised within an infectious adeno-associated viral particle, a virion, or within one or more of a plurality of infectious AAV particles. As such, the invention also emcompasses virions, viral particles, as well as isolated recombinant host cells that contain one or more of the disclosed rAAV genetic constructs. Particularly preferred host cells for the practice of the invention include, without limitation, isolated mammalian host cells that include one or more of: an rAAV vector, an AAV virion, or a plurality of infectious viral particles.

In other aspects, the invention provides novel and useful compositions that include one or more of (a) an rAAV vector, an rAAV virion, an rAAV infectious viral particle, a plurality of such virions or infectious particles, or an isolated mammalian host cell that comprises the vector, the virion, the infectious particle, or a plurality thereof. Preferably, such compositions will further optionally include one or more pharmaceutically-acceptable buffers, carriers, vehicles, diluents, and such like, and may further optionally include one or more lipids, liposomes, lipid complexes, ethosomes, niosomes, nanoparticles, microparticles, lipospheres, nanocapsules, or any combination thereof. Preferably such compositions are preferably formulated for administration to the human eye, and may be used in therapy or prophylaxis, and in the therapy or prophylaxis of a human retinal dystrophy, disease, or disorder (such as LCA1), in particular.

As noted below, the invention also includes diagnostic, therapeutic, and prophylactic kits that include one or more of the rAAV vector constructs disclosed herein. Such kits may further optionally include one or more protocols, dosing regimens, or instructions for using the component in the diagnosis, prevention, treatment, or amelioration of one or more symptoms of a retinal dystrophy, disease, disorder, or abnormal condition in a human. In certain aspects, therapeutic kits for the treatment of human patients diagnosed with Leber congenital amaurosis-1 (LCA-1) are particularly contemplated.

The present invention also encompasses the use of one or more of the disclosed rAAV-based compositions in therapy, or in prophylaxis of mammalian diseases or disorders. Likewise, the invention include use of the disclosed compositions in the manufacture of a medicament for diagnosing, preventing, treating or ameliorating one or more symptoms of a disease, disorder, dysfunction, or abnormal condition of a mammalian eye, and in particular, for treating or ameliorating one or more symptoms of Leber congenital amaurosis-1 (LCA-1) in a human.

The invention also provides a method for preventing, treating or ameliorating one or more symptoms of a disease, dysfunction, disorder, deficiency, or abnormal condition in a mammal. Such method generally involves administering to a mammal in need thereof, an effective amount of an rAAV composition disclosed herein for a time sufficient to prevent, treat and/or ameliorate the one or more symptoms of the disease, dysfunction, disorder, deficiency, or abnormal condition in the mammal. Such a mammal preferably has, is suspected of having, is at risk for developing, or has been diagnosed with at least a first retinal disorder, disease, or dystrophy, including, for example, Leber congenital amaurosis-1 (LCA-1), or wherein the mammal is at risk for developing, or has been diagnosed with one or more deficiencies, defects, or absence of biologically-active, functional guanylate cyclase protein, peptide, or polypeptide. The mammal may be of any age, but will more preferably be a neonate, newborn, infant, or juvenile that is at risk for developing or has been diagnosed with a congenital retinal dystrophy such as Leber congenital amaurosis-1 (LCA-1).

The invention also further includes a method for providing a mammal with a therapeutically-effective amount of a biologically-active mammalian guanylate cyclase peptide, polypeptide, or protein to a mammal in need thereof. Such a method generally involves at least the step of introducing into suitable cells of a mammal in need thereof, an effective amount of one or more of the rAAV vectors disclosed herein, for a time sufficient to produce a biologically-active guanylate cyclase peptide, polypeptide or protein therefrom in at least a first population of cells or at least a first tissue of the mamma into which the rAAV vector has been introduced. In the practice of the method, mammal in need thereof will preferably have one or more defects, deficiencies, or a substantial or total absence of functional, biologically-active retGC1 protein in one or more tissues within or about the body of the mammal, when compared to the level of biologically-active retGC1 protein in a normal mammal. In certain applications of the method, a plurality of cells from the mammal is provided with the rAAV vector ex vivo or in vitro, with the method further including an additional step of subsequently introducing the plurality of provided cells into at least a first tissue site within or about the body of the mammal. For example, the plurality of obtained cells may be introduced into at least a first site within one or both eyes of the mammal, including for example, by direct injection into the retina, the sub-retinal space, or to one or more tissues surrounding the retina, or to the entire eye, or to tissues surrounding the eye.

In particular aspects, the introduction of the rAAV-vectored guanylate cyclase gene construct into the cell, and its subsequent expression permits translation of functional guanylate cyclase peptide, protein, or polypeptide, and as a result, cone photoreceptors are preserved, and cone-mediated function is restored. Importantly, such method provides for a return of normal visual behavior in the eye of the mammal, and preferably, a return of vision.

Administration of the rAAV vectors of the invention may be part of a one-time therapy, or may be part of an ongoing therapy regimen repeated two or more times during the lifetime of the subject being treated. In certain aspects, a single administration of the rAAV constructs produces sustained guanylate cyclase protein formation, with preservation of the cone photoreceptors, and restoration of cone-mediated function and visual behavior over a period of at least one month, at least two months, at least three months, or longer following administration. More preferably, long-term therapy or prophylaxis is achieved using one or more subsequent administrations of the therapeutic constructs to the mammalian eye for periods of several months to several years. Preferably, cone photoreceptors are preserved, and cone-mediated function and visual behavior are restored in the mammal for a period of at least four months, at least five months, at least six months, or more following administration. In certain aspects, preservation of photoreceptors, cone-mediated function, and visual behavior are restored in the mammal for a period of at least one year, at least two years, at least three years, or at least four years or longer following completion of a treatment regimen that includes the compositions disclosed herein. The invention further provides a method for increasing the level of biologically-active retGC1 protein in one or more retinal cells of a mammal that has, is suspected of having, is diagnosed with, or is at risk for developing, LCA1. Such a method generally involves introducing into at least a first population of retinal cells of a mammal in need thereof, one or more of the disclosed rAAV-guanylate cyclase viral vector constructs, in an amount and for a time effective to increase the level of biologically-active retGC1 protein in one or more retinal cells of the mammal. Such method is particularly contemplated for preventing, treating, or ameliorating one or more symptoms of retinal dystrophy in a mammal, and may preferably involve directly or indirectly administering to the retina, sub-retinal space, or the eye of the mammal one or more of the disclosed therapeutic constructs, in an amount and for a time sufficient to treat or ameliorate the one or more symptoms of retinal dystrophy in the mammal.

The invention also provides compositions and methods for preventing, treating or ameliorating the symptoms of a guanylate cyclase protein deficiency in a mammal, and particularly for treating or reducing the severity or extent of deficiency in a human manifesting one or more of the disorders linked to a deficiency of biologically-active guanylate cyclase polypeptides. In a general sense, the method involves administration of at least a first rAAV-based genetic construct that encodes one or more guanylate cyclase peptides, polypeptides, or proteins in a pharmaceutically-acceptable vehicle to the animal in an amount and for a period of time sufficient to treat or ameliorate the deficiency in the animal suspected of suffering from such a disorder, or one or more symptoms thereof. Exemplary guanylate cyclase polypeptides useful in the practice of the invention include, but are not limited to peptides, polypeptides and proteins that have guanylate cyclase activity, and that are substantially identical in primary amino acid sequence to any one of the sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and to biologically-functional equivalents, or derivatives thereof. Additional exemplary guanylate cyclase peptides, proteins, and polypeptides useful in the practice of the include, but are not limited to those the comprise, consist essentially of, or consist of, an amino acid sequence encoding a mammalian guanylate cyclase, and particularly those sequences as disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and to biologically-functional equivalents, or derivatives thereof.

rAAV-Guanylate Cyclase Vector Compositions

In a first embodiment, the invention provides an rAAV vector comprising a polypeptide that comprises at least a first nucleic acid segment that encodes a guanylate cyclase protein, peptide or polypeptide, and in particular, a mammalian guanylate cyclase protein, peptide, or polypeptide (or a biologically-active fragment or derivative thereof), operably linked to at least a first promoter capable of expressing the nucleic acid segment in a suitable host cell transformed with such a vector. In preferred embodiments, the nucleic acid segment encodes a mammalian, and in particular, a human, guanylate cyclase peptide, polypeptide or protein, and in particular, a peptide, polypeptide, or protein that comprises at least a first contiguous amino acid sequence that is at least 90% homologous to at least a first 30 contiguous amino acid sequence from one or more of the amino acid sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, or a biologically-active fragment or variant thereof.

Preferably, the polypeptide comprises at least a first contiguous amino acid sequence that is at least 90%, at least 95%, or at least 98% homologous to an at least 30, an at least 40, an at least 50, an at least 60, an at least 70, or an at least 80 contiguous amino acid sequence from SEQ ID NO:1, and more preferably, the polypeptide comprises at least a first contiguous amino acid sequence that is at least 99% homologous to an at least 90 contiguous amino acid sequence from SEQ ID NO:1.

Alternatively, the therapeutic constructs of the invention may encompass nucleic acid segments that encode guanylate cyclase polypeptides of any mammalian origin, such as for example nucleic acids, peptides, and polypeptides of murine, primate, ovine, porcine, bovine, equine, epine, caprine, canine, feline, and/or lupine origin, or may encompass modified or site-specifically mutagenized nucleic acid segments that were initially obtained from one or more mammalian species, and genetically modified to be expressed in human cells such that their guanylate cyclase activity is retained.

In other preferred embodiments, the preferred nucleic acid segments for use in the practice of the present invention, encodes a mammalian, and in particular, a human guanylate cyclase polypeptide or a biologically active fragment or variant thereof.

The polynucleotides comprised in the vectors and viral particles of the present invention preferably comprise at least a first constitutive or inducible promoter operably linked to a guanylate cyclase-encoding nucleic acid segment as described herein. Such promoters may be homologous or heterologous promoters, and may be operatively positioned upstream of the nucleic acid segment encoding the guanylate cyclase polypeptide, such that the expression of the guanylate cyclase-encoding segment is under the control of the promoter. The construct may comprise a single promoter, or alternatively, two or more promoters may be used to facilitate expression of the guanylate cyclase-encoding DNA sequence.

Exemplary promoters useful in the practice of the invention include, but are in no way limited to, those promoter sequences that are operable in mammalian, and in particular, human host cells, tissues, and organs, such as for example, ubiquitous promoters, such as a CMV promoter, promoter, a β-actin promoter, a hybrid CMV promoter, a hybrid CMV-β-actin promoter, a truncated CMV promoter, a truncated β-actin promoter, a truncated hybrid CMV-β-actin promoter, an EF1 promoter, a U1a promoter, or a U1b promoter; or one or more cell- or tissue-specific promoters (including, for example, a photoreceptor-specific promoter such as a rhodopsin kinase promoter [hGRK1]), or an inducible promoter such as a Tet-inducible promoter or a VP16-LexA promoter.

In illustrative embodiments, a polynucleotide encoding a therapeutic polypeptide was placed under the control of a ubiquitous truncated hybrid chicken β-actin (CBA) promoter, or under the control of a photoreceptor cell-specific hGRK1) promoter, and used to produce therapeutically-effective levels of the encoded guanylate cyclase polypeptide when suitable host cells were transformed with the genetic construct, and the DNA encoding the guanylate cyclase polypeptide was expressed in such cells. An example of a suitable hGRK1 promoter is shown in SEQ ID NO:12, while a suitable ubiquitous promoter, such as the truncated hybrid chicken β-actin (CBA) promoter is shown in SEQ ID NO:13.

The polynucleotides comprised in the vectors and viral particles of the present invention may also further optionally comprise one or more native, synthetic, homologous, heterologous, or hybrid enhancer or 5' regulatory elements, for example, a natural enhancer, such as the CMV enhancer, or alternatively, a synthetic enhancer. Cell- or tissue-specific enhancers, including for example, those that increase expression of operably linked gene sequences are also contemplated to be particularly useful in the practice of the invention. Such enhancers may include, but are not limited to, retinal-specific enhancers, rod-specific enhancers, cone-specific enhancers, and such like.

The polynucleotides and nucleic acid segments comprised within the vectors and viral particles of the present invention may also further optionally comprise one or more intron sequences. In such instances, the intron sequence(s) will preferably be mammalian in origin, and more preferably, human in origin.

The DNA sequences, nucleic acid segments, and polynucleotides comprised within a vector, virion, viral particle, host cell, or composition of the present invention may also further optionally comprise one or more native, synthetic, homologous, heterologous, or hybrid post-transcriptional or 3' regulatory elements operably positioned relative to the guanylate cyclase-encoding nucleic acid segments disclosed herein to provide greater expression, greater stability, and/or enhanced translation of the encoded polypeptides. One such example is the woodchuck hepatitis virus post-transcriptional regulatory element (WPRE), operably positioned downstream of the guanylate cyclase gene. Use of elements such as these in such circumstances is well-known to those of skill in the molecular biological arts.

In illustrative embodiments, the invention concerns administration of one or more biologically-active guanylate cyclase proteins, peptides, or polypeptides that comprise an at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at about least 100, or more contiguous amino acid sequence from the polypeptide and peptide sequences disclosed hereinbelow, and particularly those polypeptides as recited in any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

Likewise, in additional illustrative embodiments, the invention concerns administration of one or more biologically-active guanylate cyclase proteins, peptides or polypeptides that are encoded by a nucleic acid segment that comprises, consists essentially of, or consists of at least about 10, at least about 20, at least about 30, at least about 40, at least about 50, at least about 60, at least about 70, at least about 80, at least about 90, at least about 100, at least about 110, at least about 120, at least about 130, at least about 140, at least about 150, at least about 160, at least about 170, at least about 180, at least about 190, or at least about 200, about 250, about 300, about 350, about 400, about 450, about 500, about 550, about 600, about 650, about 700, about 750, or even about 800 or more contiguous nucleic acid residues from the nucleic acid segments disclosed hereinbelow, and particularly those DNA sequences that encode any one or more mammalian guanylate cyclase proteins, including for example, those that are recited in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11.

Exemplary adeno-associated viral vector constructs and polynucleotides of the present invention include those that comprise, consist essentially of, or consist of at least a first nucleic acid segment that encodes a peptide or polypeptide that is at least about 75%, at least about 80%, at least about 85%, at least about 90%, at least about 95%, at least about 96%, at least about 97%, at least about 98%, or at least about 99% identical to the sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, wherein the peptide or polypeptide has guanylate cyclase activity when expressed in selected mammalian cells and/or tissues.

In certain embodiments, the viral vector constructs and polynucleotides of the present invention will preferably include those vectors and polynucleotides that comprise, consist essentially of, or consist of at least a first nucleic acid segment that encodes a peptide or polypeptide that is at least about 82%, at least about 84%, at least about 86%, at least about 88%, at least about 92%, or at least about 94% identical to one or more of the sequences disclosed in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. Such constructs will preferably encode one or more biologically-active peptides or polypeptides that have guanylate cyclase activity when expressed in selected mammalian cells and/or tissues and in human cells and/or tissues in particular.

Exemplary polynucleotides of the present invention also include those sequences that comprise, consist essentially of, or consist of at least a first nucleic acid segment that is at least about 75%, at least about 80%, at least about 85%, at least about 90%, at least about 95%, at least about 96%, at least about 97%, at least about 98%, or at least about 99% identical to a nucleic acid sequence that encodes any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, wherein the peptide or polypeptide encoded by the nucleic acid segment has guanylate cyclase activity when expressed in selected mammalian cells and/or tissues.

rAAV Viral Particles and Virions, and Host Cells Comprising them

Other aspects of the invention concern rAAV particles and virions that comprise the rAAV-guanylate cyclase vectors of the present invention, pluralities of such particles and virions, as well as pharmaceutical compositions and host cells that comprise one or more of the rAAV-guanylate cyclase vectors disclosed herein, such as for example pharmaceutical formulations of the rAAV-guanylate cyclase vectors or virions intended for administration to a mammal through suitable means, such as, by intramuscular, intravenous, or direct injection to selected cells, tissues, or organs of the mammal, for example, one or more regions of the eye of the selected mammal. Typically, such compositions will be formulated with pharmaceutically-acceptable excipients, buffers, diluents, adjuvants, or carriers, as described hereinbelow, and may further comprise one or more liposomes, lipids, lipid complexes, microspheres, microparticles, nanospheres, or nanoparticle formulations to facilitate administration to the selected organs, tissues, and cells for which therapy is desired.

Further aspects of the invention include mammalian host cells, and pluralities thereof that comprise one or more of the rAAV vectors, virions, or infectious viral particles as disclosed herein. Particularly preferred cells are human host cells, and in particular, human ocular tissues, including, for example, retinal cells.

Therapeutic Kits and Pharmaceutical Compositions

Therapeutic kits for treating or ameliorating the symptoms of a condition resulting from a guanylate cyclase deficiency in a mammal are also part of the present invention. Exemplary kits are those that preferably comprise one or more of the disclosed AAV-guanylate cyclase vector constructs, virions, or pharmaceutical compositions described herein, and instructions for using the kit. The use of such kits in methods of treatment of guanylate cyclase deficiency, and in particular, retinal-specific guanylate cyclase-1, is preferable in the treatment of retGC1 defect or deficiency and in the treatment of retinal dystrophies such as LCA-1 in an affected mammal.

Another important aspect of the present invention concerns use of the disclosed vectors, virions, compositions, and host cells described herein in the preparation of medicaments for treating or ameliorating the symptoms of guanylate cyclase deficiency in a mammal, and in particular, a human. The use of such compositions in the preparation of medicaments and in methods for the treatment of neurological and/or central nervous system defects, including for example, conditions resulting from a deficiency or defect in retinal GC1, such as for example in retinal dystrophies such as LCA-1, generally involve administration to a mammal, and particularly to a human in need thereof, one or more of the disclosed viral vectors, virions, host cells, or compositions comprising one or more of them, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

Another aspect of the invention concerns compositions that comprise one or more of the disclosed adeno-associated viral vectors, virions, viral particles, and host cells as described herein. Pharmaceutical compositions comprising such are particularly contemplated to be useful in therapy, and particularly in the preparation of medicaments for treating affected mammals, and humans in particular.

Therapeutic Methods

The invention also provides methods for delivering therapeutically-effective amounts of a guanylate cyclase polypeptide to a mammal in need thereof. Such methods generally comprise at least the step of providing or administering to such a mammal, one or more of the guanylate cyclase compositions disclosed herein. For example, the method may involve providing to such a mammal, one or more of the rAAV vectors, virions, viral particles, host cells, or pharmaceutical compositions as described herein. Preferably such providing or such administration will be in an amount and for a time effective to provide a therapeutically-effective amount of one or more of the guanylate cyclase polypeptides disclosed herein to selected cells, tissues, or organs of the mammal, and in particular, therapeutically-effective levels to the cells of the mammalian eye. Such methods may include systemic injection(s) of the therapeuticum, or may even involve direct or indirect administration, injection, or introduction of the therapeutic compositions to particular cells, tissues, or organs of the mammal.

For example, the therapeutic composition may be provided to mammal by direct injection to the tissues of the eye or to the retina, or to the subretinal space, or to one or more particular cell types within the mammalian eye.

The invention also provides methods of treating, ameliorating the symptoms, and reducing the severity of guanylate cyclase deficiency in an animal. These methods generally involve at least the step of providing to an animal in need thereof, one or more of the rAAV guanylate cyclase vector compositions disclosed herein in an amount and for a time effective to treat retGC1 polypeptide defect or deficiency, or to treat a dysfunction resulting from such accumulation, or resulting from an underexpresison or absence of sufficient biologically-active guanylate cyclase polypeptide in the animal, including retinal dystrophies such as LCA1 and the like. As described above, such methods may involve systemic injection(s) of the therapeuticum, or may even involve direct or indirect administration, injection, or introduction of the therapeutic compositions to particular cells, tissues, or organs of the animal.

The invention further concerns the use of the adeno-associated viral vectors, virions, viral particles, host cells, and/or the pharmaceutical compositions disclosed herein in the manufacture of a medicament for treating guanylate cyclase defect or deficiency, retinal dystrophy, or LCA1 or other GC1-related ocular disease, disorder, or dysfunction in a mammal. This use may involve systemic or localized injection, infection, or administration to one or more cells, tissues, or organs of the mammal. Such use is particularly contemplated in humans that have, are suspected of having, or at risk for developing one or more retinal dystrophies such as LCA-1.

BRIEF DESCRIPTION OF THE DRAWINGS

The following drawings form part of the present specification and are included to further demonstrate certain aspects of the present invention. The invention may be better understood by reference to the following description taken in conjunction with the accompanying drawings, in which like reference numerals identify like elements, and in which:

in FIG. 4F=25 µm. OS=outer segments, IS=inner segments, ONL=outer nuclear layer;

FIG. 6C: "TX"=treated), and the smCBA-mGC1 study (FIG. 6B: "no TX=untreated; FIG. 6D: "TX"=treated) and contralateral un-injected eyes stained for cone arrestin reveal that cone photoreceptors are preserved in GC1KO mice treated with AAV-mGC1 for at least 3 months post treatment. Cone cell densities were counted in central and inferior retinas of treated and untreated mice. Significant differences were found in both areas following treatment with either viral vector;

FIG. 10 shows an amino acid sequence alignment of the bovine GC1 (bov GC1) and mouse GC1 (mGC1) with consensus sequence included. Variable region located in the N-terminal area is highlighted by the red rectangle;

FIG. 13A, FIG. 13B, and FIG. 13C show AAV-mediated restoration of retinal function in GC1KO mice. FIG. 13A: Representative photopic (cone-mediated) traces recorded from eyes of GC1KO mice treated at ~P14 with AAV5-hGRK1-mGC1 (red), AAV5-smCBA-mGC1 (green) or AAV8(Y733F)-hGRK1-mGC1 or age-matched, isogenic GC1+/+ controls. Traces were generated at 4 months (left), 7 months (middle) and 9 months (right) post-injection. FIG. 13B: Average cone b-wave amplitudes generated monthly with a 12cds/m2 stimulus in treated GC1KO mice, untreated GC1KO and age-matched isogenic GC1+/+ control mice. FIG. 13C: Scotopic (rod-mediated) responses in treated vs. untreated GC1KO mice over time. Values represent the ratio of rod b-wave amplitudes generated at 5 cds/m2 in treated vs. untreated eyes. All three vectors confer stable, long-term therapy to GC1KO mice, with AAV8(Y733F)-hGRK1-mGC1 being the most efficient;

FIG. 17 illustrates data in which GC1KO mice injected with AAV8(733)-hGRK1-mGC1 were sacrificed at 4 months and 7 months post injection. GC1KO mice injected with AAV5-smCBA-mGC1 and AAV5-hGRK1-mGC1 were sacrificed at 7 months and 10 months post injection. Age matched, naïve GC1KO mice were used as controls. Optic nerves from treated and untreated eyes, and portions of the right and left brains containing visual pathways were isolated and used for recovery of vector genomes. Note that AAV8(Y733F)-hGRK1-mGC1 was injected into the LEFT eyes of GC1KO mice whereas both AAV5 vectors were injected into RIGHT eyes of GC1KO mice. Vector genomes were recovered only from the optic nerves of treated eyes in all cases. By 10 months post-injection of AAV5 vectors, no vector genomes were recovered from brain. The highest number of vector genomes were recovered from GC1KO mice injected with the strong, fast-acting AAV8(733) vector;

FIG. 21A: Immunohistochemistry of frozen retinal cross-sections was used to localize expression of GC1 (green, top row) and cone arrestin (red, bottom row) in GC1KO mice treated with AAV8(Y733F)-hGRK1-mGC1 (7 months post-injection), AAV5-smCBA-mGC1 (10 months post-injection) or AAV5-hGRK1-mGC1 (10 months post-injection) vectors as well as retinas from 8 month old untreated GC1KO and GC1+/+ control mice. Nuclei were stained with DAPI (blue). All sections were imaged at 20× magnification and exposed at identical settings. FIG. 21B: Immunostaining of retinal whole mounts from one GC1KO mouse 11 months post-treatment with AAV5-smCBA-mGC1 (one eye only) with an antibody against cone arrestin revealed marked preservation of cone photoreceptors in the treated eye (bottom right) compared to the untreated contralateral control eye (bottom left). Retinal whole mounts were oriented similarly, with their temporal portions in the 12 o'clock position. Portions of whole mounts were imaged at 10× magnification and merged together for final presentation. OS=outer segments; ONL=outer nuclear layer; INL=inner nuclear layer;

FIG. 22A: Representative cone-mediated traces elicited by a 12 cds/m$^2$ light stimulus from GC1KO eyes treated with AAV5-hGRK1-mGC1 (red line), AAV5-smCBA-mGC1 (green line) or AAV8(Y733F)-hGRK1-mGC1 (black line) or untreated age-matched GC1+/+ control eyes. Representative traces generated between 4-months' and 1-years' post-treatment are shown (top panel). Scale: y-axis=50 µV, x-axis=20 ms. FIG. 22B: Maximum cone b-wave amplitudes (those generated at 12 cds/m$^2$) were calculated from each mouse and averaged monthly in each treatment group as well as age-matched, untreated GC1KO and GC1+/+ controls. Comparisons were made between groups of animals with an n>3. All AAV treatment groups were statistically compared for 6-months' post-treatment. AAV5 vector treated eyes were statistically compared for 9-months' post-treatment;

FIG. 23A: Rod b-wave amplitudes (top left) and a-wave amplitudes (top right) elicited by a 1 cds/m$^2$ stimulus under scotopic conditions were determined in the treated and untreated eyes of GC1KO mice treated with AAV8(Y733F)-hGRK1-mGC1 (black circles), AAV5-hGRK1-mGC1 (red circles) or AAV5-smCBA-mGC1 (green triangles) vector. Intra-mouse ratios of treated and untreated eyes were generated by dividing the maximum a- or b-wave amplitude in treated eyes by the maximum amplitude in the untreated eye. These ratios were averaged monthly in all treatment groups. Comparisons were made between groups of animals with an n>3. All AAV treatment groups were statistically compared for 6 months. AAV5 vectors were also statistically compared for 9 months. Vector-mediated improvement was defined by an average ratio>0.8. FIG. 23B: Representative rod-mediated ERG traces from one GC1KO mouse reveal that rod responses from the AAV8(Y733F)-hGRK1-mGC1-treated eye (black line) were higher than those recorded from the untreated contralateral control eye (green line). This treated rod response was restored to ~50% that of the normal GC1+/+ rod response (red line); FIG. 24A: Immunoblot of retinal lysates from one GC1KO mouse eye at 10 months after treatment with AAV8(Y733F)-hGRK1-mGC1 and probed with anti-GC1 and anti-GCAP1 antibodies. Anti-β-actin antibody was used as an internal loading control. FIG. 24B: Semiquantitative real time RT-PCR of several transcripts (GC1, GCAP1, GNAT2, and PDE6α in one GC1KO retina treated with AAV5-smCBA-mGC1, one GC1KO retina treated with AAV8(Y733F)-hGRK1-mGC1 vector, and in individual untreated GC1KO or GC1+/+ control retinas. Samples were performed in triplicate using Gapdh-specific primers as a standard. Data is presented as the fold-change in mRNA levels relative to the GC1+/+ control.

DESCRIPTION OF ILLUSTRATIVE EMBODIMENTS

Figure 1A:
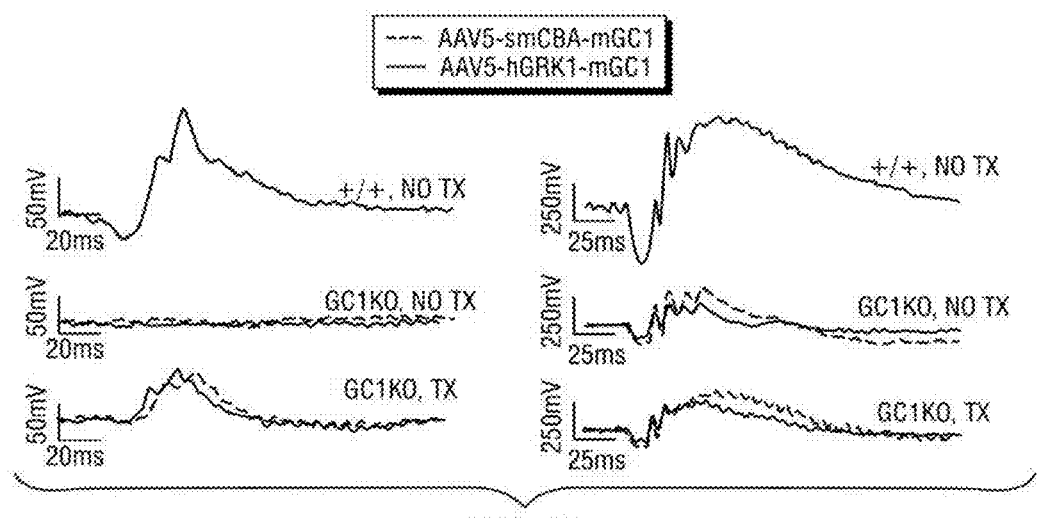
FIG. 1 shows representative cone- (left column) and rod- (right column) mediated ERG traces from +/+ (upper waveforms), untreated GC1KO (middle waveforms) and AAV-mGC1-treated (bottom waveforms) mice. Black traces correspond to eyes injected with hGRK1-mGC1 (bottom waveforms) and their un-injected contralateral eyes (middle waveforms). Red traces correspond to eyes injected with smCBA-mGC1 (bottom waveforms) and un-injected contralateral eyes (middle waveforms). Cone responses in AAV-mGC1 treated eyes are restored to approximately 45% of normal.
Figure 1B:
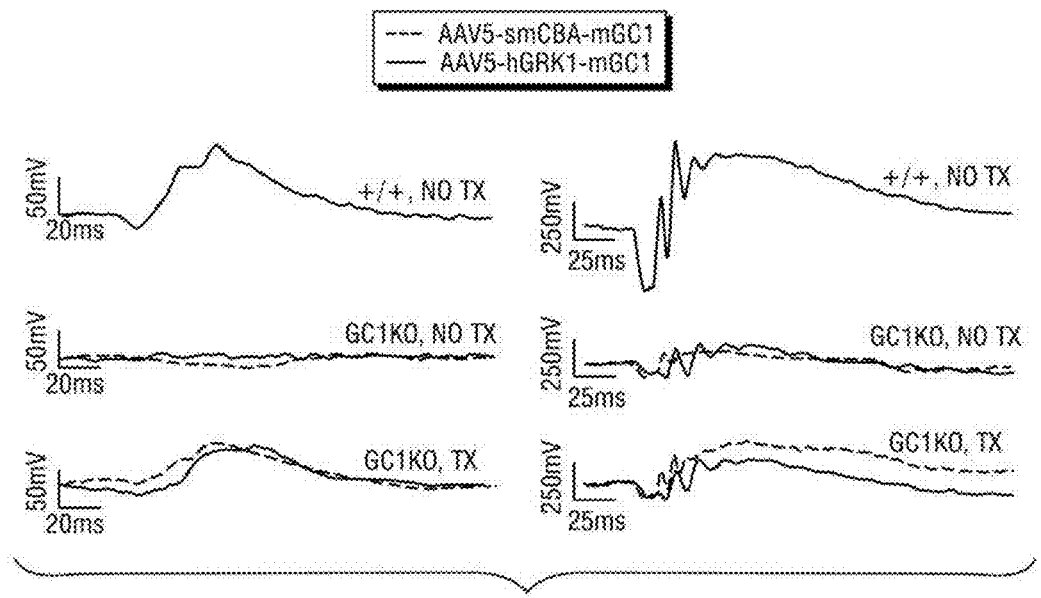

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Adeno-Associated Virus

Adeno-associated virus-2 (AAV) is a human parvovirus that can be propagated both as a lytic virus and as a provirus (Cukor et al., 1984; Hoggan et al., 1972). The viral genome consists of linear single-stranded DNA (Rose et al., 1969), 4679 bases long (Srivastava et al., 1983), flanked by inverted terminal repeats of 145 bases (Lusby et al., 1982). For lytic growth AAV requires co-infection with a helper virus. Either adenovirus (Atchinson et al., 1965; Hoggan, 1965; Parks et al., 1967) or herpes simplex (Buller et al., 1981) can supply helper function. Without helper, there is no evidence of AAV-specific replication or gene expression (Rose and Koczot, 1972; Carter et al., 1983). When no helper is available, AAV can persist as an integrated provirus (Hoggan, 1965; Berns et al., 1975; Handa et al., 1977; Cheung et al., 1980; Berns et al., 1982).

Integration apparently involves recombination between AAV termini and host sequences and most of the AAV sequences remain intact in the provirus. The ability of AAV to integrate into host DNA is apparently an inherent strategy for insuring the survival of AAV sequences in the absence of the helper virus. When cells carrying an AAV provirus are subsequently superinfected with a helper, the integrated AAV genome is rescued and a productive lytic cycle occurs (Hoggan, 1965).

AAV sequences cloned into prokaryotic plasmids are infectious (Samulski et al., 1982). For example, when the wild type AAV/pBR322 plasmid, pSM620, is transfected into human cells in the presence of adenovirus, the AAV sequences are rescued from the plasmid and a normal AAV lytic cycle ensues (Samulski et al., 1982). This renders it possible to modify the AAV sequences in the recombinant plasmid and, then, to grow a viral stock of the mutant by transfecting the plasmid into human cells (Samulski et al., 1983; Hermonat et al., 1984). AAV contains at least three phenotypically distinct regions (Hermonat et al., 1984). The rep region codes for one or more proteins that are required for DNA replication and for rescue from the recombinant plasmid, while the cap and lip regions appear to code for AAV capsid proteins and mutants within these regions are capable of DNA replication (Hermonat et al., 1984). It has been shown that the AAV termini are required for DNA replication (Samulski et al., 1983).

Laughlin et al. (1983) have described the construction of two *E. coli* hybrid plasmids, each of which contains the entire DNA genome of AAV, and the transfection of the recombinant DNAs into human cell lines in the presence of helper adenovirus to successfully rescue and replicate the AAV genome (See also Tratschin et al., 1984a; 1984b).

Adeno-associated virus (AAV) is particularly attractive for gene transfer because it does not induce any pathogenic response and can integrate into the host cellular chromosome (Kotin et al., 1990). The AAV terminal repeats (TRs) are the only essential cis-components for the chromosomal integration (Muzyczka and McLaughlin, 1988). These TRs are reported to have promoter activity (Flotte et al., 1993). They may promote efficient gene transfer from the cytoplasm to the nucleus or increase the stability of plasmid DNA and enable longer-lasting gene expression (Bartlett and Samulski, 1998). Studies using recombinant plasmid DNAs containing AAV TRs have attracted considerable interest. AAV-based plasmids have been shown to drive higher and longer transgene expression than the identical plasmids lacking the TRs of AAV in most cell types (Philip et al., 1994; Shafron et al., 1998; Wang et al., 1998).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response. AAV therefore, represents an ideal candidate for delivery of the guanylate cyclase-encoding polynucleotides of the present invention.

Production of rAAV Vectors

Traditional protocols to produce rAAV vectors have generally been based on a three-component system. One component of this system is a proviral plasmid encoding the recombinant DNA to be packaged as rAAV. This recombinant DNA is located between 145 base pair (bp) AAV-2 inverted terminal repeats (ITRs) that are the minimal cis acting AAV-2 sequences that direct replication and packaging of the vector. A second component of the system is a plasmid encoding the AAV-2 genes, rep and cap. The AAV-2 rep gene encodes four Rep proteins (Rep 78, 68, 52 and 40) that act in trans to replicate the rAAV genome, resolve replicative intermediates, and then package single-stranded rAAV genomes. The AAV-2 cap gene encodes the three structural proteins (VP1, VP2, and VP3) that comprise the virus capsid. Because AAV-2 does not proficiently replicate on its own, the third component of a rAAV packaging system is a set of helper functions from another DNA virus. These helper functions create a cellular environment in which rAAV replication and packaging can efficiently occur. The helper functions provided by adenovirus (Ad) have almost exclusively been used to produce rAAV and are encoded by the genes E1a, E1b, E2a, E4orf6, and VA RNA. While the first two components of the system are generally introduced into cells in which replication and packaging is to occur by transfection, ad helper functions are introduced by superinfection with wild type Ad virus.

The traditional rAAV production techniques are limited in their ability to produce large quantities of vector because of inherent inefficiencies in transfection. Serious difficulties are also encountered when the scale of transfection is increased. The requirement for wild type Ad may also reduce the amount of rAAV produced since Ad may compete for cellular and viral substrates that are required for viral replication but are present only in limiting amounts. Another problem encountered in traditional production protocols is that superinfection with Ad requires development of effective procedures for purification of Ad from the rAAV produced. While these purification processes are generally successful at eliminating Ad contamination of rAAV preparations, they also reduce rAAV titers. Stringent assays for Ad contamination of rAAV are also necessary.

To produce rAAV, a double co-transfection procedure is used to introduce a rAAV transfer vector plasmid together with pDG (Grimm et al., 1998) AAV helper plasmid carrying the AAV rep and cap genes, as well as Ad helper genes required for rAAV replication and packaging at a 1:1 molar ratio. Plasmid DNA used in the transfection is purified by a conventional alkaline lysis/CsCl gradient protocol. The transfection is carried out as follows: 293 cells are split 1:2 the day prior to the experiment, so that, when transfected, the cell confluence is about 75-80%. Ten 15-cm plates are transfected as one batch. To make CaPO4 precipitate 0.7 mg of pDG are mixed with 180 µg of rAAV transfer vector plasmid in a total volume of 12.5 mL of 0.25 M CaCl2. The old media is removed from the cells and the formation of the CaPO4-precipitate is initiated by adding 12.5 ml of 2×HBS (pH 7.05) that has been pre-warmed to 37° C. to the DNA-CaCl2 solution. The DNA is incubated for 1 min; and transferring the mixture into 200 mL of pre-warmed DMEM-10% FBS then stops the formation of the precipitate. Twenty two mL of the medium is immediately dispensed into each plate and cells are incubated at 37° C. for 48 hr. The CaPO4-precipitate is allowed to stay on the cells during the whole incubation period without compromising cell viability. Forty-eight hr post-transfection cells are harvested by centrifugation at 1,140×g for 10 min. Cells are then lysed in 15 ml of 0.15 M MgCl, 50 mM Tris-HCl (pH 8.5) by 3 freeze/thaw cycles in dry ice-ethanol and 37° C. baths. Benzonase (Nycomed Pharma A/S, pure grade) is added to the mixture (50 U/mL final concentration) and the lysate is incubated for 30 min at 37° C. The lysate is clarified by centrifugation at 3,700×g for 20 min and the virus-containing supernatant is further purified using a discontinuous density gradient.

The typical discontinuous step gradient is formed by underlayering and displacing the less dense cell lysate with Iodixanol, 5,5"[(2-hydroxi-1-3-propanediyl)-bis(acetylamino)]bis[N,N'bi,(2,3-dihydroxypropyl-2-4,6-triiodo-1,3-enzenecarboxamide], prepared using a 60% (wt./vol.) sterile solution of OptiPrep (Nycomed). Specifically, 15 mL of the clarified lysate are transferred into Quick-Seal Ultra-Clear 25×89-mm centrifuge tube (Beckman) using a syringe equipped with a 1/27×89 mm spinal needle. Care is taken to avoid bubbles, which would interfere with subsequent filling and sealing of the tube. A variable speed peristaltic pump, Model EP-1 (Bio-Rad), is used to underlay in order: 9 mL of 15% iodixanol and 1 M NaCl in PBS-MK buffer containing Phenol Red (2.5 µL of a 0.5% stock solution per ml of the iodixanol solution); 5 mL of 40% iodixanol in PBS-MK buffer; and finally, 5 mL of 60% iodixanol in PBS-MK buffer containing Phenol Red (0.1 µL/L). Tubes are sealed and centrifuged in a Type 70 Ti rotor (Beckman) at 350,000×g for 1 hr at 18° C. Four mL of the clear 40% step is aspirated after puncturing the tube on the side with a syringe equipped with an 18-gauge needle with the bevel uppermost. The iodixanol fraction is further purified using conventional Heparin agarose affinity chromatography.

For chromatography, typically, a pre-packed 2.5-mL Heparin agarose type I column (Sigma) is equilibrated with 20 mL of PBS-MK under gravity. The rAAV iodixanol fraction is then applied to the pre-equilibrated column, and the column is washed with 10 mL of PBS-MK. rAAV is eluted with the same buffer containing 1 M NaCl. After applying the elution buffer, the first 2 ml of the eluant are discarded, and the virus is collected in the subsequent 3.5 mL of elution buffer.

Virus is then concentrated and desalted by centrifugation through the BIOMAX® 100 K filter (Millipore, Bedford, Mass., USA) according to the manufacturer's instructions. The high salt buffer is changed by repeatedly diluting the concentrated virus with Lactated Ringer's solution, and repeating the titer both genome containing particles and infectious rAAV particles. A conventional dot-blot assay, quantitative competitive PCR (QC PCR) assay, or more recently quantitative real-time PCR (aRT-PCR) are used to determine physical particle titers (Zolotukhin et al., 2002; Jacobson et al., 2006) Infectious titers are determined by infectious center assay (ICA) and fluorescent cell assay (FCA), which scores for expression of GFP (Zolotukhin et al., 2002).

QC PCR method is based on competitive co-amplified of a specific target sequence with internal standard plasmid of known concentration in on reaction tube. It provides precise and fast quantitation of viral particles. The internal standard must hare primer recognition sites with the specific template. Both the specific template and the internal standard must be PCR-amplified with the same efficiency and it must be possible to analyze the PCR-amplified products separately. The easiest way to distinguish between the template and the internal standard is to incorporate a size difference in the two products. This can be achieved, for example, by constructing standards having the same sequence as the specific target but containing a deletion. Quantitation is then performed by comparing the PCR signal of the specific template with the PCR signal obtained with known concentrations of the competitor (the internal standard). Quantitative real-time PCR (qRT-PCR) is a standard method for evaluating DNA concentration of an unknown sample by comparison of PCR product formation in real-time to a known DNA standard.

The purified viral stock is first treated with DNAseI to digest any contaminating unpackaged DNA. Ten µL of a purified virus stock is incubated with 10 µL of DNAseI (Boehringer, Ingelheim am Rhein, Germany) in a 100 µL reaction mixture, containing 50 mM Tris-HCl (pH 7.5), 10 mM MgCl$_2$ for 1 hr at 37° C. At the end of the reaction, 10 µL of 10× Proteinase K buffer (10 mM Tris-HCl [pH 8.0], 10 mM EDTA, 1% SDS final concentration) was added, followed by the addition of 1 µL of Proteinase K (18.6 mg/mL, Boehringer). The mixture was incubated at 37° C. for 1 hr. Viral DNA was purified by phenol/chloroform extraction (twice), followed by chloroform extraction and ethanol precipitation using 10 µg of glycogen as a carrier. The DNA pellet was dissolved in 100 µL of water. QC PCR reaction mixtures each contained 1 µL of the diluted viral DNA and two-fold serial dilutions of the internal standard plasmid DNA, such as pdl-GFP. The most reliable range of standard DNA was found to be between 1 and 100 pg. An aliquot of each reaction was then analyzed by 2% agarose gel electrophoresis, until two PCR products were resolved. The analog image of the ethidium bromide stained gel was digitized using and ImageStore 7500 system (UVP; Upland, Calif., USA). The densities of the target and competitor bands in each lane were measured using the ZERO-Dscan Image Analysis System, version 1.0 (Scanalytics, Rockville, Md., USA) and their ratios are plotted as a function of the standard DNA concentration. A ratio of 1.0, at which the number of viral DNA molecules equals the number of competitor DNA molecules was used to determine the DNA concentration of the virus stock.

A modification of the previously published protocol (McLaughlin et al., 1988) was used to measure the ability of the virus to infect C12 cells, unpackage, and replicate. Briefly, C2 cells containing integrated wtAAV rep and cap genes (Clark et al., 1995) were plated in a 96-well dish at about 75% confluence, then infected with Ad5 at a M.O.I of 20. One µL of serially diluted rAAV-sCNTF was visually scored using a fluorescence microscope. High sensitivity CHROMA filter #41012 HighQ FITC LP (Chroma Technology, Bellows Fall, Va., USA) was used to monitor the fluorescence. To calculate the titer by hybridization, cells were harvested and processed essentially as previously described (McLaughlin et al., 1988).

Pharmaceutical Compositions

In certain embodiments, the present invention concerns formulation of one or more of the rAAV-guanylate cyclase compositions disclosed herein in pharmaceutically acceptable solutions for administration to a cell or an animal, either alone, or in combination with one or more other modalities of therapy.

It will also be understood that, if desired, the nucleic acid segment, RNA, DNA or PNA compositions that express a therapeutic gene product as disclosed herein may be administered in combination with other agents as well, such as, e.g., proteins or polypeptides or various pharmaceutically-active agents, including one or more systemic or topical administrations of guanylate cyclase polypeptides. In fact, there is virtually no limit to other components that may also be included, given that the additional agents do not cause a significant adverse effect upon contact with the target cells or host tissues. The rAAV-vectored guanylate cyclase compositions may thus be delivered along with various other agents as required in the particular instance. Such compositions may be purified from host cells or other biological sources, or alternatively may be chemically synthesized as described herein. Likewise, such compositions may further comprise substituted or derivatized RNA, DNA, or PNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intramuscular, and direct administration to one or more cells or tissue types within the animal, including for example, ocular, retinal, and sub-retinal injection or such like.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one of ordinary skill in the art of preparing such pharmaceutical formulations, and as such, a variety of dosages and treatment regimens may be desirable.

In certain circumstances it will be desirable to deliver the pharmaceutical compositions disclosed herein parenterally, intravenously, intramuscularly, or even intraperitoneally as described (see e.g., U.S. Pat. No. 5,543,158; U.S. Pat. No. 5,641,515 and U.S. Pat. No. 5,399,363, each of which is specifically incorporated herein in its entirety by express reference thereto). Solutions of the active compounds as freebase or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (see e.g., U.S. Pat. No. 5,466,468, specifically incorporated herein in its entirety by express reference thereto). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 mL of hypodermoclysis fluid or injected at the proposed site of infusion, (see, e.g., *Remington's Pharmaceutical Sciences* 15th Ed., pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by the United States Food and Drug Administration's (FDA) Office of Biologics Standards.

Sterile injectable solutions are prepared by incorporating the active compounds in the required amount in the appropriate solvent with various other ingredients as enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

Sequence Comparison, Identity, and Homology

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm can then be used to calculate the percent sequence identity for the test sequence(s) relative to the reference sequence, based on the designated program parameters.

Optimal alignment of sequences for comparison can be conducted, e.g., by the local homology algorithm (see e.g., Smith and Waterman, 1981), by the homology alignment algorithm (see e.g., Needleman and Wunsch, 1970), by the search similarity comparison method (see e.g., Pearson and Lipman, 1988), by computerized implementations of algorithms such as GAP, BESTFIT, FASTA, and TFASTA in the Wisconsin Genetics Software Package, Genetics Computer Group, Madison, Wis., USA, or by visual inspection. One example of an algorithm that is suitable for determining percent sequence identity and sequence similarity is the BLAST algorithm (Altschul et al., 1990) and BLOSUM62 scoring matrix (see, e.g., Henikoff and Henikoff, 1989). Software for performing BLAST analyses is publicly available through the website of the National Center for Biotechnology Information.

In addition to calculating percent sequence identity, the BLAST algorithm also performs a statistical analysis of the similarity between two sequences (see, e.g., Karlin and Altschul, 1993). Another example of a useful sequence alignment algorithm is the PILEUP program, which creates a multiple sequence alignment from a group of related sequences using progressive, pairwise alignments. It can also plot a tree showing the clustering relationships used to create the alignment. PILEUP uses a simplification of the progressive alignment comparison method (see e.g., Feng and Doolittle, 1987), and employs a general alignment matrix similar to that described by Higgins and Sharp (1989).

Therapeutic and Diagnostic Kits

The invention also encompasses one or more compositions together with one or more pharmaceutically-acceptable excipients, carriers, diluents, adjuvants, and/or other components, as may be employed in the formulation of particular rAAV-guanylate cyclase formulations, and in the preparation of therapeutic agents for administration to a mammal, and in particularly, to a human, for one or more of the guanylate cyclase-deficient conditions, such as a retinal dystrophy like LCA1, as described herein. In particular, such kits may comprise one or more rAAV-vectored guanylate cyclase composition in combination with instructions for using the viral vector in the treatment of such disorders in a mammal, and may typically further include containers prepared for convenient commercial packaging.

As such, preferred animals for administration of the pharmaceutical compositions disclosed herein include mammals, and particularly humans. Other preferred animals include non-human primates, murines, epines, bovines, ovines, equines, hircines, lupines, leporines, vulpines, porcines, canines, felines, and the like. The composition may include partially or significantly purified rAAV-guanylate cyclase compositions, either alone, or in combination with one or more additional active ingredients, which may be obtained from natural or recombinant sources, or which may be obtainable naturally or either chemically synthesized, or alternatively produced in vitro from recombinant host cells expressing DNA segments encoding such additional active ingredients.

Therapeutic kits may also be prepared that comprise at least one of the compositions disclosed herein and instructions for using the composition as a therapeutic agent. The container means for such kits may typically comprise at least one vial, test tube, flask, bottle, syringe or other container means, into which the disclosed rAAV composition(s) may be placed, and preferably suitably aliquotted. Where a second guanylate cyclase composition is also provided, the kit may also contain a second distinct container means into which this second composition may be placed. Alternatively, the plurality of guanylate cyclase compositions may be prepared in a single pharmaceutical composition, and may be packaged in a single container means, such as a vial, flask, syringe, bottle, or other suitable single container means. The kits of the present invention will also typically include a means for containing the vial(s) in close confinement for commercial sale, such as, e.g., injection or blow-molded plastic containers into which the desired vial(s) are retained.

Expression in Animal Cells

The inventors contemplate that a polynucleotide comprising a contiguous nucleic acid sequence that encodes a therapeutic guanylate cyclase polypeptide of the present invention may be utilized to treat one or more cellular defects in a transformed host cell. Such cells are preferably animal cells, including mammalian cells such as those obtained from a human or a non-human primate, or from one or more mammalian species including without limitation, murines, canines, bovines, equines, epines, felines, ovines, hircines, lupines, leporines, porcines, and the like. The use of such constructs for the treatment and/or amelioration of one or more symptoms of a retinal dystrophy such as LCA1, or of a related retinal or ocular disease, disorder, condition, or dysfunction in a human subject suspected of suffering from such a disorder, or at risk for developing such a condition is particularly contemplated by the present inventors.

The cells may be transformed with one or more rAAV vectors comprising one or more therapeutic guanylate cyclase genes of interest, such that the genetic construct introduced into and expressed in the host cells of the animal is sufficient to alter, reduce, ameliorate or prevent the deleterious or disease condition(s) or one or more symptoms thereof, either ex vivo, in vitro, ex situ, in situ, and/or in vivo.

Guanylate Cyclase

Guanylate cyclase (GC) (EC 4.6.1.2) is a lyase that catalyzes the conversion of guanosine triphosphates (GTP) to 3',5'-cyclic guanosine monophosphate (cGMP) and pyrophosphate. Referred to alternatively in the literature as "guanyl cyclase" or "guanylyl cyclase," both membrane-bound (type 1) and soluble (type 2) forms of GC exist.

Leber Congenital Amaurosis

Leber congenital amaurosis (LCA) is an autosomal recessive group of diseases that represent the earliest and most severe form of all inherited retinal dystrophies. The first gene implicated in the onset of this genetically and clinically heterogeneous disease, and therefore assigned to the LCA1 locus was retinal-specific Guanylate cyclase-1 (Gucy2d) (Perrault et al., 1996). Gucy2d encodes for the retinal specific protein guanylate cyclase (retGC1) which is expressed predominantly in photoreceptor outer segment membranes and plays a role in the regulation of cGMP and Ca2+ levels within these cells. Following light stimulation, levels of cGMP within photoreceptor outer segments rapidly fall due to hydrolysis by cGMP phosphodiesterase (PDE). This reduction of cGMP leads to a closure of cGMP-gated channels, reduced Ca2+ influx, and hyperpolarization of the cell. This decrease in intracellular Ca2+ stimulates recovery of light-stimulated photoreceptors to the dark state via its interaction with guanylate cyclase activating proteins (GCAPs), a family of calcium binding proteins that regulate the activity of GC. In the dark adapted photoreceptor, Ca2+-bound GCAPs inhibit the activity of GC. Upon light stimulation, however, Ca2+-free GCAPs stimulate GC activity which produces an increase in cGMP levels, a reopening of the cGMP-gated channels and a return of the cell to a depolarized state. Mutations which reduce or abolish the ability of GC to replenish intracellular cGMP and reopen cGMP-gated cation channels, as is the case in LCA1, are thought to create the biochemical equivalent of chronic light exposure in rod and cone photoreceptors.

Mutations in Gucy2d account for ~15% of all cases of LCA making it one of the leading causes of this disease. The number of patients affected by LCA1 is approximately double that affected by the well known RPE65 version of the disease (LCA2), a form for which successful AAV-mediated gene therapy trials have recently garnered worldwide attention. Diagnosis of LCA1 is typically made within the first few months of life in an infant with total blindness or severely impaired vision, extinguished electroretinogram (ERG) and pendular nystagmus (Perrault et al., 1999; Chung and Traboulsi, 2009). Despite these functional deficits, LCA1 patients present with normal fundus (Perrault et al., 1999) and retain some rod and cone photoreceptors in both their macular and peripheral retina for years (Milam et al., 2003; Simonelli et al., 2007; Pasadhika et al., 2009). Using spectral-domain optical coherence tomography (SDOCT) to scan the central macular and perifoveal areas, a recent study revealed that LCA1 patients (age range, 20-53 years) retained all 6 retinal layers with visible photoreceptor inner/outer segment juncture. Maintenance of retinal structure in LCA1 is unlike other forms of the disease which exhibit marked retinal thinning that generally worsens with age (Pasadhika et al., 2009). While the preservation of retinal structure does not parallel better visual acuity in LCA1 patients, it does suggest that they are better suited for future therapeutic strategies.

Animal Models

Two animal models carrying null mutations in the retGC1 gene have been used to evaluate gene replacement therapy, the naturally occurring GUCY1*B chicken and the guanylate-cyclase-1 (GC1) knockout mouse (see e.g., Williams et al., 2006; Haire et al., 2006). The GUCY1*B chicken is blind at hatch, exhibits extinguished scotopic (rod-mediated) and photopic (cone-mediated) ERG and retinal degeneration (see e.g., Ulshafer et al., 1984; Huang et al., 1998; Semple-Rowland et al., 1998). Lentiviral-mediated transfer of Gucy2d to the GUCY1*B retina restored vision to these animals as evidenced by behavioral testing and ERG (see e.g., Williams et al., 2006). Despite the short term therapeutic success, this therapy fell short of preserving retinal structure or function in the long term. The transient nature of this result, obtained in a non-mammalian species with an integrating viral vector delivered in ovo suggested the need for more appropriate translational studies towards the development of clinical application.

A mammalian model of LCA1, the GC1KO mouse, exhibits cone photoreceptor degeneration (see e.g., Yang et al., 1999; Coleman et al., 2004). Like LCA1 patients, loss of cone function in this mouse model precedes cone degeneration (Yang et al., 1999). In addition, light-induced translocation of cone arrestin is disrupted. Rod photoreceptors in this model do not degenerate and continue to generate electrical responses to light (Yang et al., 1999), a result likely owed to the presence of GC2, a close relative of GC1 in these cells (see e.g., Lowe et al., 1995; Yang et al., 1995; Yang and Garbers, 1997; Karan et al., 2010). AAV-mediated transfer of Gucy2d to the post-natal GC1KO retina restored light-driven translocation of cone arrestin in transduced cells, but failed to restore cone ERG responses or prevent cone degeneration (Haire et al., 2006). In both the chicken and mouse studies, which were conducted by the same investigators, the therapeutic cDNA was of bovine origin which is the protein species historically used in biochemical assays evaluating GC1 functionality (Otto-Bruc et al., 1997; Williams et al., 2006).

Exemplary Definitions

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

In accordance with long standing patent law convention, the words "a" and "an" when used in this application, including the claims, denotes "one or more."

As used herein, the term "about" should generally be understood to refer to both numbers in a range of numerals. For example, "about 1 to 10" should be understood as "about 1 to about 10." Moreover, all numerical ranges herein should be understood to include each whole integer within the range, as well as each tenth. The term "about," as used herein, should generally be understood to mean "approximately", and typically refers to numbers approximately equal to a given number recited within a range of numerals. Moreover, all numerical ranges herein should be understood to include each whole integer within the range.

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

As used herein, the term "nucleic acid" includes one or more types of polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

Similarly, the term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

In the context of the invention the term "expression" is intended to include the combination of intracellular processes, including transcription and translation undergone by a polynucleotide such as a structural gene to synthesize the encoded peptide or polypeptide.

The term "e.g.," as used herein, is used merely by way of example, without limitation intended, and should not be construed as referring only those items explicitly enumerated in the specification.

As used herein, the term "promoter" is intended to generally describe the region or regions of a nucleic acid sequence that regulates transcription.

As used herein, the term "regulatory element" is intended to generally describe the region or regions of a nucleic acid sequence that regulates transcription. Exemplary regulatory elements include, but are not limited to, enhancers, post-transcriptional elements, transcriptional control sequences, and such like.

As used herein, the term "structural gene" is intended to generally describe a polynucleotide, such as a gene, that is expressed to produce an encoded peptide, polypeptide, protein, ribozyme, catalytic RNA molecule, or antisense molecule.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the term "transformed cell" is intended to mean a host cell whose nucleic acid complement has been altered by the introduction of one or more exogenous polynucleotides into that cell.

As used herein, the term "transgenic cell" is generally intended to mean any cell that is derived or regenerated from a transformed cell or derived from another transgenic cell, or from the progeny or offspring of any generation of such a transformed or transgenic host cell.

As used herein, the term "vector" is generally intended to mean a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The terms "substantially corresponds to," "substantially homologous," or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, about 77, about 78, about 79, about 80, about 81, about 82, about 83, about 84 or even about 85 percent sequence identity, and more preferably at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, or at least about 95% percent or greater sequence identity. More preferably still, highly homologous sequences often share greater than at least about 96% sequence identity, at least about 97% sequence identity, at least about 98% sequence identity, or at least about 99% sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome.

However, in the case of sequence homology of two or more polynucleotide sequences, the reference sequence and the target sequence will typically comprise at least about 18 to about 25 contiguous identical nucleotides, more typically at least about 26 to about 35 contiguous nucleotides that are identical, and even more typically at least about 40, about 50, about 60, about 70, about 80, about 90, or even about 100 or so contiguous nucleotides that are identical. Desirably, which highly homologous fragments are desired, the extent of overall percent sequence identity between two given sequences will be at least about 80% identical preferably at least about 85% identical, and more preferably about 90% identical, about 91% identical, about 92% identical, about 93% identical, about 94% identical, or even about 95% or greater identical, as readily determined by one or more of the sequence comparison algorithms well-known to those of skill in the art, such as, e.g., the FASTA program analysis described by Pearson and Lipman (1988).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The phrase "substantially identical," in the context of two nucleic acids refers to two or more sequences or subsequences that have at least about 90%, preferably 91%, most preferably about 92%, about 93%, about 94%, about 95%, about 96%, about 97%, about 98%, about 98.5%, about 99%, about 99.1%, about 99.2%, about 99.3%, about 99.4%, about 99.5%, about 99.6%, about 99.7%, about 99.8%, or about 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of about 2 to about 20 amino acid residues in length, oligopeptides of about 10 to about 100 amino acid residues in length, and polypeptides of about 100 to about 5,000 or more amino acid residues in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "substantially homologous" encompasses two or more biomolecular sequences that are significantly similar to each other at the primary nucleotide sequence level. For example, in the context of two or more nucleic acid sequences, "substantially homologous" can refer to at least about 75%, preferably at least about 80%, and more preferably at least about 85%, or at least about 90% identity, and even more preferably at least about 95%, more preferably at least about 97% identical, more preferably at least about 98% identical, more preferably at least about 99% identical, and even more preferably still, entirely identical (i.e., 100% or "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" can refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, entirely identical (i.e., 100% identical or "non-degenerate").

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will be greater than about 80 percent complementary (or "% exact-match") to a corresponding nucleic acid target sequence to which the nucleic acid specifically binds, and will, more preferably be greater than about 85 percent complementary to the corresponding target sequence to which the nucleic acid specifically binds. In certain aspects, as described above, it will be desirable to have even more substantially complementary nucleic acid sequences for use in the practice of the invention, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

As used herein, the terms "protein," "polypeptide," and "peptide" are used interchangeably, and include molecules that include at least one amide bond linking two or more amino acid residues together. Although used interchangeably, in general, a peptide is a relatively short (e.g., from 2 to about 100 amino acid residues in length) molecule, while a protein or a polypeptide is a relatively longer polymer (e.g., 100 or more residues in length). However, unless specifically defined by a chain length, the terms peptide, polypeptide, and protein are used interchangeably.

As used herein, the term "patient" (also interchangeably referred to as "host" or "subject") refers to any host that can serve as a recipient for one or more of the rAAV-based guanylate cyclase compositions as discussed herein. In certain aspects, the recipient will be a vertebrate animal, which is intended to denote any animal species (and preferably, a mammalian species such as a human being). In certain embodiments, a "patient" refers to any animal host, including but not limited to, human and non-human primates, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals, exotics or zoological specimens, as well as companion animals, pets, and any animal under the care of a veterinary practitioner.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal or acceptable for a diagnostic purpose, as applicable. The use of one or more delivery vehicles for gene therapy constructs, viral particles, vectors, and the like, is well known to those of ordinary skill in the pharmaceutical and molecular arts. Except insofar as any conventional media or agent is incompatible with the active ingredient, its use in the prophylactic, and/or therapeutic compositions is contemplated. One or more supplementary active ingredient(s) may also be incorporated into, or administered in association with, one or more of the disclosed compositions.

As used herein, "an effective amount" would be understood by those of ordinary skill in the art to provide a therapeutic, prophylactic, or otherwise beneficial effect to a recipient patient.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardts' solution, 5×SSC, 25 mM sodium phosphate, 0.1% SDS and 100 µg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardts' solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to by 40, from the second by of the sequence to by 41, from the third by to by 42, and so forth, while for 50-mers, such probes or primers may correspond to a nucleotide sequence extending from by 1 to by 50, from by 2 to by 51, from by 3 to by 52, from by 4 to by 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—AAV-Mediated Gene Therapy Restores Visual Function and Behavior to a Mouse Model of LCA1

In this example, the inventors evaluated whether delivery of a species-specific version of retGC1 (i.e., murine) to cone cells of the postnatal GC1KO mouse could restore function to these cells. Serotype 5 AAV vectors were used to deliver mGC1 to photoreceptors of postnatal day 14 (P14) GC1KO mice. Electroretinogram (ERG) and behavioral testing were used to assess visual function and immunocytochemistry was used to examine therapeutic transgene expression, cone arrestin localization and cone photoreceptor densities in treated and untreated eyes.

This example demonstrates that an AAV vector subretinally delivered to one eye of P14 GC1 KO mice facilitated expression of wild type retGC1, restoration of visual function and behavior, and preservation of cone photoreceptors. Four weeks following injection, visual function (ERG) was analyzed in treated and untreated eyes. ERG was performed every two weeks thereafter until 3 months post injection (the latest time point evaluated). Mice with positive ERG responses as well as isogenic wild type and un-injected control mice were evaluated for restoration of visual behavior using optokinetic reflex testing. At 3 months post injection, all animals were sacrificed and their treated and untreated retinas were evaluated for expression of GC1 and localization of cone arrestin.

The results also confirm that cone-mediated function was restored to treated eyes of GC1KO mice (ERG amplitudes were ~60% of normal). Moreover, the treatment effect was stable for at least 3 months post-administration. Behavior testing revealed robust improvements in cone-mediated visual behavior, with responses of treated mice being similar or identical to that of wild type mice. Histology revealed AAV-mediated GC1 expression in photoreceptors and a restoration of cone arrestin translocation in treated mice. In addition, cone cell densities were higher in treated eyes than untreated contralateral controls. This result suggests that treatment is capable of preserving cone photoreceptors for at least three months post treatment. This is the first demonstration that postnatal gene therapy is capable of restoring visual function and behavior to, and preserving retinal structure in, a mammalian model of LCA1. Importantly, results were obtained using a well characterized, clinically relevant AAV vector; the in vivo animal model data thus obtained provide the foundation for an AAV-based gene therapy vector for treatment of children affected with LCA1.

Materials and Methods:

Experimental Animals:

GC1 +/− heterozygote embryos were removed from a cryopreserved stock at The Jackson Laboratory (Bar Harbor, Me., USA). Heterozygotes were mated at the inventors' facilities to produce GC1KO (−/−) and isogenic +/+ control offspring. All mice were bred and maintained in a centralized facility at the inventors' institution under a 12 hr/12 hr light/dark cycle. Food and water were available ad libitum. All animal studies were approved by the local Institutional Animal Care and Use Committee and conducted in accordance with the ARVO Statement for the Use of Animals in Ophthalmic and Vision Research and NIH regulations.

Figure 11A:
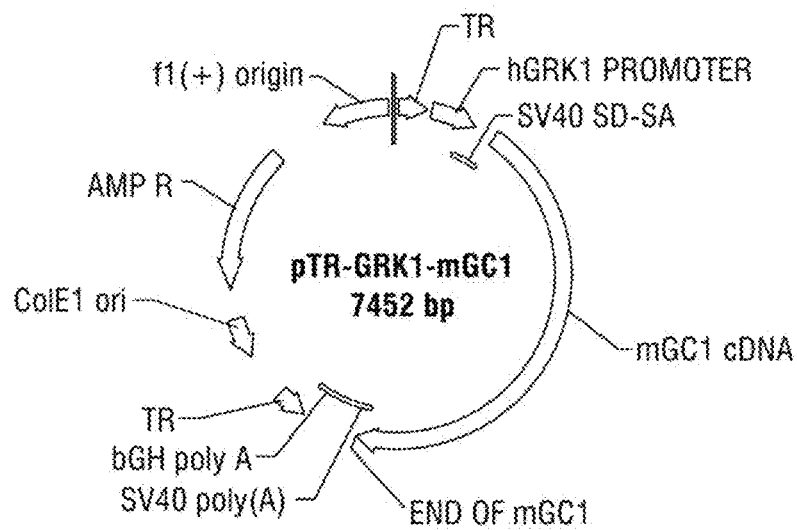
FIG. 11 shows maps of the two illustrative vectors. One contains the ubiquitous promoter smCBA, while the other utilizes the photoreceptor-specific promoter, hGRK1.
Figure 11B:
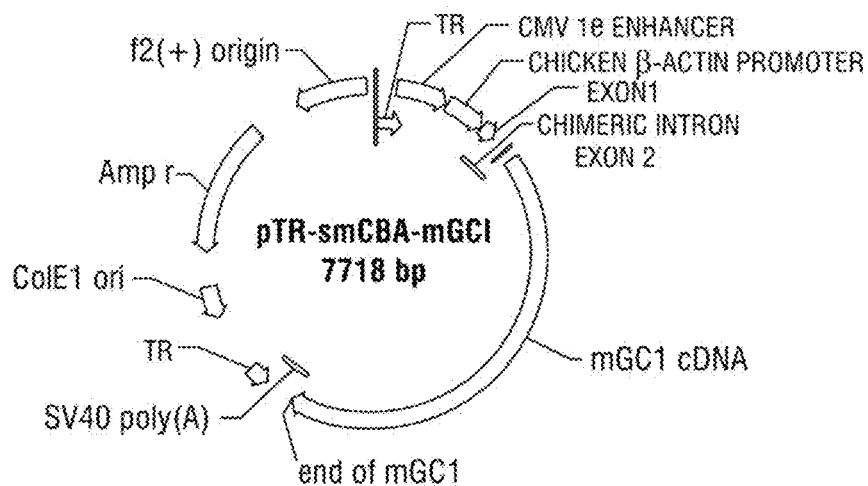
Figure 12:
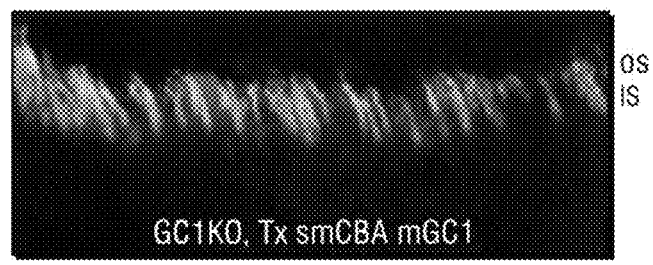
FIG. 12 shows representative retinal section from a GC1KO eye injected with AAV5-smCBA-mGC1 stained for GC1 (red) and PNA lectin (green) reveals GC1 expression in cone outer segments (yellow overlay) as well as in rod outer segments (red alone). hGRK1-mGC1 injected eyes revealed the same pattern.
Figure 13C:
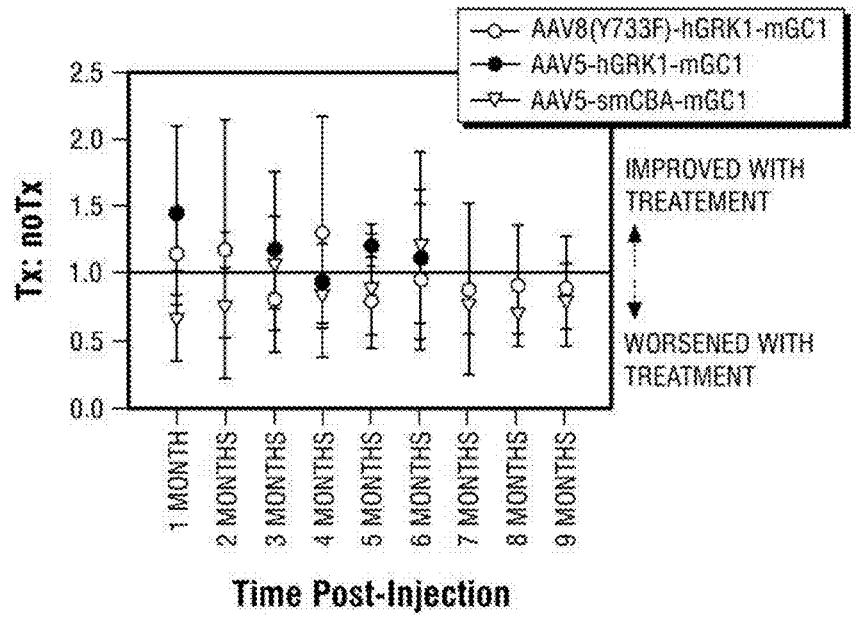
Figure 14:
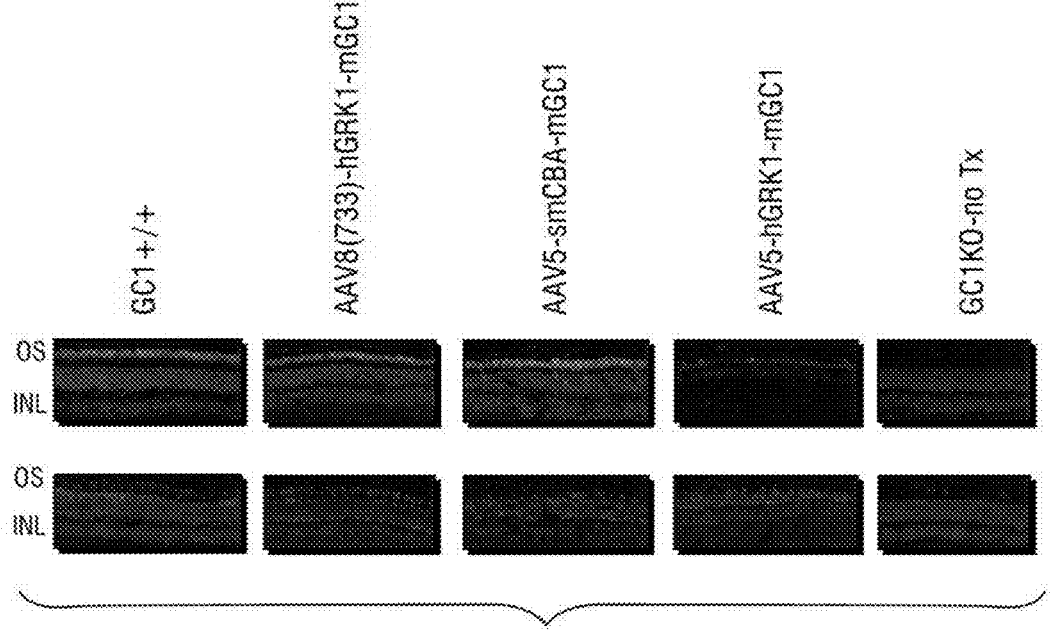
FIG. 14 shows GC1KO mice treated with AAV8(Y733F)-hGRK1-mGC1 were sacrificed at 7 months post injection. AAV5-smCBA-mGC1 and AAV5-hGRK1-mGC1-treated mice were sacrificed at 9 months post-injection. These eyes as well as that of an ~11 month old GC1+/+ mice were sectioned and retinas stained with antibodies raised against GC1 (green, top row) and cone arrestin (red, bottom row). All three therapeutic vectors drove GC1 expression exclusively in photoreceptors of GC1KO mice. Some retinal thinning was observed in AAV5-hGRK1-mGC1 treated mice, a result likely due to the high titer of this vector. GC1 expression and cone density/morphology in AAV8(Y733F)- and AAV5-smCBA-treated mice resembled that seen in age-matched GC1+/+ controls. On the contrary, retinas of an age-matched GC1KO mouse revealed an absence of GC1 expression and a marked reduction in cone cell density.
Figure 15:
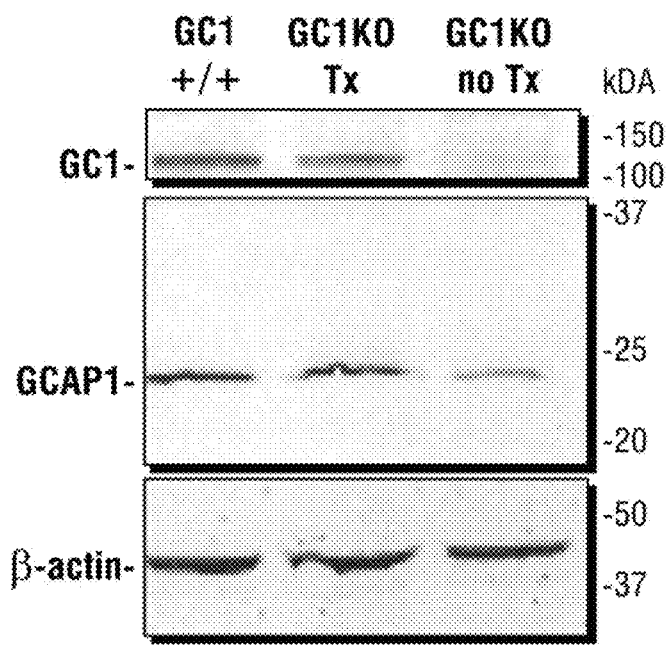
FIG. 15 shows at 7.5 months post-injection with AAV8(Y733F)-hGRK1-mGC1, one GC1KO mouse was sacrificed and its retinas used for western blot. Antibodies directed against GC1 show that the level of AAV-mediated GC1 expression in the treated GC1KO eye are similar to that seen in the age-matched, isogenic GC1+/+ control eye. Levels of guanylate cyclase activating protein-1 (GCAP1) expression (a biochemical partner of guanylate cyclase) was also evaluated in treated and untreated GC1KO as well as GC1+/+ control eyes. Consistent with previous reports, GCAP1 protein was downregulated in the untreated GC1KO eyes. AAV-mediated GC1 expression results in increased GCAP1 expression, similar to levels seen in the isogenic GC1+/+ control.
Figure 16A:
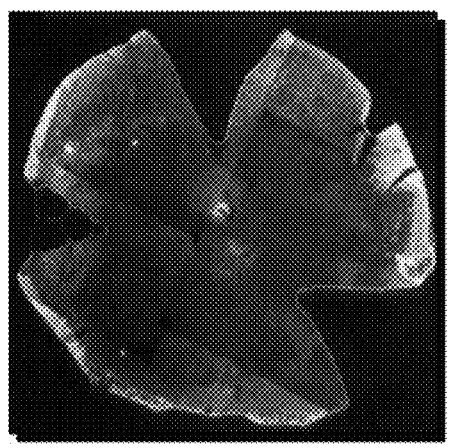
FIG. 16A and FIG. 16B show results at 11 months post injection with AAV5-smCBA-mGC1, one GC1KO mouse was sacrificed, its retinas whole-mounted and stained with an antibody raised against cone arrestin. The immunostain revealed that cones are absent in the untreated GC1KO eye (FIG. 16A) except in the superior retina. AAV-mediated GC1 expression preserves cone photoreceptors throughout the retina of the treated eye (FIG. 16B) for at least 11 months (the latest time point studied)
Figure 16B:
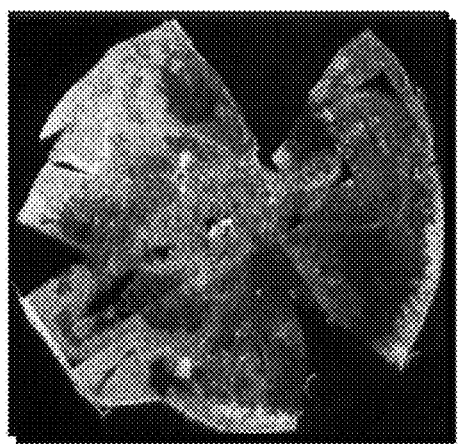

Construction of AAV Vectors:

Serotype 5 Adeno-associated virus (AAV5) vectors were used to deliver murine GC1 (mGC1) as they have been shown to exhibit robust transduction efficiency and a faster onset of expression in retinal photoreceptors than other AAV serotypes (Yang et al., 2002). Both a cell-specific and a ubiquitous promoter were selected to drive expression of mGC1. The cell-specific, G protein-coupled receptor kinase 1 (GRK1), also known as rhodopsin kinase promoter was chosen for its ability to specifically target robust transgene expression in rod and cone photoreceptors when used in conjunction with AAV (Khani et al., 2007). The ubiquitous smCBA promoter which exhibits a similar expression pattern to full-length CBA in retina was chosen for its ability to efficiently target the neural retina (Haire et al., 2006). Polymerase chain reaction utilizing the following forward primer:

(SEQ ID NO: 14)
5'-AAAAGCGGCCGCATGAGCGCTTGGCTCCTGCCAGCC-3' and the following reverse primer:

(SEQ ID NO: 15)
5'-AAAAGCGGCCGCTCACTTCCCAGTAAACTGGCCTGG-3' was used to amplify mGC1 from a plasmid containing a mGC1-eGFP fusion (Bhowmick et al., 2009). The resulting fragment was cloned into pCRblunt plasmid (Invitrogen, Carlsbad, Calif., USA) and sequence verified. AAV vector plasmid containing smCBA driving expression of mGC1 (pTR-smCBA-mGC1) was created by replacing full-length CBA with smCBA in plasmid pTR-CB$^{SB}$-hRPE65 (Jacobson et al., 2006) via EcoRI digestion and subsequent ligation. Subsequently, hRPE65 was replaced with mGC1 via NotI digestion and ligation, resulting in the creation of pTR-smCBA-mGC1 (FIG. 11). An AAV vector plasmid containing human GRK1 promoter driving expression of mGC1, pTR-GRK1-mGC1 was created by removing hGFP from pTR-hGRK1-hGFP (Beltran et al., 2010) and replacing it with mGC1 via NotI digest and ligation (FIG. 11). AAV vectors were packaged according to previously published methods (Haire et al., 2006). Viral particles were resuspended in Balanced Salt Solution (Alcon, Fort Worth, Tex., USA) and titered by quantitative real-time PCR (Jacobson et al., 2006). Resulting titers were $4.69 \times 10^{12}$ viral genomes per mL (vg/mL) and $4.12 \times 10^{13}$ vg/mL for AAV5-smCBA-mGC1 and AAV5-hGRK1-mGC1, respectively.

Subretinal Injections:

One µL of AAV5-GRK1-mGC1 ($4.12 \times 10^{10}$ delivered vector genomes) or AAV5-smCBA-mGC1 ($4.69 \times 10^9$ delivered vector genomes) was delivered subretinally at postnatal day 14 (P14) to the right eye of each GC1KO mouse, leaving the left eye as a contralateral control. Subretinal injections were performed as previously described (Timmers et al., 2001; Pang et al., 2006). Further analysis was carried out only on animals which received comparable, successful injections (>60% retinal detachment and minimal complications). It is well established that the area of retinal detachment corresponds to the area of viral transduction (Cideciyan et al., 2008; Timmers et al., 2001).

Electroretinographic Analysis:

Electroretinograms (ERGs) of treated GC1KO (n=14) and isogenic +/+ controls (n=2) were recorded using a PC-based control and recording unit (Toennies Multiliner Vision; Jaeger/Toennies, Höchberg, Germany) according to methods previously described with minor modifications (Haire et al., 2006). Initial ERG measurements were recorded at 4 weeks' post-injection, and each subsequent 2 weeks thereafter, until 3 months' post-injection (the latest time point evaluated in the study). Age matched +/+ isogenic controls were recorded alongside treated animals at every time point. Mice were dark-adapted overnight (more than 12 hours) and anesthetized with a mixture of 100 mg/kg ketamine, 20 mg/kg xylazine and saline in a 1:1:5 ratio, respectively. Pupils were dilated with 1% tropicamide and 2.5% phenylephrine hydrochloride. A heated circulating water bath was used to maintain the body temperature at 38° C. Hydroxypropyl methylcellulose 2.5% was applied to each eye to prevent corneal dehydration. Full-field ERGs were recorded using custom, gold wire loop corneal electrodes. Reference and ground electrodes were placed subcutaneously between the eyes and in the tail, respectively. Scotopic rod recordings were elicited with a series of white flashes of seven increasing intensities (0.01 mcds/m$^2$ to 5 cds/m$^2$). Interstimulus intervals for low intensity stimuli were 1.1 second. At the three highest intensities (100 mcds/m$^2$, 1 cds/m$^2$ and 5 cds/m$^2$), interstimulus intervals were 2.5, 5.0 and 20.0 seconds, respectively. Ten responses were recorded and averaged at each intensity. Mice were then light adapted to a 100 cds/m$^2$ white background for 2 min. Photopic cone responses were elicited with a series of five increasing light intensities (100 mcds/m$^2$ to 12 cds/m$^2$). Fifty responses were recorded and averaged at each intensity. All stimuli were presented in the presence of the 100 cds/m$^2$ background. B-wave amplitudes were defined as the difference between the a-wave troughs to the positive peaks of each waveform.

Figure 2A:
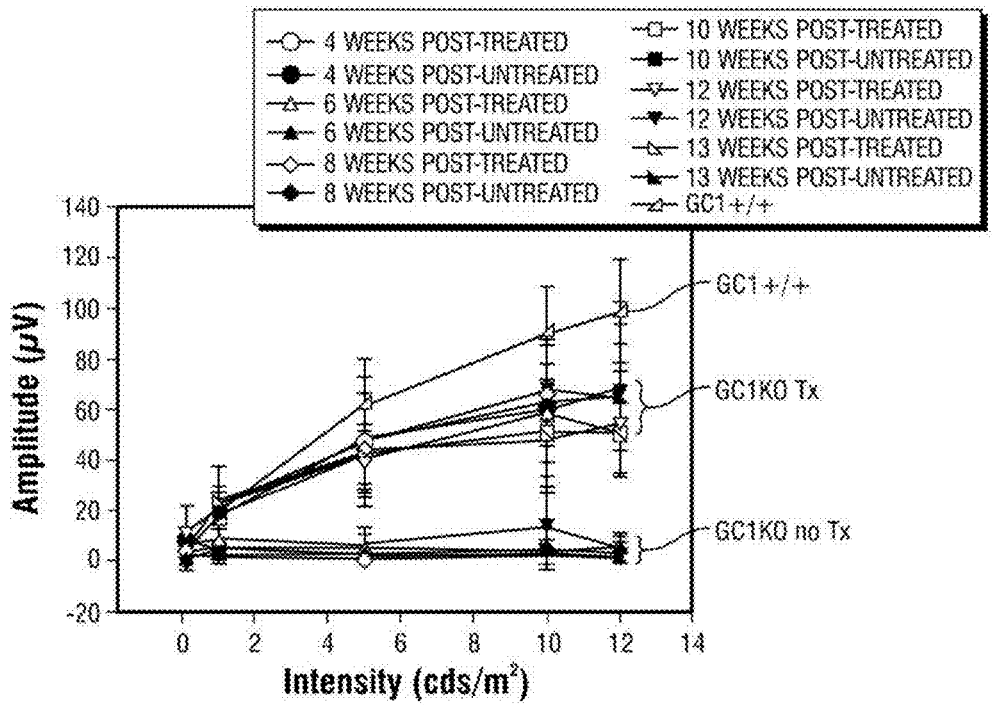
FIG. 2A and FIG. 2B show average photopic b-wave maximum amplitudes in GC1KO, isogenic +/+ controls, smCBA-mGC1-treated (FIG. 2A) and hGRK1-mGC1-treated (FIG. 2B) GC1KO mice over time. Cone responses of both smCBA-mGC1 and hGRK1-mGC1-treated mice are approximately 45% of normal for at least 3 months post injection.
Figure 2B:
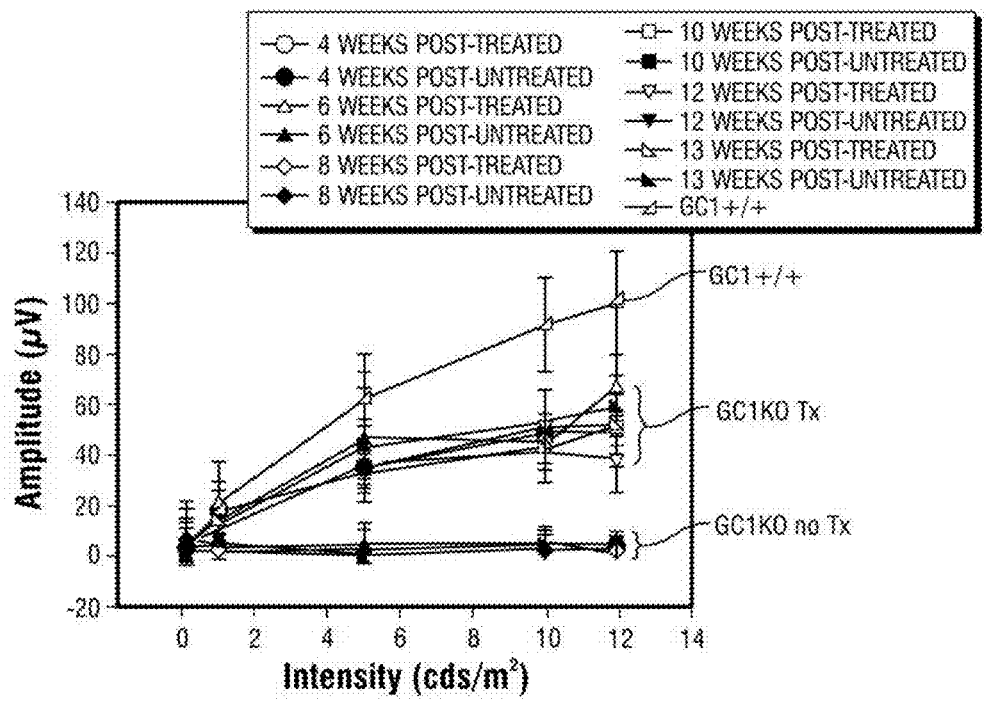

Photopic b-wave maximum amplitudes (those generated at 12 cds/m$^2$) of all smCBA-mGC1-treated (n=6) and hGRK1-mGC1-treated (n=8) GC1KO (both treated and untreated eyes) and isogenic +/+ control mice were averaged and used to generate standard errors. These calculations were made at every time point (4 weeks'-13 weeks' post-injection). This data was imported into Sigma Plot for final graphical presentation. The paired t-test was used to calculate P-values between treated and untreated eyes within each promoter group (smCBA or hGRK1) and between each promoter group over time (4 weeks post-injection vs. 3 months' post-injection). The standard t-test was used to calculate P-values between smCBA-mGC1 vs. hGRK1-mGC1 treated eyes. Significant difference was defined as a P-value<0.05. Because some of the mice from each treated group were temporarily removed from the study for behavioral analyses, the total number of mice averaged and presented at each time point in FIG. 2A and FIG. 2B differs. Three mice from the smCBA-mGC1-treated group were sent for optomotor testing, leaving an "n" of 3 mice used for ERG analysis during the 8, 10 and 12 week measurements (FIG. 2A). Two mice from the hGRK1-mGC1-treated group were sent for optomotor testing, leaving an "n" of 6 used for ERG analysis during the 6, 8, 10 and 12 week measurements (FIG. 2B). All mice sent for behavioral analysis were measured at 13 weeks' post-injection upon their return to the inventors' laboratories (smCBA-mGC1: n=3, hGRK1-mGC1: n=2) following completion of behavioral analyses.

Optomotor Testing:

Photopic visual acuities and contrast sensitivities of treated and untreated GC1KO mouse eyes were measured using a two-alternative forced choice paradigm as described previously (see e.g., Umino et al., 2008; Alexander et al., 2007). To test the sensitivity of individual eyes from the same animal we took advantage of the fact that mouse vision has minimal binocular overlap and that the left eye is more sensitive to clockwise rotation and the right to counterclockwise rotation (Douglas et al., 2005). Thus in the inventors' "randomize-separate" optomotor protocol, each eye's acuity and contrast sensitivity threshold was determined separately and simultaneously via stepwise functions for correct responses in both the clockwise and counterclockwise directions. Correct detection of patterns rotating in the clockwise direction was driven primarily by visual signals originating from the left eye and correct responses in the counterclockwise direction were derived from visual signals originating from the right eye. Acuity was defined the highest spatial frequency (100% contrast) yielding a threshold response, and contrast sensitivity was defined as 100 divided by the lowest percent contrast yielding a threshold response. For photopic acuity, the initial stimulus was a 0.200 cycles/degree sinusoidal pattern with a fixed 100% contrast. For photopic contrast sensitivity measurements, the initial pattern was presented at 100% contrast, with a fixed spatial frequency of 0.128 cycles/degree. Photopic vision was measured at a mean luminance of 70 cd/m². Visual acuities and contrast sensitivities were measured for both eyes of each mouse four to six times over a period of 1 week. Age matched, isogenic +/+ control animals (M1, M2) and naïve GC1KO mice (M3, M4) are presented along with the smCBA-mGC1-treated (M5, M6, M7) and hGRK1-mGC1-treated mice (M8, M9) in FIG. 3. Cone-mediated ERG amplitudes generated from a 12 cds/m² stimulus of all mice (M1-M9) are presented alongside the behavior results. Unpaired t-tests were carried out on acuity and percent contrast values to determine significance of results.

Tissue Preparation:

Three months' post-injection, P14-treated GC1KO mice and age matched isogenic +/+ controls were dark adapted for 2 hr. Immediately following dark adaptation, mice were sacrificed under dim red light (>650 nm). The limbus of injected and un-injected eyes was marked with a hot needle at the 12:00 position, facilitating orientation. Enucleation was performed under dim red light and eyes were placed immediately in 4% paraformaldehyde. Eyes that were to be used for cryosectioning were prepared according to previously described methods (Haire et al., 2006). Briefly, corneas were removed from each eye, leaving the lens inside the remaining eye cup. A small "V" shaped cut was made into the sclera adjacent to the burned limbus to maintain orientation. After overnight fixation, the lens and vitreous were removed. The remaining retina/RPE-containing eyecup was placed in 30% sucrose in PBS for at least 1 hr at 4° C. Eyecups were then placed in cryostat compound (Tissue Tek OCT 4583; Sakura Finetek, Inc., Torrance, Calif., USA) and snap-frozen in a bath of dry ice/ethanol. Eyes were serially sectioned at 10 μm with a cryostat (Microtome HM550; Walldorf, Germany). Eyes that were to be used for whole mount analysis were prepared according to previously described methods (Pang et al., 2010). Orientation was achieved as previously mentioned. After overnight fixation, cornea, lens, vitreous and retinal pigment epithelia were removed from each eye without disturbing the retina. A cut was made in the superior (dorsal) portion of the retina adjacent to the original limbus burn to maintain orientation.

Immunohistochemistry and Microscopy:

Retinal cryosections and whole mounts were washed 3× in 1×PBS. Following these washes, samples were incubated in 0.5% Triton X-100® for 1 hr in the dark at room temperature. Next, samples were blocked in a solution of 1% bovine serum albumin (BSA) in PBS for 1 hr at room temperature. Retinal sections were incubated overnight at 37° C. with a rabbit polyclonal GC1 antibody (1:200, sc-50512, Santa Cruz Biotechnology, Inc., Santa Cruz, Calif., USA) or rabbit polyclonal cone arrestin antibody ("Lumij" 1:1000; provided by Dr. Cheryl Craft, University of Southern California, Los Angeles, Calif., USA) diluted in 0.3% Triton X-100®/1% BSA. Retinal whole mounts were incubated overnight at room temperature with the same cone arrestin antibody, diluted 1:1000 in 0.3% Triton X-100®/1% BSA. Following primary incubation, retinal sections and whole mounts were washed 3× with 1×PBS.

Retinal sections were incubated for 1 hr at room temperature with IgG secondary antibodies tagged with either Alexa-594 or Alexa-488 fluorophore (Molecular Probes, Eugene, Oreg., USA) diluted 1:500 in 1×PBS. Following incubation with secondary antibodies, sections and whole mounts were washed with 1×PBS. Retinal sections were counterstained with 4',6'-diamino-2-phenylindole (DAPI) for 5 min at room temperature. After a final rinse with 1×PBS and water, sections were mounted in an aqueous-based medium (DAKO) and cover-slipped. Retinal whole mounts were oriented on slides with the superior (dorsal) portion of the retina positioned at the 12:00 position. Samples were mounted in DAKO and cover-slipped.

Retinal sections were analyzed with confocal microscopy (Leica TCS SP2 AOBS Spectral Confocal Microscope equipped with LCS Version 2.61, Build 1537 software, (Bannockburn, Ill., USA). All images were taken with identical exposure settings at either 20× or 63× magnification. Excitation wavelengths used for DAP1, GC1 and cone arrestin stains were 405 nm, 488 nm, and 594 nm, respectively. Emission spectra were 440-470 nm, 500-535 nm and 605-660 nm, respectively. Retinal whole mounts were analyzed with a widefield fluorescent microscope (Axioplan 2) (Zeiss, Thornwood, N.Y., USA) equipped with a QImaging Retiga 4000R Camera and QImaging QCapture Pro software (QImaging, Inc., Surrey, BC, Canada). Quadrants of each whole mount were imaged at 5× under identical exposure settings and then merged together in Photoshop® (Version 7.0) (Adobe, San Jose, Calif., USA)

Image Analysis:

Cone photoreceptor densities were analyzed in retinal whole mounts by counting cells labelled with secondary fluorophore directed against cone arrestin antibody in the central and inferior retina using ImageJ® software (National Institutes of Health, Bethesda, Md., USA). These values were obtained by zooming in on the 5×TIFF files shown in FIG. 6. Five squares (500 μm²) were placed over identical areas in central and inferior retina of both treated and untreated GC1KO eyes. For central retina, squares were placed at an equal eccentricity around the optic nerve head in all eyes (125 μm). Cone photoreceptors were counted in each respective retinal area, values were averaged and standard deviations calculated. The standard t-test was used to calculate P-values between desired samples. Significant difference was defined as a P-value<0.05.

Results

Figures 1, 18A:
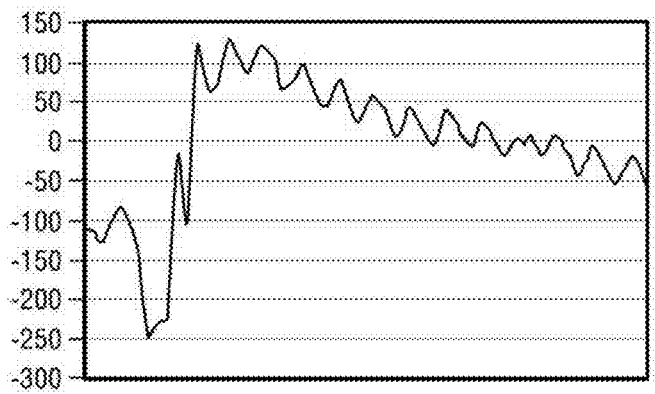
FIG. 18A and FIG. 18B illustrate data in which OCT and rod/cone ERGs from a GCdko mouse TWO months post injection with AAV8(Y733F)-hGRK1-mGC1.
Figures 2, 18A:
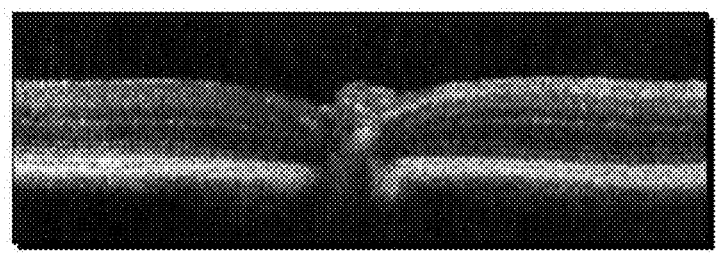
Figures 1, 18B:
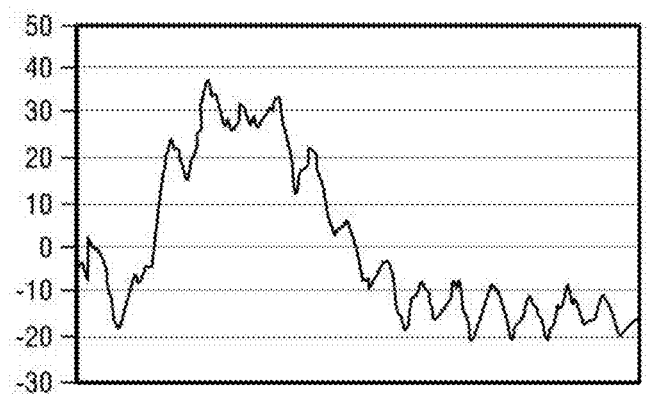
Figures 2, 18B:
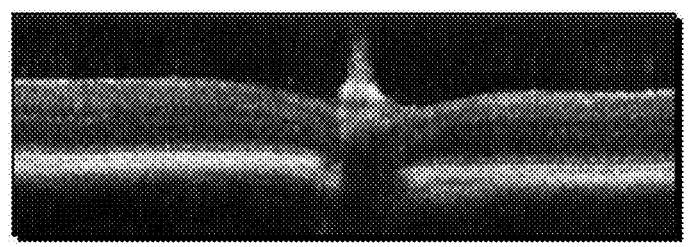
Figure 19A:
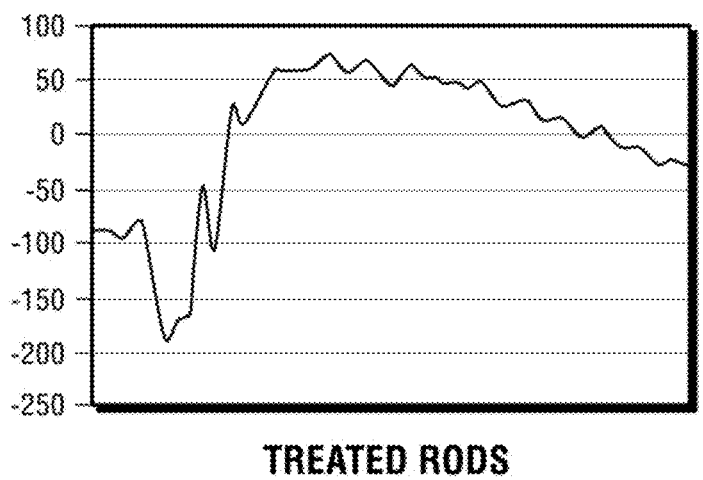
FIG. 19A and FIG. 19B illustrate data in which representative rod and cone ERGs from a GCdko mouse one month post injection with AAV8(Y733F)-hGRK1-mGC1.
Figure 19B:
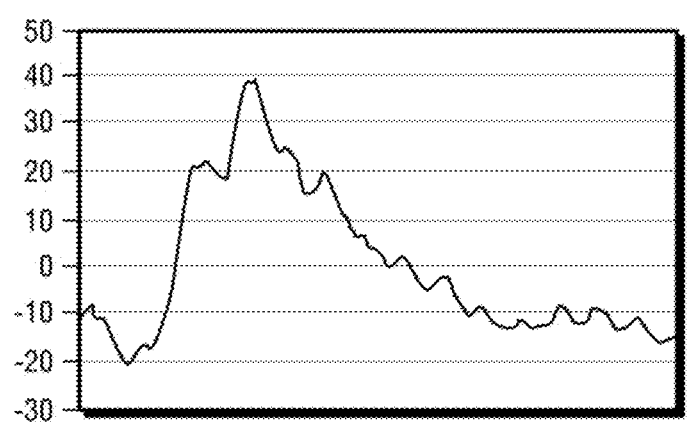

Photoreceptor Function (ERG) was Restored in AAV-Treated GC1KO Mice:

It was previously reported that cone responses in the GC1KO mouse are barely detectable by 1 month of age. Here the inventors have shown that P14-treatment of this mouse with an AAV vector carrying the mouse GC1 gene under the control of either a photoreceptor-specific (hGRK1) or ubiquitous (smCBA) promoter led to substantial restoration of cone photoreceptor function as measured by ERG. Representative cone traces (FIG. 1) (as well as the average photopic b-wave amplitudes (FIG. 2A and FIG. 2B) from hGRK1-mGC1-treated, smCBA-mGC1-treated, GC1KO and isogenic +/+ controls) showed that cone function in treated eyes was restored to approximately 45% of normal at four weeks' post-injection. Similar to previous reports, cone responses in contralateral, untreated eyes were ablated by this time point. At 4 weeks' post-injection, the average cone-mediated b-wave amplitude in smCBA-mGC1-treated eyes (65.1 μV) was significantly higher (P=0.006) than that in the untreated eyes (3.9 μV). The average cone mediated b-wave amplitude in hGRK1-mGC1-treated eyes (59.1 μV) was significantly higher (P<0.001) than that in untreated eyes (3.2 μV). The level of restoration achieved four weeks' post-delivery of the photoreceptor-specific hGRK1-mGC1 vector was not significantly different from that achieved with the ubiquitous promoter-containing smCBA-mGC1 vector (P=0.604). At 3 months' post-injection, the average cone-mediated b-wave amplitude in smCBA-mGC1-treated eyes (53.3 μV) was significantly higher (P<0.001) than that in the untreated eyes (2.8 μV). The average cone mediated b-wave amplitude in hGRK1-mGC1-treated eyes (45.3 μV) was significantly higher (P<0.001) than that in untreated eyes (3.4 μV). The level of restoration achieved 3 months following delivery of the photoreceptor-specific GRK1-mGC1 vector was not significantly different from that achieved with the ubiquitous promoter-containing smCBA-mGC1 vector (P=0.331). Both promoters conferred similar levels of functional restoration to cones in treated eyes of the GC1KO mouse in the short term. Importantly, restoration of cone photoreceptor function remained stable for 3 months (the latest time point evaluated in this study (see FIG. 1, FIG. 2A and FIG. 2B). There was no significant difference in photopic b-wave amplitudes of smCBA-mGC1-treated or hGRK1-mGC1-treated eyes between 4 weeks and 3 months post treatment (P=0.174 and 0.125, respectively).

ERG implicit times which are an important feature in the diagnosis of various retinal disorders including other forms of LCA (Sun et al., 2010) were also determined. While no such measurement can be obtained from a GC1KO eye (there are no ERG responses in these eyes), it was possible to compare cone b-wave implicit times in AAV-mGC1 treated and isogenic +/+ control mice. At 4 weeks post injection, there was no significant difference between cone b-wave implicit times in treated and +/+ control eyes (P=0.884); average values in AAV-mGC1-treated and +/+ eyes at this time point were 50.8 ms and 50.4 ms, respectively. At 3 months post injection, there was also no significant difference between the two groups (P=0.697); averages of all cone b-wave implicit times in treated and +/+ control eyes were 59.7 ms and 58.3 ms, respectively. The response kinetics of cones in the treated GC1KO retina (as determined by implicit time measurements) appeared to be normal and stable in the short term.

It was previously reported that rod ERGs in the GC1KO mouse show alterations by 1 month of age, with the rod a-wave and b-wave both markedly reduced (Yang et al., 1999). This reduction plateaus at 5 months of age with responses approximately 50-70% that of a wild-type (WT) mouse. While some instances of AAV-mGC1-mediated improvements were observed in treated eyes of GC1KO mice relative to untreated controls (example seen in FIG. 1), this result was not as consistent as that seen in the cone-mediated responses.

Figure 3A:
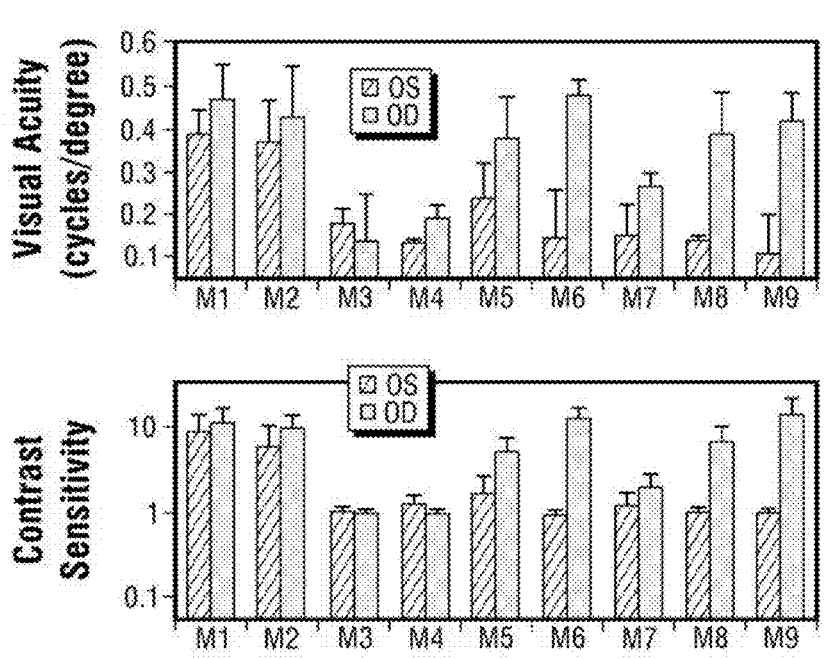
FIG. 3A, FIG. 3B, and FIG. 3C illustrate by optomotor analysis that visually-elicited behavior was restored in GC1KO mice treated with either smCBA-mGC1 or hGRK1-mGC1. M1 to M9 correspond to the nine mice used for testing. Photopic acuities and contrast sensitivities of +/+ control mice (M1, M2), naïve GC1KO (M3, M4), smCBA-mGC1 (M5, M6, M7) and hGRK1-mGC1-treated (M8, M9) mice reveal that treated mice behave like normal-sighted mice (FIG. 3B and FIG. 3C). Averages of all +/+ eyes (n=4), GC1KO eyes (n=9) and AAV-mGC1-treated eyes (n=5) are shown (FIG. 3C). Cone-mediated ERG responses from each mouse (M1-M9) are shown for electrophysiological comparison (FIG. 3A)
Figure 3B:
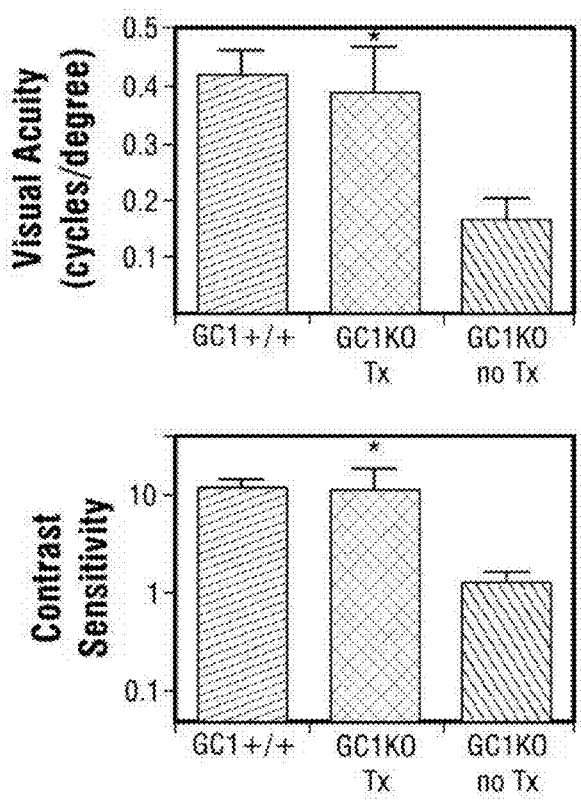
Figure 3C:
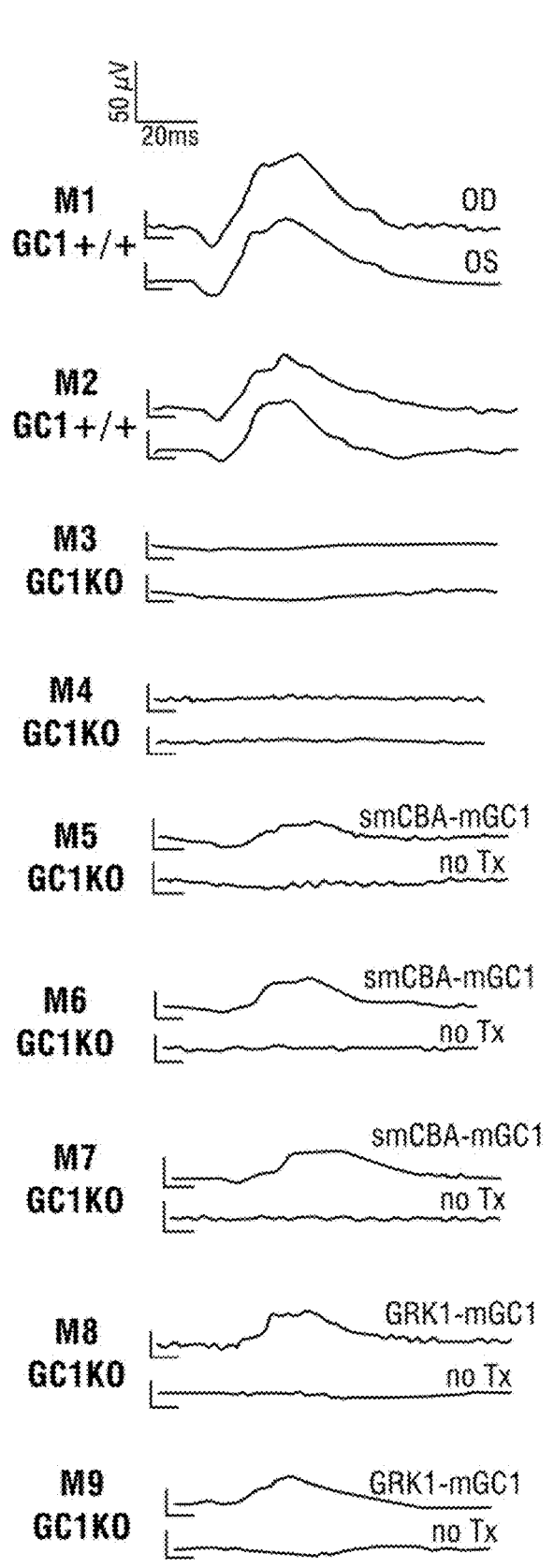

Visual Behavior was Restored in AAV-Treated GC1KO Mice:

Optomotor analysis revealed that eyes of GC1KO mice treated with either smCBA-mGC1 (M5, M6, M7) or hGRK1-mGC1 (M8, M9) responded significantly better than untreated eyes under all photopic, cone-mediated conditions. Untreated GC1KO eyes perform poorly with a visual acuity of 0.163±0.040 cycles per degree (FIG. 3B and FIG. 3C, bar, mean±s.d., n=9 eyes). Isogenic GC1$^{+/+}$ control eyes (M1, M2) respond significantly better, showing an average acuity of 0.418±0.046 cycles per degree (n=4 eyes). AAV-mGC1-treated eyes (M5-M9) have an average acuity of 0.392±0.077 cycles per degree (n=5 eyes), a level essentially identical to control +/+ eyes and significantly better than untreated GC1KO eyes (P<0.0001). Photopic contrast sensitivities (FIG. 3B and FIG. 3C) paralleled the photopic acuity results, with AAV-mGC1-treated eyes (contrast sensitivity of 11.9±7.37, n=5 eyes) showing contrast thresholds nearly identical to +/+ mice (11.94±3.03, n=4 eyes). Again, GC1KO eyes treated at P14 with AAV-mGC1 performed significantly better than untreated eyes, which showed an average contrast sensitivity of 1.27±0.31 (n=9, P<0.0001). In all photopic tests, untreated GC1KO eyes perform extremely poorly, essentially equivalent to no cone-mediated function. Statistical comparisons of these measurements are shown in Table 1. Cone-mediated ERG traces of all GC1$^{+/+}$ (M1, M2), GC1KO (M3, M4), smCBA-mGC1-treated (M5, M5, M7) and hGRK1-mGC1-treated (M8, M9) mice used in behavior analysis are shown in FIG. 3A to relate visual function (optmotor behavior) to retinal function (electrophysiology).

Rod retinal function (ERG) is partially preserved in the GC1KO mouse. Studies have shown that even very small ERG amplitudes translate into robust visual behavior (Williams et al., 2006). In fact, LCA2 patients who received AAV-RPE65 therapy were found to exhibit behavioral restoration despite a complete lack of ERG response (Maguire et al., 2008). Optomotor testing revealed that scotopic, rod-mediated visual acuities and contrast sensitivities of GC1KO eyes are very similar to +/+ controls. For this reason, it was impossible to compare visual restoration of treated vs. untreated eyes on a behavioral level. Statistical comparisons of these measurements are shown in Table 1:

TABLE 1

STATISTICAL COMPARISON OF THE PHOTOPIC VISUAL FUNCTIONS OF WT, AAV-MGC1- TREATED AND UNTREATED GC1KO EYES AS MEASURED BY OPTOMOTOR BEHAVIOR

| Photopic Acuity | Wild Type(WT) | Treated | Untreated |
| --- | --- | --- | --- |
| Number of Values | 4 | 5 | 9 |
| Mean | 0.4183 | 0.3919 | 0.163 |
| Standard Deviation | 0.0456 | 0.07731 | 0.03954 |
|  |  | P-value |  |
| WT vs. Treated |  | 0.5671 | Not significant |
| WT vs. Untreated |  | <0.0001 | * |
| Treated vs. Untreated |  | <0.0001 | * |
| Photopic Contrast Sensitivity | WT | Treated | Untreated |
| Number of Values | 4 | 5 | 9 |
| Mean | 11.94 | 11.16 | 1.27 |
| Standard Deviation | 3.03 | 7.37 | 0.31 |
|  |  | P-value |  |
| WT vs. Treated |  | 0.4186 | Not significant |
| WT vs. Untreated |  | <0.0001 | * |
| Treated vs. Untreated |  | <0.0001 | * |

* = p < 0.0001

Figure 4A:
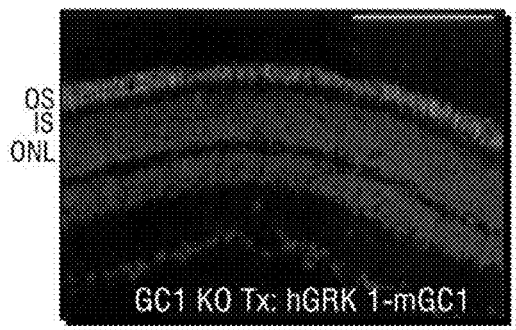
FIG. 4A, FIG. 4B, FIG. 4C, FIG. 4D, FIG. 4E, and FIG. 4F show AAV5-hGRK1-mGC1 drives expression of GC1 in photoreceptor outer segments of GC1KO mice (FIG. 4A). No GC1 expression is seen in untreated contralateral control eye (FIG. 4B). AAV5-smCBA-mGC1 drives expression of GC1 in photoreceptor outer segments (FIG. 4C) and occasionally in photoreceptor cell bodes (white arrows in FIG. 4F). No such GC1 expression is seen in the untreated contralateral control eye (FIG. 4D). Levels of therapeutic transgene expression in AAV5-mGC1-treated eyes are similar to that seen in isogenic +/+ control eyes (FIG. 4E). All retinas were taken from mice 3 months' post treatment or age matched untreated controls. Scale bars in FIG. 4A=100 µm.
Figure 4B:
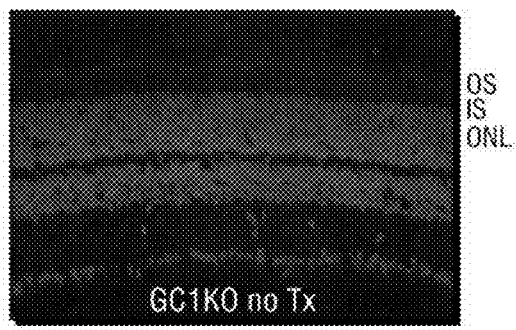
Figure 4C:
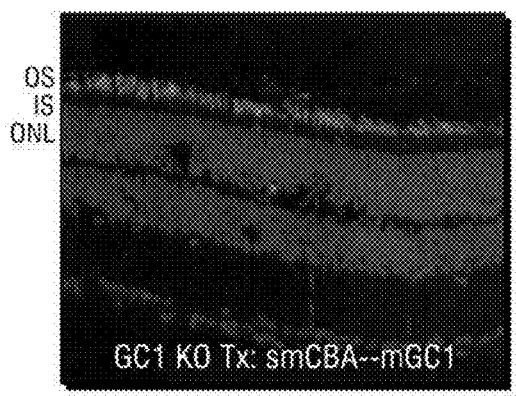
Figure 4D:
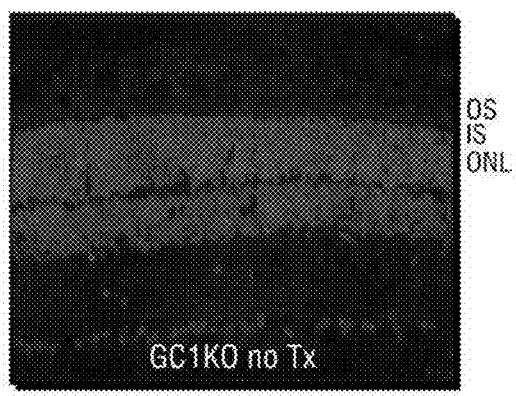
Figure 4E:
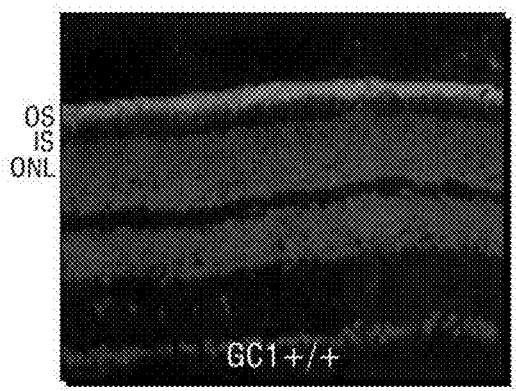
Figure 4F:
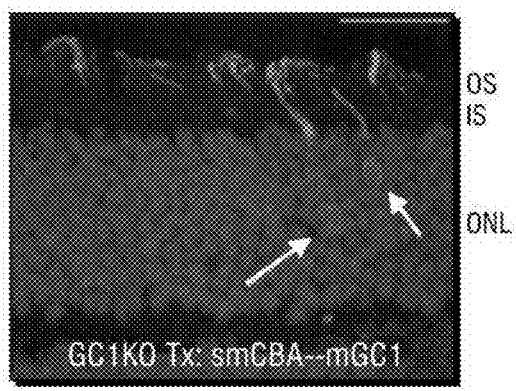

Photoreceptor-Specific and Ubiquitous Promoters Both Drive mGC1 Transgene Expression in Rods and Cones of GC1KO Mice GC1-deficiency affects both rod and cone photoreceptors in LCA1 patients. The photoreceptor-specific human RK promoter and the ubiquitous smCBA promoter were therefore chosen for this study as a means of targeting both cell types. The human RK promoter was chosen for its small size and ability to efficiently drive transgene expression specifically in photoreceptor cells. Immunostaining of GC1KO retinas 3 months' post-treatment with AAV-hGRK1-mGC1 revealed that this promoter drove robust GC1 expression in photoreceptor outer segments. A representative image of a retinal cross section from an eye injected with this therapeutic vector (FIG. 4A) shows intense GC1 staining in the OS layer whereas the contralateral, untreated eye from the same mouse lacks any GC1 expression (FIG. 4B). The smCBA promoter also efficiently drove GC1 expression in photoreceptor cells. Photoreceptor OS exhibited robust smCBA-mediated GC1 expression in treated eyes (FIG. 4C), relative to the contralateral, untreated eye (FIG. 4D). Levels of hGRK1 and smCBA-mediated GC1 expression approached that seen in isogenic, +/+ control eyes (FIG. 4E). GC1 expression in hGRK1-mGC1-treated eyes was restricted to OS. In smCBA-mGC1-treated eyes, GC1 expression was occasionally found in photoreceptor cell bodies of the outer nuclear layer (see e.g., arrows FIG. 4F). Notably however, neither promoter construct drove therapeutic GC1 expression outside the photoreceptor cells. This lack of off-target expression is relevant to the development of future clinical applications.

Figure 5A:
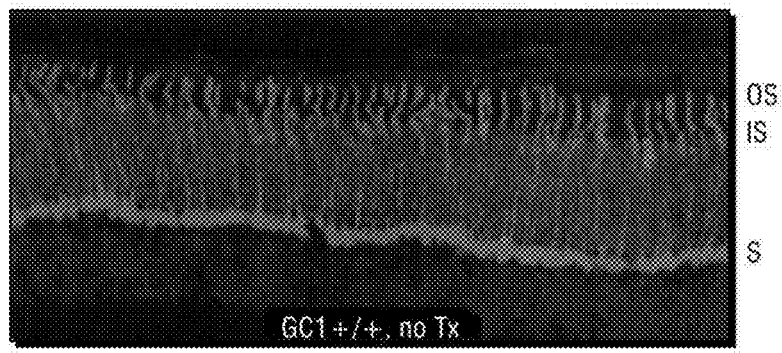
FIG. 5A, FIG. 5B, FIG. 5C, and FIG. 5D show cone arrestin expression in cone photoreceptors of +/+, GC1KO, AAV5-smCBA-mGC1-treated and AAV5-hGRK1-mGC1-treated mice. Untreated GC1KO retinas contain characteristic disorganized, detached cone outer segments (FIG. 5B), whereas cone outer segments were intact and cone arrestin distribution appeared normal in treated GC1KO (FIG. 5C and FIG. 5D) and +/+ (FIG. 5A) retinal sections. All retinas were taken from mice 3 months post treatment or age matched untreated controls. Scale bars in FIG. 5D=100 µm. OS=outer segments, IS=inner segments, S=synaptic terminals.
Figure 5B:
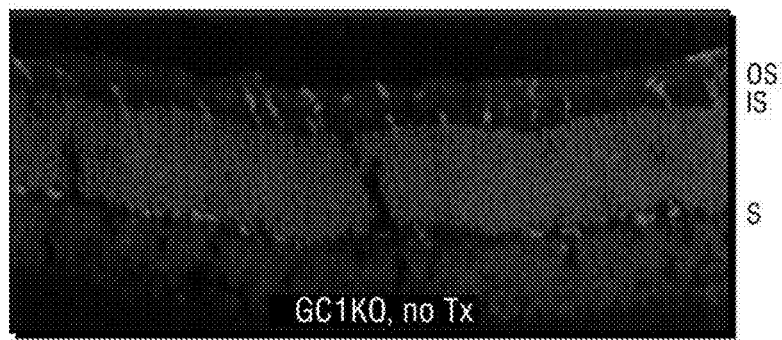
Figure 5C:
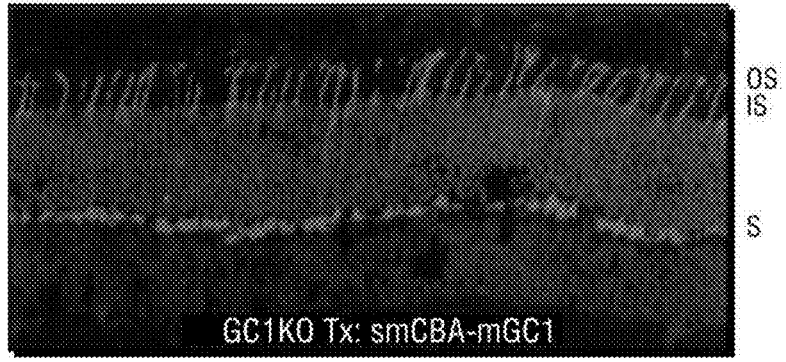
Figure 5D:
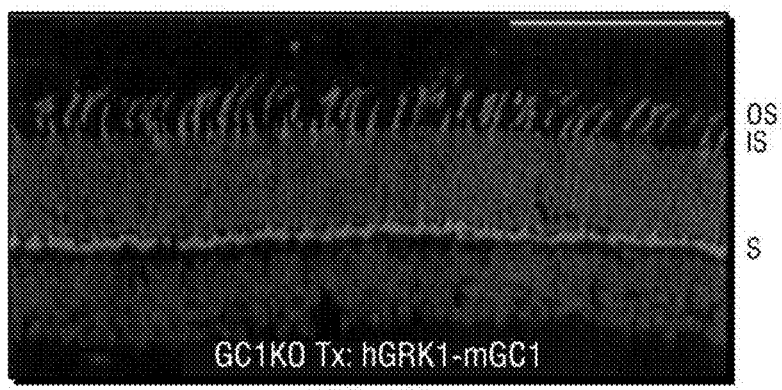
Figure 6A:
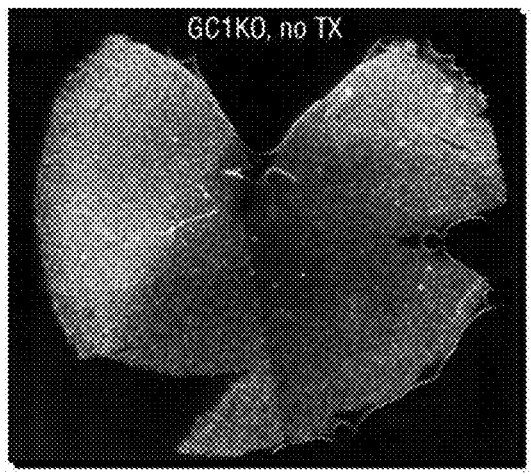
FIG. 6A, FIG. 6B, FIG. 6C and FIG. 6D show that AAV-mGC1 treatment results in preservation of cone photoreceptors in treated eyes for at least three months post treatment. Representative retinal whole mounts from the hGRK1-mGC1 study (FIG. 6A: "no TX"=untreated.
Figure 6B:
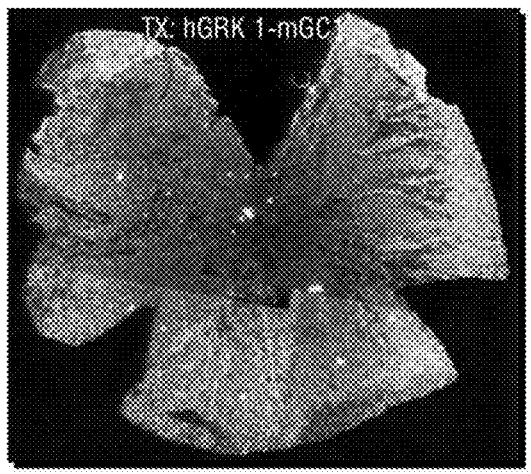
Figure 6C:
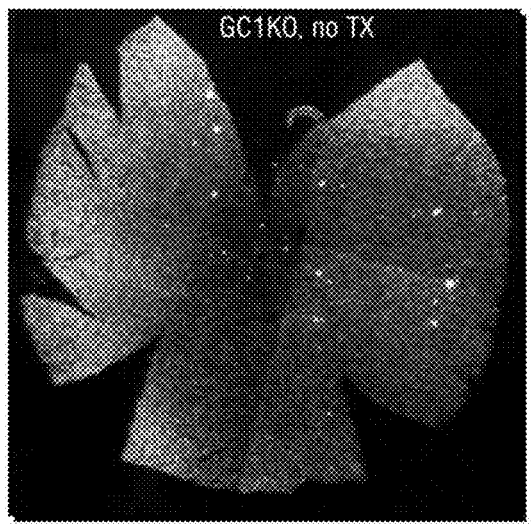
Figure 6D:
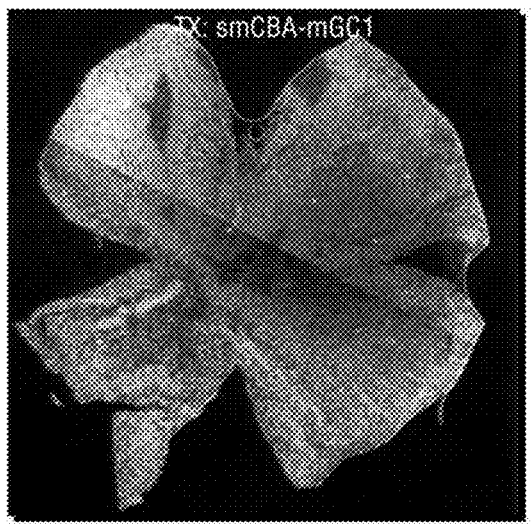
Figure 7:
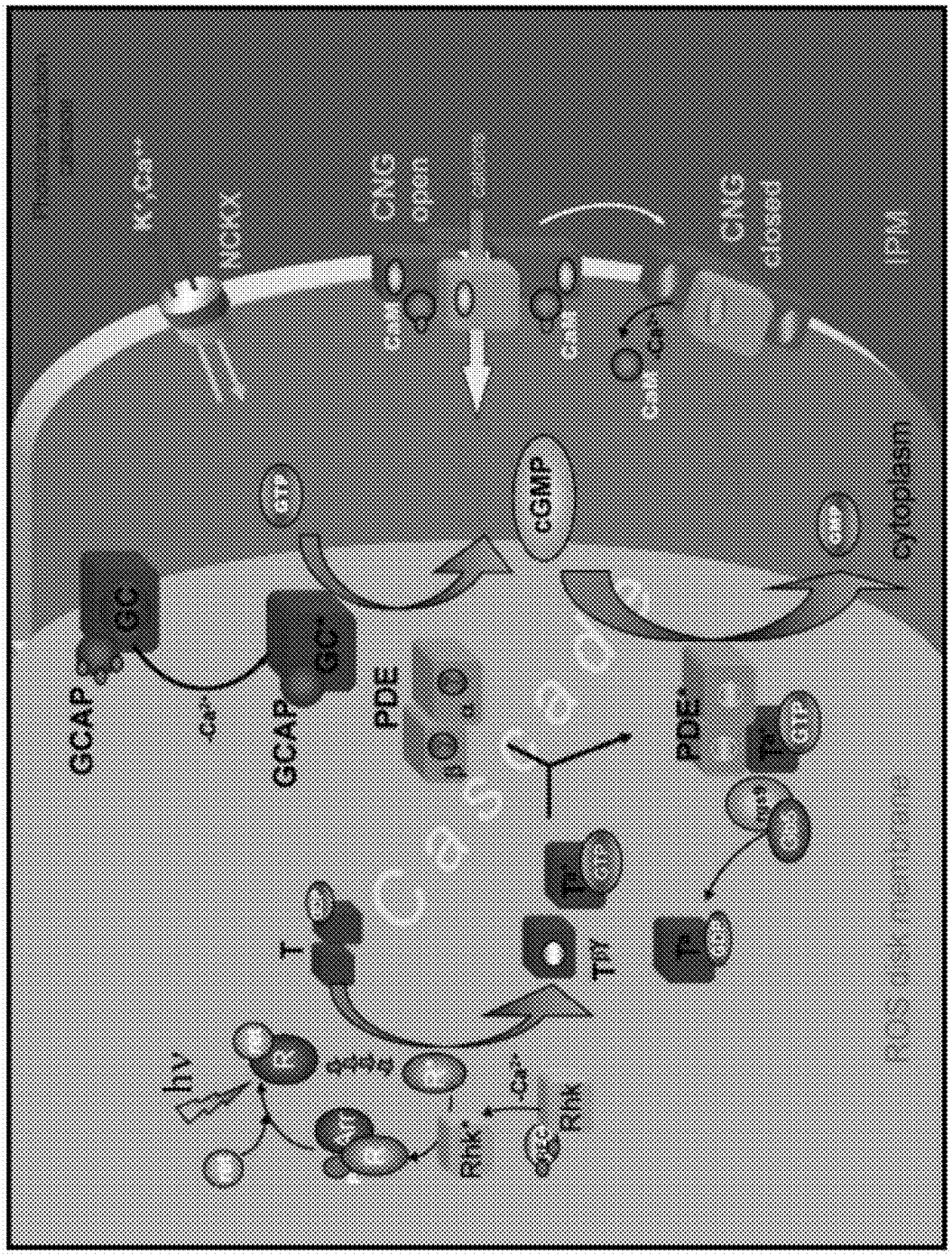
FIG. 7 illustrates the vertebrate phototransduction cascade. Upon light stimulation, conformational changes in rhodopsin (R) stimulate a cascade of events including activation of transducin (T) and cGMP phosphodiesterase (PDE) eventually resulting in the hydrolysis of cGMP. This lowering of intracellular cGMP causes a closure of the cyclic nucleotide-gated channels (CNG) in photoreceptor outer segment membranes. Closure of these channels causes hyperpolarization of the cell and therefore a dramatic drop in intracellular calcium. When calcium levels fall, unbound guanylate cyclase activating protein (GCAP) is free to stimulate guanylate cyclase (GC). GC plays a role in the recovery phase of phototransduction in that its purpose is to produce cGMP. When levels of cGMP are sufficiently increased by GC, cGMP-gated channels re-open causing depolarization of the cell and a return to the dark-adapted state.
Figure 8:
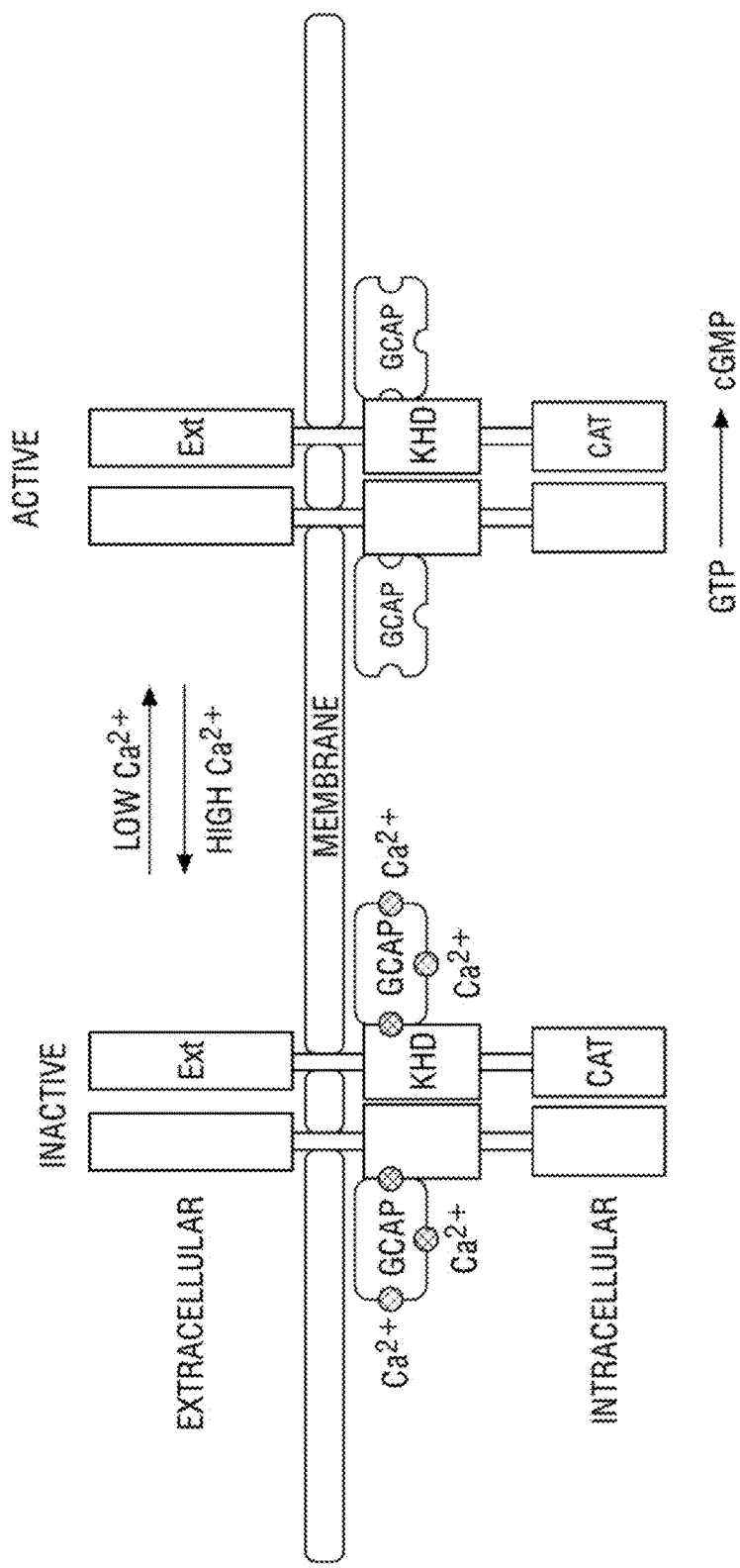
FIG. 8 shows the predicted structure and topology of retGC1 shows homology to other guanylate cyclases with a single transmembrane spanning region, an intracellular and extracellular domain. The intracellular domain is further divided in a "kinase-like" region and catalytic domain. The calcium and GCAP1-dependent regulation of retGC1 is regulated through the intracellular domains (KHD). When calcium concentration in the photoreceptor cell is high (in the dark/depolarized state), calcium-bound GCAP1 prevents activation of retGC1. Upon light stimulation, calcium levels decrease. Calcium is unbound from GCAP1, thereby allowing GCAP1 to activate retGC1. The role of retGC1 is to produce cGMP.
Figure 9B:
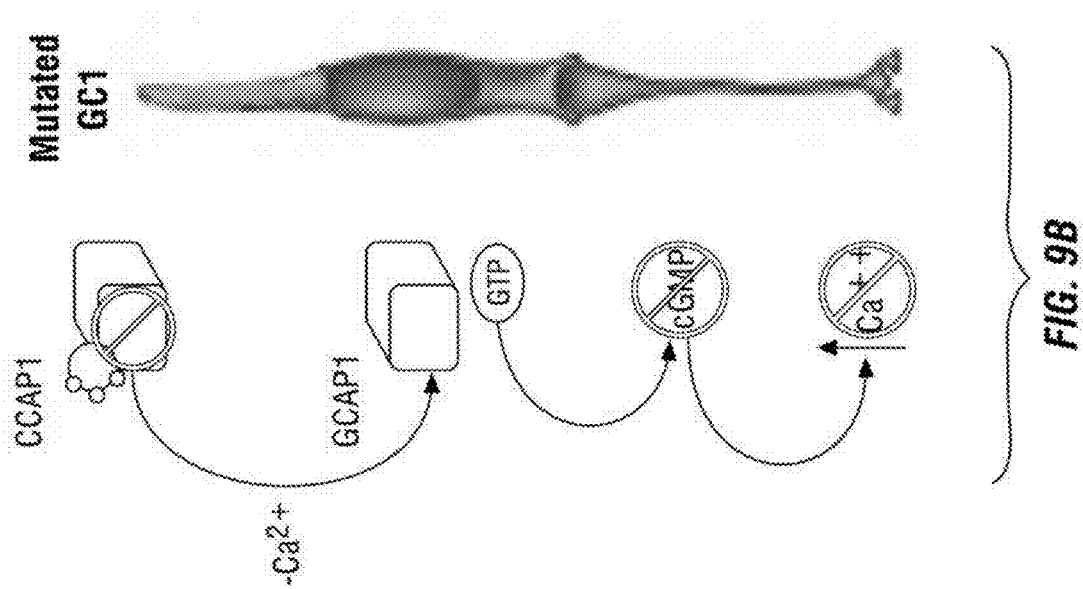
FIG. 9 shows cone photoreceptors in normal (WT) vs. GC1KO mice. In WT cones, GC1 functions normally to produce cGMP which can effectively reopen CNG gated channels and return the cell to its dark-adapted/depolarized state. In cone photoreceptors of the GC1KO mouse, GC1 fails to produce cGMP. This failure prevents reopening of CNG-gated channels. These cells are in essence, chronically hyperpolarized (light-adapted). They do not transduce light for vision (as evidenced by a lack of ERG) and will eventually degenerate.
Figure 9A:
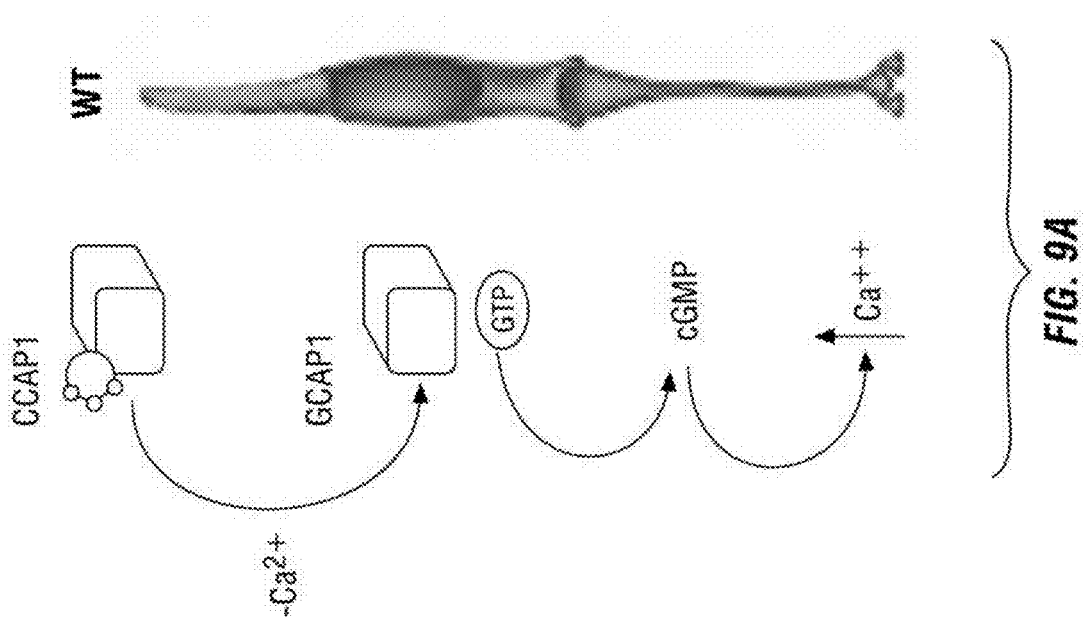

Cone Arrestin Translocation was Restored in AAV-mGC1-Treated GC1KO Mice:

AAV-mGC1 treatment restored light-induced cone arrestin translocation to cone photoreceptors in the treated GC1KO retina. Representative treated, untreated and +/+ retinal cross sections immunostained with an antibody generated against cone arrestin showed that cone arrestin was localized to the outer segments, inner segments, axons and synaptic termini of +/+, smCBA-mGC1-treated and hGRK1-mGC1-treated cone photoreceptors (FIG. 5A, FIG. 5C, and FIG. 5D, respectively). On the contrary, cone arrestin remained localized mostly to the outer segments of cones in untreated GC1KO retinas (FIG. 5B). This result was consistent with the notion that cones in the GC1KO mouse retina are chronically hyperpolarized. Not only was a restoration of cone arrestin localization in dark-adapted, treated retinas observed, but an apparent up-regulation of the protein was seen in treated eyes relative to untreated controls. Significantly, cone cell densities also appeared higher in treated eyes relative to untreated controls (see e.g., FIG. 5A, FIG. 5B, and FIG. 5C).

Cone Photoreceptors were Preserved in AAV-mGC1-Treated GC1KO Mice:

Analysis of smCBA-mGC1 and hGRK-mGC1 treated and un-injected, contralateral retinal whole mounts 3 months' post-injection with therapeutic vector that were stained with an antibody directed against cone arrestin revealed that cone photoreceptors were preserved as a result of treatment with the therapeutic vector (FIG. 6). Counts of cone photoreceptors in inferior and central retinas of both treated and untreated retinal whole mounts revealed that there was a statistically significant difference in the cone cell densities of treated vs. untreated eyes. This result was consistent with the observation that robust electrophysiological and behavioral restoration was clearly evident. P14-treatment of GC1KO mice with either therapeutic construct was capable of preserving cone photoreceptor structure for at least three months.

Example 2—Animal Model Containing a GC1/GC2 Double Knockout

It is important to note that while only cone photoreceptors are affected in the GC1KO mouse (rods only lose partial function and they do not degenerate), LCA1 patients exhibit rod function loss and rod degeneration. The reason for this difference is speculated to be a species-specific difference in the dependence on GC2, a close relative of GC1 that is expressed in rod photoreceptors. Mouse rods are able to function in the absence of GC1 presumably because GC2 is capable of reconstituting activity; however in humans this is not the case. GC1 is required for rod function, hence the rod degeneration. A GC1/GC2 double knockout mouse model was generated and shown to have rod function loss (in addition to cone function loss as seen in the GC1 K/O) (Baehr et al., 2007). It was proven through biochemical studies with this model that GC2 is what provides rod function in the absence of GC1. Having said that, it is the GC1/GC2 double knockout mouse that more reliably mimics the human condition (both cones and rods affected) (Karan et al., 2010). To test both the rAAV-smCBA-mGC1 and rAAV-hGRK1-mGC1 vectors in the GC1/GC2 double knock-out mouse, rAAV vectors are delivered in precisely the same manner and time (post-natal day 14) as with the aforementioned GC1 knock-out study. Analysis of restoration of vision, both physiologically and behaviorally, is also performed in the same manner as described above for the GC1 knock-out study. Particular emphasis is paid to scotopic (i.e., rod) responses, as a measurable recovery of rod function is expected in GC1/GC2 double knock-out mice treated with a GC1 vector construct.

Example 3—'Humanized' Murine Animal Model of LCA1

This example describes the creation of a "humanized" murine animal model of LCA1. In one embodiment, the mouse model contains a GC1/GC2/GCAP1 knockout. GCAP1 is the protein that activates GC1. To create an in-vivo system in which human GC1 expressed from a clinical grade rAAV vector designed for use in humans can be evaluated for function, a GC1/GC2/GCAP1 triple knock-out hGCAP1 transgenic mouse is utilized. In this mouse, visual function is resorted by rAAV-mediated hGC1 interacting with hGCAP1 only (i.e., no endogenous murine GCAP1 is present). From this study, it is possible to determine whether the human GCAP1 protein is required to stimulate human GC1 activity in the mouse model, and whether function can be restored to cones and rods when the two human polypeptides are reconstituted and expressed in the non-human (i.e., murine) model of the disease. To generate the GC1/GC2/GCAP1 triple knockout hGCAP1 transgenic mouse the GC1/GC2 double knockout mouse (Baehr et al., 2007) is crossed with the GCAP1 knock-out mouse (Mendez et al., 2001). Human GCAP1 is then trangenically-expressed in the animal model to generate a GC1/GC2/GCAP1 triple knockout hGCAP1 transgenic mouse. Studies in which rAAV-vectored hGC1 is provided to these animals are conducted in a manner substantially identical to the methods used in the GC1 knock-out study. Analysis of restoration of vision, both physiologically and behaviorally, is then performed in the same manner as was carried in the GC1 knock-out study.

Example 4—Exemplary Vector Constructs Useful in the Practice of the Invention

Maps of the two illustrative vectors are shown in FIG. 11. One contains the nonspecific promoter smCBA and the other has the rod/cone limited promoter GRK1. Both have been packaged into serotype 5 AAV. All vector doses tested to date are safe in the mouse retina. Cohorts of GC1−/− mice were then sub-retinally injected at postnatal day 14 (P14) and then analyzed periodically by ERG and by photopic optokinetic (cone mediated) behavior. Since the GC1$^{-/-}$ mouse maintains a rod mediated ERG, monitoring functional rescue focused primarily on restoration of cone function. For the smCBA vector ERGs were assessed at 4 weeks post-treatment and every 2 weeks thereafter until 12-13 weeks post-treatment. All 9 eyes treated in 9 mice responded to treatment. The results, shown below demonstrate a significant restoration of photopic ERG amplitudes from essentially unrecordable in control untreated eyes to approximately 50% of normal in partner vector treated eyes.

Four GC1$^{-/-}$ mice were then analyzed by scotopic optokinetic behavior for differences mediated by treated vs. untreated partner eyes (shown below). All four treated eyes (289, 290, 294, 295, red bars) showed significant improvement in visual acuity over their control eyes, and three of the four showed significantly improved contrast sensitivity. Mice 297 and 298 were wild type controls, and mouse 299 was an untreated GC1$^{-/-}$ mouse. The results demonstrate that the vector achieved functional and behavioral restoration of cone mediated vision in the animal model of LCA1.

For the GRK1 vector that limits expression to rods and cones, ERGs were assessed in 14 GC1$^{-/-}$ mice treated in one eye at 4 weeks post-treatment and every 2 weeks thereafter until 12-13 weeks post-treatment. Twelve of the 14 treated eyes in 12 animals responded. The results (shown below) revealed a significant restoration of photopic ERG amplitudes from essentially unrecordable in control untreated eyes to approximately 40% of normal in partner vector treated eyes.

One GC1$^{-/-}$ mouse (#293) was then analyzed by scotopic optokinetic behavior for differences in treated vs. untreated partner eyes (shown above). This mouse showed significant improvement in both visual acuity and contrast sensitivity in the vector treated right eye (red bar) relative to its control left eye (blue bar). Responses were nearly equivalent to control wild type mice (297 and 298) and significantly improved over an untreated GC1-/- mouse (299). It was therefore concluded that the GRK1 vector also achieves functional and behavioral restoration of cone mediated vision in this model of LCA1.

Example 5—Specific Cone Targeting of wtGC1 Improves Rescue

The data presented above clearly demonstrate that cone function and cone-mediated behavior can be rescued with the rod/cone limited GRK1 promoter. Since human LCA1 shows both rod and cone deficits (unlike the GC1$^{-/-}$ mouse that shows primarily cone deficits), expression need not be further limited to gain pure cone specificity. However, there is one final cone phenotype in the mouse model which is important to study: in dark adapted conditions, cone arrestin does not move normally from cone outer segments into inner segments, axons and synaptic termini as it does in the wild type retina. Studies were therefore performed to assess whether this cell biological phenotype was also corrected in vector-treated GC1$^{-/-}$ eyes. In the results shown, a GC1$^{-/-}$ mouse was treated in one eye with the GRK1 vector, then at 7 weeks post-injection the mouse was dark adapted. Treated (bottom panel) and control (top panel) retinas were then analyzed for cone arrestin localization by immunohistochemistry. In the untreated GC1$^{-/-}$ retina (top panel), cone arrestin remained largely in cone outer segments (OS) and the synaptic layer (SL). In contrast, in the contralateral treated retina (bottom panel) a substantial fraction (~50%) has translocated into the inner segments and synaptic termini. It was concluded, therefore, that vector treatment also restored correct translocation of cone arrestin.

Example 6—Long-Term Therapy of LCA1 Using rAAV-Vectored Genetic Constructs

The previous examples have demonstrated that subretinal injection of rAAV vectors containing the murine GC1 cDNA (driven by either the photoreceptor-specific human rhodopsin kinase [hGRK1] or the ubiquitous [smCBA] promoter) were capable of restoring cone-mediated function and visual behavior and preserving cone photoreceptors in the GC1KO mouse for at least three months.

In the present Example, the inventors evaluated whether long-term therapy was also achievable in the rodent model of LCA1. Additionally, the inventors examined whether delivery of GC1 to photoreceptors of the GC1/GC2 double knockout mouse (GCdko), a model which exhibits loss of both rod and cone structure and function and phenotypically resembles human LCA1, would confer therapy to these cells.

Methods

Subretinal injections of AAV5-hGRK1-mGC1, AAV5-smCBA-mGC1 or the highly efficient capsid tyrosine mutant AAV8(Y733F)-hGRK1-mGC1 were performed in one eye of GC1KO or GCdko mice between postnatal day 14 (P14) and P25. Rod and cone photoreceptor function were assayed electroretinographically. Localization of therapeutic GC1 expression and extent of cone photoreceptor preservation were determined by immunohistochemistry. Biodistribution studies were used to evaluate the presence of vector genomes in optic nerves and brains of treated animals.

Results

Cone photoreceptor function was restored in GC1KO mice treated with all vectors, with AAV8(733) being the most efficient. Responses were stable for at least 10 months post-treatment. Therapeutic GC1 was found in photoreceptor outer segments. By 10 months post-injection, AAV5 and AAV8(733) vector genomes were detected only in the optic nerves of treated eyes of GC1KO mice. AAV8(733)-vectored mGC1 restored function to both rods and cones in treated GCdko mice.

Conclusion

Long-term therapy is achievable in a mammalian model of GC1 deficiency, the GC1KO mouse, using the rAAV vector constructs disclosed herein. Importantly, therapy was also achievable in the GCdko mouse which mimics the LCA1 rod/cone phenotype. These results provide evidence for the use of rAAV-based gene therapy vectors for treatment of retinal dystrophies, and LCA1 in particular.

Example 7—Long Term Preservation of Cone Photoreceptors and Restoration of Cone Function by Gene Therapy in the GC1KO Mouse In previous examples, it was shown that subretinal AAV5 vectors containing murine GC1 cDNA driven by either the photoreceptor-specific (hGRK1) or the ubiquitous (smCBA) promoter were capable of restoring cone-mediated function and visual behavior and preserving cone photoreceptors in the GC1KO mouse for three months. In the present example, long term therapy is evaluated using the same murine model. AAV5-hGRK1-mGC1, AAV5-smCBA-mGC1 or the highly efficient capsid tyrosine mutant AAV8(Y733F)-hGRK1-mGC1 were delivered subretinally to GC1KO mice between postnatal day 14 (P14) and postnatal day (P25). Retinal function was assayed by electroretinograms (ERGs). Localization of AAV-mediated GC1 expression and cone survival were assayed with immunohistochemistry and the spread of vector genomes beyond the retina was quantified by PCR of optic nerve and brain tissue. Cone function was restored with all vectors tested, with AAV8(Y733F) being the most efficient. AAV-mediated expression of GC1 was found exclusively in photoreceptors. By 10 months post-injection, AAV genomes were detected only in optic nerve of treated eyes. These results demonstrate for the first time that long-term therapy is achievable in a mammalian model of GC1 deficiency.

Retinal guanylate cyclase-1 (GC1) encoded by GUCY2D serves a key function in vertebrate phototransduction (Pugh et al., 1997). Following light stimulus, second messenger cyclic GMP (cGMP) is rapidly hydrolyzed by phosphodi-esterase (PDE6) within photoreceptor cells leading to a closure of cGMP-gated cation channels and hyperpolarization of the cell. When cytoplasmic [$Ca^{2+}$] drops below 50 nM, GC1 is activated by small $Ca^{2+}$-binding proteins, GCAPs (guanylate cyclase activating proteins). GC1 synthesizes cGMP which binds and reopens cGMP-gated channels, returning the photoreceptor to the "dark", depolarized state (Pugh et al., 1997; Polans et al., 1996; Wensel, 2008; Lamb and Pugh, 2006; Arshaysky et al, 2002). Thus, GC1 plays a vital role in the light-dark and recovery cycles, anchoring, via cGMP, the feedback loop linking intracellular calcium levels and the polarization state of photoreceptors.

GC1 is expressed in the outer segments of rod and cone photoreceptors of human, monkey and mouse retinas (Dizhoor et al., 1994; Liu et al., 1994; Haire et al., 2006). Like other membrane guanylate cyclases, it contains an N'-terminal signal sequence, an extracellular domain (ECD), a single transmembrane domain, a kinase-like homology domain (KHD), a dimerization domain (DD) and a C'-terminal catalytic domain (CCD), and is present likely as homomeric dimers (Yang and Garbers, 1997). Mutations in GUCY2D are associated with recessive Leber congenital amaurosis-1 (LCA1) as well as dominant and recessive forms of cone-rod dystrophy, CORD6 and CORD, respectively (Perrault et al., 1996; Perrault et al., 2000; Kelsell et al., 1998; Perrault et al., 1998; Gregory-Evans et al., 2000; Weigell-Weber et al., 2000; Ugur et al., 2010). LCA1 is a severe, early onset, autosomal recessive blinding disorder characterized by extinguished electroretinogram (ERG) which precedes photoreceptor degeneration (Perrault et al., 1999; Chung and Traboulsi, 2009). CORD6 is a dominant disorder characterized by progressive degeneration of photoreceptors beginning with cones causing early loss of visual acuity and color vision followed by degeneration of rods leading to progressive night blindness and peripheral visual field loss (Kelsell et al., 1998; Perrault et al., 1998). CORD6 mutations are restricted to the dimerization domain (DD) and generally cause an increase in GCAP-mediated activation of GC1 (Payne et al., 2001; Downes et al., 2001; Wilkie et al., 2000). A recently found recessive CORD-causing mutation is located in the catalytic domain (CD) of GC1 and is thought to reduce overall enzyme function (Ugur et al., 2010). LCA1-causing mutations are distributed throughout the ECD, KHD, DD and CCD domains of GC1 (Karan et al., 2010). These mutations alter enzyme structure and stability, may impact retrograde transport of other peripheral membrane associated proteins and are frequently null.

The GC1KO mouse carries a null mutation in Gucy2e, the murine homologue of GUCY2D. Like LCA1 patients, loss of cone function in this model precedes cone degeneration (Timmers et al., 2001). Rods retain 30-50% of their function and do not degenerate due to the presence of GC2, another functional guanylate cyclase in murine photoreceptors (Yang and Garbers, 1997; Jacobson et al., 2006; Timmers et al., 2001; Cideciyan et al., 2008; Song et al., 2002). In the earlier examples, it was shown that subretinal injection of serotype 5 adeno-associated viral (AAV) vectors containing the murine GC1 cDNA driven by either the photoreceptor-specific human rhodopsin kinase (hGRK1) or the ubiquitous (smCBA) promoter were capable of restoring cone-mediated function and visual behavior and preserving cone photoreceptors in the GC1KO mouse for three months. In the present study, AAV-mediated gene replacement therapy was evaluated for its ability to provide therapy to the GC1KO mouse over the long term. AAV5-hGRK1-mGC1 and AAV5-smCBA-mGC1 and the highly efficient capsid tyrosine mutant vector AAV8(Y733F)-hGRK1-mGC1 were delivered subretinally to GC1KO mice between postnatal day 14 (P14) and postnatal day 25 (P25). These findings demonstrate for the first time that long-term therapy is achievable in a mammalian model of GC1 deficiency. Vector genome biodistribution was also evaluated for AAV5- and AAV8(733)-based vectors. These findings have direct bearing on the development of an AAV-based gene therapy clinical trial for LCA1 (and possibly cone-rod dystrophies), and help to develop a standardized vector design for a wide range of recessive retinal degenerations mediated by defects in photoreceptor-associated genes.

Materials and Methods

Experimental Animals:

GC1KO and congenic +/+ controls derived from heterozygous matings of GC1+/− mice provided by The Jackson Laboratory (Bar Harbor, Me., USA) were bred and maintained in the inventors' institutional animal care facility under a 12 hr/12 hr light/dark cycle. Food and water were available ad libitum. All studies were conducted in accordance with the ARVO Statement for the Use of Animals in Ophthalmic and Vision Research and NIH regulations.

Construction of AAV Vectors:

Serotype 5 Adeno-associated virus (AAV5) vector plasmids containing either the ubiquitous (smCBA) or photoreceptor-specific human rhodopsin kinase (hGRK1) promoter driving murine GC1 (mGC1) cDNA were generated according to previously described methods (Boye et al., 2010). Site-directed mutagenesis of surface-exposed tyrosine residues on the AAV2 capsid have been reported (Zhong et al., 2008). Similar methods were used to generate the AAV8 (Y733F) capsid mutant described here. All vectors were packaged, purified and titered according to previously described methods (Zolotukhin et al., 2002; Jacobson et al., 2006). Resulting titers for AAV5-smCBA-mGC1, AAV5-hGRK1-mGC1 and AAV8(Y733F)-hGRK1-mGC1 were $4.69 \times 10^{12}$ vector genomes per ml (vg/mL), $4.12 \times 10^{13}$ vg/mL and $1.08 \times 10^{13}$ vg/mL, respectively.

Subretinal Injections:

One μL of AAV5-smCBA-mGC1 ($4.69 \times 10^9$ vector genomes), AAV5-hGRK1-mGC1 ($4.12 \times 10^{10}$ vector genomes) or AAV8(Y733F)-hGRK1-mGC1 ($1.08 \times 10^{10}$ vector genomes) were injected subretinally into one eye of GC1KO mice between postnatal day 14 (P14) and postnatal day 25 (P25). The contralateral control eye remained uninjected. Subretinal injections were performed as previously described (Timmers et al., 2001). Further analysis was carried out only on animals which received comparable, successful injections (>60% retinal detachment with minimal complications). Approximately 75% of all cohorts received "successful" injections. It is well established that the area of vector transduction corresponds to at least the area of retinal detachment (Timmers et al., 2001; Cideciyan et al., 2008).

Electroretinographic Analysis:

ERGs of treated GC1KO and age-matched, congenic (+/+) controls were recorded using a PC-based control and recording unit (Toennies Multiliner Vision; Jaeger/Toennies, Höchberg, Germany) according to methods previously described with minor modifications (Haire et al., 2006; Boye et al., 2010). Recordings of AAV5-smCBA-mGC1-treated GC1KO mice (n=10), AAV5-hGRK1-mGC1-treated GC1KO mice (n=6), AAV8(Y733F)-treated GC1KO mice (n=6) and congenic (+/+) controls (n=8) commenced on different dates and therefore each subset of mice was monitored for slightly different lengths of time. ERGs of treated GC1KO mice were recorded 4-weeks' post-injection and every month thereafter until 1 year post-injection (AAV5-treated mice) or 9 months post-injection (AAV8[Y733F]-treated mice). Age-matched, congenic (+/+) control mice were followed for 8 months. Mice were removed from the study at different time points throughout the experiment for various postmortem studies (biodistribution studies, retinal immunohistochemical analysis, real time RT-PCR of retinal tissue) or unexpected sickness/death. ERG data was presented only for groups of animals with an n>3. Therefore, this study compares findings out to 9 months post-injection for AAV5-treated mice and 6 months post-injection for AAV8(Y733F)-treated mice. Treated mice continued to exhibit ERG responses beyond these time points, however sample sizes were sufficiently reduced such that statistical analysis was no longer practical. Representative cone-mediated traces from individual mice 1 year post-treatment with AAV5 vectors and 9 months post-treatment with AAV8 (Y733F) are presented to support this contention. Scotopic (rod-mediated) and photopic (cone-mediated) recordings were elicited using recording parameters previously described (Boye et al., 2010). B-wave amplitudes were defined as the difference between the a-wave troughs and the subsequent positive peak of each waveform. Rod-mediated ERG responses in untreated GC1KO mice are variable from animal to animal (Yang et al., 1999), hence, large standard deviations were observed when averaging scotopic a- and b-wave amplitudes from different animals. Rod ERG data is presented in ratio form (the average of intra-individual, treated versus untreated rod a- and b-wave amplitudes). As such, any value above 1 indicates AAV-mGC1 treatment improved the rod response. Ratios were calculated using amplitudes generated with a 1 cds/m$^2$ stimulus. Photopic, cone-mediated b-wave maximum amplitudes in injected and uninjected eyes of all treated GC1KO mice and congenic (+/+) control mice generated at 12 cds/m$^2$ were averaged at each time point and used to generate standard errors. All data was imported into Sigma Plot for final graphical presentation. The standard t-test was used to calculate P-values between data sets. Significant difference was defined as a P-value<0.05.

Biodistribution:

The spread of vector DNA in tissues of the treated GC1KO mice was determined in samples collected at sacrifice according to previously described methods with minor modifications (Jacobson et al., 2006). Vector-treated mice were sacrificed at the following time points: AAV8(Y733F)-hGRK1-mGC1-treated mice (4-months' post-injection: n=1; 7-months' post-injection: n=1), AAV5-smCBA-mGC1 (7-months' post-injection: n=1; 10-months' post-injection: n=5), AAV5-hGRK1-mGC1 (7-months' post injection: n=1; 10-months' post-injection: n=1). Control tissues from GC1KO mice age-matched to the 7-month-post injection or 10-month-post injection time points were also evaluated alongside experimental animals. Following sacrifice, different new forceps were used to enucleate treated and untreated eyes which retained approximately 0.5 cm of proximal optic nerve. Different, new dissection scissors were then used to cut the optic nerves away from the eyeballs after which they were snap frozen in liquid nitrogen and transferred to −80° C. where they remained until the time of DNA extraction. Eyeballs were immersed in 4% paraformaldehyde (PAF) and processed for immunohistochemistry (see below).

Brains were removed and a stainless steel mouse coronal brain matrix (Harvard Apparatus, Holliston, Mass., USA) was used to isolate visual-specific regions. Right and left lateral geniculate nuclei were collected from one mouse per treatment group (at the latest time point), formalin fixed and saved in the event that vector genomes were recovered from brain and immunohistochemistry was necessary. Separate portions of right and left brain containing visual pathways were collected, snap frozen in liquid nitrogen and transferred to −80° C. where they remained until the time of DNA extraction. Precautions were taken to avoid cross-contamination while harvesting tissues. Genomic DNA was extracted from tissues according to the manufacturer's protocol (Qiagen DNeasy tissue kit). Resulting DNA concentrations were determined using an Eppendorf Biophotomoter (Model 6131; Eppendorf, Hamburg, Germany). Quantitative PCRs were performed according to previously described methods with minor modifications (Jacobson et al., 2006; Song et al., 2002; Poirier et al., 2004).

Primer pairs were designed to the SV40 poly-adenylation signal (SV40 polyA) region in each vector genome and standard curves established using known concentrations of plasmid DNA containing the same SV40 polyA target sequence. DNA samples were assayed in triplicate. In order to rule out false negatives due to inhibition of PCR, the third replicate was 'spiked' with plasmid DNA containing target (SV40 polyA) at a ratio of 100 copies/μg of genomic DNA. If >40 copies of the spike-in DNA were detected, the sample was considered acceptable for reporting vector genome copies. In some cases samples failing 'spike in' were reanalyzed using less than 1 μg of genomic DNA in PCR reactions, thereby diluting out PCR inhibitors copurifying with DNA in the extracted tissue. Spike-in copy number was reduced proportionally to maintain the 100 copies/μg DNA ratio. Criteria for reporting vector genome copies were established according to previously described methods (Jacobson et al., 2006). Briefly, greater than 100 genome copies/μg was considered positive and the measured copy number/pig reported. Fewer than 100 copies/μg was considered negative.

Tissue Preparation, Immunohistochemistry and Microscopy:

At sacrifice, concomitant with biodistribution studies performed at 7 months post-[AAV8(Y733F)-hGRK1-mGC1] and 10 months post- (AAV5-smCBA-mGC1 and AAV5-hGRK1-mGC1) injection, the limbus of treated GC1KO mice, age-matched, untreated GC1KO mice as well as age-matched congenic GC1+/+ mice were marked with a hot needle at the 12 o'clock position, facilitating orientation. Untreated GC1KO and GC1+/+ controls were age-matched to the AAV8(Y733F)— treated mice (8 months of age at the time of sacrifice). Eyes designated for cryosectioning were processed and immunostained according to previously described methods (Haire et al., 2006). Briefly, 10 μm retinal sections were incubated with antibodies directed against GC1 (rabbit polyclonal 1:200, sc-50512 Santa Cruz Biotechnology, USA) or mouse cone arrestin (rabbit polyclonal "LUMIj", 1:1000, provided by Dr. Cheryl Craft, University of Southern California, Los Angeles, Calif., USA). Following primary incubation, IgG secondary antibodies Alexa-488 or Alexa-594, respectively, were applied for 1 hour at room temperature (1:500 in 1×PBS). Sections were counterstained with 4',6'-diamino-2-phenyl-indole (DAPI) for 5 min at room temperature. At 11-months' post-injection, one GC1KO mouse that received treatment with AAV5-smCBA-mGC1 in one eye only was sacrificed and retinal whole mounts from treated and untreated eyes processed according to previously described methods (Pang et al., 2010). Briefly, whole mounts were stained with LUMIj (1:1000) followed by IgG secondary Alexa-594 (1:500 in 1×PBS) and positioned on slides with the superior (dorsal) portion of the retina oriented at 12-o'clock. Retinal sections were analyzed by confocal microscopy (Leica TCS SP2 AOBS Spectral Confocal Microscope equipped with LCS Version 2.61, Build 1537 software). Images were taken at identical exposure settings at 20× magnification. Retinal whole mounts were analyzed with a wide-field fluorescent microscope (Zeiss Axioplan 2) equipped with QImaging Retiga 4000R Camera and QImaging QCapture Pro software. Quadrants of each whole mount were imaged at 10× under identical exposure settings and then merged together in Adobe Photoshop.

Immunoblotting:

At 7 months post-injection, one mouse injected with AAV8(Y733F)-hGRK1-mGC1 and an age-matched, congenic GC1+/+(control) mouse were sacrificed, their eyes enucleated and placed in 1×PBS. Retinas were immediately dissected and processed as follows. Individual retinas were solubilized in PBS (137 mM NaCl, 2.7 mM KCl, 10 mM $Na_2HPO_4$, 1.8 mM $KH_2PO_4$) with 1% Triton X-100 and complete protease inhibitor (Roche) for 1 hour at 4° C., followed by centrifugation at 14000 rpm. The protein concentration of the supernatant was determined by BCA (Pierce) and 15 µg of each sample was separated on a 12% polyacrylamide gel (Bio-Rad) and transferred onto Immobilon-FL membranes for 1 hour in transfer buffer (25 mM Tris, 192 mM glycine) containing 15% methanol. Blots were treated with blocking buffer (Li-Cor) and labeled for 1 hour with a mouse monoclonal antibody recognizing GC1 (IS4, 1:3000, provided by Dr. Kris Palcweski, Case Western University, USA.) and rabbit polyclonal antibodies raised against GCAP1 (pAb UW14, 1:25,000, provided by Dr. Wolfgang Baehr, University of Utah) and β-actin (1:5000, Abcam). Secondary antibodies (goat anti-mouse Ig conjugated to CW800 and goat anti-rabbit conjugated with IR680) were applied for 1 hour and blots imaged with an Odyssey Infrared Imaging System (Licor, Lincoln, Nebr., USA).

mRNA Quantification by rtPCR, Retinal Genome Recovery and Optic Nerve IHC

Individual treated eyes with optic nerve attached were harvested from GC1KO mice 1 year post-treatment with either AAV8(Y733F)-hGRK1-mGC1 or AAV5-smCBA-mGC1 and an age-matched, untreated GC1 +/+ mouse. Retinas were dissected from the eye immediately and snap frozen in liquid nitrogen. Optic nerves were dissociated from the eyes, fixed in 4% paraformaldehyde overnight at 4° C., immersed in 30% sucrose for 2 hours at 4° C., and then quick frozen in cryostat compound (Tissue Tek® OCT 4583; Sakura Finetek USA, Inc., Torrance, Calif., USA) in a bath of dry ice/ethanol. Optic nerves were sectioned at 10 µM and stained according to previously described methods (Boye et al., 2010). Retinas were homogenized in 350 mL of Buffer RLT (RNeasy® Protect Mini Kit, Qiagen, Inc., Valencia, Calif., USA) plus BME for 45 sec. Samples were centrifuged and the lysate was split in half (one half designated for genome recovery and the other half for RNA extraction) (Traint and Whitehead, 2009). Genome recovery was performed as described above. RNA extraction was performed with an RNeasy® Protect Mini Kit (Qiagen, Inc.). RNA was reverse transcribed (iScript® cDNA synthesis kit, Biorad Laboratories, Hercules, Calif., USA) and used in real-time PCR (iQ SYBR® Green Supermix and MyiQ real-time PCR detection system interfaced with iCycler® thermal cycler, Biorad Laboratories) to measure the following retinal specific mRNAs: guanylate cyclase-1 (GC1), guanylate cyclase activating protein-1 (GCAP1), cone transducin α (GNAT2), rod cGMP-specific 3',5' cyclic phosphodiesterase subunit alpha (PDE6α) and the housekeeping gene, glyceraldehyde 3-phosphate dehydrogenase (GAPDH).

Figure 20A:
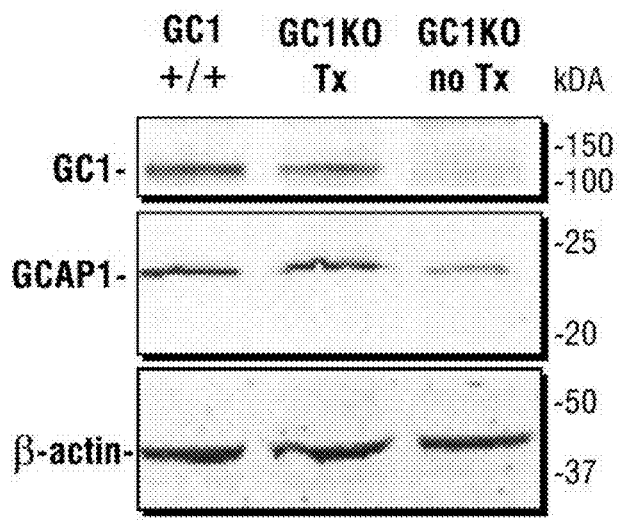
FIG. 20A and FIG. 20B shows real time RT-PCR standards. Fluorescence (log units in Y-axis) is plotted against cycle threshold $C\tau$ values (X-axis). Each panel represents the standard curves (generated by a dilution series of total retina cDNA) for GC1 and Gapdh transcript using retinal cDNA from either a wild type, GC1+/+ mouse (a) or a GC1KO mouse treated with AAV8(Y733F)-hGRK1-mGC1. The standard curves generated by GC1 and Gapdh primer sets were parallel using either template indicating similar amplification kinetics. $C_\tau$ cycle value increases with decreasing amount of template.
Figure 20B:
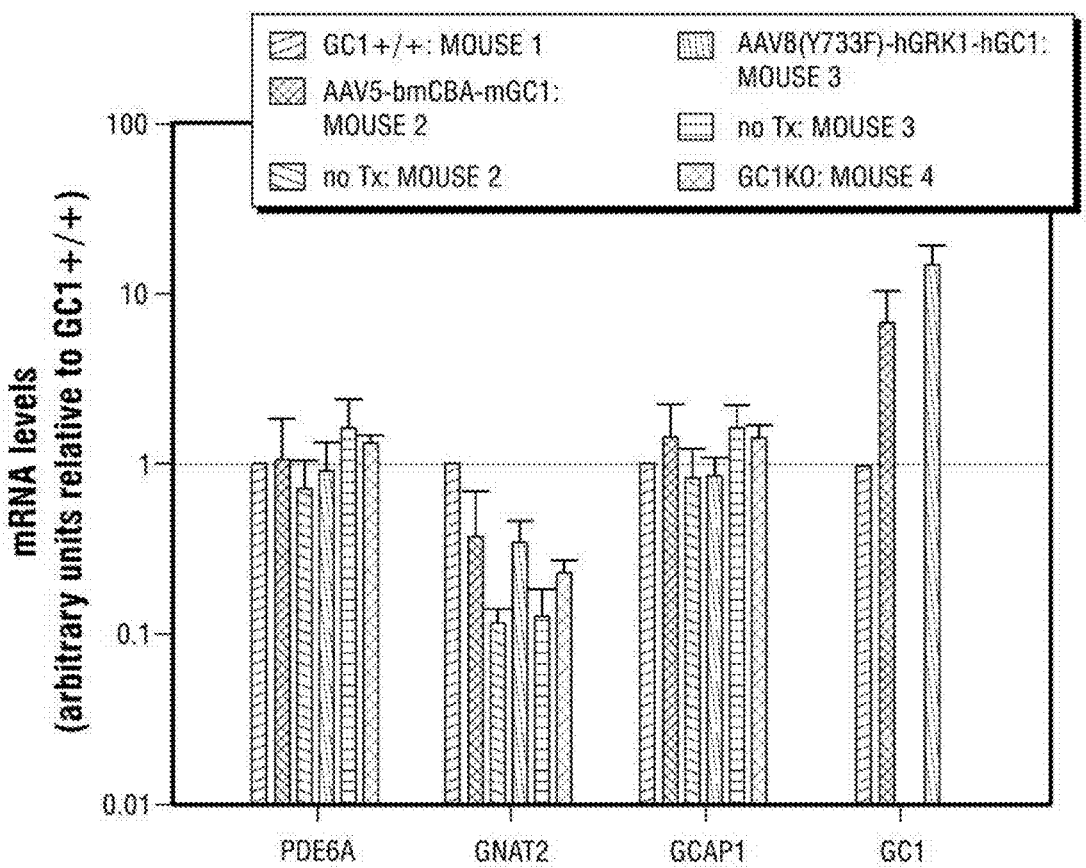

Primer pairs for GCAP1, GNAT2, PDEα and GAPDH were identical to those used by Baehr et al. (2007). Primers for murine GC1 (forward primer: 5'-GACCCTTCCT-GCTGGTTCGATCCA-3' [SEQ ID NO:16], reverse primer: 5"-CTGCATGTGTAGCAGCCTGTGCCTC-3' [SEQ ID NO:17]) were designed to flank exon 5, the site of gene disruption in the GC1KO mouse (Yang et al., 1999) and generate an amplicon of 151 bp. PCR produced appropriately sized amplicons in GC1 +/+ and AAV-mGC1-treated GC1KO retina samples, but not in untreated GC1KO retina as expected. Amplicon identity was verified by restriction digest with StuI (NEB) which cleaves within the target sequence to yield fragments of 56 bps and 95 bps. rtPCR with GC1 and GAPDH primers on dilution series of reverse transcribed DNA (from both GC1 +1+ and AAV-mGC1-treated GC1KO retina samples) resulted in similar slopes, indicating suitability of GC1 primers for quantifying both endogenous and vector mediated GC1 message (FIG. 20A and FIG. 20B).

Results are the average of 3 replicate reactions and were calculated using the $2^{-\Delta\Delta C}\tau$ method (Livak and Schmittgen, 2001) with GAPDH signal used to normalize samples and the GC1 +/+ sample serving as the calibrator. Standard deviations were calculated from the 3 replicate reactions done for each sample. Data is presented as the fold change in mRNA levels relative to the GC1 +/+ sample.

Results

Figure 21A:
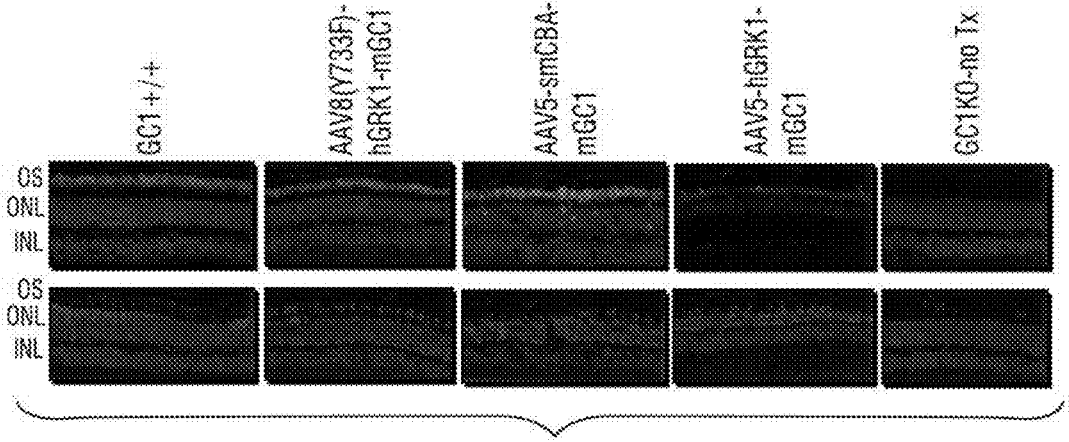
FIG. 21A and FIG. 21B show GC1 and cone arrestin expression in retinas of treated and untreated GC1KO mice and GC1+/+ controls.
Figure 21B:
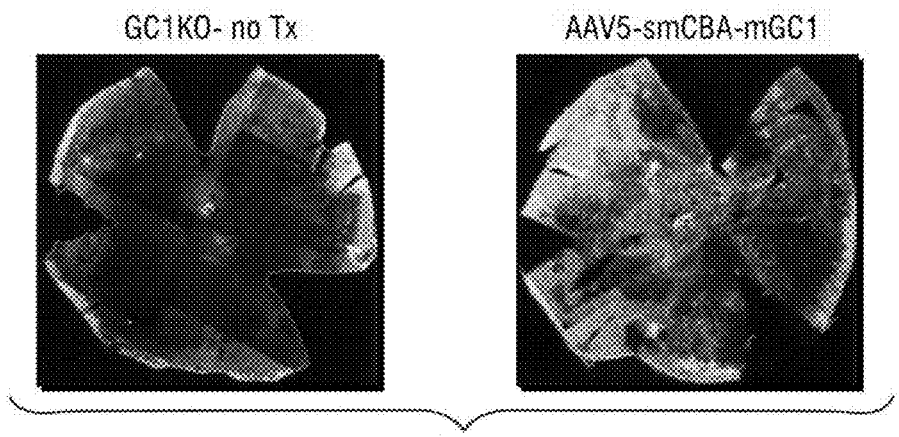

Long-Term, Photoreceptor-Specific GC1 Expression:

Immunostaining with an antibody directed against GC1 revealed that AAV-vectored therapeutic protein expression persisted exclusively in photoreceptors of treated GC1KO mice for a significant fraction of the animal's lifetime; AAV8(Y733F)-hGRK1-mGC1 for at least 7 months, AAV5-smCBA-mGC1 for at least 10 months, and AAV5-hGRK1-mGC1 for at least 10 months (FIG. 21A and FIG. 21B). GC1 expression was limited to the outer segments of rods and cones treated with AAV8(Y733F)-hGRK1-mGC1 vector whereas it was found in both outer segments and more rarely in photoreceptor cell bodies of eyes treated with AAV5-smCBA-mGC1, a result consistent with the strength of this ubiquitous promoter relative to photoreceptor-specific, hGRK1 (Beltran et al., 2010). Two examples of retinal thinning were observed. The first was a GC1KO retina treated with AAV5-smCBA-mGC1 ($4.69 \times 10^9$ total vector genomes delivered). The outer nuclear layer (ONL) was slightly thinned relative to that seen in naïve GC1KO or GC1+/+ control retinas (both 8 months of age). This may be a result of over-expression of GC1 mediated by the smCBA promoter (Beltran et al., 2010).

The second involved a GC1KO retina treated with the more concentrated AAV5-hGRK1-mGC1 and as before showed photoreceptor-specific GC1 expression but with profound thinning of the outer nuclear layer. It should be noted that this vector was the most concentrated of the three evaluated in this study ($4.12\times10^{10}$ vector genomes delivered versus $4.69\times10^9$ and $1.08\times10^{10}$, for the AAV5-smCBA-mGC1 prep and AAV8(Y733F)-hGRK1-mGC1, respectively), and again highlights that over expression of GC1 may be the cause of the observed thinning. At a minimum, these results suggest that a dose limiting toxicity may be observable in the mouse. GC1 expression was absent from the untreated GC1KO retina (FIG. 21A and FIG. 21B).

Long Term Cone Photoreceptor Survival is Achieved by AAV-Vectored GC1

Cone photoreceptors in treated and untreated GC1KO mice as well as GC1+/+ controls were identified by staining for mouse cone arrestin. Retinal cross sections from mice sacrificed for the final biodistribution study and retinal whole mounts from a GC1KO mouse 11 months post-treatment with AAV5-smCBA-mGC1 (right eye only) were analyzed. Here it was shown that cone photoreceptor densities were markedly reduced in untreated GC1KO retinas by 10 months of age and confirm previous reports that cones are lost in a topographically specific manner in this mouse model (Coleman et al., 2004) (FIG. 21A and FIG. 21B). Whole mount analysis revealed the 11 month old, untreated retina exhibited a sparse cone density, with residual cones found exclusively in superior retinal regions whereas the partner, P14-treated retina retained much higher cone density throughout, with the exception of a small patch of temporal retina which likely was not exposed to vector during the subretinal injection and therefore did not contain transgene product. Compared to that seen in AAV5-treated retinas, cone densities and structure in retinal cross sections of AAV8(Y733F)-treated mice appeared qualitatively most similar to that seen in the normal, GC1+/+ retina (FIG. 21A and FIG. 21B). While their densities were increased relative to untreated controls, cones in AAV5-treated retinas appeared slightly disorganized, a result likely due to the slight overall disorder/thinning of the outer nuclear layers in these mice.

Long-term Restoration of Photoreceptor Function (ERG) in AAV-Treated GC1KO Mice

Figure 22A:
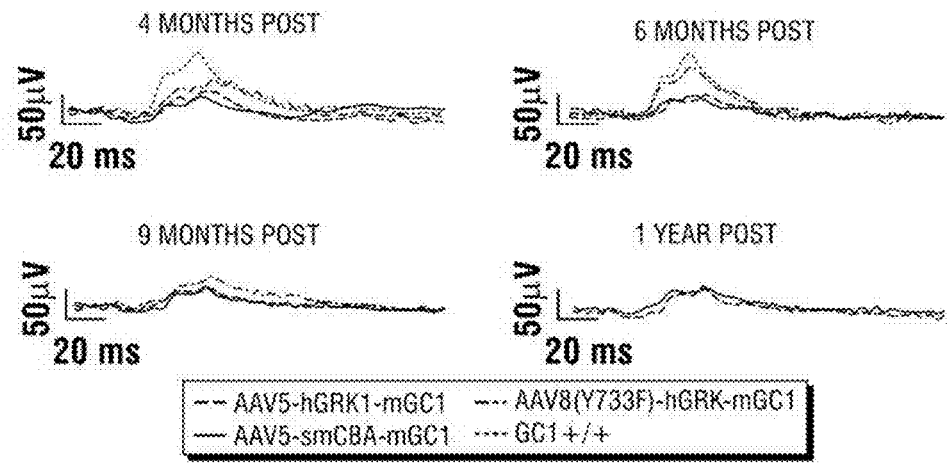
FIG. 22A and FIG. 22B show cone-mediated electroretinograms (ERGs) of treated and untreated GC1KO and untreated GC1+/+ control eyes.
Figure 22B:
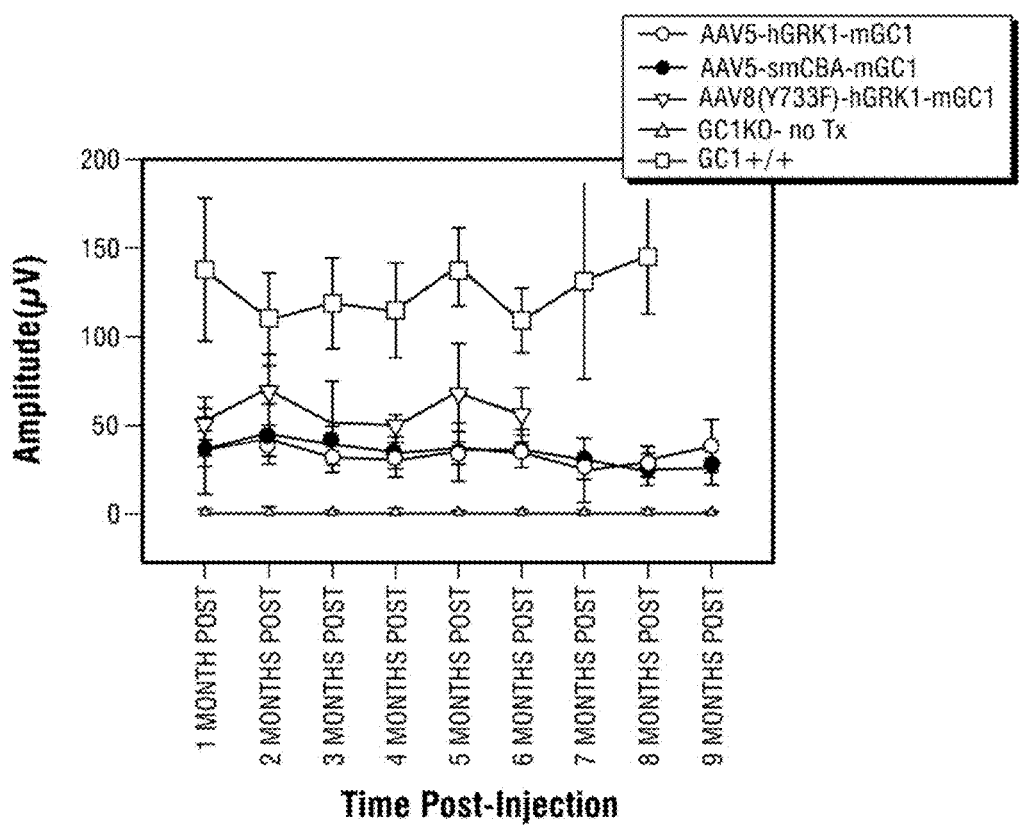

In the previous examples, cone-mediated function could be restored to GC1KO mice for 3 months following P14 delivery of AAV5-smCBA-mGC1 or AAV5-hGRK1-mGC1 (Boye et al., 2010). Average photopic b-wave amplitudes in treated mice were partially restored at 4 weeks post-injection and remained stable throughout that study. In the present example, cone-mediated responses out to 9 months post-treatment were compared in GC1KO mice injected between P14 and P25 with identical vectors used in the previous study. All remaining mice treated with AAV5-mGC1 vector continued to exhibit measurable cone-mediated function out to at least 1 year post-treatment. Representative traces elicited at 12 cds/m$^2$ from an individual mouse treated with AAV5-hGRK1-mGC1 are shown in FIG. 22A and FIG. 22B. Cone responses were stable over time and were significantly higher than responses generated from untreated, contralateral controls ($p<0.001$), suggesting that restoration of cone function is possible over the lifetime of the animal (FIG. 22A). Consistent with the previous example, the level of restoration achieved following delivery of the photoreceptor-specific promoter (hGRK1)-containing vector was not significantly different from that achieved with the ubiquitous promoter (smCBA)-containing vector at any post-treatment time point. Representative traces reveal that the kinetics of the restored cone ERG appeared normal throughout the course of the study (FIG. 22B). In addition, it was shown in this example that cone photoreceptor function was stably restored for at least 6 months following injection with AAV8(Y733F)-hGRK1-mGC1.

Cone b-wave amplitudes in GC1KO mice injected with this strong, fast-acting AAV8 tyrosine capsid mutant were higher than those seen in GC1KO mice injected with either AAV5 vector at every time point evaluated. At 6 months post-treatment, the latest time point in which all vectors could be compared in parallel, there was a significant difference between cone b-wave amplitudes in AAV8 (Y733)-hGRK1-mGC1 vs. AAV5-hGRK1-mGC1-treated mice ($p=0.033$) and AAV(Y733F)-hGRK1-mGC1 vs. AAV5-smCBA-mGC1-treated mice ($p=0.025$). A representative trace recorded 9 months post-injection with AAV8 (Y733F)-hGRK1-mGC1 (n=1) was noticeably smaller than that recorded at 6-months' post-injection.

Figures 1, 23A:
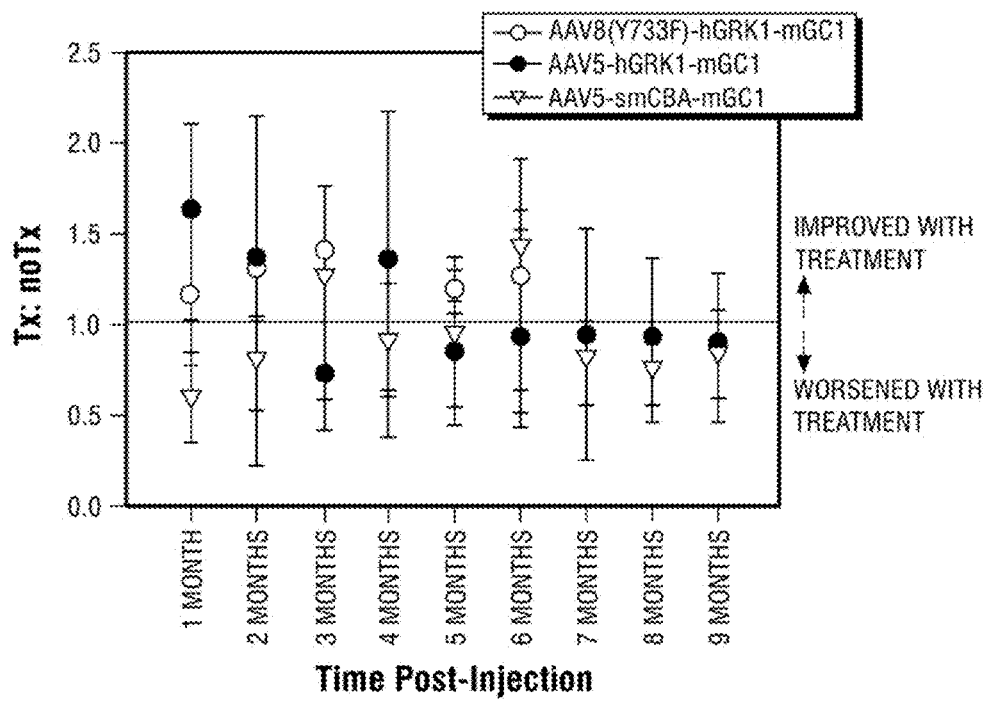
FIG. 23A and FIG. 23B illustrate rod-mediated electroretinograms (ERGs) of treated and untreated GC1KO and GC1+/+ control eyes.
Figures 2, 23A:
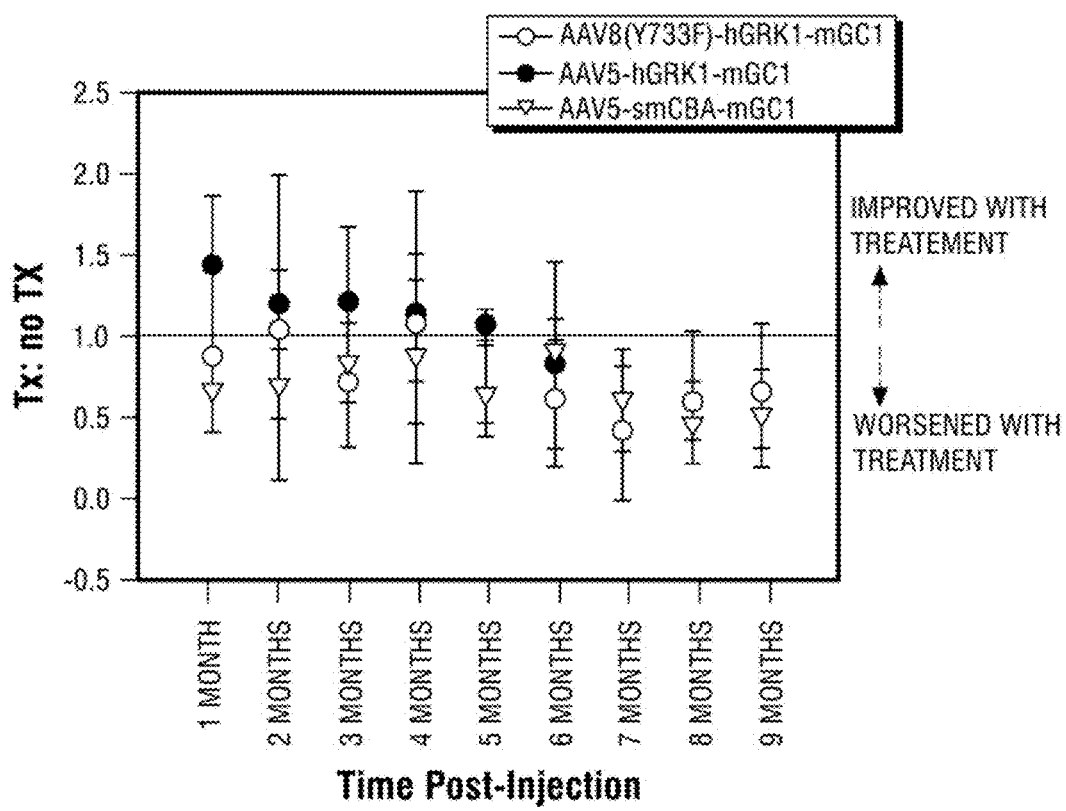
Figure 23B:
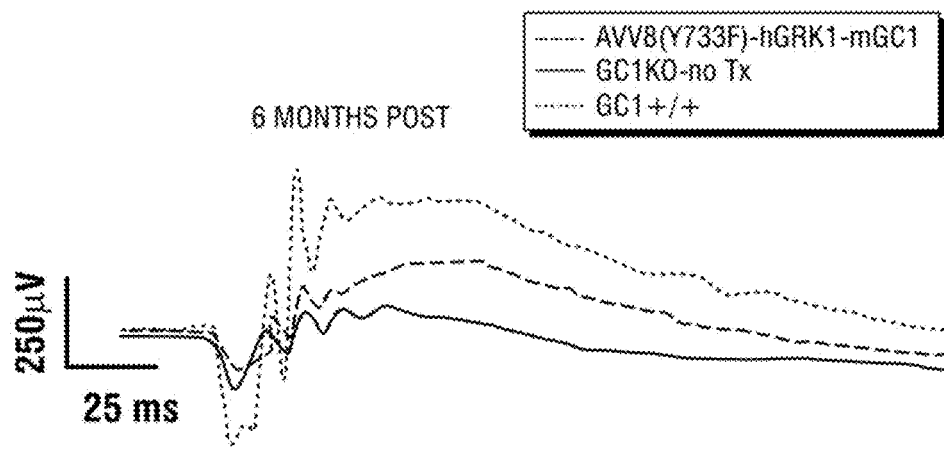

Due to the inter-mouse variability in untreated GC1KO rod responses (50-70% of WT by 5 months of age (23)), statistical comparison of average rod responses of treated vs. untreated eyes is problematic. However, within an animal, rod ERG amplitudes are nearly equal between partner eyes, therefore we calculated the average intra-mouse rod a- and b-wave amplitude ratios for treated versus untreated eyes and then plotted these ratios over time (FIG. 23A and FIG. 23B). AAV-mediated restoration of rod function is indicated by ratios with a value>1.0. FIG. 23A and FIG. 23B show that, with the exception of one time point (4 months post-treatment), the average ratios of rod b-wave amplitudes in AAV8(Y733F)-hGRK1-mGC1-treated vs. untreated eyes were all >1.0. Ratios of AAV5-treated vs. untreated eyes were only occasionally >1.0. Similarly, rod a-wave ratios were consistently higher in AAV8(Y733F)-hGRK1-mGC1-treated mice, whereas they often declined following treatment with either AAV5 vector (FIG. 23B). These results suggest that while the therapeutic effects on rods were subtle, AAV8(Y733F) conferred the most robust rod-mediated functional improvement to the GC1KO mouse (FIG. 23B). Representative rod-mediated scotopic ERG traces elicited by a 1 cds/m$^2$ stimulus were demonstrated in an AAV8(Y733F)-hGRK1-mGC1-treated GC1KO mouse (6 months post-treatment), the untreated contralateral control eye and an age-matched GC1+/+ control. AAV8(Y733F)-mediated improvements in rod ERG amplitudes are clear in this example and indicate that aside from the sub-wild type amplitudes, treated eye response kinetics resemble that seen in the GC1+/+ control.

Vector Biodistribution:

Biodistribution studies were performed in GC1KO mice treated with each vector to establish whether AAV5 or AAV8(Y733F)-delivered vector genomes could be detected in the optic nerves and/or brains of treated mice after a period of months. Mice injected with AAV5 vectors were evaluated at 7 (n=2) and 10 (n=5) months post-treatment and mice injected with AAV8(Y733F)-hGRK1-mGC1 were evaluated at 4 (n=1) and 7 (n=1) months post-treatment. The optic nerves from injected and uninjected eyes were examined as well as portions of left and right brain that contained visual pathways. AAV5 vectors were injected in the right eyes of GC1KO mice. Accordingly, vector genomes were detected in the right optic nerve of AAV5-treated mice at both 7 and 10 months post-injection. At 7 months post-injection, vector genomes were also detected in the left brain of one mouse injected with AAV5-hGRK1-mGC1. No vector genomes were detected from the right brain of that animal. The observation that right (injected) optic nerve and left brain were positive is anatomically consistent since the left hemisphere is predominantly "wired" to the right eye.

By 10 months post-injection, AAV5 delivered vector genomes were still detected in right (injected) optic nerve but were absent from both brain hemispheres. AAV8(Y733) vector was injected into the left eyes of GC1KO mice. Accordingly, AAV8(Y733F)-delivered vector genomes were detected in the left optic nerves at both 4 and 7 months post-injection. At no time point were vector genomes in the AAV8(733)-treated mouse detected in either brain hemisphere. A higher average number of vector genomes were detected in optic nerves of eyes injected with AAV5-GRK1-mGC1 compared to AAV5-smCBA-mGC1. This result is likely due to the higher titer of the former ($4.12 \times 10^{13}$ vg/mL) compared to the latter ($4.69 \times 10^{12}$ vg/mL).

In addition, only AAV5-hGRK1-mGC1-delivered genomes were detected in brain tissue over the course of this study, another observation likely due to the relatively high titer of this vector. Despite the fact that the titer of AAV8 (Y733F)-hGRK1-mGC1 vector used ($1.08 \times 10^{13}$ vg/mL) was less than that of the AAV5-hGRK1-mGC1 vector, a higher average number of vector genomes was detected in optic nerves of AAV8(Y733F)-treated eyes. While AAV5 is known to be ineffective for transducing ganglion cells of the mouse retina (Stieger et al., 2008), it was shown that AAV8 does transduce this cell type (Jacobson et al., 2006). Some exposure of vector to retinal ganglion cells is expected as the syringe transverses the inner retina during subretinal injection and because the ratio of injection volume to total eye size is high in mouse. The higher number of vector genomes detected in optic nerves of AAV8(Y733F)-treated eyes therefore could be due to the increased affinity of AAV8 (Y733F), relative to AAV5, for retinal ganglion cells. As expected, no AAV vector genomes were recovered from any tissue of naïve GC1KO control mice.

AAV-mGC1 Treatment Restores Wild-Type Levels of GC1 and GCAP1 to Treated GC1KO Retina At 7 months post-injection with AAV8(Y733F)-hGRK1-mGC1, treated and untreated retinas from one GC1KO mouse as well as one age-matched GC1+/+ control mouse were used to assay levels of GC1 and GCAP1 protein expression. The goal of this experiment was not to compare GC1 levels across treatment groups but rather to compare levels of vector-mediated GC1 expression to levels of GC1 in a wild type animal. Similarly we evaluated the effects of AAV-delivered GC1 on GCAP1 expression. As expected, GC1 protein was absent from the untreated eye of the GC1KO mouse. In contrast, levels of GC1 in the AAV8 (Y733F)-treated eye approached that seen in the normal, GC1+/+ control (FIG. 4). Consistent with previous reports that GCAP1 is post-translationally downregulated in the GC1KO mouse, we show that GCAP1 was downregulated in untreated GC1KO retina relative to the GC1+/+ control (39). However, AAV8(Y733F)-mediated delivery of GC1 leads to an upregulation in GCAP1 expression in the treated GC1KO mouse retina. Levels of GCAP1 expression were also comparable to that seen in GC1+/+ controls.

Figure 24A:
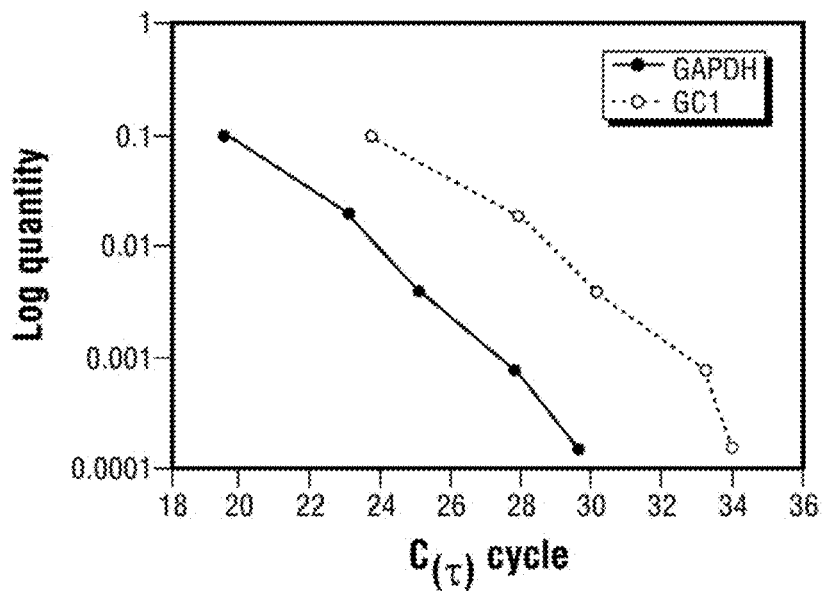
FIG. 24A and FIG. 24B show protein and transcript levels in treated and untreated GC1KO mice and GC1+/+ controls.
Figure 24B:
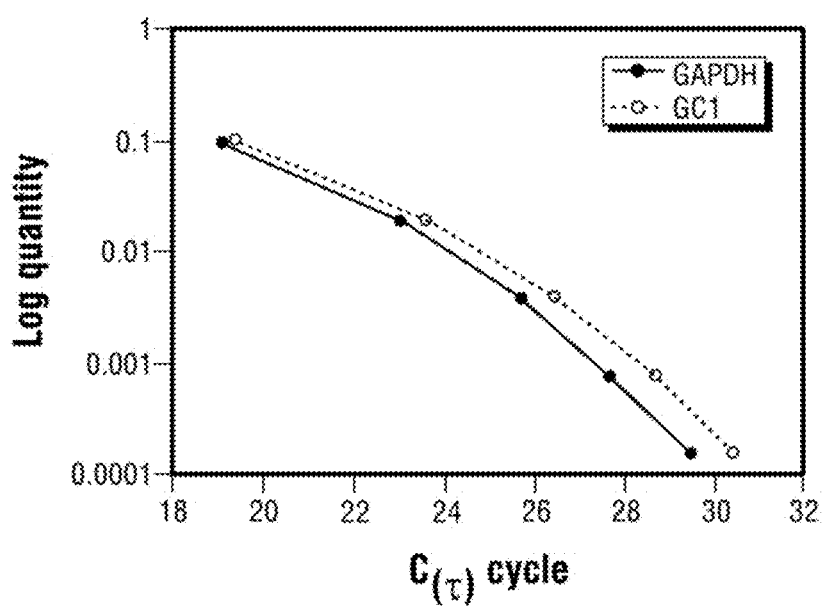

In treated GC1KO mice, GC1 mRNA is present and GNAT2 mRNA levels are increased relative to untreated GC1KO mice. Using a GC1 primer pair that flanks the neomycin gene disruption located within Exon 5 of the GC1KO mouse (Timmers et al., 2001) it was possible to measure GC1 mRNA in both GC1 +/+ and vector-treated GC1KO mice. Interestingly a second GC1 primer pair targeted to exon 18 and 19 of GC1, well downstream of the gene disruption, produced a PCR product in the untreated GC1KO mouse sample and therefore these primers were not used. At one-year post-treatment, levels of GC1 mRNA in treated retinas were approximately seven-fold (AAV5-treated) and 14-fold [AAV8(YY733F)-treated] higher than that seen in the age-matched GC1+/+ control mouse (FIG. 24A and FIG. 24B). By using a nucleic acid recovery technique that enabled homogeneous partitioning of the sample into 2 equal halves, one for RNA extraction and the other for DNA (Pang et al., 2011), albeit was possible to measure mRNA levels and determine the number of vector genomes within the same sample. It was found that high levels of GC1 mRNA in treated retinas corresponded to recovery of many vector genomes; $1.57 \times 10^7$ vector genomes/μg of DNA for AAV8(Y733F) and $4.7 \times 10^6$ vector genomes/μg for AAV5. Despite the high levels of GC1 mRNA in treated retinas, no GC1 expression was detected in optic nerves of treated eyes. This result further supports the notion that vectors evaluated in this study did not result in off-target transgene expression. Consistent with previous reports that the reduction of GCAP1 in GC1KO mice is post-translational (i.e., mRNA levels are unchanged), we found no substantial changes in the levels of GCAP1 mRNA across samples (FIG. 24A and FIG. 24B).

As an initial estimate of treatment on other cone specific RNAs, several other transcripts were also evaluated in these samples. To establish a baseline for levels of cone transducin α (GNAT2), GNAT2 RNA was evaluated in untreated GC1KO samples and found to be reduced relative to GC1+/+ controls, a result likely due to the loss of cone photoreceptors in these retinas (FIG. 24A and FIG. 24B). In contrast, there were appreciable increases GNAT2 mRNA levels in eyes treated with either AAV5 or AAV8(Y733F) vectors, a result which further supports the notion that cone photoreceptors are preserved in AAV-mGC1-treated GC1KO mice. Levels of rod PDE6α were relatively unchanged across samples likely because rod photoreceptors do not degenerate in the GC1KO mouse (FIG. 24A and FIG. 24B).

In conclusion, these studies demonstrate that persistent AAV-mediated GC1 expression is capable of restoring long term retinal function and preserving cone photoreceptors in the GC1KO mouse. Cohorts of AAV5- and AAV8(Y733F)-treated GC1KO mice were evaluated for ERG recovery for 9 months and 6 months post-injection, respectively. While the statistical comparison of cone ERG amplitudes did not continue beyond these time points due to dwindling sample sizes, all treated mice continued to exhibit functional (ERG) rescue. A variety of assays performed on subsets of these remaining mice all show clear indications of continuing therapy. This therapeutic longevity was validated on a number of different levels: 1) the existence of GC1 protein in treated eyes at 10 months post-treatment, 2) the restoration of cone function as measured by ERG at 12 months post-treatment, 3) the increased cone survival in treated eyes at 11 months post-treatment and 4) the recovery of vector genomes and GC1 mRNA in retinas at 12 months post-treatment. When viewed as individual, discrete analyses, the sample sizes used in these assays were often small. However when all are considered as correlates of therapeutic efficacy in mice exhibiting clear signs of functional rescue, the sample size is effectively much larger. Within this context, therefore, it appears that therapy persists beyond the period statistically evaluated for ERG rescue. This is the first demonstration of long-term therapy in an animal model of GC1 deficiency.

Restored cone ERGs were observed in AAV5 and AAV8 (Y733)-treated GC1KO mice for at least 9 months and 6 months post-treatment, respectively. Responses were stable and significantly higher than untreated GC1KO cone responses throughout the course of the study. Recovery was most pronounced in mice treated with AAV8(Y733F) vector. Average cone b-wave amplitudes in AAV8(Y733F)-treated mice were consistently ~20 µV higher than those recorded from GC1KO mice treated with standard AAV5 vectors (55 µV vs. ~35 µV, respectively). At 6 months post-treatment, the latest time point that all vectors were statistically compared, this difference remained significant. This result confirms that an AAV8(Y733F) vector stably restored retinal structure and function to the rd10 mouse, a model refractory to treatment with standard AAV vectors.

Quantifying differences in rod amplitudes between treated and untreated eyes in the GC1KO mouse is complicated by the fact that rod function in this model is partially subserved by guanylate cyclase-2 (GC2) (Sun et al., 2010). Rod ERG responses are therefore variable from animal to animal (30-50% of normal). Therefore, unlike comparisons of treated and untreated cone responses, treated rod responses cannot be compared to a zero baseline. Nevertheless, paired GC eyes have comparable rod ERG amplitudes, and the intra-animal ratio of rod ERGs in partner eyes, one treated and the other untreated, provides a valid metric for evaluating treatment effects on rod function. Improvements in rod-mediated responses in AAV8(Y733F)-treated GC1KO mice were observed more consistently than those recorded from AAV5-treated mice as indicated by comparing the intra-individual ratio of rod a- and b-wave amplitudes from the treated and untreated eye. This suggests that aggressive expression of GC1 in the GC eye can supplement the partial effect of GC2 on murine rod function.

Long-term cone photoreceptor survival (11 months post-injection) was demonstrated by immunostaining treated and untreated retinal whole mounts from one mouse treated with AAV5-smCBA-mGC1 with an antibody directed against cone arrestin. Cones were identified throughout the treated GC retina. AAV5-smCBA-mGC1-treated retina also clearly contained more cones than the untreated eye which, consistent with previous reports, retained only a small fraction of cones in its superior hemisphere (Provost et al., 2005). While the preserved cones in treated GC1KO retina were not examined on an ultrastructural level (e.g., electron microscopy), the observation that cones remained functional over time by ERG analysis suggests that their structure was intact. Long term preservation of cone photoreceptors mediated by therapeutic AAV-GC1 has obvious clinical relevance because it suggests the potential to preserve macular cones and restore usable daytime/color vision to patients with GC1 deficiency.

AAV-mediated GC1 expression persisted for at least 10 months post-treatment (the latest time point evaluated by IHC), and was located exclusively in photoreceptors, regardless of the serotype used or whether a photoreceptor-specific (hGRK1) or ubiquitous (smCBA) promoter drove its expression. While transgene expression was limited to the target cell type, the hGRK1 promoter was more specific in that it resulted in expression exclusively within the proper compartment of the target cell (photoreceptor outer segments). This result, along with other successful proof-of-concept studies utilizing this promoter suggests that the hGRK1 promoter should be considered in the design of a clinical AAV vector targeting photoreceptors.

Immunostaining of transverse GC1KO retinal sections at 10 months post-treatment with AAV5-smcBA-mGC1 revealed moderate thinning of the ONL relative to the wild type and untreated GC1KO controls. Additionally, in this retina GC1 was occasionally found in cell bodies of photoreceptors. It is possible that the strong, ubiquitous smCBA promoter drove expression of GC1 at levels that overwhelmed the trafficking machinery of some photoreceptors and that the accumulation of transgene product in photoreceptor cell bodies constituted a stress-initiated apoptosis in these cells. More dramatic ONL thinning was observed in one mouse injected with AAV5-hGRK1-mGC1. With an n of 1, it cannot be definitively conclude that retinal thinning was present in all mice treated with this vector. Nevertheless, consistent with the notion of overexpression toxicity, the titer of the AAV5-hGRK1-mGC1 vector was the highest of the three vectors evaluated in this study. However, it should also be noted that there was no accumulation of GC1 in photoreceptor cell bodies with the high titer AAV5-hGRK1-mGC1 vector.

Despite the photoreceptor-exclusive nature of AAV-mediated GC1 expression, the inventors were interested in evaluating the spread of vector genomes to tissues outside the subretinal space. Importantly, these data were collected from 'diseased' animals. This is relevant based on evidence that the pattern of vector transduction is different in diseased vs. healthy retina (Kolstad et al., 2010). This would suggest that biodistribution patterns may also be different. For this reason, it was important to evaluate the spread of genomes within the rescued animal model itself (i.e., within subjects that exhibited clear ERG recovery). Although the sample size was limited, useful information was collected about the distribution of AAV5- and AAV8(Y733F)-delivered genomes in optic nerve and brain.

This is the first evaluation of biodistribution for an AAV vector containing a capsid surface exposed tyrosine mutation. AAV5- and AAV8(Y733F)— delivered vector genomes were detected in the optic nerves of injected eyes at all time points assessed. At only one time point (7 months post-injection) were AAV5 vector genomes detected in the brain of a treated GC1KO mouse. Genomes were recovered only in the hemisphere opposite the injected eye. This result contrasts the finding by Provost et al., 2005 who reported a lack of AAV5-delivered sequence in brains of subretinally-injected rats and dogs. By 10 months post-injection, no vector genomes were recovered from brains of AAV5-treated GC1KO mice nor from brains of mice treated with AAV8(Y733F) at any time point. However, due to the relatively small number of mice analyzed, it cannot unequivocally be excluded that AAV5-delivered genomes were present in brains at 10 months post-injection or that AAV8(Y733F) delivered genomes are never present in brains of treated GC1KO mice at any time.

Despite recovering vector genomes from optic nerves of treated eyes, immunostaining revealed a lack of GC1 expression in optic nerves of eyes treated with either AAV5-smCBA-mGC1 or AAV8(Y733F)-hGRK1-mGC1 vectors. A previous study by Stieger, et al., (2005) detected transgene expression in optic nerves and brains of rats and dogs at 2 months and 4 weeks post-subretinal injection with AAV8 containing green fluorescent protein (GFP). Taking into account that the AAV8(Y733F) vector contained the photoreceptor-specific hGRK1 promoter and the previous finding that GC1 expression was limited to photoreceptors even when under the control of a ubiquitous promoter like smCBA, a lack of GC1 expression in optic nerves is not unexpected. Stieger et al., (2005) incorporated the strong, ubiquitous CMV promoter into their vector to drive GFP, a protein which is capable of being stably expressed in a wide variety of tissues when delivered via viral vectors.

While both AAV5 and AAV8(Y733F) vectors were capable of providing long term therapy to the GC1KO mouse, there are apparent advantages associated with using AAV8(Y733F). First and foremost, AAV8(Y733F) with a photoreceptor-specific promoter conferred significantly higher cone ERG responses to treated mice than either AAV5 vector. The reason for this may be due to the ability of AAV8 vectors to transduce areas outside of the injection bleb in rodent retina whereas the area of retina transduced by AAV5 remains largely confined to the bleb (47). Thus, AAV8(733F) may simply transduce on average a larger area of retina relative to AAV5 vectors and in turn result in more cone transduction and a robust full-field cone ERG response, through either or both an increased overall cone survival and/or an increased level of light response in each transduced cone.

Example 8—Exemplary Mammalian GC1 Polypeptide Sequences

Exemplary amino acid sequences useful in the practice of the present invention include, without limitation, one or more amino acid sequences that encode a biologically-active mammalian guanylate cyclase protein. Such sequences include, without limitation, those of human, non-human primate, murine, bovine, and canine origin, such as those guanylate cyclase proteins set forth in SEQ ID NO:1, SEQ ID NO:2, SEQ ID NO:4, SEQ ID NO:5, SEQ ID NO:6, SEQ ID NO:7, SEQ ID NO:8, SEQ ID NO:9, SEQ ID NO:10 and SEQ ID NO:11, hereinbelow:

```
Homo sapiens (human; GenPept Accession Number: NP 000171)
                                                      (SEQ ID NO: 1)
MTACARRAGGLPDPGLCGPAWWAPSLPRLPRALPRLPLLLLLLLLQPPALSAVFTVGVLGPWACDP

IFSRARPDLAARLAAARLNRDPGLAGGPRFEVALLPEPCRTPGSLGAVSSALARVSGLVGPVNPAA

CRPAELLAEEAGIALVPWGCPWTQAEGTTAPAVTPAADALYALLRAFGWARVALVTAPQDLWVEAG

RSLSTALRARGLPVASVTSMEPLDLSGAREALRKVRDGPRVTAVIMVMHSVLLGGEEQRYLLEAAE

ELGLTDGSLVFLPFDTIHYALSPGPEALAALANSSQLRRAHDAVLTLTRHCPSEGSVLDSLRRAQE

RRELPSDLNLQQVSPLFGTIYDAVFLLARGVAEARAAAGGRWVSGAAVARHIRDAQVPGFCGDLGG

DEEPPFVLLDTDAAGDRLFATYMLDPARGSFLSAGTRMHFPRGGSAPGPDPSCWFDPNNICGGGLE

PGLVFLGFLLVVGMGLAGAFLAHYVRHRLLHMQMVSGPNKIILTVDDITFLHPHGGTSRKVAQGSR

SSLGARSMSDIRSGPSQHLDSPNIGVYEGDRVWLKKFPGDQHIAIRPATKTAFSKLQELRHENVAL

YLGLFLARGAEGPAALWEGNLAVVSEHCTRGSLQDLLAQREIKLDWMFKSSLLLDLIKGIRYLHHR

GVAHGRLKSRNCIVDGRFVLKITDHGHGRLLEAQKVLPEPPRAEDQLWTAPELLRDPALERRGTLA

GDVFSLAIIMQEVVCRSAPYAMLELTPEEVVQRVRSPPPLCRPLVSMDQAPVECILLMKQCWAEQP

ELRPSMDHTFDLFKNINKGRKTNIIDSMLRMLEQYSSNLEDLIRERTEELELEKQKTDRLLTQMLP

PSVAEALKTGTPVEPEYFEQVTLYFSDIVGFTTISAMSEPIEVVDLLNDLYTLFDAIIGSHDVYKV

ETIGDAYMVASGLPQRNGQRHAAEIANMSLDILSAVGTFRMRHMPEVPVRIRIGLHSGPCVAGVVG

LTMPRYCLFGDTVNTASRMESTGLPYRIHVNLSTVGILRALDSGYQVELRGRTELKGKAEDTFWL

VGRRGFNKPIPKPPDLQPGSSNHGISLQEIPPERRRKLEKARPGQFS

Mus musculus (mouse; GenPept Accession Number: NP 032218)
                                                      (SEQ ID NO: 2)
MSAWLLPAGGLPGAGFCVPARQSPSSFSRVLRWPRPGLPGLLLLLLLPSPSALSAVFKVGVLGPWA

CDPIFARARPDLAARLAANRLNRDFALDGGPRFEVALLPEPCLTPGSLGAVSSALSRVSGLVGPVN

PAACRPAELLAQEAGVALVPWGCPGTRAAGTTAPAVTPAADALYVLLRAFRWARVALITAPQDLWV

EAGRALSTALRARGLPVALVTSMETSDRSGAREALGRIRDGPRVRVVIMVMHSVLLGGEEQRYLLE

AAEELALTDGSLVFLPFDTLHYALSPGPEALAAFVNSSQLRRAHDAVLTLTRRCPPGGSVQDSLRR

AQEHQELPLDLNLKQVSPLFGTIYDAVFLLAGGVKRARTAVGGGWVSGASVARQVREAQVSGFCGV

LGRTEEPSFVLLDTDASGEQLFATHLLDPVLGSLRSAGTPMHFPRGGPAPGPDPSCWFDPDVICNG

GVEPGLVFVGFLLVIGMGLTGAFLAHYLRHRLLHMQMASGPNKIILTLEDVTFLHPPGGSSRKVVQ

GSRSSLATRSASDIRSVPSQPQESTNVGLYEGDWVWLKKFPGEHHMAIRPATKTAFSKLRELRHEN

VALYLGLFLAGTADSPATPGEGILAVVSEHCARGSLHDLLAQREIKLDWMFKSSLLLDLIKGMRYL
```

-continued

HHRGVAHGRLKSRNCVVDGRFVLKVTDHGHGRLLEAQRVLPEPPSAEDQLWTAPELLRDPSLERRG

TLAGDVFSLAIIMQEVVCRSTPYAMLELTPEEVIQRVRSPPPLCRPLVSMDQAPMECIQLMTQCWA

EHPELRPSMDLTFDLFKSINKGRKTNIIDSMLRMLEQYSSNLEDLIRERTEELEQEKQKTDRLLTQ

MLPPSVAEALKMGTSVEPEYFEEVTLYFSDIVGFTTISAMSEPIEVVDLLNDLYTLFDAIIGAHDV

YKVETIGDAYMVASGLPQRNGQRHAAEIANMSLDILSAVGSFRMRHMPEVPVRIRIGLHSGPCVAG

VVGLTMPRYCLFGDTVNTASRMESTGLPYRIHVNMSTVRILRALDQGFQMECRGRTELKGKGIEDT

YWLVGRLGFNKPIPKPPDLQPGASNHGISLQEIPPERRKKLEKARPGQFTGK

*Rattus norvegicus* (Norway rat; GenPept Accession Number: NP 077356)
(SEQ ID NO: 3)
MSAWLLPAGGFPGAGFCIPAWQSRSSLSRVLRWPGPGLPGLLLLLLLPSPSAFSAVFKVGVLGPWA

CDPIFARARPDLAARLATDRLNRDLALDGGPWFEVTLLPEPCLTPGSLGAVSSALTRVSGLVGPVN

PAACRPAELLAQEAGVALVPWGCPGTRAAGTTAPAVTPAADALYVLLKAFRWARVALITAPQDLWV

EAGRALSTALRARGLPVALVTSMVPSDLSGAREALRRIRDGPRVRVVIMVMHSVLLGGEEQRYLLE

AAEELGLTDGSLVFLPFDTLHYALSPGPEALAAFVNSSKLRRAHDAVLTLTRRCPPGGSVQDSLRR

AQEHQELPLDLDLKQVSPLFGTIYDAVFLLAGGVTRARAAVGGGWVSGASVARQMREAQVFGFCGI

LGRTEEPSFVLLDTDAAGERLFTTHLLDPVLGSLRSAGTPVHFPRGAPAPGPDPSCWFDPDVICNG

GVEPGLVFVGFLLVIVVGLTGAFLAHYLRHRLLHMQMVSGPNKIILTLEDVTFLHPQGGSSRKVAQ

GSRSSLATRSTSDIRSVPSQPQESTNIGLYEGDWVWLKKFPGEHHMAIRPATKMAFSKLRELRHEN

VALYLGLFLAGTADSPATPGEGILAVVSEHCARGSLHDLLAQRDIKLDWMFKSSLLLDLIKGMRYL

HHRGVAHGRLKSRNCVVDGRFVLKVTDHGHGRLLEAQRVLPEPPSAEDQLWTAPELLRDPALERRG

TLAGDVFSLGIIMQEVVCRSTPYAMLELTPEEVIQRVRSPPPLCRPLVSMDQAPMECIQLMAQCWA

EHPELRPSMDLTFDLFKGINKGRKTNIIDSMLRMLEQYSSNLEDLIRERTEELEQEKQKTDRLLTQ

MLPPSVAEALKMGTSVEPEYFEEVTLYFSDIVGFTTISAMSEPIEVVDLLNDLYTLFDAIIGSHDV

YKVETIGDAYMVASGLPQRNGQRHAAEIANMSLDILSAVGSFRMRHMPEVPVRIRIGLHSGPCVAG

VVGLTMPRYCLFGDTVNTASRMESTGLPYRIHVNMSTVRILRALDQGFQMECRGRTELKGKGVEDT

YWLVGRVGFNKPIPKPPDLQPGASNHGISLQEIPPERRKKLEKARPGQFTGK

*Bos taurus* GC1 (bovine; GenPept Accession Number: NP 776973)
(SEQ ID NO: 4)
MTACTFLAGGLRDPGLCAPTRWSPSPPGLPPIPPRPRLRLRPPLLLLLLLPRSVLSAVFTVGVLGP

WACDPIFARARPDLAARLAASRLNHAAALEGGPRFEVALLPEPCRTPGSLGAVSSALTRVSGLVGP

VNPAACRPAELLAQEAGVALVPWGCPGTRAAGTTAPVVTPAADALYALLRAFRWAHVALVTAPQDL

WVEAGHALSTALRARGLPVALVTSMEPSDLSGAREALRRVQDGPRVRAVIMVMHSVLLGGEEQRCL

LEAAEELGLADGSLVFLPFDTLHYALSPGPDALAVLANSSQLRKAHDAVLTLTRHCPLGGSVRDSL

RRAQEHRELPLDLNLQQVSPLFGTIYDSVFLLAGGVARARVAAGGGWVSGAAVARHIRDARVPGFC

GALGGAEEPSFVLLDTDATGDQLFATYVLDPTQGFFHSAGTPVHFPKGGRGPGPDPSCWFDPDTIC

NGGVEPSVVFIGFLLVVGMGLAGAFLAHYCRHRLLHIQMVSGPNKIILTLDDITFLHPHGGNSRKV

AQGSRTSLAARSISDVRSIHSQLPDYTNIGLYEGDWVWLKKFPGDRHIAIRPATKMAFSKIRELRH

ENVALYLGLFLAGGAGGPAAPGEGVLAVVSEHCARGSLQDLLAQRDIKLDWMFKSSLLLDLIKGIR

YLHHRGVAHGRLKSRNCVVDGRFVLKVTDHGHGRLLEAQRVLPEPPSAEDQLWTAPELLRDPVLER

RGTLAGDVFSLGIIMQEVVCRSAPYAMLELTPEEVVKRVQSPPPLCRPSVSIDQAPMECIQLMKQC

WAEQPELRPSMDRTFELFKSINKGRKMNIIDSMLRMLEQYSSNLEDLIRERTEELELEKQKTDRLL

TQMLPPSVAEALKMGTPVEPEYFEEVTLYFSDIVGFTTISAMSEPIEVVDLLNDLYTLFDAIIGSH

DVYKVETIGDAYMVASGLPQRNGHRHAAEIANMALDILSAVGTFRMRHMPEVPVRIRIGLHSGPCV

-continued

AGVVGLTMPRYCLFGDTVNTASRMESTGLPYRIHVNRSTVQILSALNEGFLTEVRGRTELKGKGAE

ETYWLVGRRGFNKPIPKPPDLQPGASNHGISLHEIPPDRRQKLEKARPGQFSGK

*Canis lupus familiaris* (canine; GenPept Accession Number:
NP 001003207)

(SEQ ID NO: 5)

MSACALLAGGLPDPRLCAPARWARSPPGVPGAPPWPQPRLRLLLLLLLPPSALSAVFTVGVLGPW

ACDPIFARARPDLAARLAAARLNRDAALEDGPRFEVTLLPEPCRTPGSLGAVSSALGRVSGLVGPV

NPAACRPAELLAQEAGVALVPWSCPGTRAGGTTAPAGTPAADALYALLRAFRWARVALITAPQDLW

VEAGRALSAALRARGLPVALVTTMEPSDLSGAREALRRVQDGPRVRAVIMVMHSVLLGGEEQRCLL

QAAEELGLADGSLVFLPFDTLHYALSPGPEALAVLANSSQLRRAHDAVLILTRHCPPGGSVMDNLR

RAQEHQELPSDLDLQQVSPFFGTIYDAVLLLAGGVARARAAAGGGWVSGATVAHHIPDAQVPGFCG

TLGGAQEPPFVLLDTDAAGDRLFATYMLDPTRGSLLSAGTPVHFPRGGGTPGSDPSCWFEPGVICN

GGVEPGLVFLGFLLVVGMGLTGAFLAHYLRHRLLHIQMVSGPNKIILTLDDVTFLHPHGGSTRKVV

QGSRSSLAARSTSDIRSVPSQPLDNSNIGLFEGDWVWLKKFPGDQHIAIRPATKTAFSKLRELRHE

NVVLYLGLFLGSGGAGGSAAGEGVLAVVSEHCARGSLHDLLAQRDIKLDWMFKSSLLLDLIKGMRY

LHHRGVAHGRLKSRNCVVDGRFVLKVTDHGHARLMEAQRVLLEPPSAEDQLWTAPELLRDPALERR

GTLPGDVFSLGIIMQEVVCRSAPYAMLELTPEEVVERVRSPPPLCRPSVSMDQAPVECIQLMKQCW

AEHPDLRPSLGHIFDQFKSINKGRKTNIIDSMLRMLEQYSSNLEDLIRERTEELELEKQKTDRLLT

QMLPPSVAEALKMGTPVEPEYFEEVTLYFSDIVGFTTISAMSEPIEVVDLLNDLYTLFDAIIGSHD

VYKVETIGDAYMVASGLPQRNGQRHAAEIANMALDILSAVGSFRMRHMPEVPVRIRIGLHSGPCVA

GVVGLTMPRYCLFGDTVNTASRMESTGLPYRIHVNMSTVRILHALDEGFQTEVRGRTELKGKGAED

TYWLVGRRGFNKPIPKPPDLQPGASNHGISLQEIPLDRRWKLEKARPGQFSGK

*Macaca mulatta* (Rhesus macaque; predicted sequence from
XP 001111670)

(SEQ ID NO: 6)

MTACARRAGGLPDPRLCGPARWAPALPRLPRALPRLPLLLLLLLLQPPALSAVFTVGVLGPWACDP

IFSRARADLAARLAAARLNRDPDLAGGPRFEVALLPEPCRTPGSLGAVSSALTRVSGLVGPVNPAA

CRPAELLAEEAGIALVPWGCPGTQAAGTTAPALTPAADALYALLRAFGWARVALVTAPQDLWVEAG

HSLSTALRARGLPVASVTSMEPLDLSGAREALRKVRDGPRVTAVIMVMHSVLLGGEEQRYLLEAAE

ELGLTDGSLVFLPFDTVHYALSPGPEALAALANSSQLRRARDAVLTLTRHCPSEGSVLDSLRRAQE

RRELPSDLNLQQVSPLFGTIYDAVFLLVRGVAEARAAAGGRWVSGAAVARHVWDAQVPGFCGDLGG

DEEPPFVLLDTDAVGDRLFATYMLDPTRGSLLSAGTPMHFPRGGSAPGPDPSCWFDPNNICGGGLE

PGLVFLGFLLVVGMGLAGAFLAHYVRHQLLHIQMVSGPNKIILTVDDITFLHPHGGTSRKVAQGSR

SSLAARSMSDVRSGPSQPTDSPNVGVYEGDRVWLKKFPGDQHIAIRPATKTAFSKLQELRHENVAL

YLGLFLAQGAEGPAALWEGNLAVVSEHCTRGSLQDLLAQREIKLDWMFKSSLLLDLIKGIRYLHHR

GVAHGRLKSRNCIVDGRFVLKITDHGHGRLLEAQKVLPEPPRAEDQLWTAPELLRDPALERRGTLA

GDVFSLAIIMQEVVCRSAPYAMLELTPEEVVQRVRSPPPLCRPLVSMDQAPVECIHLMKQCWAEQP

ELRPSMDHTFDLFKNINKGRKTNIIDSMLRMLEQYSSNLEDLIRERTEELELEKQKTDRLLTQMLP

PSVAEALKTGTPVEPEYFEQVTLYFSDIVGFTTISAMSEPIEVVDLLNDLYTLFDAIIGSHDVYKV

ETIGDAYMVASGLPQRNGQRHAAEIANMSLDILSAVGTFRMRHMPEVPVRIRIGLHSGPCVAGVVG

LTMPRYCLFGDTVNTASRMESTGLPYRIHVNLSTVGILRALDSGYQVELRGRTELKGKGAEDTFWL

VGRRGFNKPIPKPPDLQPGSSNHGISLQEIPPERRRKLEKARPGQFS.

*Pongo abelii* (Sumatran Orangutan; predicted sequence from XP_002827037)

(SEQ ID NO: 7)

MTACARRAGGLPDPGLCGPARWAPSLPRLPRALPRLPLLLLLLLQPPALSAVFTVGVLG

PWACDPIFSRARPDLAARLAAARLNRDPGLAGGPRFEVALLPEPCRTPGSLGAVSSALAR

VSGLVGPVNPAACRPAELLADNPGIALVPWGCPWTQAEGTTAPCVTPAADALYALLRAFG

WARVALVTAPQDLWVEAGRSLSTALRARGLPVASVTSMEPLDLSGAREALRKVRDGPRVT

AVIMVMHSVLLGGEEQRYLLEAAEELGLTDGSLVFLPFDTIHYALSPGPEALAALANSSQ

LRRAHDAVLTLTRHCPSEGSVLDSLRRAQERRELPSDLNLQQVSPLFGTIYDAVFLLARG

VAEAWAAAGGRWVSGAAVARHIRDAQVPGFCGDLGGDEPPFVLLDTAAGDRLFATYML

DPARGSFLSAGTRMHFPRGGSAPGPDPSCWFDPNNICGGGLEPGLVFLGFLLVVGMGLAG

AFLAHYVRHRLLHIQMVSGPNKIILTVNDITFLHPHGGTSRKVAQGSRSSLAARSMSDIR

SGPSQPLDSPNVGVYEGDRVWLKKFPGDQHIAIRPATKTAFSKLQELRHENVALYLGLFL

ARGAEGPAALWEGNLAVVSEHCTRGSLQDLLSQREIKLDWMFKSSLLLDLIKGIRYLHHR

GVAHGRLKSRNCIVDGRFVLKITDHGHGRLLEAQKVLPEPPRAEDQLWTAPELLRDPALE

RRGTLAGDVFSLAIIMQEVVCRSAPYAMLELTPEEVVQRVRSPPPLCRPLVSMDQAPVEC

IHLMKQCWAEQPELRPSMDHTFDLFKNINKGRKTNIIDSMLRMLEQYSSNLEDLIRERTE

ELELEKQKTDRLLTQMLPPSVAEALKTGTPVEPEYFEQVTLYFSDIVGFTTISAMSEPIE

VVDLLNDLYTLFDAIIGSHDVYKVETIGDAYMVASGLPQRNGQRHAAEIANMSLDILSAV

GTFRMRHMPEVPVRIRIGLHSGPCVAGVVGLTMPRYCLFGDTVNTASRMESTGLPYRIHV

NLSTVGILRALDSGYQVELRGRTELKGKGAEDTFWLVGRRGFNKPIPKPPDLQPGSSNHG

ISLQEIPPERRRKLEKARPGQFS

*Callithrix jacchus* (white tufted-ear marmoset; predicted sequence from XP_002747985)

(SEQ ID NO: 8)

MTACARRAGGLPDPGLCGPARWAPALSRLPRALPRLPLLLLLLLQPPALSAQFTVGVLG

PWACDPIFSRARPDLAARLAAARLNRDPSLAGGPRFEVALLPEPCRTPGSLGAVSSALAR

VSGLVGPVNPAACRPAELLAEEAGIALVPWGCPGTQAAGTTAPVVTPAADALYALLRAFG

WARVALVTAPQDLWVEAGLSLSTALRARGLPVVSVTSMEPLDLSGAREALRKVRNGPRVT

AVIMVMHSVLLGGEEQRYLLEAAEELGLTDGSLVFLPFDTIHYALSPGREALAALVNSSQ

LRRAHDAVLTLTRHCSSEGSVLDSLRKAQQRRELPSDLNLEQVSPLFGTIYDAVVLLARG

VADARAAVGGRWVSGAAVARHVWDAQASGFCGDLGRDEEPSFVLLDTAAGDQLFATYML

DPARGSLLSAGTPMHFPRGGPAPGPDPSCWFDPNNICDGGLEPGFIFLGFLLVVGMGLAG

ALLAHYVRHQLLHIQMVSGPNKIILTVDDITFLHPHGGASRKVAQGSRSSLAAHSTSDIR

SGPSQPSDSPNIGVYEGDRVWLKKFPGEQHIAIRPATKTAFSKLQELRHENVALYLGLFL

AQGAEGPAALWEGNLAVVSEHCTRGSLQDLLAQREIKLDWMFKSSLLLDLIKGIRYLHHR

GVAHGRLKSRNCIVDGRFVLKITDHGHGRLLEAQKVLPEPPKAEDQLWTAPELLRDPALE

RRGTLAGDVFSLGIIMQEVVCRSAPYAMLELTPDEVVQRVRSPPPLCRPFVSMDQAPVEC

IHLMKQCWAEQPELRPSMDLTFDLFKNINKGRKTNIIDSMLRMLEQYSSNLEDLIRERTE

ELELEKQKTDRLLTQMLPPSVAEALKTGTPVEPEYFEQVTLYFSDIVGFTTISAMSEPIE

VVDLLNDLYTLFDAIIGSHDVYKVETIGDAYMVASGLPQRNGQRHAAEIANMSLDILSAV

```
GTFRMRHMPEVPVRIRIGLHSGPCVAGVVGLTMPRYCLFGDTVNTASRMESTGLPYRIHV

NLSTVGILRALDSGYQVELRGRTELKGKGAEDTFWLVGRRGFNKPIPKPPDLQPGASNHG

ISLQEIPPERRRKLEKARPGQFS
```

Ailuropoda melanoleuca (giant panda; predicted sequence from XP_002921218)

(SEQ ID NO: 9)

```
MRACALLAGGLPYPRLCAPTRWAPARPGVSRALPWPRPRLRLLLLLLLRPPSVLSAVFTV

GVLGPWACDPIFARARPDLXXXXXXXXXXDALYVLLRAFRWARVALVTAPQDLWVEAGRAL

SAALRARGLPVALVTTMEPSDLSGAREALRRVQHGPRVSAVIMVMHSVLLGGEEQRCLLQ

AAEELGLADGSLVFLPFDTLHYALSPGPEALAALANSSQLRRAHDAVLTLTRHCPPGGSV

MDSLRRAQERQELPSDLNLEQVSPLFGTIYDAVFLLAGGVARARAAAADSRVPGFCGALG

GAEEPPFVLLDTDAAGDRFFATYVLDPTRGSLHSAGTPVHFPRGGGAPGPDPSCWFEPDS

ICNGGVEPGLVFTGFLLVVGMGLMGAFLAHYVRHRLLHIQMVSGPNKIILTLDDITFLHP

QGGSARKVVQGSRSSLAARSTSDVRSVPSQPSDGGNIGLYEGDWVWLKKFPGSQHIAIRP

ATKTAFSKLRELRHENVALYLGLFLGGGEGGSAAAGGGMLAVVSEHCTRGSLHDLLAQRD

IKLDWMFKSSLLLDLIKGMRYLHHRGVAHGRLKSRNCVVDGRFVLKVTDHGHGRLLEAQK

VLAEPPSAEDQLWTAPELLRDPALERRGTLAGDVFSLGIIMQEVVCRSSPYAMLELSARE

VVQRVRSPPPLCRPSVSVDQAPAECIQLMKQCWAEQPELRPSLDRTFDQFKSINKGRKTN

IIDSMLRMLEQYSSNLEGLIRERTEELELEKRKTDRLRAASLPSSVAEALKMGTPVEPEY

FEEVTLYFSDIVGFTTISAMSEPIEVVDLLNDLYTLFDAIIGSHDVYKVETIGDAYMVAS

GLPQRNGQRHAAEIANMALDILSAVGSFRMRHMPEVPVRIRIGLHSGPCVAGVVGLTMPR

YCLFGDTVNTASRMESTGLPYRIHVNMSTVRILRALDEGFQTEVRGRTELKGKGAEDTYW

LVGXXXXXXXXXPIPKPPDLQPGASNHGISLQEIPLDRRQKLEKARPGQFSGK
```

Monodelphis domestica (gray short-tailed opossum; predicted sequence from XP_001369029)

(SEQ ID NO: 10)

```
MLVPSINGLFHHPPWCFPPLPLPLFFLFLLLLLPVPVLPATFTIGVLGPWSCDPIFSRAR

PDLAARLAATRMNHDQALEGGPWFEVILLPEPCRTSGSLGALSPSLARVSGLVGPVNPAA

CHPAELLAQEAGVPLVPWGCPQGKARTTAPALPLALDALYALLRAFHWAKVALITAPQDL

WVEAGQALAGGLRSRGLPVAMVTSLETTDLESAKNALKRVRDGPKVKVLIMVMHSVLLGG

EEQRLLLEAAEELGLVEGTMVFLPFDTLHYALPPGPEALRPITNSSRLRKAHDAVLTLTR

YCPKGSVSASLRQAQEHRELPLDLKPQQVSPLFGTIYDAIYLLAGAVAGAQVAGGGGWVS

GAAVARHIPNTLVSGFCGDLGGTKEPPFVLLDTDGMRDQLLPTYTLDPAQGVLHHAGNPI

HFPHGGQGPGPDPPCWFDPNVICSGGIEPRFILLVILIIIGGGLVVATLAYYVRRQLLHA

QMVSGPNKMILTLEDITFFPRQGSSSRKATEGSRSSLIAHSASDMRSIPSQPPDNSNIGM

YEGDWVWLKKFPGEHYTEIRPATKMAFSKLRELRHENVAVQMGLFLAGSMEGAAAGGLGG

GILAVVSEYCSRGSLQDLLIQRDIKLDWMFKSSLLLDLIKGLRYLHHRGVAHGRLKSRNC

VVDGRFVLKITDRAHGRLLEAQRVSLEPPQAEDRLWTAPELLRNEALERQGTLQGDVFSV

GIIMQEVVCRCEPYAMLELTPEEIIQKVQSPPPMCRPSVSVDQAPMECIQLMKQCWAEQP

DLRPNMDTTFDLFKNINKGRKTNIIDSMLRMLEQYSSNLEDLIRERTEELELEKQKTDKL
```

-continued

LTQMLPPSVAEALKLGIPVEPEYFEEVTLYFSDIVGFTTISAMSEPIEVVDLLNDLYTLF

DAIIGSHDVYKVETIGDAYMVASGLPKRNGQRHAAEIANMSLDILSSVGSFRMRHMPEVP

VRIRIGLHSGPCVAGVVGLTMPRYCLFGDTVNTASRMESTGLPYRIHVNLSTVKILQGLN

EGFQIEIRGRTELKGKGVEDTYWLVGRKGFDKPIPIPPDLLPGASNHGISLQEIPEDRRK

KLEKARPGQPLGK

*Equus caballus* (horse; predicted sequence from XP_001918412)
(SEQ ID NO: 11)

MVMHSVLLGGEEQRCLLEAAEELGLADGSLVFLPFDTLHYALSPGPEALAVLANNSQLRR

AHDAVLTLTRHCPLGGSVLDSLRRAQEHQELPSDLNLQQVSPLFGTIYDAVYLLAGGVAR

ARAAAGGSWVSGAAVAHHVRDAQVPGFCGALGGAEEPQFVLLDTDAAGDRLFATYMLDPT

RGSLWSAGTPVHFPRGGRGPGPDPWCWFDPDDICNGGVEPRLVFIGFLLAVGMGLAGVFL

AHYVRHRLLHIQMASGPNKIILTLDDITFLHPQGGSSRKVIQGSRSSLAARSVSDIRSVP

SQPMDSSNIGLYEGDWVWLKKFPGDQHIAIRPATKTAFSKLRELRHENVALYLGLFLAGG

SSGAAAPREGMLAVVSEHCARGSLHDLLAQRDIKLDWMFKSSLLLDLIKGMRYLHHRGVA

HGRLKSRNCVVDGRFVLKVTDHGHGRLLEAQKVLPEPPSAEDQLWTAPELLRDPALERQG

TLAGDVFSLGIIIQEVVCRSTPYAMLELTPEEVVQRLQSPPPLCRPSVSMDQAPMECIQL

MKQCWAEQPDLRPSMDRTFDLFKSINKGRKTNIIDSMLRMLEQYSSNLEDLIRERTEELE

LEKQKTDRLLTQMLPPSVAEALKMGTPVEPEYFEEVTLYFSDIVGFTTISAMSEPIEVVD

LLNDLYTLFDAIIGSHDVYKVETIGDAYMVASGLPQRNGQRHAAEIANMALDILSAVGSF

RMRHMPEVPVRIRIGLHSGPCVAGVVGLTMPRYCLFGDTVNTASRMESTGLPYRIHVNMS

TVRILRALDEGFQVEVRGRTELKGKGVEDTYWLVGRRGFNKPIPKPPDLQPGASNHGISL

QEIPPERRQKLEKARPGQFSGK

Example 9—Sequence Analysis of Known Mammalian GC1 Polypeptides

All GC1 alignment data generated using amino acid sequence for the following species: *Bos taurus* (bovine; 1110 residues), *Canis lupus familiaris* (canine; 1109 residues), *Mus musculus* (murine; 1108 residues), and *Homo sapiens* (human; 1103 residues). Positions of consensus and variable regions are based on numerical residues corresponding to *Bos taurus* as this is the longest GC1 protein, 1110 residues, and has no gaps in the alignment.

Figure 25:
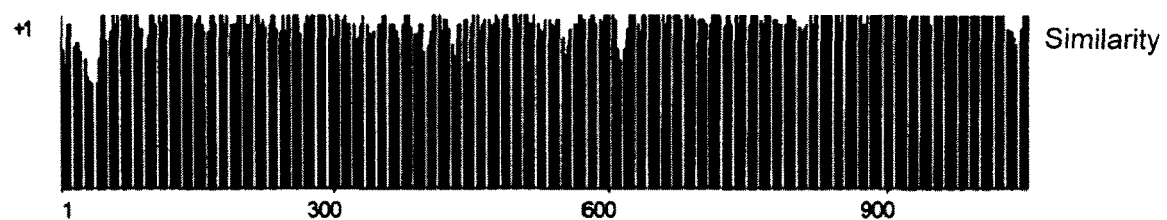
FIG. 25 shows a similarity graph of alignment of GC1 proteins from *Bos taurus, Canis lupus familiaris, Mus musculus,* and *Homo sapiens*.

A similarity graph of alignment of GC1 proteins from *Bos taurus, Canis lupus familiaris, Mus musculus,* and *Homo sapiens* is shown in FIG. 25.

GC1 Consensus Regions:

Amino acid positions: 44-49, 55-90, 98-155, 164-321, 464-549, 561-604, 620-761, 813-1026, 1045-1054, and 1060-1110.

Variable Regions:

Amino acid positions: 4-43, 50-54, 91-97, 156-163, 322-463, 550-560, 605-619, 762-812, 1027-1044, and 1055-1059.

Other notable regions of the GC1 consensus alignment include:

(1) Kinase homology domain: amino acid positions 531 to 541 of the consensus sequence (known to be essential for activity in photoreceptors—see, e.g., Bereta et al., 2010).

(2) Phosphorylated serine residues within the kinase homology domain of murine GC1 protein (consensus/bovine position shown in parenthesis): 530 (532), 532 (534), 533 (535) and 538(540).

Example 10—Nucleotide Sequence of the smCBA Promoter

The nucleic acid sequence of an illustrative human GRK1 (hGRK1) promoter which was used in the studies described above is shown below:

(SEQ ID NO: 12)

GGGCCCCAGAAGCCTGGTGGTTGTTTGTCCTTCTCAGGGGAAAAGTGAGGCGGCCCCTTGGAGGAAGG

GGCCGGGCAGAATGATCTAATCGGATTCCAAGCAGCTCAGGGGATTGTCTTTTTCTAGCACCTTCTTG

CCACTCCTAAGCGTCCTCCGTGACCCCGGCTGGGATTTAGCCTGGTGCTGTGTCAGCCCCGGTCTCCC

AGGGGCTTCCCAGTGGTCCCCAGGAACCCTCGACAGGGCCCGGTCTCTCTCGTCCAGCAAGGGCAGGG

ACGGGCCACAGGCCAAGGGC

The nucleic acid sequence of an illustrative smCBA promoter which was used in the studies described above is shown below:

(SEQ ID NO: 13)
```
AATTCGGTACCCTAGTTATTAATAGTAATCAATTACGGGGTCATTAGTTCATAGCCCATATATGGA
GTTCCGCGTTACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACGTCAATGGGT
GGACTATTTACGGTAAACTGCCCACTTGGCAGTACATCAAGTGTATCATATGCCAAGTACGCCCCC
TATTGACGTCAATGACGGTAAATGGCCCGCCTGGCATTATGCCCAGTACATGACCTTATGGGACTT
TCCTACTTGGCAGTACATCTACGTATTAGTCATCGCTATTACCATGGTCGAGGTGAGCCCCACGTT
CTGCTTCACTCTCCCCATCTCCCCCCCCTCCCCACCCCCAATTTTGTATTTATTTATTTTTTAATT
ATTTTGTGCAGCGATGGGGCGGGGGGGGGGGGGGCGCGCGCCAGGCGGGGCGGGGCGGGGCGA
GGGGCGGGGCGGGGCGAGGCGGAGAGGTGCGGCGGCAGCCAATCAGAGCGGCGCGCTCCGAAAGTT
TCCTTTTATGGCGAGGCGGCGGCGGCGGCGGCCCTATAAAAAGCGAAGCGCGCGGCGGGCGGGAGT
CGCTGCGACGCTGCCTTCGCCCCGTGCCCCGCTCCGCCGCCGCCTCGCGCCGCCCGCCCCGGCTCT
GACTGACCGCGTTACTCCCACAGGTGAGCGGGCGGGACGGCCCTTCTCCTCCGGGCTGTAATTAGC
GCTTGGTTTAATGACGGCTTGTTTCTTTTCTGTGGCTGCGTGAAAGCCTTGAGGGGCTCCGGGAGC
TAGAGCCTCTGCTAACCATGTTCATGCCTTCTTCTTTTTCCTACAGCTCCTGGGCAACGTGCTGGT
TATTGTGCTGTCTCATCATTTTGGCAAAG
```

REFERENCES

The following references, to the extent that they provide exemplary procedural or other details supplementary to those set forth herein, are specifically incorporated herein by reference.

U.S. Pat. No. 4,237,224, issued Dec. 2, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,883,750, issued Nov. 28, 1989.
U.S. Pat. No. 4,987,071, issued Jan. 22, 1991.
U.S. Pat. No. 5,145,684, issued Sep. 8, 1992.
U.S. Pat. No. 5,334,711, issued Aug. 2, 1994.
U.S. Pat. No. 5,354,855, issued Oct. 11, 1994.
U.S. Pat. No. 5,399,363, issued Mar. 21, 1995.
U.S. Pat. No. 5,466,468, issued Nov. 14, 1995.
U.S. Pat. No. 5,543,158, issued Apr. 6, 1996.
U.S. Pat. No. 5,552,157, issued Sep. 3, 1996.
U.S. Pat. No. 5,565,213, issued Oct. 15, 1996.
U.S. Pat. No. 5,567,434, issued Oct. 22, 1996.
U.S. Pat. No. 5,602,306, issued Feb. 11, 1997.
U.S. Pat. No. 5,631,359, issued May 20, 1997.
U.S. Pat. No. 5,639,940, issued Jun. 17, 1997.
U.S. Pat. No. 5,641,515, issued Jun. 24, 1997.
U.S. Pat. No. 5,656,016, issued Aug. 12, 1997.
U.S. Pat. No. 5,697,899, issued Dec. 16, 1997.
U.S. Pat. No. 5,720,936, issued Feb. 24, 1998.
U.S. Pat. No. 5,738,868, issued Apr. 14, 1998.
U.S. Pat. No. 5,741,516, issued Apr. 21, 1998.
U.S. Pat. No. 5,770,219, issued Jun. 23, 1998.
U.S. Pat. No. 5,779,708, issued Jul. 14, 1998.
U.S. Pat. No. 5,783,208, issued Jul. 21, 1998.
U.S. Pat. No. 5,789,655, issued Aug. 4, 1998.
U.S. Pat. No. 5,795,587, issued Aug. 18, 1998.
U.S. Pat. No. 5,797,898, issued Aug. 25, 1998.
Int. Pat. Appl. No. PCT/US87/00880.
Int. Pat. Appl. No. PCT/US88/10315.
Int. Pat. Appl. No. PCT/US89/01025.
Int. Pat. Appl. Publ. No. WO 89/06700.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Eur. Pat. Appl. Publ. No. EP 0329822.
Eur. Pat. Appl. Publ. No. EP 0360257.
Eur. Pat. Appl. Publ. No. EP 92110298.4.
Eur. Pat. Appl. Publ. No. 320,308.
Great Britian Appl. No. 2202328.
Acland G M, Aguirre G D, Ray J, Zhang Q, Aleman T S, Cideciyan A V, Pearce-Kelling S E, Anand V, Zeng Y, Maguire A M, Jacobson S G, Hauswirth W W, Bennett J., "Gene therapy restores vision in a canine model of childhood blindness," *Nat. Genet.*, 28(1):92-5, 2001.
Alexander J J, Umino Y, Everhart D, Chang B, Min S H, et al., "Restoration of cone vision in a mouse model of achromatopsia," *Nat. Med.*, 13:685-687, 2007.
Alstrom, C. H. "Heredo-retinopathia congenitalis monohybrida recessiva autosomalis: a genetical-statistical study in clinical collaboration with Olof Olson," *Hereditas*, 43:1-178, 1957.
Arshaysky V Y, Lamb T D, Pugh E N Jr, "G proteins and phototransduction," *Annu. Rev. Physiol.*, 64:153-187, 2002.
Azadi S et al., "RD3, the protein associated with Leber congenital amaurosis type 12, is required for guanylate cyclase trafficking in photoreceptor cells," *Proc Natl Acad Sci USA*, 107:21158-63, 2010.
Baehr W, Karan S, Maeda T, Luo D G, Li S, Bronson J D, Watt C B, Yau K W, Frederick J M, Palczewski K., "The function of guanylate cyclase 1 and guanylate cyclase 2 in rod and cone photoreceptors," *J. Biol. Chem.*, 282(12):8837-47, 2007.

Bainbridge J W, Smith A J, Barker S S, Robbie S, Henderson R, Balaggan K et al., "Effect of gene therapy on visual function in Leber's congenital amaurosis," *N. Engl. J. Med.*, 358:2231-2239, 2008.

Beltran W, Boye S L, Boye S E, Chiodo V, Lewin A S et al., "rAAV2/5 gene-targeting to rods: dose-dependent efficiency and complications associated with different promoters," *Gene Ther.*, 17:1162-1174, 2010.

Bereta G, Wang B, Kiser P D, Baehr W, Jang G F, Palczewski K., "A functional kinase homology domain is essential for the activity of photoreceptor guanylate cyclase 1," *J. Biol. Chem.*, 285(3):1899-908, 2010.

Bhowmick R, Li M, Sun J, Baker S A, Insinna C, Besharse J C, "Photoreceptor IFT complexes containing chaperones, guanylyl cyclase 1 and rhodopsin," *Traffic*, 10:648-63, 2009.

Boye S E, Boye S L, Pang J, Ryals R, Everhart D, Umino Y et al., "Functional and behavioral restoration of vision by gene therapy in the guanylate cyclase-1 (GC1) knockout mouse," *PLoS One*, 5:e11306, 2010.

Burns M E and Arshaysky V Y, "Beyond counting photons: trials and trends in vertebrate visual transduction," *Neuron*, 48:387-401, 2005.

Camuzat, A.; Dollfus, H.; Rozet, J.-M.; Gerber, S.; Bonneau, D.; Bonnemaison, M.; Briard, M.-L.; Duffer, J.-L.; Ghazi, I.; Leowski, C.; Weissenbach, J.; Frezal, J.; Munnich, A.; Kaplan, J., "A gene for Leber's congenital amaurosis maps to chromosome 17p," *Hum. Molec. Genet.*, 4:1447-1452, 1995.

Camuzat, A.; Rozet, J.-M.; Dollfus, H.; Gerber, S.; Perrault, I.; Weissenbach, J.; Munnich, A.; Kaplan, J., "Evidence of genetic heterogeneity of Leber's congenital amaurosis (LCA) and mapping of LCA1 to chromosome 17p13," *Hum. Genet.*, 97:798-801, 1996.

Chung D C and Traboulsi E I, "Leber congenital amaurosis: clinical correlations with genotypes, gene therapy trials update, and future directions," *J. AAPOS.*, 13:587-92, 2009.

Cideciyan A V, Aleman T S, Boye S L, Schwartz S B, Kaushal S et al., "Human gene therapy for RPE65 isomerase deficiency activates the retinoid cycle of vision but with slow rod kinetics. *Proc. Natl. Acad. Sci. USA*, 105:15112-7, 2008.

Cideciyan A V, Hauswirth W W, Aleman T S, Kaushal S, Schwartz S B, Boye S L et al., "Vision one year after gene therapy for Leber congenital amaurosis," *N. Engl. J. Med.*, 361:725-727, 2009.

Coleman J E and Semple-Rowland S L, "GC1 deletion prevents light-dependent arrestin translocation in mouse cone photoreceptor cells," *Invest. Ophthalmol. Vis. Sci.* 46:12-6, 2005.

Coleman J E, Zhang Y, Brown G A, Semple-Rowland S L, "Cone cell survival and downregulation of GCAP1 protein in the retinas of GC1 knockout mice," *Invest. Ophthalmol. Vis. Sci.*, 45:3397-403, 2004.

Cremers, F. P. M.; van den Hurk, J. A. J. M.; den Hollander, A. I., "Molecular genetics of Leber congenital amaurosis," *Hum. Molec. Genet.* 11:1169-1176, 2002.

den Hollander A I, Roepman R, Koenekoop R K, Cremers R P "Leber congenital amaurosis: genes, proteins and disease mechanisms," *Prog Ret Eye Res* 27:301-419, 2008.

Dizhoor A M, Lowe D G, Olshevskaya E V, Laura R P and Hurley J B, "The human photoreceptor membrane guanylyl cyclase, RetGC, is present in outer segments and is regulated by calcium and a soluble activator," *Neuron*, 12:1345-52, 1994.

Douglas R M, Alam N M, Silver B D, McGill T J, Tschetter W W et al., "Independent visual threshold measurements in the two eyes of freely moving rats and mice using a virtual-reality optokinetic system," *Vis. Neuro.*, 22:677-684, 2005.

Downes S M, Payne A M, Kelsell R E, Fitzke F W, Holder G E, Hunt D M et al., "Autosomal dominant cone-rod dystrophy with mutations in the guanylate cyclase 2D gene encoding retinal guanylate cyclase-1. *Arch. Ophthalmol.*, 119:1667-1673, 2001.

Ehara, H.; Nakano, C.; Ohno, K.; Goto, Y.-I.; Takeshita, K., "New autosomal-recessive syndrome of Leber congenital amaurosis, short stature, growth hormone insufficiency, mental retardation, hepatic dysfunction, and metabolic acidosis," *Am. J. Med. Genet.* 71:258-266, 1997.

Ek, J.; Kase, B. F.; Reith, A.; Bjorkhem, I.; Pedersen, J. I., "Peroxisomal dysfunction in a boy with neurologic symptoms and amaurosis (Leber disease): clinical and biochemical findings similar to those observed in Zellweger syndrome," *J. Pediat.* 108:19-24, 1986.

Francois, J., "Leber's congenital tapetoretinal degeneration," *Int. Ophthal. Clin.*, 8:929-947, 1968.

Gillespie, F. D., "Congenital amaurosis of Leber," *Am. J. Ophthal.*, 61:874-880, 1966.

Glushakova L G et al., "Does recombinant adeno-associated virus-vectored proximal region of mouse rhodopsin promoter support only rod-type specific expression in vivo? *Mol. Vis.* 12:298-309, 2006.

Gorczyca W A et al., "Purification and physiological evaluation of a guanylate cyclase activating protein from retinal rods," *Proc Natl Acad Sci USA*, 91:4014-8, 1994.

Haire S E, Pang J, Boye S L, Sokal I, Craft C M et al., "Light-driven cone arrestin translocation in cones of postnatal guanylate cyclase-1 knockout mouse retina treated with AAV-GC1," *Invest. Ophthalmol. Vis. Sci.*, 47(9):3745-53, 2006.

Hanein, S.; Perrault, I.; Gerber, S.; Tanguy, G.; Barbet, F.; Ducroq, D.; Calvas, P.; Dollfus, H.; Hamel, C.; Lopponen, T.; Munier, F.; Santos, L.; Shalev, S.; Zafeiriou, D.; Dufier, J.-L.; Munnich, A.; Rozet, J.-M.; Kaplan, J., "Leber congenital amaurosis: comprehensive survey of the genetic heterogeneity, refinement of the clinical definition, and genotype-phenotype correlations as a strategy for molecular diagnosis," *Hum. Mutat.* 23:306-317, 2004.

Hanein, S.; Perrault, I.; Olsen, P.; Lopponen, T.; Hietala, M.; Gerber, S.; Jeanpierre, M.; Barbet, F.; Ducroq, D.; Hakiki, S.; Munnich, A.; Rozet, J.-M.; Kaplan, J., "Evidence of a founder effect for the RETGC1 (GUCY2D) 2943DelG mutation in Leber congenital amaurosis pedigrees of Finnish origin," (Abstract) *Hum. Mutat.*, 20:322-323, 2002.

Hauswirth W, Aleman T S, Kaushal S, Cideciyan A V, Schwartz S B, Wang L et al., "Treatment of Leber congenital amaurosis due to RPE65 mutations by ocular subretinal injection of adeno-associated virus gene vector: short-term results of a phase I trial," *Hum. Gene Ther.*, 19:979-990, 2008.

Hayasaka, S.; tiara, S.; Mizuno, K.; Narisawa, K.; Tada, K., "Leber's congenital amaurosis associated with hyperthreoninemia," *Am. J. Ophthal.*, 101:475-479, 1986.

Huang Y, Cideciyan A V, Papastergiou G I, Banin E, Semple-Rowland S L et al., "Relation of optical coherence tomography to microanatomy in normal and rd chickens," *Invest. Ophthalmol. Vis. Sci.*, 39:2405-16, 1998.

Jacobson S G et al., "Safety in nonhuman primates of ocular AAV2-RPE65, a candidate treatment for blindness in Leber congenital amaurosis," *Hum Gene Ther.* 17:845-58, 2006.

Jacobson S G, Acland G M, Aguirre G D, Aleman T S, Schwartz S B et al., "Safety of recombinant adeno-associated virus type 2-RPE65 vector delivered by ocular subretinal injection," *Mol. Ther.,* 13:1074-84, 2006.

Karan S, Frederick J M and Baehr W, "Novel functions of photoreceptor guanylate cyclases revealed by targeted deletion," *Mol. Cell. Biochem.,* 334:141-55, 2010.

Khani S C, Pawlyk B S, Bulgakov O V, Kasperek E, Young J E, "AAV-mediated expression targeting of rod and cone photoreceptors with a human rhodopsin kinase promoter," *Invest. Ophthalmol. Vis. Sci.,* 48:3954-61, 2007.

Khanna, H.; Davis, E. E.; Murga-Zamalloa, C. A.; Estrada-Cuzcano, A.; Lopez, I.; den Hollander, A. I.; Zonneveld, M. N.; Othman, M. I.; Waseem, N.; Chakarova, C. F.; Maubaret, C.; Diaz-Font, A. et al., "A common allele in RPGRIP1L is a modifier of retinal degeneration in ciliopathies," *Nature Genet.,* 41:739-745, 2009.

Kolstad K D et al., "Changes in adeno-associated virus-mediated gene delivery in retinal degeneration," *Hum. Gene Ther.,* 21:571-8, 2010.

Komáromy A M, Alexander J J, Rowlan J S, Garcia M M, Chiodo V A, Kaya A et al "Gene therapy rescues cone function in congenital achromatopsia." *Hum Mol. Genet.* April 21 [Epub ahead of print], 2010.

Lamb T D, Pugh E N Jr, "Phototransduction, dark adaptation, and rhodopsin regeneration the proctor lecture," *Invest. Ophthalmol. Vis. Sci.,* 47:5138-5152, 2006.

Lambert, S. R.; Sherman, S.; Taylor, D.; Kriss, A.; Coffey, R.; Pembrey, M., "Concordance and recessive inheritance of Leber congenital amaurosis," *Am. J. Med. Genet.,* 46:275-277, 1993.

Leber, T., "Ueber anomale formen der retinitis pigmentosa," *Albrecht von Graefes Arch. Ophthal.,* 17:314-340, 1871.

Leber, T., "Ueber retinitis pigmentosa and angeborene amaurose," *Albrecht von Graefes Arch. Ophthal.* 15:1-25, 1869.

Li T, Pawlyk B S, Bulgakov O V, Liu X, Xu X, Adamian M, Sun X, Khani S C, Berson E L, Sandberg M, "Replacement gene therapy with a human RPGRIP1 sequence slows photoreceptor degeneration in a murine model of Leber congenital amaurosis," *Hum. Gene Ther.,* 21(8): 993-1004, 2010.

Li W et al., "Gene therapy following subretinal AAV5 vector delivery is not affected by a previous intravitreal AAV5 vector administration in the partner eye," *Mol. Vis.,* 14:267-75, 2009.

Liu X, Seno K, Nishizawa Y, Hayashi F, Yamazaki A et al., "Ultrastructural localization of retinal guanylate cyclase in human and monkey retinas," *Exp. Eye Res.,* 59:761-8, 1994.

Liu, L, Barone I, Dai X, Lei B, Boye S L, Chiodo V, Chang B, Hauswirth W W, Strettoi E, Pang J J, "Gene therapy preserves inner retinal neurons and their connectivity in rd10 mice, a model of recessive retinitis pigmentosa with PDEβ mutations," *Abstr. ARVO Annu. Meet,* #3112, 2010.

Livak K J and Schmittgen "Analysis of relative gene expression data using real-time quantitative PCR and the 2(-Delta Delta C(T)) Method. *Methods,* 25:402-8, 2001.

Lotery A J et al "Adeno-associated virus type 5 transduction efficiency and cell-type specificity in the primate retina," *Hum Gene Ther.,* 14:1663-71, 2003.

Lowe D G, Dizhoor A M, Liu K, Gu Q, Spencer M et al., "Cloning and expression of a second photoreceptor-specific membrane retina guanylyl cyclase (RetGC), RetGC-2," *Proc. Natl. Acad. Sci. USA,* 92:5535-9, 1995.

Maguire A M, Simonelli F, Pierce E A, Pugh Jr E N, Mingozzi F, Bennicelli J et al., "Safety and efficacy of gene transfer for Leber's congenital amaurosis," *N. Engl. J. Med.,* 358:2240-2248, 2008.

Mah et al., "Dual vectors expressing murine factor VIII result in sustained correction of hemophilia A mice,"*Hum. Gene Ther.,* 14(2):143-152, 2003.

Mancuso K et al "Gene therapy for red-green colour blindness in adult primates," *Nature* 461:784-7, 2009.

McCarty et al., "Adeno-associated virus terminal repeat (TR) mutant generates self-complementary vectors to overcome the rate-limiting step to transfuction in vivo," *Gene Ther.,* 10(26):2112-2118, 2003.

Mendez A, Burns M E, Sokal I, Dizhoor A M, Baehr W, Palczewski K, Baylor D A, Chen J., "Role of guanylate cyclase-activating proteins (GCAPs) in setting the flash sensitivity of rod photoreceptors," *Proc. Natl. Acad. Sci. USA,* 98(17):9948-53, 2001.

Milam, A. H.; Barakat, M. R.; Gupta, N.; Rose, L.; Aleman, T. S.; Pianta, M. J.; Cideciyan, A. V.; Sheffield, V. C.; Stone, E. M.; Jacobson, S. G., "Clinicopathologic effects of mutant GUCY2D in Leber congenital amaurosis," *Ophthalmology,* 110:549-558, 2003.

Moore, A. T.; Taylor, D. S. I. "A syndrome of congenital retinal dystrophy and saccade palsy—a subset of Leber's amaurosis, *Brit. J. Ophthal.,* 68:421-431, 1984.

Nakamura, M.; Ito, S.; Miyake, Y. "Novel de novo mutation in CRX gene in a Japanese patient with Leber congenital amaurosis," *Am. J. Ophthal.,* 134:465-467, 2002.

Natkunarajah M et al., "Assessment of ocular transduction using single-stranded and self-complementary recombinant adeno-associated virus serotype 2/8," *Gene Ther.,* 15:463-7, 2008.

Nickel, B.; Hoyt, C. S. "Leber's congenital amaurosis. Is mental retardation a frequent associated defect?" *Arch. Ophthal.,* 100:1089-1092, 1982.

Otto-Bruc A, Buczylko J, Surgucheva I, Subbaraya I, Rudnicka-Nawrot M et al., "Functional reconstitution of photoreceptor guanylate cyclase with native and mutant forms of guanylate cyclase-activating protein 1,*" Biochemistry,* 36:4295-302, 1997.

Palczewski K et al., "Molecular cloning and characterization of retinal photoreceptor guanylyl cyclase-activating protein," *Neuron* 13:395-404, 1994.

Pang J, Boye S E, Lei B, Boye S L, Everhart D, Ryals R, Umino Y, Rohrer B, Alexander J, Li J, Dai X, Li Q, Chang B, Barlow R, Hauswirth W W, "Self-complementary AAV-mediated gene therapy restores cone function and prevents cone degeneration in two models of Rpe65 deficiency," *Gene Ther.,* 17(7):815-826, 2010.

Pang J J, Boye S L, Kumar A, Dinculescu A, Deng W, Li J, Li Q, Rani A, Foster T C, Chang B, Hawes N L, Boatright J H, Hauswirth W W, "AAV-mediated gene therapy for retinal degeneration in the rd10 mouse containing a recessive PDEbeta mutation," *Invest. Ophthalmol. Vis. Sci.,* 49(10):4278-83, 2008.

Pang J J, Chang B, Kumar A, Nusinowitz S, Noorwez S M, Li J, Rani A, Foster T C, Chiodo V A, Doyle T, Li H, Malhotra R, Teusner J T, McDowell J H, Min S H, Li Q, Kaushal S, Hauswirth W W, "Gene therapy restores vision-dependent behavior as well as retinal structure and function in a mouse model of RPE65 Leber congenital amaurosis," *Mol. Ther.,* 13(3):565-72. 2006.

Pang J J, Dai X, Boye S E, Barone I, Boye S L, Mao S et al., "Long-term retinal function and structure rescue using capsid mutant AAV8 vector in the rd10 mouse, a model of recessive retinitis pigmentosa," *Mol. Ther.* 19:234-42, 2011.

Pang J J, Dai X, Everhart D, 3, Lei B, Boye S L, Dinculescu A, Umino Y, Chang B, Barlow R, Hauswirth W W., "Long-term rescue following gene therapy with capsid mutant AAV8 in the rd10 mouse, a model of recessive retinitis pigmentosa," *ARVO Abstract* 2527, Annu. Meet., 2010.

Pasadhika S, Fishman G A, Stone E M, Lindeman M, Zelkha R et al., "Differential macular morphology in patients with RPE65, CEP290, GUCY2D and AIPL1 related Leber congenital amaurosis," *Invest. Ophthalmol. Vis. Sci.*, 51(5):2608-2614, 2010.

Pawlyk B S et al., "Replacement gene therapy with a human RPGRIP1 sequence slows photoreceptor degeneration in a murine model of leber congenital amaurosis," *Hum Gene Ther.*, April 12 [Epub ahead of print], 2010.

Payne A M, Morris A G, Downes S M, Johnson S, Bird A C, Moore A T et al., "Clustering and frequency of mutations in the retinal guanylate cyclase (GUCY2D) gene patients with dominant cone-rod dystrophies," *J Med. Genet.* 38:611-614, 2001.

Perrault et al., "Retinal-specific guanylate cyclase gene mutations in Leber's congenital amaurosis," *Nat. Genet.*, 14(4):461-4, 1996.

Perrault I, Rozet J M, Gerber S, Ghazi I, Ducroq D et al., "Spectrum of retGC I mutations in Leber's congenital amaurosis," *Eur. J. Hum. Genet.*, 8:578-82, 2000.

Perrault I, Rozet J M, Gerber S, Ghazi I, Leowski C et al., "Leber congenital amaurosis," *Mol. Genet. Metab.*, 68:200-8, 1999.

Perrault, I.; Rozet, J. M.; Calvas, P.; Gerber, S.; Camuzat, A.; Dollfus, H.; Chatelin, S.; Souied, E.; Ghazi, I.; Leowski, C.; Bonnemaison, M.; Le Paslier, D.; Frezal, J.; Dufier, J.-L.; Pittler, S.; Munnich, A.; Kaplan, J., "Retinal-specific guanylate cyclase gene mutations in Leber's congenital amaurosis," *Nature Genet.*, 14:461-464, 1996.

Perrault, I.; Rozet, J.-M.; Gerber, S.; Ghazi, I.; Leowski, C.; Ducroq, D.; Souied, E.; Dufier, J.-L.; Munnich, A.; Kaplan, J., "Leber congenital amaurosis," *Molec. Genet. Metab.*, 68:200-208, 1999.

Petrs-Silva H, Dinculescu A, Li Q, Min S H, Chiodo V, Pang J J, et al. "High-efficiency transduction of the mouse retina by tyrosine-mutant AAV serotype vectors," *Mol. Ther.* 17:463-71, 2009.

Poirier, A et al. "Toxicology and biodistribution studies of a recombinant adeno-associated virus 2-α-1 antitrypsin vector," *Preclinica* 2:43-51, 2004.

Polans A, Baehr W, Palczewski K "Turned on by $Ca^{2+}$! The physiology and pathology of $Ca^{2+}$ binding proteins in the retina," *Trends Neurosci* 19:547-554, 2006.

Provost N et al., "Biodistribution of rAAV vectors following intraocular administration: evidence for the presence and persistence of vector DNA in the optic nerve and in the brain," *Mol. Ther.*, 11:275-83, 2005.

Pugh E N Jr, Duda T, Sharma R K, Sitaramayya A "Photoreceptor guanylate cyclases: a review," *Biosci Rep.*, 17:429-473, 1997.

Rahn, E. K.; Falls, H. F.; Knaggs, J. G.; Proux, D. J., "Leber's congenital amaurosis with an Ehlers-Danlos-like syndrome: study of an American family," *Arch. Ophthat,* 79:135-141, 1968.

Riess, O.; Weber, B.; Noeremolle, A.; Shaikh, R. A.; Hayden, M. R.; Musarella, M. A., "Linkage studies and mutation analysis of the PDEB gene in 23 families with Leber congenital amaurosis," *Hum. Mutat.*, 1:478-485, 1992.

Russell-Eggitt, I. M.; Taylor, D. S. I.; Clayton, P. T.; Garner, A.; Kriss, A.; Taylor, J. F. N. "Leber's congenital amaurosis—a new syndrome with a cardiomyopathy," *Brit. J. Ophthal.*, 73:250-254, 1989.

Schappert-Kimmijser, J.; Henkes, H. E.; Van den Bosch, J. "Amaurosis congenita (Leber)," *Arch. Ophthal.*, 61:211-218, 1959.

Schroeder, R.; Mets, M. B.; Maumenee, I. H. "Leber's congenital amaurosis: retrospective review of 43 cases and a new fundus finding in two cases," *Arch. Ophthal.*, 105:356-359, 1987.

Schuil, J.; Meire, F. M.; Delleman, J. W. "Mental retardation in amaurosis congenita of Leber," *Neuropediatrics,* 29:294-297, 1998.

Semple-Rowland S L, Lee N R, Van Hooser J P, Palczewski K, Baehr W, "A null mutation in the photoreceptor guanylate cyclase gene causes the retinal degeneration chicken phenotype," *Proc. Natl. Acad. Sci. USA*, 95:1271-6, 1998.

Simonelli F, Ziviello C, Testa F, Rossi S, Fazzi E et al., "Clinical and molecular genetics of Leber's congenital amaurosis: a multicenter study of Italian patients," *Invest. Ophthalmol. Vis. Sci.*, 48:4284-90, 2007.

Sohocki, M. M.; Bowne, S. J.; Sullivan, L. S.; Blackshaw, S.; Cepko, C. L.; Payne, A. M.; Bhattacharya, S. S.; Khaliq, S.; Mehdi, S. Q.; Birch, D. G.; Harrison, W. R.; Elder, F. F. B.; Heckenlively, J. R.; Daiger, S P, "Mutations in a new photoreceptor-pineal gene on 17p cause Leber congenital amaurosis," *Nature Genet.* 24:79-83, 2000.

Song S et al. "Intramuscular administration of recombinant adeno-associated virus 2 a-1 antitrypsin (rAAV-SER-PINA1) vectors in a nonhuman primate model: safety and immunologic aspects," *Mol. Ther.*, 6:329-335, 2002.

Sorsby, A.; Williams, C. E., "Retinal aplasia as a clinical entity," *Brit. Med. J.* 1:293-297, 1960.

Stephen R et al., "Stabilizing function for myristoyl group revealed by the crystal structure of a neuronal calcium sensor, guanylate cyclase-activating protein 1," *Structure* 15:1392-402, 2007.

Stieger K et al., "Subretinal delivery of recombinant AAV serotype 8 vector in dogs results in gene transfer to neurons in the brain," *Mol. Ther.* 16:916-23, 2008.

Sun X, Pawlyk B, Xu X, Liu X, Bulgakov O V et al., "Gene therapy with a promoter targeting both rods and cones rescues retinal degeneration caused by AIPL1 mutations," *Gene Ther.*, 17:117-31, 2010.

Surace E M and Auricchio A. "Versatility of AAV vectors for retinal gene transfer," *Vis. Res.*, 48:353-359, 2007.

Tan M H, Smith A J, Pawlyk B, Xu X, Liu X et al., "Gene therapy for retinitis pigmentosa and Leber congenital amaurosis caused by defects in AIPL1: effective rescue of mouse models of partial and complete Aipl1 deficiency using AAV2/2 and AAV2/8 vectors," *Hum. Mol. Genet.*, 18:2099-114, 2009.

Timmers A M, Zhang H, Squitieri A, Gonzalez-Pola C, "Subretinal injections in rodent eyes: effects on electrophysiology and histology of rat retina," *Mol. Vis.*, 7:131-7, 2001.

Traint and Whitehead, "Simultaneous Extraction of High-Quality RNA and DNA from Small Tissue Samples," *J. Heredity,* 100:246-250, 2009.

Ulshafer R J, Allen C, Dawson W W and Wolf E D, "Hereditary retinal degeneration in the Rhode Island Red chicken. I. Histology and ERG," *Exp. Eye Res.*, 39:125-35, 1984.

Umino Y, Solessio E, Barlow R B, "Speed, spatial, and temporal tuning of rod and cone vision in mouse," *J. Neurosci.*, 28:189-198, 2008.

Waardenburg, P. J.; Schappert-Kimmijser, J., "On various recessive biotypes of Leber's congenital amaurosis," *Acta Ophthal.*, 41:317-320, 1963.

Wagner, R. S.; Caputo, A. R.; Nelson, L. B.; Zanoni, D., "High hyperopia in Leber's congenital amaurosis," *Arch. Ophthal.*, 103:1507-1509, 1985.

Weiss E R, et al., "Species-specific differences in expression of G-protein-coupled receptor kinase (GRK) 7 and GRK1 in mammalian cone photoreceptor cells: implications for cone cell phototransduction," *J. Neurosci.*, 21:9175-84, 2001.

Wensel T G "Signal transducing membrane complexes of photoreceptor outer segments," *Vis Res.* 48:2052-2061, 2008.

Wilkie S E, Newbold F J, Deery E, Walker C E, Stinton I, Ramamurthy V et al., "Functional characterization of missense mutations at codon 838 in retinal guanylate cyclase correlates with disease severity in patients with autosomal dominant cone-rod dystrophy," *Hum Mol. Genet.*, 9:3065-3073, 2000.

Williams G A and Jacobs G H "Cone-based vision in the aging mouse," *Vision Res* 47:2037-46, 2007.

Williams M L, Coleman J E, Haire S E, Aleman T S, Cideciyan A V, "Lentiviral expression of retinal guanylate cyclase-1 (RetGC1) restores vision in an avian model of childhood blindness," *PLoS. Med.*, 3:e201, 2006.

Yang G S, Schmidt M, Yan Z, Lindbloom J D, Harding T C et al., "Virus-mediated transduction of murine retina with adeno-associated virus: effects of viral capsid and genome size," *J. Virol.*, 76:7651-60, 2002.

Yang R B and Garbers D L, "Two eye guanylyl cyclases are expressed in the same photoreceptor cells and form homomers in preference to heteromers," *J. Biol. Chem.*, 272:13738-42, 1997.

Yang R B, Foster D C, Garbers D L, Rifle H J, "Two membrane forms of guanylyl cyclase found in the eye," *Proc. Natl. Acad. Sci. USA*, 92:602-6, 1995.

Yang R B and Garbers D L "Two eye guanylyl cyclases are expressed in the same photoreceptor cells and form homomers in preference to heteromers," *J. Biol. Chem.*, 272:13738-13742, 1997.

Yang R B, Robinson S W, Xiong W H, Yau K W, Birch D G et al., "Disruption of a retinal guanylyl cyclase gene leads to cone-specific dystrophy and paradoxical rod behavior," *J. Neurosci.*, 19:5889-97, 1999.

Yano, S.; Oda, K.; Watanabe, Y.; Watanabe, S.; Matsuishi, T.; Kojima, K.; Abe, T.; Kato, H. "Two sib cases of Leber congenital amaurosis with cerebellar vermis hypoplasia and multiple systemic abnormalities," *Am. J. Med. Genet.*, 78:429-432, 1998.

Yin L, Greenberg K, Hunter J J, Dalkara D, Kolstad K D, Masella B D et al., "Intravitreal injection of AAV2 transduces macaque inner retina," *Invest. Ophthalmol. Vis. Sci.*, Feb. 10, 2011.

Zernant, J.; Kuhn, M.; Dharmaraj, S.; den Hollander, A. I.; Perrault, I.; Preising, M. N.; Lorenz, B.; Kaplan, J.; Cremers, F. P. M.; Maumenee, I.; Koenekoop, R. K.; Allikmets, R., "Genotyping microarray (disease chip) for Leber congenital amaurosis: detection of modifier alleles," *Invest. Ophthal. Vis. Sci.*, 46:3052-3059, 2005.

Zhang H, Huang W, Zhang H, Zhu X, Craft C M et al., "Light-dependent redistribution of visual arrestins and transducin subunits in mice with defective phototransduction," *Mol. Vis.*, 9:231-7, 2003.

Zhong L, et al., "Next generation of adeno-associated virus 2 vectors: point mutations in tyrosines lead to high-efficiency transduction at lower doses. *Proc. Natl. Acad. Sci. USA*, 105:7827-32, 2008.

Zhu X, Li A, Brown B, Weiss E R, Osawa S, Craft C M, "Mouse cone arrestin expression pattern: light induced translocation in cone photoreceptors," *Mol. Vis.*, 8:462-71, 2002.

Zolotukhin S et al., "Production and purification of serotype 1, 2, and 5 recombinant adeno-associated viral vectors," *Methods*, 28(2):158-67, 2002.

All of the compositions and methods disclosed and claimed herein can be made and executed without undue experimentation in light of the present disclosure. While the compositions and methods of this invention have been described in terms of preferred embodiments, it will be apparent to those of ordinary skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those of ordinary skill in the art are deemed to be within the spirit, scope and concept of the invention as defined by the appended claims.

What is claimed is:

1. A method for treating a human suffering from Leber congenital amaurosis-1 (LCA1), wherein the human has a defect, deficiency, or total absence of biologically-active retGC1 protein in at least one eye, as compared to the level of biologically-active retGC1 protein in an eye of a normal, untreated human, the method comprising: introducing into at least a first population of human photoreceptor cells an rAAV vector comprising at least a first polynucleotide that comprises a photoreceptor-specific human rhodopsin kinase promoter, operably linked to at least a first nucleic acid segment that encodes a first biologically-active, retinal-specific human guanylate cyclase polypeptide that comprises a first contiguous amino acid sequence region that is at least about 95% identical to a first sequence region of at least 80-contiguous-amino-acid sequence from SEQ ID NO:1, wherein the rAAV vector is contained within a AAV5 or AAV8 particle and wherein the rAAV vector is administered subretinally into at least a first site within one or both eyes of the human in an amount effective to produce a biologically-active human retGCI polypeptide in the one or more photoreceptor cells, such that production of the biologically-active human retGCI polypeptide in the one or more photoreceptor cells rescues and provides sustained restoration of photoreceptor function, thereby treating Leber congenital amaurosis-1 (LCA1).

2. The method of claim 1, wherein the human is a neonate, a newborn, an infant, or a juvenile.

3. The method of claim 1, wherein production of the biologically active retGCI polypeptide in the one or more photoreceptor cells a) preserves one or more cone photoreceptors, b) restores one or more cone-mediated functions, c) restores visual behavior in one or both eyes, or d) any combination thereof.

4. The method of claim 1, wherein production of the biologically active retGCI polypeptide persists in the one or more photoreceptor cells for a period of at least about three months following a single administration of the rAAV vector into the first population of human photoreceptor cells within the one or both eyes of the human.

5. The method of claim 4, wherein production of the biologically active retGCI polypeptide persists in the one or more-photoreceptor cells for a period of at least about six months following a single administration of the rAAV vector into the first population of human photoreceptor cells within the one or both eyes of the human.

6. The method of claim 5, wherein production of the biologically active retGCI polypeptide persists in the one or more photoreceptor cells for a period of at least about ten months following a single administration of the rAAV vector into the first population of human-photoreceptor cells within the one or both eyes of the human.

7. The method of claim 1, wherein the rAAV vector is contained within a AAV5 particle.

* * * * *

UNITED STATES PATENT AND TRADEMARK OFFICE
CERTIFICATE OF CORRECTION

PATENT NO. : 9,816,108 B2
APPLICATION NO. : 13/643074
DATED : November 14, 2017
INVENTOR(S) : Shannon E. Boye et al.

It is certified that error appears in the above-identified patent and that said Letters Patent is hereby corrected as shown below:

In the Claims

At Column 147, Line 40, Claim 1 the text:
"retGCI"
Should be replaced with the text:
--retGC1--

At Column 147, Line 42, Claim 1 the text:
"retGCI"
Should be replaced with the text:
--retGC1--

At Column 148, Line 21, Claim 3 the text:
"retGCI"
Should be replaced with the text:
--retGC1--

At Column 148, Line 28, Claim 4 the text:
"retGCI"
Should be replaced with the text:
--retGC1--

At Column 148, Line 34, Claim 5 the text:
"retGCI"
Should be replaced with the text:
--retGC1--

Signed and Sealed this
Nineteenth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,816,108 B2

At Column 148, Line 40, Claim 6 the text:
"retGCI"
Should be replaced with the text:
--retGC1--